United States Patent
Higuchi et al.

(10) Patent No.: US 6,462,038 B1
(45) Date of Patent: Oct. 8, 2002

(54) ANDROGEN RECEPTOR MODULATOR COMPOUNDS AND METHODS

(75) Inventors: Robert Higuchi, Solana Beach; Kristen L. Arienti, San Diego; Mani Neelakandha, San Diego; Barbara Pio, San Diego; Lin Zhi, San Diego; Penghui Chen, San Diego; Thomas R. Caferro, San Diego, all of CA (US)

(73) Assignee: Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/648,684

(22) Filed: Aug. 25, 2000

Related U.S. Application Data
(60) Provisional application No. 60/150,988, filed on Aug. 27, 1999.

(51) Int. Cl.[7] .................. A61K 31/536; A61K 31/545; C07D 265/34; C07D 279/14
(52) U.S. Cl. .............. 514/224.5; 514/229.8; 514/250; 514/291; 544/34; 544/101; 544/345; 546/80; 546/89; 546/90
(58) Field of Search ............. 544/34, 101, 345; 514/224.5, 229.8, 250, 291; 546/80, 89, 90

(56) References Cited

U.S. PATENT DOCUMENTS

| | | | |
|---|---|---|---|
| 3,755,332 A | 8/1973 | Wasley et al. ........ 260/288 R |
| 3,798,031 A | 3/1974 | Janssens et al. .......... 96/1.8 |
| 3,830,647 A | 8/1974 | Janssens et al. .......... 96/1.5 |
| 3,832,171 A | 8/1974 | Janssens et al. .......... 96/1.5 |
| 3,928,686 A | 12/1975 | Poot et al. ............. 428/457 |
| 3,936,461 A | 2/1976 | Schwender et al. ..... 260/289 R |
| 3,979,394 A | 9/1976 | Janssens et al. .......... 260/283 |
| 3,993,656 A | 11/1976 | Rooney et al. ........ 260/296 N |
| 4,138,490 A | 2/1979 | Brittain et al. ........... 424/258 |
| 4,193,931 A | 3/1980 | Loeliger ................. 424/308 |
| 4,326,055 A | 4/1982 | Loeliger ................. 542/429 |
| 4,415,572 A | 11/1983 | Tominaga et al. ........ 424/250 |
| 4,427,654 A | 1/1984 | Austin ..................... 424/95 |
| 4,505,852 A | 3/1985 | Rasnick et al. ........ 260/112.5 |
| 4,534,979 A | 8/1985 | Loev et al. .............. 514/529 |
| 4,539,134 A | 9/1985 | Martin et al. ........... 252/156 |
| 4,578,498 A | 3/1986 | Frickel et al. ............. 560/8 |
| 4,710,507 A | 12/1987 | Campbell et al. ........ 514/312 |
| 4,728,653 A | 3/1988 | Campbell et al. ........ 514/312 |
| 4,801,733 A | 1/1989 | Wuest et al. ............ 560/56 |
| 4,831,052 A | 5/1989 | Shudo ................... 514/455 |
| 4,833,240 A | 5/1989 | Maignan et al. ........ 536/55.2 |
| 4,874,747 A | 10/1989 | Shroot et al. ............ 514/23 |
| 4,879,284 A | 11/1989 | Lang et al. ............. 514/62 |
| 4,898,864 A | 2/1990 | Maignan et al. ........ 514/237.5 |
| 4,925,979 A | 5/1990 | Shudo ................... 562/462 |
| 4,933,336 A | 6/1990 | Martin et al. ........... 514/222.5 |
| 4,943,502 A | 7/1990 | Terrell et al. ............ 430/58 |
| 4,981,784 A | 1/1991 | Evans et al. ............. 435/6 |
| 5,004,730 A | 4/1991 | Philippe et al. .......... 514/29 |
| 5,071,773 A | 12/1991 | Evans et al. ............ 436/501 |
| 5,081,242 A | 1/1992 | Combs .................... 544/52 |
| 5,091,528 A | 2/1992 | Gluchowski ............ 544/105 |
| 5,124,473 A | 6/1992 | Shroot et al. ............ 560/56 |
| 5,147,844 A | 9/1992 | Weber et al. ............ 503/227 |
| 5,198,567 A | 3/1993 | Lang et al. .............. 560/56 |
| 5,320,833 A | 6/1994 | Deckers et al. .......... 424/59 |
| 5,391,569 A | 2/1995 | Brion et al. ............. 514/456 |
| 5,391,766 A | 2/1995 | Klaus et al. .............. 549/23 |
| 5,688,808 A | 11/1997 | Jones et al. ............. 514/285 |
| 5,688,810 A | 11/1997 | Jones et al. ............. 514/311 |
| 5,693,646 A | 12/1997 | Jones et al. ............. 514/285 |
| 5,693,647 A | 12/1997 | Jones et al. ............. 514/285 |
| 5,696,127 A | 12/1997 | Jones et al. ............. 514/285 |
| 5,696,130 A | 12/1997 | Jones et al. ............. 514/291 |
| 5,705,167 A | 1/1998 | Bernardon et al. ....... 424/401 |
| 5,721,103 A | 2/1998 | Boehm et al. ............ 435/7.1 |
| 5,776,699 A | 7/1998 | Klein et al. .............. 435/7.2 |
| 5,910,508 A | 6/1999 | Thoreau et al. .......... 514/432 |
| 5,968,908 A | 10/1999 | Epstein et al. ........... 514/42 |
| 5,972,935 A | * 10/1999 | Gaster ................. 514/229.8 |
| 5,977,108 A | 11/1999 | Kikuchi et al. .......... 514/249 |
| 5,977,125 A | 11/1999 | Hibi et al. ............... 514/277 |
| 6,030,964 A | 2/2000 | Hibi et al. ............... 514/183 |
| 6,133,309 A | 10/2000 | Bollag et al. ............ 514/437 |
| 6,147,224 A | 11/2000 | Vuligonda et al. ........ 548/518 |

FOREIGN PATENT DOCUMENTS

| | | |
|---|---|---|
| DE | 2111938 | 10/1971 |
| DE | 2611824 | 9/1976 |
| DE | 38 10 706 | 10/1989 |
| EP | 0 272 910 | 6/1988 |
| EP | 0 356 230 | 2/1990 |
| EP | 0542609 | 11/1992 |
| EP | 0 718 285 | 6/1996 |
| GB | 2058788 | 4/1981 |
| SU | 555119 | 6/1977 |
| WO | 89/07441 | 8/1989 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |
| WO | 94/20093 | 9/1994 |

(List continued on next page.)

OTHER PUBLICATIONS

Korshak et al., Chemical Abstracts, vol. 106:196899, 1987.*
Potts et al., Chemical Abstracts, vol. 107:7167, 1987.*
Gaster, Chemical Abstracts, vol. 126:251157, 1997.*

(List continued on next page.)

*Primary Examiner*—Richard L. Raymond
(74) *Attorney, Agent, or Firm*—Brobeck, Phleger & Harrison LLP

(57) ABSTRACT

Compounds, pharmaceutical compositions, and methods for modulating processes mediated by steroid receptors. In particular, preparation and methods of use of non-steroidal compounds and compositions that are agonists, partial agonists, and antagonists for the androgen receptor (AR) are described. Further, described are the methods of making and use of critical intermediates including a stereoselective synthetic route to intermediates for the AR modulators.

69 Claims, No Drawings

FOREIGN PATENT DOCUMENTS

| WO | 9524394 | 9/1995 |
|---|---|---|
| WO | 96/05165 | 2/1996 |
| WO | 96/19458 | 6/1996 |
| WO | 96/20913 | 7/1996 |
| WO | 9700876 | 1/1997 |
| WO | 97/12853 | 4/1997 |
| WO | 97/49709 | 12/1997 |
| WO | 99/43708 | 9/1999 |
| WO | 99/58486 | 11/1999 |
| WO | 00/53562 | 9/2000 |
| WO | 00/66680 | 11/2000 |

OTHER PUBLICATIONS

Patent Abstracts of Japan, vol. 009:188, Pub. Date: Aug. 3, 1985, Pub. No. 60056985.

Patent Abstracts of Japan, vol. 004:019, Pub. Date: Dec. 6, 1979, Pub. No. 54154797.

Patent Abstracts of Japan, vol. 1999:14, Pub. Date: Sep. 7, 1999, Pub. No. 11242304.

Atarashi, et al., "Asymmetric Reduction of 7,8–Difluoro–3–methyl–2H–1,4–benzoxazine. Synthesis of a Key Intermediate of (S)–(–)–Ofloxacin (DR–3355)," *J. Heterocyclic Chem.* 28:329–31 (1991).

Barluenga, et al., "A New Method for the Syntheis of Pyridines," *Synthesis* 191 (1975).

Berger, et al., "Interaction of Glucocorticoid Analogues with the Human Glucocorticoid Receptor," *J. Steroid Biochem. Mol. Biol.* 41:733–38 (1992).

Edwards, et al., "New Nonsteriodal Androgen Receptor Modulators Based on 4–(Trifluormethyl)–2(1H)–Pyrrolidino[3,2–g]Quinolinone," *Bioorg. Med. Chem. Lett.* 8:745–750 (1998).

Evans, "The Steriod and Thyroid Hormone Receptor Superfamily," *Science* 240:889–95 (1988).

Goralski, et al., "Boranes in Synthesis. 3. Conversion of the Morpholine and Pyrrolidine Enamines of Symmetrical Dialkylketones to the Corresponding threo–β–Amino Alcohols via Hydroboration/Oxidation," *Tetrahedron Lett.* 35:3251–54 (1994).

Hamann, et al., "Synthesis and Biological Activity of a Novel Series of Nonsteriodal, Peripherally Selective androgen Receptor Antagonists Derived from 1,2–Dihydropyridono[5,6–g]quinolines," *J. Med. Chem.*, 41:623–639 (1997).

Hershberger, et al., "Myotrophic Activity of 19–Nortestosterone and Other Steroids Determined by Modified Levator Ani Muscle Method" *Proc. Soc. Exptl. Biol. Med.* 83:175–178 (1953).

Jones, "The Structure, Reactions, Synthesis and Uses of Heterocyclic Compounds," *Comprehensive Heterocyclic Chemistry* vol. 2, Chap. 2.08, 421–426 (1984).

Labrie, et al., "Science behind total androgen blockade: from gene to combination therapy," *Clin. Invest. Med.* 16:475–492 (1993).

Luke, et al., "The Male Sex Accessory Tissues; Structure, Androgen Action, and Physiology," *The Physiology of Reproduction*, 1435–1487 (1994).

Matsumoto, et al., "Novel Potassium Channel Activators: Synthesis and Structure–Activity Relationship Studies of 3,4–Dihydro–2H–1,4–benzoxazine Derivatives," *Chem. Pharm. Bull.*, 44:103–114 (1996).

Mitscher, et al., "Chiral DNA Gyrase Inhibitors. 2. Asymmetric Synthesis and Biological Activity of the Enantiomers of 9–Fluoro–3–methyl–10–(4–methyl–1–piperazinyl)–7–oxo–2,3–dihydro–7H–pyrido[1,2,3–de]–1, 4–benzoxazine–6–carboxylic Acid (Ofloxacin)," *J. Med. Chem.* 30:2283 (1987).

Okuda, et al., "Testosterone Dependent Regulation of the Enzymes Involved in DNA Synthesis in the Rats Ventral Prostate," *J. Urol.* 145:188–191 (1991).

Pine, et al., "Carbonyl Methylenation Using a Titanium–Aluminum (Tebbe) Complex," *J. Org. Chem.* 50:1212–1216 (1985).

Sala, et al., "Depsidone Synthesis. Part 14. The Total Synthesis of Psoromic Acid: Isopropyl Ethers as Useful Phenolic Protective Groups," *J. Chem. Soc. Perkin. Trans.* I:2593 (1979).

Sato, et al., "CsF in Organic Synthesis. Tuning of N– or O–Alkylation of 2–Pyridone," *Synlett* 845–846 (1995).

Shridhar, et al., "A General and Convenient Synthesis of 2H–1,4–Benzoxazin–3(4H)–ones," *Org. Prep. Proc. Int.* 14:195 (1982).

Simental, et al., "Transcriptional activation and nuclear targeting signals of the human androgen receptor," *J. Biol. Chem.* 266:510–518 (1991).

Voss, "2,4–Bis(4–methoxyphenyl)–1,3,2,4–dithiadiphosphetane 2,4–Disulfide," *Encyclopedia of Reagents for Organic Synthesis*, 1:530–533 (1995).

Wagaw, et al., "Palladuim–Catalyzed Coupling of Optically Active Amines with Aryl Bromides," *J. Am. Chem. Soc.* 119:8451–8458 (1997).

Walsh, et al., "Inhibition of extratesticular stimuli to prostatic growth in the castrated rat by antiandrogens," *Endrocrinology* 86:624 (1970).

Xie, et al., *Chinese Chemical Letters* 6:857 (1995).

Allegretto, et al., "Transactivation Properties of Retinoic Acid and Retinoid X Receptors in Mammalian Cells and Yeast," J. Biol. Chem., 268(35):26625–26633 (1993).

Apfel, et al., "A retinoic acid receptor α antagonist selectively counteracts retinoic acid effects," *Proc. Natl. Acad. Sci.* 89:7129 (1992).

Atkins, R.L. et al., "Substituted Coumarins and Azacoumarins. Synthesis and Flourescent Properties," *J. Org. Chem.*, 43(10):1975–1980 (1978).

Aurell, et al., "Trienediolates of Hexadienoic Acids in Synthesis. Synthesis of Retinoic and nor–Retinoic Acids." *Tetrahedron* 49:6089 (1993).

Beard, et al., "Synthesis and Structure–Activity Relationships of Stilbene Retinoid Analogs Substituted with Heteroaromatic Carboxylic Acids," *J. Med. Chem.* 38:2820 (1995).

Bestmann, et al., "Cumulated Ylides as Building Blocks for the Synthesis of Heterocycles," *Angew. Chem. Int. Ed. Engl.* 15(2):115–116 (1976).

Bissell, E.R. et al., "Synthesis and Chemistry of 7–Amino–4–(trifluormethyl)coumarin and Its Amino Acid and Peptide Derivatives," *J. Org. Chem.*, 45:2283–7 (1980).

Bissonnette, et al., "9–cis Retinoic Acid Inhibition of Activation–Induced Apoptosis Is Mediated via Regulation of Fas Ligand and Requires Retinoic Acid Receptor and Retinoid X Receptor Activation," *Mol. Cell. Biol.* 15: 5576–5585 (1995).

Biswas, et al., "Montmorillonite clay as condensing agent in Pechmann reaction for the synthesis of courmarin derivatives," *Indian J. Chem.* 31B:628 (1992).

Blatt, *The Fries Reaction Chapter 11 Org. React.* 1:342 (1942).

Boehm, et al. "Synthesis and Structure–Activity Relationships of Novel Retinoid X Receptor Selective Retinoids," *J. Med. Chem.* 37:2930 (1994).

Boehm, et al., "Design and Synthesis of Potent Retinoid X Receptor Selective Ligands That Induce Apoptosis in Leukemia Cells," *J. Med. Chem.* 38:3146 (1995).

Boehm, et al., "Synthesis of High Specific activity [3H]–9–Cis Retinoic Acid and its Application for Identifying Retinoids with Unusual Binding Properties," *J. Med. Chem.*, 37:408 (1994).

Canan–Koch, et al., "Identification of the First Retinoid X Receptor Homodimer Antagonist," *J. Med. Chem.* 39(17):3229 (1996).

Catellani, et al., "A New Palladium–catalyzed Synthesis of 3,4–Disubstituted Coumarins from 3–Alkenoates of ortho–Iodophenol, Phenylacetylene and Carbon Monoxide," *Tetrahedron Lett.* 35(32):5923 (1994).

*Chemistry and Biology of Synthetic Retinoids*, Dawson and Okamuna, Eds., CRC Press, Florida: Chapters 3,8,14, and 16 (1990).

Clark and Miller, "Hydrogen Bonding in Organic Synthesis V: Potassium Fluoride in Carboxylic Acids as an Alternative To Crown Ether With Acid Salts in The Preparation of Phenacyl Esters," *Tetrahedron Lett.* 7:599 (1977).

Dawson and Hobbs, "Ch. 2—The Synthetic Chemistry of Retinoids," in *The Retinoids: Biology, Chemistry and Medicine*, 2nd edition, edited by Sporn et al., Raven Press, New York, pp. 5–178 (1994).

Dawson, et al., "Effects of Structural Modification in the C7–C11 Region of the Retinoid Skeleton on Biological Activity in a Series of Aromatic Retinoids," *J. Med. Chem.* 32:1504 (1989).

Edwards, et al., "5–Ayrl–1, 2–dihydro–5H–Chromeno[3,4–f]quinolines as Potent, Orally Active, Nonsteriodal Progesterone Receptor Agonists: The Effect of D–Ring Substituents," *J. Med. Chem.*, 41:303–331 (1998).

Edwards, J.P., et al., "Preparation, Resolution, and Biological Evaluation of 5–Aryl–1,2–dihydro–5H–chromeno[3,4–f]quinolines: Potent, Orally Active, Nonsteriodal Progesterone Receptor Agonists," *J. Med. Chem.*, 41(15):2779–85 (1998).

Eyrolles, et al., "Retinobenzoic Acids. 6. Retoid Antagonists with a Heterocyclic Ring," *J. Med. Chem* 37:1508 (1994).

Eyrolles, et al., "Retinoid Antagonists: Molecular Design Based on the Ligand Superfamily in Concept," *Med. Chem. Res.*, 2:361–367 (1992).

Forman, et al., "Unique Response Pathways Are Established by Allosteric Interactions among Nuclear Hormone Receptors," *Cell* 81:541–550 (1995).

Fries and Fink, "Uber Homologe des Cumaranons und ihre Abkommlinge," *Ber.* 41:4271 (1908).

Fries and Pfaffendorf, "Uber ein Kondensationsprodukt des Cumaranons und seine Umwandlung in Oxindirubin," *Ber.* 43:212 (1910).

Giguere et al., "Identification of a receptor for the morphogen retinoic acid," *Nature* 330:624–629 (1987).

Gromova, G.N. et al., *Khim Prom St.*, 43(2):97–8 (1967).

Hamann, L.G., et al., "Discovery of a Potent, Oraly Active, Nonsteriodal Androgen Receptor Agonist: 4–Ethyl–1,2,3,4–tetrahydro–6–(trifluoromethyl)–8–pyridono[5,6–g]–quinoline," *J. Med. Chem.*, 42(2):210–12 (1999).

Heyman et al., "9–Cis Retenoic Acid is a High Affinity Ligand for the Retinoid X Receptor," *cell* 68:397–406 (1992).

Hollenberg and Evans, "Multiple and Cooperative Trans-–Activation Domains of the Human Glucocorticoid Receptor," *Cell* 55:899–906 (1988).

Ishikawa et al., "A Functional Retinoic Acid Receptor Encoded by the Gene on Human Chromosome 12," *Molecular Endocrinology* 4(6):837–844 (1990).

Ivanov, et al., Chem Abstracts No. 95:97624, "Synthesis and properties of derivatives of 2,2,4–trimethyl substituted quinolines and some of their analogs," *Izv. Akad. Nauk. SSSR Ser. Khim.*, 3:628–633 (1981).

Jow, et al., "The Human Peroxisome Proliferator–activated Receptor (PPAR) Subtype NUC1 Prepresses the Activation of hPPARα and Thyroid Hormone Receptors," *J. Biol. Chem*, 270(8):3836–3840 (1995).

Kagechika, et al. "Retinobenzoic Acids. 2. Structure–Activity Relationship of Chalcone–4–carboxylic Acids and Glavone–4'–carboxylic Acids," *J. Med. Chem.*, 32(4):834 (1989).

Kagechika, et al., "Retinobenzoic Acids. 3. Structure–Activity Relationships of Retinoidal Azobenzene–4–carboxylic Acids and Stilbene–4–carboxylic Acids," *J. Med. Chem.* 32(5):1098 (1989).

Kagechika, et al., "Retinobenzoic Acids. 4. Conformation of Aromatic Amides with Retinoidal Activity. Importance of trans–Amide Structure for the Activity," *J. Med. Chem.* 32(10):2292 (1989).

Kaneko, et al., "Retinoid Antagonists," *Med. Chem. Res.*, 1:220–225 (1991).

Keidel, et al., "Different Agonist– and Antagonist–Induced Conformational Changes in Retinoic Acid Receptors Analyzed by Protease Mapping," *Mol. cell. Biol.* 14(1):287 (1994).

Kliewer et al., "Convergence of 9–cis retinoic acid and peroxisome proliferator signalling pathways through heterodimer formation of their receptors," *Nature* 358:771–774 (1992).

Kong, et al., "Effects of isosteric pyridone replacements in androgen antagonists based on 1,2–dihydro–and 1,2,3,4–tetrahydro–2,2–dimethyl–6–trifluoromethyl–8–pyridono 5,6–g quinolines" *Bioorg. Med. Chem. Lett.* 10(5), 411–414 (2000).

Kurokawa, et al., "Regulation of retinoid signalling by receptor polarity and allosteric control of ligand binding," *Nature* 371:528–531 (1994).

Lee, et al., "A synthetic retinoid antagonist inhibits the human immunodeficiency virus type 1 promoter," *Proc. Natl. Acad. Sci.* 91:5632 (1994).

Levin, et al., "9–Cis retinoic acid stereoisomer binds and activates the nuclear receptor RXRα," *Nature*, 355:359–361 (1992).

Ley et al., "Tetrapropylammonium Perruthenate, $Pr_4N^+$ $RuO^{-4}$, TPAP: A Catalytic Oxidant for Organic Synthesis," *Synthesis* 639 (1994).

Li, et al., "Montmorillonite Clay Catalysts. Part 7. An Environmentally Friendly Procedure for the Synthesis of Coumarins via Pechmann Condensation of Phenols with Ethyl Acetoacetate," *J. Chem. Res.* 38–39 (1998).

Liu and Asato, "Photochemistry and Synthesis of Stereoisomers of Vitamin A," *Tetrahedron* 40(11):1931–1969 (1984).

Loeliger, et al., "Arotinoids, a new class of highly active retinoids," *Eur. J. Med. Chem* 15:9 (1980).

Mangelsdorf et al., "A Direct Repeat in the Cellular Retinol–Binding Protein Type II Gene Confers Differential Regulation by RXR and RAR," *Cell* 66:555–561 (1991).

Mangelsdorf et al., "Ch. 8—The Retinoid Receptors," in *The Retinoids: Biology, Chemistry and Medicine, 2nd edition*, Sporn ed., Raven Press Ltd., New York, pp. 319–349 (1994).

Mangelsdorf et al., "Nuclear receptor that identifies a novel retinoic acid response pathway," *Nature* 345:224–229 (1990).

Maryanoff and Reitz,, "The Wittig Olefination Reaction and Modifications Involving Phosphoryl–Stabalized Carbanions. Stereochemistry, Mechanism, and Sepected Synthetic Aspects," *Chem. Rev.* 89(4):863–927 (1989).

McDonnell, et al., "Analysis of Estrogen Receptor Function in Vitro Reveals Three Distinct Classes of Antiestrogens," *Mol. Endo.* 9(6):659–669 (1995).

Mukherjee et al., "Human and Rat Peroxisome Proliferator Activated Receptors (PPARs) Demonstrate Similar Tissue Distribution but Different Responsiveness to PPAR Activators," *J. Steroid Biochem. Molec. Biol.* 51(3–4):157–166 (1994).

Mukherjee, et al., "Identification, characterization, and Tissue Distribution of Human Peroxisome Proliferator–activated Receptor (PPAR) Isoforms PPARγ2 versus PPARγ1 and Activation with Retinoid X Receptor Agonists and Antagonists," *Journ. Biol. Chem.* 272(12): 8071–8076 (1997).

Petkovich et al., "A human retinoic acid receptor which belongs to the family of nuclear receptors," *Nature* 330:444–450 (1987).

Quast, et al., "Synthesis and reactions of some pyrido 3,2-g!quinolines (1,8–diazaanthracenes)," *Liebigs Ann. Chem.*, 133–46 (1984).

Rodbard, D. "Mathematics and statistics of ligand assays: an illustrated guide" In: J. Langon and J.J. Clapp, eds., Ligand Assay, Masson Publishing U.S.A, Inc., New York, pp. 45–99, (1981).

Roy, et al., "Synergistic Activation of Retinoic Acid (RA)–Responsive Genes and Induction of Embryonal Carcinoma Cell Differentiation by an RA Receptor α (RARα)–, RARβ–, or RARγ–Selective Ligand in Combination with a Retinoid X Receptor–Specific Ligand," *Mol. Cell. Biol.* 15(12):6481–6487 (1995).

Sato and Otera, "CsF in Organic Synthesis. A Practical Method for Inversion of Secondary Mesylates," *Syn. Lett.* 336(1995).

Sethna and Phadke, *The Pechmann Reaction Organic Reactions* 7:1–58 (1953).

Sherman, et al., "Central Hypothyroidism Associated with Retinoid X Receptor–Selective Ligands," *N. Engl. J. Med.* 340(14):1075–1079 (1999).

Strickland et al., "Structure–Activity Relationships of a New Series of Retinoidal Benzoic Acid Derivatives as Measured by Induction of Differentiation of Murine F9 Teratocarcinoma Cells and Human HL–60 Promyelocytic Leukemia Cells," *Cancer Research* 43:5268–5272 (1983).

Tegley, C.M., et al., "5–Benzylidene 1,2–Dihydrochromeno [3,4–f]quinolines, A Novel Class of Nonsteriodal Human Progesterone Receptor Agonists," *J. Med. Chem.*, 41(22):4354–9 (1998).

Trost and Toste, "A New Palladium–Catalyzed Addition: A Mild Method for the Synthesis of Coumarins," *J. Am. Chem. Soc.* 118(26):6305 (1996).

Tzukerman et al., "Human estrogen receptor transactivational capacity is determined by both cellular and promoter context and mediated by two functionally distinct intramolecular regions," *Molecular Endocrinology* 8:21–30 (1994).

Umesono, et al. "Retinoic acid and thyroid hormone induce gene expression through a common responsive element," *Nature* 336:262 (1988).

Yoshimura, et al. "A Novel Type of Retinoic Acid Receptor Antagonist: Synthesis and Structure–Activity Relationships of Heterocyclic Ring Containing Benzoic Acid Derivatives," *J. Med. Chem.* 38(16):3163 (1995).

Zhi, et al., "5–Aryl–1,2–dihydrochromeno [3,4–f]quinolines: A Novel Class of Nonsteriodal Human Progesterone Recepetor Agonists," *J. Med. Chem.*, 41(3):291–302 (1998).

Chapelo, et al., "Heteroaromatoc Analogues of the $α_2$_Adrenoreceptor Partial Agonist Clonidine," *J. Med. Chem.*, 32:1627–1630 (1989).

Munk, et al., "Synthesis and Evaluation of 2–[(5–Methylbenz–1–ox–4–azin–6–yl) imino]imidazoline, a Potent, Peripherally Acting $α_2$ Adrenoreceptor Agonist," *J. Med. Chem.*, 39:3533–3538 (1996).

\* cited by examiner

ANDROGEN RECEPTOR MODULATOR COMPOUNDS AND METHODS

This application claims priority to U.S. Provisional Application Ser. No. 60/150,988, filed Aug. 27, 1999, the entire disclosure of which is incorporated by reference herein.

FIELD OF THE INVENTION

This invention relates to non-steroidal compounds that are modulators (i.e. agonists and antagonists) of androgen receptors, and to methods for the making and use of such compounds.

BACKGROUND OF THE INVENTION

Intracellular receptors (IRs) form a class of structurally-related genetic regulators scientists have named "ligand dependent transcription factors." R. M. Evans, *Science*, 240:889 (1988). Steroid receptors are a recognized subset of the IRs, including the progesterone receptor (PR), androgen receptor (AR), estrogen receptor (ER), glucocorticoid receptor (GR) and mineralocorticoid receptor (MR). Regulation of a gene by such factors requires both the IR itself and a corresponding ligand, which has the ability to selectively bind to the IR in a way that affects gene transcription.

Ligands to the IRs can include low molecular weight native molecules, such as the hormones progesterone, estrogen and testosterone, as well as synthetic derivative compounds such as medroxyprogesterone acetate, diethylstilbesterol and 19-nortestosterone. These ligands, when present in the fluid surrounding a cell, pass through the outer cell membrane by passive diffusion and bind to specific IR proteins to create a ligand/receptor complex. This complex then translocates to the cell's nucleus, where it binds to a specific gene or genes present in the cell's DNA. Once bound to DNA, the complex modulates the production of the protein encoded by that gene. In this regard, a compound that binds an IR and mimics the effect of the native ligand is referred to as an "agonist", while a compound that inhibits the effect of the native ligand is called an "antagonist."

Ligands to the steroid receptors are known to play an important role in health of both women and men. For example, the native female ligand, progesterone, as well as synthetic analogues, such as norgestrel (18-homonorethisterone) and norethisterone (17α-ethinyl-19-nortestosterone), are used in birth control formulations, typically in combination with the female hormone estrogen or synthetic estrogen analogues, as effective modulators of both PR and ER. On the other hand, antagonists to PR are potentially useful in treating chronic disorders, such as certain hormone dependent cancers of the breast, ovaries, and uterus, and in treating non-malignant conditions such as uterine fibroids and endometriosis, a leading cause of infertility in women. Similarly, AR antagonists, such as cyproterone acetate and flutamide, have proved useful in the treatment of prostatic hyperplasia and cancer of the prostate.

The effectiveness of known modulators of steroid receptors is often tempered by their undesired side-effect profile, particularly during long-term administration. For example, the effectiveness of progesterone and estrogen agonists, such as norgestrel and diethylstilbesterol respectively, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a GR antagonist. Accordingly, identification of compounds that have good specificity for one or more steroid receptors, but have reduced or no cross-reactivity for other steroid or intracellular receptors, would be of significant value in the treatment of male and female hormone responsive diseases.

A group of quinolinone and coumarin analogs having a fused ring system of the aryl, piperidine, pyrrolidine, or indoline series have been described as androgen modulators. See U.S. Pat. No. 5,696,130; Int. Patent Appl. WO 97/49709; L. G. Hamann, et. al. *J. Med. Chem.*, 41:623–639 (1998); J. P. Edwards, et. al., *Bioorg. Med. Chem. Lett.*, 8:745–750 (1998).

In addition, novel enantioselective synthetic routes to N-alkyl or N-aryl 3,4-dihydro-2H-1,4-benzoxazine compounds are described. Such compounds are key intermediates in the preparation of quinolinones and other fused ring structures of the instant invention. Often, when such fused-ring compounds are chiral and possess biological activity, only one enantiomer is biologically active, or the enantiomers possess different biological activity. Isolating and testing such enantiomers often yields a compound with enhanced selectivity, lower toxicity, and greater potency. Therefore, it would be highly advantageous to selectively prepare these types of compounds in the desired configuration. See Atarashi S., et al., *J. Heterocyclic Chem.*, 28:329 (1991); Xie, L. J., *Chinese Chemical Letters*, 6:857 (1995); Mitscher, L. A., et al., *J. Med. Chem.*, 30:2283 (1987).

The entire disclosures of the publications and references referred to above and hereafter in this specification are incorporated herein by reference.

SUMMARY OF THE INVENTION

The present invention is directed to novel compounds, pharmaceutical compositions, and methods for modulating processes mediated by steroid receptors. More particularly, the invention relates to non-steroidal compounds and compositions that are high-affinity, high-specificity agonists, partial agonists (i.e., partial activators and/or tissue-specific activators) and antagonists for the androgen receptor (AR). Also provided are methods of making and using such compounds and pharmaceutical compositions, as well as critical intermediates used in their synthesis.

In another aspect of the invention, a stereoselective synthetic route to intermediate compounds for these AR modulators is described. This aspect of the invention relates to preparing N-alkylated amino alcohol intermediates stereoselectively.

These and various other advantages and features of novelty that characterize the invention are pointed out with particularity in the claims annexed hereto and forming a part hereof. The following detailed description of the invention provides a better understanding of the invention, its advantages, and objects obtained by its use, as well as preferred embodiments of the invention.

DETAILED DESCRIPTION OF THE INVENTION

In accordance with the present invention, we have developed novel compounds, compositions, and methods of preparation of non-steroidal compounds that are AR modulators. Specifically, we have developed high affinity, high specificity agonists, partial agonists (i.e., partial activators and/or tissue-specific activators) and antagonists for the androgen receptor and methods of preparing these compounds and compositions.

In accordance with the present invention and as used herein, the following structure definitions are provided for nomenclature purposes. Furthermore, in an effort to maintain consistency in the naming of compounds of similar structure but differing substituents, the compounds described herein are named according to the following general guidelines. The numbering system for the location of substituents on such compounds is also provided.

The term "alkyl" refers to an optionally substituted straight-chain or branched-chain hydrocarbon radical having from 1 to about 10 carbon atoms, more preferably from 1 to about 6 carbon atoms, and most preferably from 1 to about 4 carbon atoms. Examples of alkyl radical include methyl, ethyl, n-propyl, isopropyl, n-butyl, isobutyl, sec-butyl, tert-butyl, pentyl, hexyl, octyl and the like.

The term "alkenyl" refers to a straight-chain or branched-chain hydrocarbon radical having one or more carbon-carbon double-bonds and having from 2 to about 10 carbon atoms, preferably from 2 to about 6 carbon atoms, and most preferably from 2 to about 4 carbon atoms. Preferred alkenyl groups include allyl. Examples of alkenyl radicals include ethenyl, propenyl, 1,4-butadienyl and the like.

The term "allyl" refers to the radical $CH_2=CH-CH_2$.

The term "alkynyl" refers to a straight-chain or branched-chain hydrocarbon radical having one or more carbon-carbon triple-bonds and having from 2 to about 10 carbon atoms, preferably from 2 to about 6 carbon atoms, and most preferably from 2 to about 4 carbon atoms. Examples of alkynyl radicals include ethynyl, propynyl, butynyl and the like.

The term aryl refers to optionally substituted aromatic ring systems. The term aryl includes monocyclic aromatic rings, polycyclic aromatic ring systems, and polyaromatic ring systems. The polyaromatic and polycyclic ring systems may contain from two to four, more preferably two to three, and most preferably two, rings.

The term "heteroaryl" refers to optionally substituted aromatic ring systems having one or more heteroatoms such as, for example, oxygen, nitrogen and sulfur. The term heteroaryl may include five- or six-membered heterocyclic rings, polycyclic heteroaromatic ring systems, and polyheteroaromatic ring systems where the ring system has from two to four, more preferably two to three, and most preferably two, rings. The terms heterocyclic, polycyclic heteroaromatic, and polyheteroaromatic include ring systems containing optionally substituted heteroaromatic rings having more than one heteroatom as described above (e.g., a six membered ring with two nitrogens), including poly-heterocyclic ring systems from two to four, more preferably two to three, and most preferably two, rings. The term heteroaryl includes ring systems such as, for example, pyridine, quinoline, furan, thiophene, pyrrole, imidazole and pyrazole.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy" refers to an aryl ether radical wherein the term aryl is defined as above. Examples of aryloxy radicals include phenoxy, benzyloxy and the like.

The term "cycloalkyl" refers to a saturated or partially saturated monocyclic, bicyclic or tricyclic alkyl radical wherein each cyclic moiety has about 3 to about 8 carbon atoms. Examples of cycloalkyl radicals include cyclopropyl, cyclobutyl, cyclopentyl, cyclohexyl and the like.

The term "cycloalkylalkyl" refers to an alkyl radical as defined above which is substituted by a cycloalkyl radical having from about 3 to about 8 carbon atoms.

The term "arylalkyl" refers to an alkyl radical as defined above in which one hydrogen atom is replaced by an aryl radical as defined above, such as, for example, benzyl, 2-phenylethyl and the like. Preferably, arylalkyl refers to arylmethyl.

The terms alkyl, alkenyl, and alkynyl include optionally substituted straight-chain, branched-chain, cyclic, saturated and/or unsaturated structures, and combinations thereof.

The terms cycloalkyl, allyl, aryl, arylalkyl, heteroaryl, alkynyl, and alkenyl include optionally substituted cycloalkyl, allyl, aryl, arylalkyl, heteroaryl, alkynyl, and alkenyl groups.

The terms haloalkyl, haloalkenyl and haloalkynyl include alkyl, alkenyl and alkynyl structures, as described above, that are substituted with one or more fluorines, chlorines, bromines or iodines, or with combinations thereof.

The terms heteroalkyl, heteroalkenyl and heteroalkynyl include optionally substituted alkyl, alkenyl and alkynyl structures, as described above, in which one or more skeletal atoms are oxygen, nitrogen, sulfur, or combinations thereof.

The substituents of an "optionally substituted" structure include, for example, one or more, preferably one to four, more preferably one to two, of the following preferred substituents: alkyl, alkenyl, alkynyl, aryl, heteroaryl, alkoxy, aryloxy, cycloalkyl, cycloalkylalkyl, arylalkyl, amino, alkylamino, dialkylamino, F, Cl, Br, I, CN, $NO_2$, $NR^{10}R^{11}$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$ and $C(O)NH_2$, $C_1-C_4$ alkyl, $C_1-C_4$ haloalkyl, $C_3-C_8$ cycloalkyl, $C_1-C_4$ heteroalkyl, and $OR^9$.

A 2H-1,4-benzoxazin-3(4H)-one is represented by the following structure:

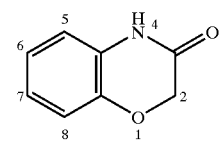

A 2H-1,4-benzoxazin is represented by the following structure:

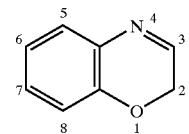

A 7H-[1,4]oxazino[3,2-g]quinolin-7-one is represented by the following structure:

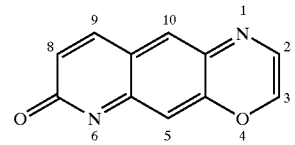

A 1H-[1,4]oxazino[3,2-g]quinoline is represented by the following structure:

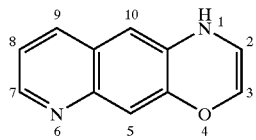

A 1H-[1,4]oxazino[3,2-g]quinoline-2(3H)-one is represented by the following structure:

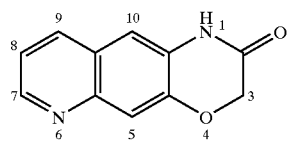

A 3H-[1,4]oxazino[3,2-g]quinolin-2,7-dione is represented by the following structure:

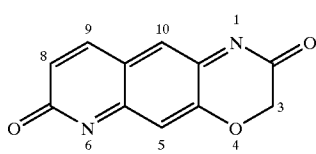

A pyrido[1',2':4,5][1,4]oxazino[3,2-g]quinolin-9(8H)-one is represented by the following structure:

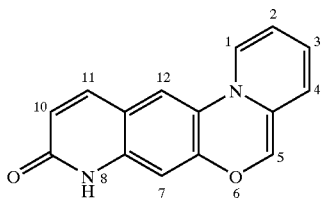

A 1H-pyrrolo[1',2':4,5][1,4]oxazino[3,2-g]quinolin-8(7H)-one is represented by the following structure:

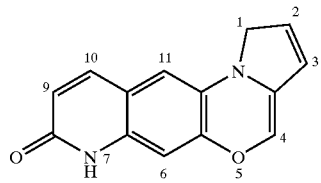

A quinoxalin-2(1H)-one is represented by the following structure:

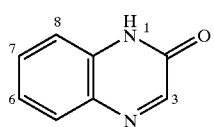

A quinoxaline is represented by the following structure:

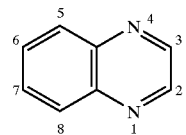

A pyrazino[3,2-g]quinolin-2,7-dione is represented by the following structure:

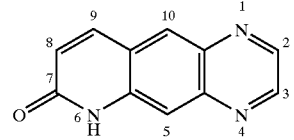

A pyrazino[3,2-g]quinolin-7(6H)-one is represented by the following structure:

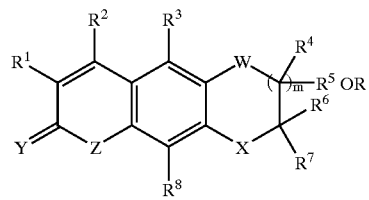

Compounds of the present invention are represented by those having the formulas:

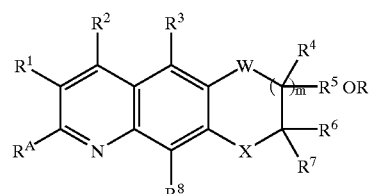

(I)

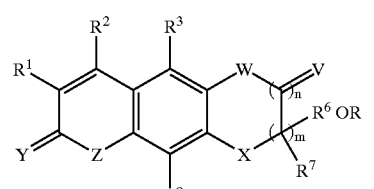

(II)

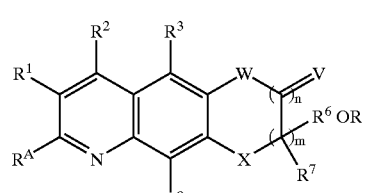

(III)

(IV)

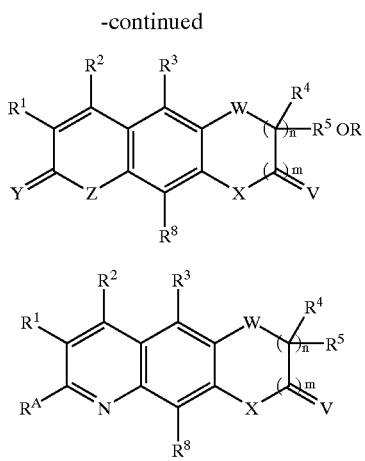

(V)

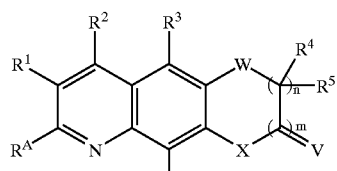

(VI)

wherein:
$R^1$ represents hydrogen, F, Cl, Br, I, $NO_2$, $OR^9$, $NR^{10}R^{11}$, $S(O)_mR^9$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, or $C_2$–$C_8$ alkenyl, wherein the alkyl, cycloalkyl, heteroalkyl, haloalkyl, aryl, arylalkyl, heteroaryl, alkynyl, and alkenyl groups may be optionally substituted;

$R^2$ is hydrogen, F, Cl, Br, I, $CF_3$, $CF_2H$, $CFH_2$, $CF_2OR^9$, $CH_2OR^9$, $OR^9$, $S(O)_mR^9$, $NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, or $C_2$–$C_8$ alkenyl, wherein the alkyl, cycloalkyl, heteroalkyl, haloalkyl, aryl, arylalkyl, heteroaryl, alkynyl, and alkenyl groups may be optionally substituted;

$R^3$ is hydrogen, F, Cl, Br, I, $OR^9$, $S(O)_mR^9$, $NR^{10}R^{11}$, or $C_1$–$C_6$ alkyl, $C_1$–$C_6$ heteroalkyl, or $C_1$–$C_6$ haloalkyl and wherein the alkyl, heteroalkyl, and haloalkyl groups may be optionally substituted;

$R^4$ and $R^5$ each independently are hydrogen, $OR^9$, $S(O)_mR^9$, $NR^{10}R^{11}$, $C(Y)OR^{11}$, $C(Y)NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, or $C_2$–$C_8$ alkenyl, wherein the alkyl, cycloalkyl, heteroalkyl, haloalkyl, aryl, arylalkyl, heteroaryl, alkynyl, and alkenyl groups may be optionally substituted; or $R^4$ and $R^5$ taken together can form a saturated or unsaturated three- to seven-membered ring that may be optionally substituted;

$R^6$ and $R^7$ each independently are hydrogen, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, or $C_2$–$C_8$ alkenyl, wherein the alkyl, cycloalkyl, heteroalkyl, haloalkyl, aryl, arylalkyl, heteroaryl, alkynyl, and alkenyl groups may be optionally substituted; or $R^6$ and $R^7$ taken together can form a saturated or unsaturated three- to seven-membered ring that may be optionally substituted; or $R^6$ and $R^5$ taken together can form a saturated or unsaturated three- to seven-membered ring that may be optionally substituted;

$R^8$ is hydrogen, $C_1$–$C_4$ alkyl, $C_1$–$C_4$ heteroalkyl, $C_1$–$C_4$ haloalkyl, F, Cl, Br, I, $NO_2$, $OR^9$, $NR^{10}R^{11}$ or $S(O)_mR^9$, wherein the alkyl, heteroalkyl, and haloalkyl groups may be optionally substituted;

$R^9$ is hydrogen, $C_1$–$C_6$ alkyl, $C_1$–$C_6$ heteroalkyl, $C_1$–$C_6$ haloalkyl, aryl, heteroaryl, $C_2$–$C_8$ alkenyl or arylalkyl, wherein the alkyl, heteroalkyl, haloalkyl, aryl, heteroaryl, alkenyl and arylalkyl groups may be optionally substituted;

$R^{10}$ is hydrogen, $C_1$–$C_6$ alkyl, $C_1$–$C_6$ heteroalkyl, $C_1$–$C_6$ haloalkyl, aryl, heteroaryl, $C_2$–$C_8$ alkenyl, arylalkyl, $SO_2R^{12}$ or $S(O)R^{12}$, wherein the alkyl, heteroalkyl, haloalkyl, aryl, heteroaryl, alkenyl and arylalkyl groups may be optionally substituted;

$R^{11}$ is hydrogen, $C_1$–$C_6$ alkyl, $C_1$–$C_6$ heteroalkyl, $C_1$–$C_6$ haloalkyl, aryl, heteroaryl, $C_2$–$C_8$ alkenyl or arylalkyl, wherein the alkyl, heteroalkyl, haloalkyl, aryl, heteroaryl, alkenyl and arylalkyl groups may be optionally substituted;

$R^{12}$ is hydrogen, $C_1$–$C_6$ alkyl, $C_1$–$C_6$ heteroalkyl, $C_1$–$C_6$ haloalkyl, aryl, heteroaryl, $C_2$–$C_8$ alkenyl or arylalkyl, wherein the alkyl, heteroalkyl, haloalkyl, aryl, heteroaryl, alkenyl and arylalkyl groups may be optionally substituted;

$R^{13}$ is hydrogen, $C_1$–$C_8$ alkyl, $C_3$–$C_8$ cycloalkyl, $C_1$–$C_8$ heteroalkyl, $C_1$–$C_8$ haloalkyl, aryl, heteroaryl, or arylalkyl, wherein the alkyl, heteroalkyl, haloalkyl, aryl, heteroaryl and arylalkyl groups may be optionally substituted; or $R^{13}$ and $R^4$ taken together can form a saturated or unsaturated three- to seven-membered ring that may be optionally substituted;

$R^{14}$ and $R^{15}$ each independently are hydrogen, $C_1$–$C_8$ alkyl, $C_3$–$C_8$ cycloalkyl, $C_1$–$C_8$ heteroalkyl, $C_1$–$C_8$ haloalkyl, aryl, heteroaryl, arylalkyl, $C_2$–$C_8$ alkynyl or $C_2$–$C_8$ alkenyl, wherein the alkyl, cycloalkyl, heteroalkyl, haloalkyl, aryl, heteroaryl, arylalkyl, alkynyl and alkenyl groups may be optionally substituted;

$R^A$ is F, Br, Cl, I, CN, $C_1$–$C_6$ alkyl, $C_1$–$C_6$ haloalkyl, $C_1$–$C_6$ heteroalkyl, $OR^{16}$, $NR^{16}R^{17}$, $SR^{16}$, $CH_2R^{16}$, $COR^{17}$, $CO_2R^{17}$, $CONR^{17}R^{17}$, $SOR^{17}$ or $SO_2R^{17}$, wherein the alkyl, heteroalkyl, and haloalkyl groups may be optionally substituted;

$R^{16}$ is hydrogen, $C_1$–$C_8$ alkyl, $C_1$–$C_8$ haloalkyl, $C_1$–$C_8$ heteroalkyl, $COR^{17}$, $CO_2R^{17}$ or $CONR^{17}R^{17}$, wherein the alkyl, heteroalkyl, and haloalkyl groups may be optionally substituted;

$R^{17}$ is hydrogen, $C_1$–$C_4$ alkyl, $C_1$–$C_4$ haloalkyl or $C_1$–$C_4$ heteroalkyl, wherein the alkyl, heteroalkyl, and haloalkyl groups may be optionally substituted;

m is 0, 1 or 2;

n is 1 or 2;

V is O, S or $CR^{14}R^{15}$;

W is O, $S(O)_m$, $NR^{13}$, $NC(Y)R^{11}$, or $NSO_2R^{11}$

X and Z each independently are O, $S(O)_m$, $NR^{11}$, $NC(Y)R^{11}$, $NSO_2R^{12}$ or $NS(O)R^{12}$;

Y is O or S; and any two of $R^4$, $R^5$, $R^6$, $R^7$, and $R^{13}$ taken together can form a saturated or unsaturated three- to seven-membered ring that may be optionally substituted;

and pharmaceutically acceptable salts thereof.

Preferred $R^1$ groups include hydrogen, F, Cl, Br, I, $NO_2$, $OR^9$, $NR^{10}R^{11}$, $S(O)_mR^9$, $C_1$–$C_8$ alkyl, $C_1$–$C_8$ cycloalkyl, $C_1$–$C_8$ heteroalkyl, $C_1$–$C_8$ haloalkyl, allyl, $C_1$–$C_8$ aryl, $C_1$–$C_8$ arylalkyl, $C_1$–$C_8$ heteroaryl, $C_2$–$C_8$ alkynyl, and $C_2$–$C_8$ alkenyl. The alkyl, cycloalkyl, heteroalkyl, haloalkyl, allyl, aryl, arylalkyl, heteroaryl, alkynyl, and alkenyl groups may be optionally substituted. More preferred $R^1$ groups include H, F, Cl, $OR^9$, $NR^{10}R^{11}$, $S(O)_mR^9$, and $C_1$–$C_2$ alkyl. Particularly preferred $R^1$ groups include H, F, and Cl.

Preferred $R^2$ groups include hydrogen, F, Cl, Br, I, $CF_3$, $CF_2Cl$, $CF_2H$, $CFH_2$, $CF_2OR^9$, $CH_2OR^9$, $OR^9$, $S(O)_mR^9$, $NR^{10}R^{11}$, $C_1$–$C_8$ alkyl, $C_3$–$C_8$ cycloalkyl, $C_1$–$C_8$ heteroalkyl, $C_1$–$C_8$ haloalkyl, allyl, aryl, arylalkyl, heteroaryl, $C_2$–$C_8$ alkynyl, or $C_2$–$C_8$ alkenyl. The alkyl, cycloalkyl, heteroalkyl, haloalkyl, allyl, aryl, arylalkyl, heteroaryl, alkynyl, and alkenyl groups may be optionally substituted. More preferred $R^2$ groups include H, F, Cl, methyl, ethyl, $CF_3$, $CF_2H$, $CF_2Cl$, $CFH_2$, and $OR^9$. Particularly preferred $R^2$ groups include H, Cl, methyl, ethyl, $CF_3$, $CF_2H$, $CF_2Cl$.

Preferred $R^3$ groups include hydrogen, F, Cl, Br, I, $OR^9$, $S(O)_mR^9$, $NR^{10}R^{11}$, $C_1$–$C_6$ alkyl, $C_1$–$C_6$ heteroalkyl and $C_1$–$C_6$ haloalkyl. The alkyl, heteroalkyl, and haloalkyl groups may be optionally substituted. More preferred $R^3$ groups include hydrogen, F, Cl, $OR^9$, $NR^{10}R^{11}$, and $S(O)_mR^9$.

Preferred $R^4$ groups include H, $OR^9$, $C(Y)OR^{11}$, $C_1$–$C_8$ alkyl, $C_3$–$C_8$ cycloalkyl, $C_1$–$C_8$ heteroalkyl, $C_1$–$C_8$ haloalkyl, $C_2$–$C_8$ alkynyl, $C_2$–$C_8$ alkenyl, aryl, arylalkyl, and heteroaryl. The alkyl, cycloalkyl, heteroalkyl, haloalkyl, alkynyl, alkenyl, aryl, arylalkyl and heteroaryl groups may be optionally substituted. More preferred $R^4$ groups include H, $OR^9$, $C(Y)OR^{11}$, $C_1$–$C_4$ alkyl, $C_1$–$C_4$ heteroalkyl, $C_1$–$C_4$ haloalkyl, $C_2$–$C_4$ alkynyl, and $C_2$–$C_4$ alkenyl. Particularly preferred $R^4$ groups include H, $OR^9$, $C(Y)OR^{11}$, $C_1$–$C_4$ alkyl, $C_1$–$C_4$ haloalkyl, and where $R^4$ and $R^{13}$ together form a five- or six-membered ring.

Also preferred are compounds where $R^4$ and $R^{13}$ together form a saturated or unsaturated three- to seven-membered ring optionally substituted with 1–2 substituents. Examples of such substituents include, for example, hydrogen, F, Cl, Br, $C_1$–$C_4$ alkyl, $C_3$–$C_8$ cycloalkyl, $C_1$–$C_4$ heteroalkyl, $C_1$–$C_4$ haloalkyl, $OR^9$ and $NR^{10}R^{11}$. The alkyl, cycloalkyl, heteroalkyl, haloalkyl groups may be optionally substituted.

Also preferred are compounds where $R^4$ and $R^{13}$ together form a five- to seven-membered ring optionally substituted with 1–2 substituents. Examples of such substituents include F, $C_1$–$C_4$ alkyl, $C_1$–$C_4$ heteroalkyl, $C_1$–$C_4$ haloalkyl, and $OR^9$. The alkyl, heteroalkyl, and haloalkyl groups may be optionally substituted.

Preferred $R^5$ groups include H, $OR^9$, $C(Y)OR^{11}$, $C_1$–$C_8$ alkyl, $C_3$–$C_8$ cycloalkyl, $C_1$–$C_8$ heteroalkyl, $C_1$–$C_8$ haloalkyl, $C_2$–$C_8$ alkynyl, $C_2$–$C_8$ alkenyl, aryl, arylalkyl, and heteroaryl. The alkyl, cycloalkyl, heteroalkyl, haloalkyl, alkynyl, alkenyl, aryl, arylalkyl and heteroaryl groups may be optionally substituted. More preferred $R^5$ groups include hydrogen, $OR^9$, $C(Y)OR^{11}$, $C_1$–$C_4$ alkyl, and $C_1$–$C_4$ haloalkyl.

Also preferred are compounds where $R^4$ and $R^5$ taken together form a saturated or unsaturated three- to seven-membered ring that may be optionally substituted.

Preferred $R^6$ groups include hydrogen, $C_1$–$C_8$ alkyl, $C_3$–$C_8$ cycloalkyl, allyl, $C_1$–$C_8$ heteroalkyl, $C_1$–$C_8$ haloalkyl, $C_2$–$C_8$ alkynyl, $C_2$–$C_8$ alkenyl, aryl, arylalkyl and heteroaryl. The alkyl, cycloalkyl, allyl, heteroalkyl, haloalkyl, alkynyl, alkenyl, aryl, arylalkyl and heteroaryl groups may be optionally substituted. More preferred $R^6$ groups include hydrogen, $CH_3$, and $CH_2CH_3$.

Also preferred are compounds where $R^6$ and $R^5$ taken together form a saturated or unsaturated three- to seven-membered ring that may be optionally substituted.

Preferred $R^7$ groups include hydrogen, $C_1$–$C_8$ alkyl, $C_3$–$C_8$ cycloalkyl, $C_1$–$C_8$ heteroalkyl, $C_1$–$C_8$ haloalkyl, $C_2$–$C_8$ alkynyl, $C_2$–$C_8$ alkenyl, aryl, arylalkyl and heteroaryl. The alkyl, cycloalkyl, heteroalkyl, haloalkyl, alkynyl, alkenyl, aryl, arylalkyl and heteroaryl groups may be optionally substituted. More preferred $R^7$ groups include hydrogen, $CH_3$, and $CH_2CH_3$.

Also preferred are compounds where $R^6$ and $R^7$ taken together form a saturated or unsaturated three- to seven-membered ring that may be optionally substituted.

Preferred $R^8$ groups include hydrogen, F, Cl, Br, I, $NO_2$, $OR^9$, $S(O)_mR^9$, $C_1$–$C_4$ alkyl, $C_1$–$C_4$ heteroalkyl, $C_1$–$C_4$ haloalkyl, and $NR^{10}OR^{11}$. The alkyl, heteroalkyl and haloalkyl groups may be optionally substituted. More preferred $R^8$ groups include hydrogen and F.

Preferred $R^9$ groups include hydrogen, $C(Y)R^{12}$, $C_1$–$C_6$ alkyl, $C_1$–$C_6$ heteroalkyl, $C_1$–$C_6$ haloalkyl, aryl, heteroaryl, arylalkyl, $C_2$–$C_8$ alkynyl and $C_2$–$C_8$ alkenyl. The alkyl, heteroalkyl, haloalkyl, aryl, heteroaryl, arylalkyl, alkynyl, and alkenyl groups may be optionally substituted. More preferred $R^9$ groups include hydrogen, $C(Y)R^{12}$, and $C_1$–$C_6$ alkyl. Particularly preferred $R^9$ groups include $CH_3$, $CH_2CH_3$, $CH_2CH_2CH_3$, and $C(O)CH_3$.

Preferred $R^{10}$ groups include hydrogen, $C(Y)R^{12}$, $C(Y)OR^{12}$, $SO_2R^{12}$, $S(O)R^{12}$, $C_1$–$C_6$ alkyl, $C_1$–$C_6$ heteroalkyl, $C_1$–$C_6$ haloalkyl, aryl, heteroaryl, arylalkyl, $C_2$–$C_8$ alkynyl, and $C_2$–$C_8$ alkenyl. The alkyl, heteroalkyl, haloalkyl, aryl, heteroaryl, arylalkyl, alkynyl, and alkenyl groups may be optionally substituted. More preferred $R^{10}$ groups include hydrogen, $C_1$–$C_6$ alkyl, $C(Y)R^{12}$, $C(Y)OR^{12}$, $SO_2R^{12}$.

Preferred $R^{11}$ groups include hydrogen, $C_1$–$C_6$ alkyl, $C_1$–$C_6$ heteroalkyl, $C_1$–$C_6$ haloalkyl, aryl, heteroaryl, arylalkyl, $C_2$–$C_8$ alkynyl, and $C_2$–$C_8$ alkenyl. The alkyl, heteroalkyl, haloalkyl, aryl, heteroaryl, arylalkyl, alkynyl, and alkenyl groups may be optionally substituted. More preferred $R^{11}$ groups include hydrogen and $C_1$–$C_4$ alkyl.

Preferred $R^{12}$ groups include hydrogen, $C_1$–$C_6$ alkyl, $C_1$–$C_6$ heteroalkyl, $C_1$–$C_6$ haloalkyl, aryl, heteroaryl, allyl, arylalkyl, $C_2$–$C_8$ alkynyl, $C_2$–$C_8$ alkenyl. The alkyl, heteroalkyl, haloalkyl, aryl, heteroaryl, allyl, arylalkyl, alkynyl, and alkenyl groups may be optionally substituted. More preferred $R^{12}$ groups include hydrogen and $C_1$–$C_4$ alkyl.

Preferred $R^{13}$ groups include hydrogen, $C_1$–$C_8$ alkyl, $C_1$–$C_8$ heteroalkyl, $C_1$–$C_8$ haloalkyl, $C_3$–$C_8$ cycloalkyl, aryl, heteroaryl, arylalkyl, heteroarylalkyl, $C_2$–$C_8$ alkynyl, and $C_2$–$C_8$ alkenyl. The alkyl, heteroalkyl, haloalkyl, cycloalkyl, aryl, heteroaryl, arylalkyl, heteroarylalkyl, alkynyl, and alkenyl groups may be optionally substituted. More preferred $R^{13}$ groups include $C_1$–$C_4$ alkyl, $C_2$–$C_4$ alkenyl, $C_2$–$C_4$ alkynyl, $C_1$–$C_4$ heteroalkyl and $C_1$–$C_4$ haloalkyl. Particularly preferred $R^{13}$ groups include $CH_3$, $CH_2CH_3$, $CH_2CH_2CH_3$, $CH(CH_3)_2$, $CH_2CH_2(CH_3)$, $CH_2$ (cyclopropyl), $CH_2CClF_2$, $CH_2CHF_2$, and $CH_2CF_3$.

Preferred $R^{14}$ groups include hydrogen, $C_1$–$C_8$ alkyl, $C_1$–$C_8$ heteroalkyl, $C_1$–$C_8$ haloalkyl, $C_2$–$C_8$ alkynyl, $C_2$–$C_8$ alkenyl, aryl, arylalkyl, and heteroaryl. The alkyl, heteroalkyl, haloalkyl, aryl, heteroaryl, arylalkyl, alkynyl, and alkenyl groups may be optionally substituted. More preferred $R^{14}$ groups include hydrogen and $C_1$–$C_4$ alkyl.

Preferred $R^{15}$ groups include hydrogen, $C_1$–$C_8$ alkyl, $C_1$–$C_8$ heteroalkyl, $C_1$–$C_8$ haloalkyl, $C_2$–$C_8$ alkynyl, $C_2$–$C_8$ alkenyl, aryl, arylalkyl, and heteroaryl. The alkyl, heteroalkyl, haloalkyl, aryl, heteroaryl, arylalkyl, alkynyl, and alkenyl groups may be optionally substituted. More preferred $R^{15}$ groups include hydrogen and $C_1$–$C_4$ alkyl.

Preferred $R^{16}$ groups include hydrogen, $C_1$–$C_8$ alkyl, $C_1$–$C_8$ heteroalkyl, $C_1$–$C_8$ haloalkyl, $C_2$–$C_8$ alkynyl, $C_2$–$C_8$ alkenyl, $COR^{17}$, $CO_2R^{17}$, $CONR^{17}R^{17}$, aryl, and heteroaryl. The alkyl, heteroalkyl, haloalkyl, aryl, heteroaryl, alkynyl, and alkenyl groups may be optionally substituted. More preferred $R^{16}$ groups include hydrogen and $C_1$–$C_4$ alkyl.

Preferred $R^A$ groups include hydrogen, F, Cl, Br, I, CN, $C_1$–$C_6$ alkyl, $C_1$–$C_6$ heteroalkyl, $C_1$–$C_6$ haloalkyl, $OR^{16}$, $NR^{16}R^{17}$, $SR^{16}$, $CH_2R^{16}$, $COR^{17}$, $CO_2R^{17}$, $CONR^{17}R^{17}$, $SOR^{17}$, and $SO_2R^{17}$. The alkyl, heteroalkyl, and haloalkyl groups may be optionally substituted. More preferred $R^A$ groups include hydrogen, F, Cl, CN, and $OR^{16}$.

Preferably n is 1 or 2. More preferably, n is 1.

Preferably, m is 1 or 2. More preferably, m is 1.

Preferred V groups include O and S. More preferably, V is O.

Preferred W groups include O, $S(O)_m$, $NR^{13}$, $NC(Y)R^{11}$, and $NSO_2R^{11}$. More preferred W groups include $NR^{13}$, $NC(Y)R^{11}$, and $NSO_2R^{11}$. Particularly preferred W groups include $NR^{13}$.

Preferred X groups include O, $S(O)_m$, $NR^{11}$, $NC(Y)R^{11}$, $NSO_2R^{12}$ and $NS(O)R^{12}$. More preferred X groups include O, $S(O)_m$, and $NR^{11}$. Particularly preferred X groups include O and $S(O)_m$. Most preferably, X is O.

Preferably Y is O.

Preferred Z groups include O, $S(O)_m$, $NR^{11}$, $NC(Y)R^{11}$, $NSO_2R^{12}$ and $NS(O)R^{12}$. More preferred Z groups include O, $S(O)_m$, and $NR^{11}$. Most preferably, Z is NH.

In one aspect, compounds of formula I are preferred.

In another aspect, compounds of formula II are preferred.

In still another aspect, compounds of formula III are preferred.

In yet another aspect, compounds of formula IV are preferred.

In one preferred aspect, $R^3$ and $R^8$ are each hydrogen; X and Y are each independently O or S; W is $NR^{13}$; and Z is $NR^{11}$.

In another preferred aspect, $R^3$ and $R^8$ are each hydrogen; X and Y are each O, W is $NR^{13}$; and Z is $NR^{11}$.

In still another preferred aspect, $R^3$ and $R^8$ are each hydrogen; $R^2$ is $CF_3$, X and Y are each O, W is $NR^{13}$; and Z is $NR^{11}$.

In yet another preferred aspect, $R^1$ $R^3$, $R^4$, $R^5$, $R^6$, $R^7$, $R^8$, $R^{11}$ and $R^A$ are each hydrogen, $R^2$ is $CF_3$, $R^{13}$ is $C_1$–$C_8$ alkyl, W is $NR^{13}$, Z is $NR^{11}$, X and Y are each O; and m is 1 or 2.

In yet another preferred aspect, $R^1$ $R^3$, $R^6$, $R^7$, $R^8$, $R^{11}$ and $R^A$ are each hydrogen, $R^2$ is $CF_3$, $R^4$, $R^5$ and $R^{13}$ are each $C_1$–$C_8$ alkyl, W is $NR^{13}$, Z is $NR^{11}$, X and Y are each O; and m is 1 or 2.

In yet another preferred aspect, $R^1$ $R^3$, $R^4$, $R^5$, $R^8$, $R^{11}$ and $R^A$ are each hydrogen, $R^2$ is $CF_3$, $R^6$, $R^7$ and $R^{13}$ are each $C_1$–$C_8$ alkyl, W is $NR^{13}$, Z is $NR^{11}$, X and Y are each O; and m is 1 or 2.

In a preferred aspect, the present invention provides a pharmaceutical compositions comprising an effective amount of an androgen receptor modulating compound of formulas I through VI shown above wherein $R^1$ through $R^{17}$, $R^A$, V, W, X, Y, Z, m and n all have the same definitions as given above.

In a further preferred aspect, the present invention comprises methods of modulating processes mediated by androgen receptors comprising administering to a patient an effective amount of a compound of the formulas I through VI shown above, wherein $R^1$ through $R^{17}$, $R^A$, V, W, X, Y, Z, m and n all have the same definitions as those given above.

Any of the compounds of the present invention can be synthesized as pharmaceutically acceptable salts for incorporation into various pharmaceutical compositions. As used herein, pharmaceutically acceptable salts include, for example, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl) aminomethane. Additional pharmaceutically acceptable salts are known to those skilled in the art.

AR agonist, partial agonist and antagonist compounds (including compounds with tissue-selective AR modulator activity) of the present invention will prove useful in the treatment of acne (antagonist), male-pattern baldness (antagonist), male hormone replacement therapy (agonist), wasting diseases (agonist), hirsutism (antagonist), stimulation of hematopoiesis (agonist), hypogonadism (agonist), prostatic hyperplasia (antagonist), osteoporosis (agonist) male contraception (agonist), impotence (agonist), sexual dysfunction (agonist), cancer cachexia (agonist), various hormone-dependent cancers, including, without limitation, prostate (antagonist) and breast cancer and as anabolic agents (agonist). It is understood by those of skill in the art that a partial agonist may be used where agonist activity is desired, or where antagonist activity is desired, depending upon the AR modulator profile of the particular partial agonist.

It is understood by those skilled in the art that while the compounds of the present invention will typically be employed as a selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare-ups. In this instance, a compound that is primarily a PR agonist, but also displays some AR and MR modulating activity, may prove useful. Specifically, the mixed MR effects would be useful to control water balance in the body, while the AR effects would help to control any acne flare-ups that occur.

Furthermore, is understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists and antagonists) according to the present invention include:

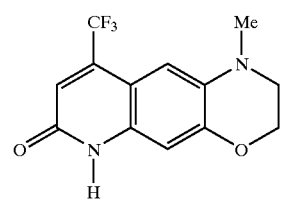

Compound 101
1,2,3,6-Tetrahydro-1-methyl-9-(trifluoromethyl)-
7H-[1,4]oxazino[3,2-g]quinolin-7-one -continued

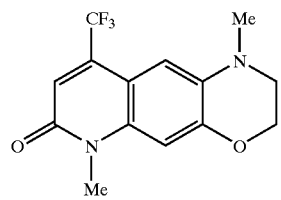

Compound 102
1,2,3,6-Tetrahydro-1,6-dimethyl-9-(trifluoromethyl)-
7H-[1,4]oxazino[3,2-g]quinolin-7-one

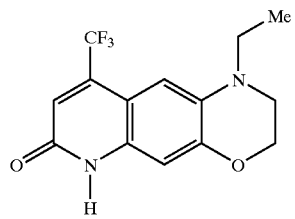

Compound 103
1-Ethyl-1,2,3,6-tetrahydro-9-(trifluoromethyl)-
7H-[1,4]oxazino[3,2-g]quinolin-7-one

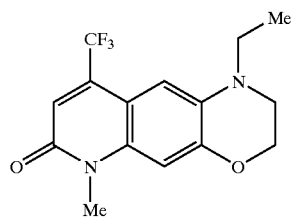

Compound 104
1-Ethyl-1,2,3,6-tetrahydro-6-methyl-9-(trifluoromethyl)-
7H-[1,4]oxazino[3,2-g]quinolin-7-one

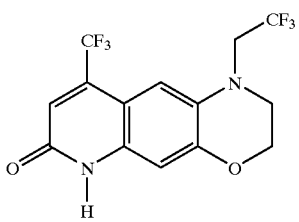

Compound 105
1,2,3,6-tetrahydro-1-(2,2,2-trifluoroethyl)-9-(trifluoromethyl)-
7H-[1,4]oxazino[3,2-g]quinolin-7-one

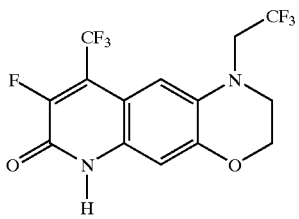

Compound 106
8-Fluoro-1,2,3,6-tetrahydro-1-(2,2,2-trifluoroethyl)-
9-(trifluoromethyl)-7H-[1,4]oxazino[3,2-g]quinolin-7-one

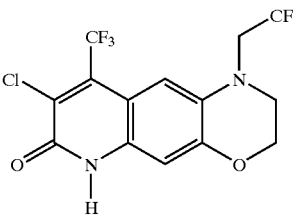

Compound 107
8-Chloro-1,2,3,6-tetrahydro-1-(2,2,2-trifluoroethyl)-
9-(trifluoromethyl)-7H-[1,4]oxazino[3,2-g]quinolin-7-one -continued

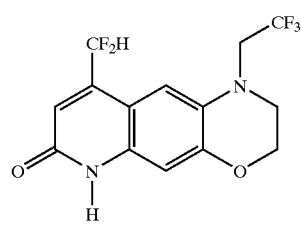

Compound 108
9-(Difluoromethyl)-1,2,3,6-tetrahydro-
1-(2,2,2-trifluoroethyl)-7H-[1,4]oxazino[3,2-g]quinolin-7-one

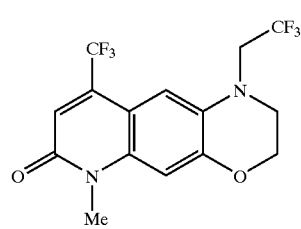

Compound 109
1,2,3,6-Tetrahydro-6-methyl-1-(2,2,2-trifluoroethyl)-
9-(trifluoromethyl)-7H-[1,4]oxazino[3,2-g]quinolin-7-one

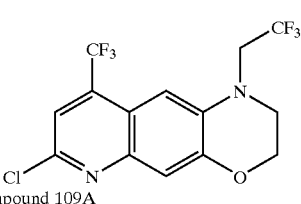

Compound 109A
7-Chloro-2,3-dihydro-1-(2,2,2-trifluoroethyl)-9-
(trifluoromethyl)-1H-[1,4]oxazino[3,2-g]quinoline

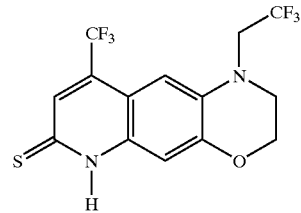

Compound 110
1,2,3,6-tetrahydro-1-(2,2,2-trifluoroethyl)-9-(trifluoromethyl)
7H-[1,4]oxazino[3,2-g]quinolin-7-thione

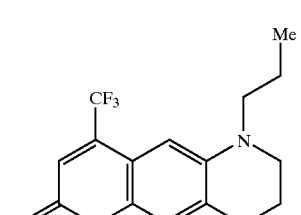

Compound 111
1,2,3,6-Tetrahydro-1-propyl-9-(trifluoromethyl)-
7H-[1,4]oxazino[3,2-g]quinolin-7-one

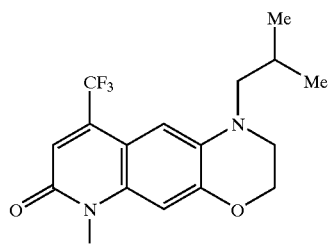

Compound 112
1,2,3,6-Tetrahydro-1-isobutyl-9-(trifluoromethyl)-
7H-[1,4]oxazino[3,2-g]quinolin-7-one

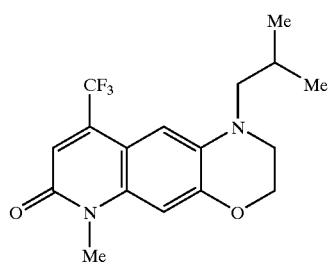

Compound 113
1,2,3,6-Tetrahydro-1-isobutyl-6-methyl-9-(trifluoromethyl)-
7H-[1,4]oxazino[3,2-g]quinolin-7-one

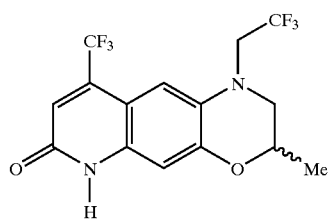

Compound 114
(±)-1,2,3,6-Tetrahydro-3-methyl-1-(2,2,2-trifluoroethyl)-
9-(trifluoromethyl)-7H-[1,4]oxazino[3,2-g]quinolin-7-one

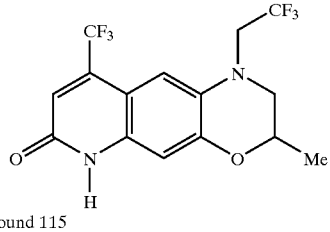

Compound 115
(−)-1,2,3,6-Tetrahydro-3-methyl-1-(2,2,2-trifluoroethyl)-
9-(trifluoromethyl)-7H-[1,4]oxazino[3,2-g]quinolin-7-one

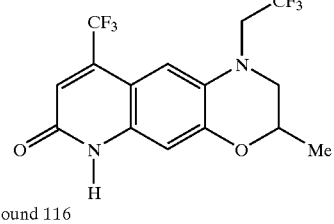

Compound 116
(+)-1,2,3,6-Tetrahydro-3-methyl-1-(2,2,2-trifluoroethyl)-
9-(trifluoromethyl)-7H-[1,4]oxazino[3,2-g]quinolin-7-one

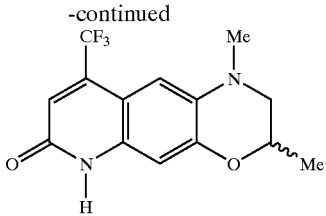

Compound 117
(±)-1,2,3,6-Tetrahydro-1,3-dimethyl-9-(trifluoromethyl)-
7H-[1,4]oxazino[3,2-g]quinolin-7-one

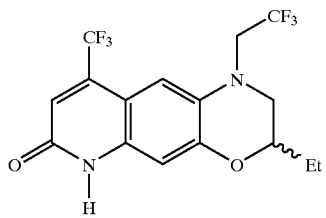

Compound 118
(±)-3-Ethyl-1,2,3,6-tetrahydro-1-(2,2,2-trifluoroethyl)-
9-(trifluoromethyl)-7H-[1,4]oxazino[3,2-g]quinolin-7-one

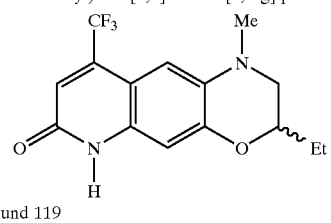

Compound 119
(±)-3-Ethyl-1,2,3,6-tetrahydro-1-methyl-9-(trifluoromethyl)
7H-[1,4]oxazino[3,2-g]quinolin-7-one

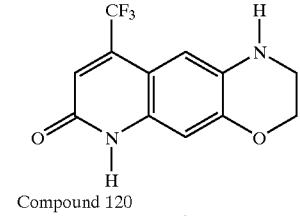

Compound 120
1,2,3,6-Tetrahydro-9-(trifluoromethyl)-
7H-[1,4]oxazino[3,2-g]quinolin-7-one

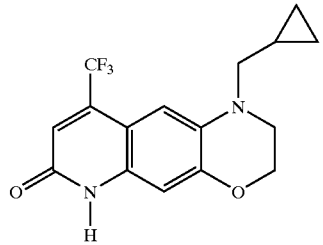

Compound 121
1-Cyclopropylmethyl-1,2,3,6-tetrahydro-9-(trifluoromethyl)-
7H-[1,4]oxazino[3,2-g]quinolin-7-one

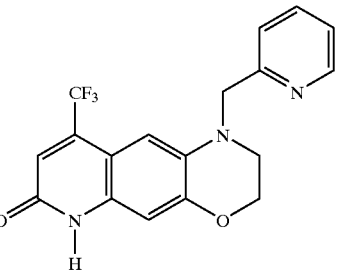

Compound 122
1,2,3,6-Tetrahydro-1-(pyridylmethyl)-9-(trifluoromethyl)-
7H-[1,4]oxazino[3,2-g]quinolin-7-one

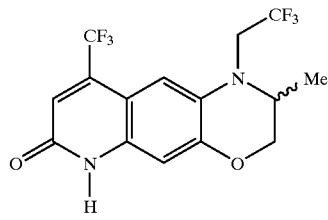

Compound 123
(±)-1,2,3,6-Tetrahydro-2-methyl-1-(2,2,2-trifluoroethyl)-
9-(trifluoromethyl)-7H-[1,4]oxazino[3,2-g]quinolin-7-one

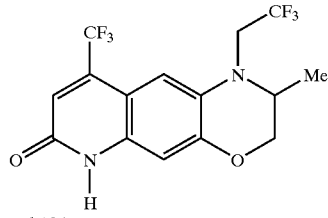

Compound 124
(+)-1,2,3,6-Tetrahydro-2-methyl-1-(2,2,2-trifluoroethyl)-
9-(trifluoromethyl)-7H-[1,4]oxazino[3,2-g]quinolin-7-one

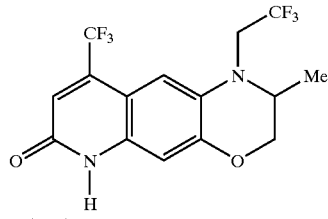

Compound 125
(−)-1,2,3,6-Tetrahydro-2-methyl-1-(2,2,2-trifluoroethyl)-
9-(trifluoromethyl)-7H-[1,4]oxazino[3,2-g]quinolin-7-one

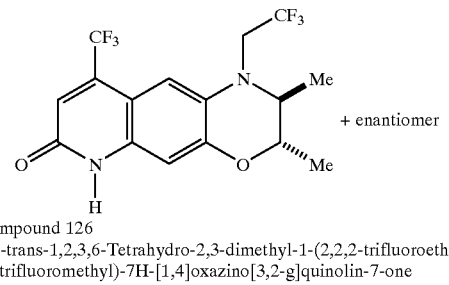

Compound 126
(±)-trans-1,2,3,6-Tetrahydro-2,3-dimethyl-1-(2,2,2-trifluoroethyl)-
9-(trifluoromethyl)-7H-[1,4]oxazino[3,2-g]quinolin-7-one

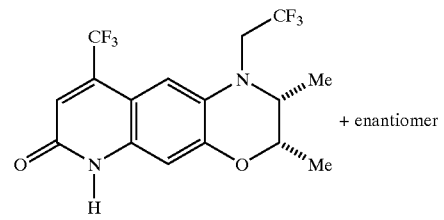

Compound 127
(±)-cis-1,2,3,6-Tetrahydro-2,3-dimethyl-1-(2,2,2-trifluoroethyl)-
9-(trifluoromethyl)-7H-[1,4]oxazino[3,2-g]quinolin-7-one

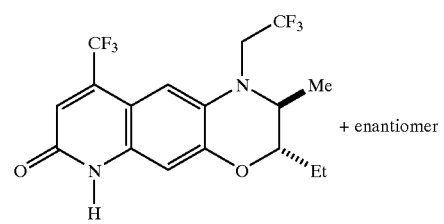

Compound 128
(±)-trans-3-Ethyl-1,2,3,6-tetrahydro-2-methyl-1-(2,2,2-trifluoroethyl)-
9-(trifluoromethyl)-7H-[1,4]oxazino[3,2-g]quinolin-7-one

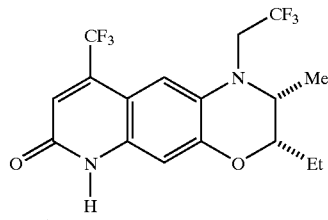

Compound 129
(±)-cis-3-Ethyl-1,2,3,6-tetrahydro-2-methyl-1-(2,2,2-trifluoroethyl)-
9-(trifluoromethyl)-7H-[1,4]oxazino[3,2-g]quinolin-7-one

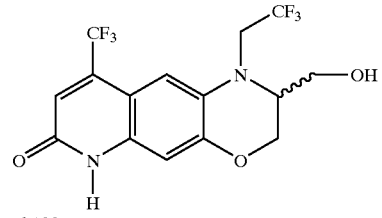

Compound 130
(±)-1,2,3,6-Tetrahydro-2-(hydroxymethyl)-1-(2,2,2-trifluoroethyl)-
9-(trifluoromethyl)-7H-[1,4]oxazino[3,2-g]quinolin-7-one

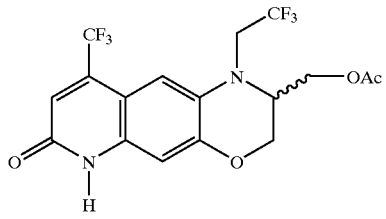

Compound 131
(±)-1,2,3,6-Tetrahydro-2-(acetoxymethyl)-1-(2,2,2-trifluoroethyl)-
9-(trifluoromethyl)-7H-[1,4]oxazino[3,2-g]quinolin-7-one

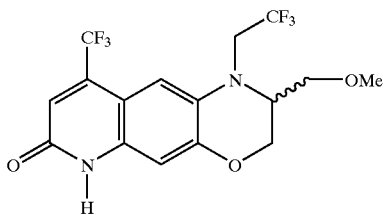

Compound 132
(±)-1,2,3,6-Tetrahydro-2-(methoxymethyl)-1-(2,2,2-trifluoroethyl)-
9-(trifluoromethyl)-7H-[1,4]oxazino[3,2-g]quinolin-7-one

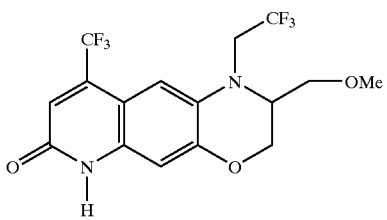

Compound 133
(+)-1,2,3,6-Tetrahydro-2-(methoxymethyl)-1-(2,2,2-trifluoroethyl)-
9-(trifluoromethyl)-7H-[1,4]oxazino[3,2-g]quinolin-7-one

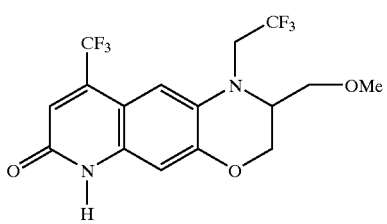

Compound 134
(−)-1,2,3,6-Tetrahydro-2-(methoxymethyl)-1-(2,2,2-trifluoroethyl)-
9-(trifluoromethyl)-7H-[1,4]oxazino[3,2-g]quinolin-7-one

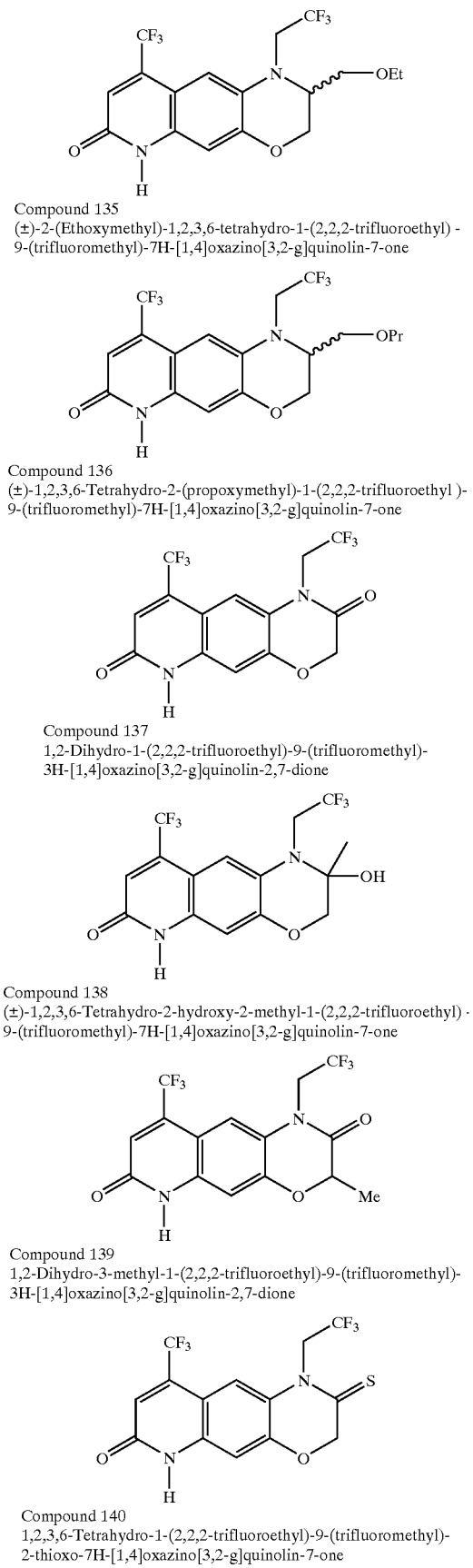

Compound 135
(±)-2-(Ethoxymethyl)-1,2,3,6-tetrahydro-1-(2,2,2-trifluoroethyl)-9-(trifluoromethyl)-7H-[1,4]oxazino[3,2-g]quinolin-7-one Compound 136
(±)-1,2,3,6-Tetrahydro-2-(propoxymethyl)-1-(2,2,2-trifluoroethyl)-9-(trifluoromethyl)-7H-[1,4]oxazino[3,2-g]quinolin-7-one Compound 137
1,2-Dihydro-1-(2,2,2-trifluoroethyl)-9-(trifluoromethyl)-3H-[1,4]oxazino[3,2-g]quinolin-2,7-dione Compound 138
(±)-1,2,3,6-Tetrahydro-2-hydroxy-2-methyl-1-(2,2,2-trifluoroethyl)-9-(trifluoromethyl)-7H-[1,4]oxazino[3,2-g]quinolin-7-one Compound 139
1,2-Dihydro-3-methyl-1-(2,2,2-trifluoroethyl)-9-(trifluoromethyl)-3H-[1,4]oxazino[3,2-g]quinolin-2,7-dione Compound 140
1,2,3,6-Tetrahydro-1-(2,2,2-trifluoroethyl)-9-(trifluoromethyl)-2-thioxo-7H-[1,4]oxazino[3,2-g]quinolin-7-one

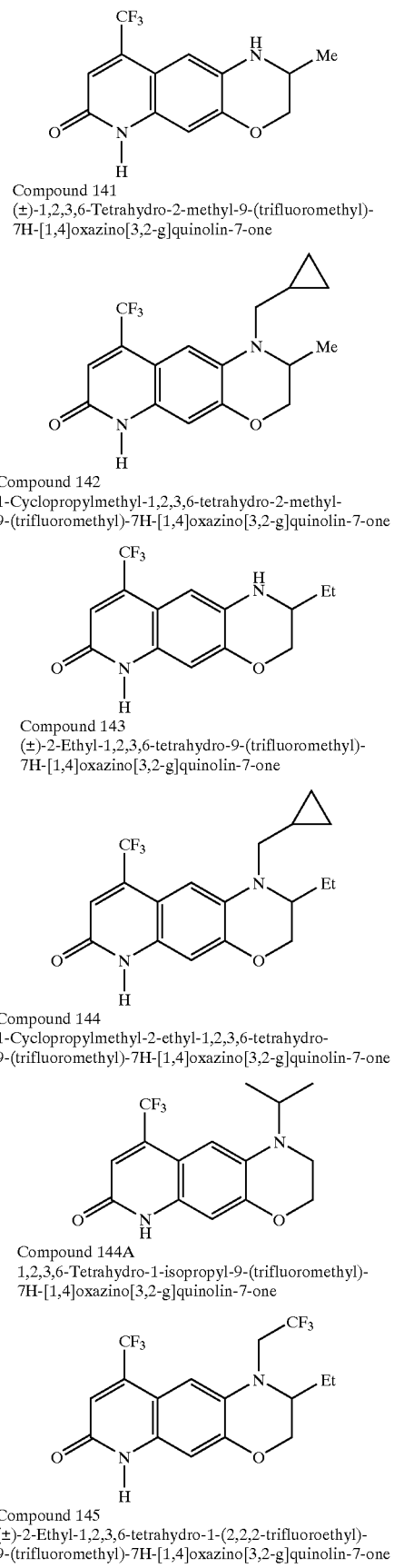

Compound 141
(±)-1,2,3,6-Tetrahydro-2-methyl-9-(trifluoromethyl)-7H-[1,4]oxazino[3,2-g]quinolin-7-one Compound 142
1-Cyclopropylmethyl-1,2,3,6-tetrahydro-2-methyl-9-(trifluoromethyl)-7H-[1,4]oxazino[3,2-g]quinolin-7-one Compound 143
(±)-2-Ethyl-1,2,3,6-tetrahydro-9-(trifluoromethyl)-7H-[1,4]oxazino[3,2-g]quinolin-7-one Compound 144
1-Cyclopropylmethyl-2-ethyl-1,2,3,6-tetrahydro-9-(trifluoromethyl)-7H-[1,4]oxazino[3,2-g]quinolin-7-one Compound 144A
1,2,3,6-Tetrahydro-1-isopropyl-9-(trifluoromethyl)-7H-[1,4]oxazino[3,2-g]quinolin-7-one Compound 145
(±)-2-Ethyl-1,2,3,6-tetrahydro-1-(2,2,2-trifluoroethyl)-9-(trifluoromethyl)-7H-[1,4]oxazino[3,2-g]quinolin-7-one

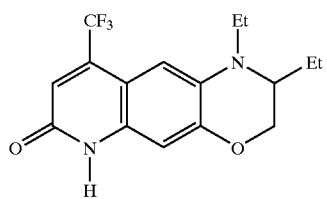

Compound 146
(±)-1,2-Diethyl-1,2,3,6-tetrahydro-9-(trifluoromethyl)-
7H-[1,4]oxazino[3,2-g]quinolin-7-one

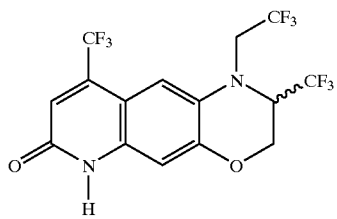

Compound 146A
(±)-1,2,3,6-Tetrahydro-(2,2,2-trifluoroethyl)-
2,9-bis(trifluoromethyl)-7H-[1,4]oxazino[3,2-g]quinolin-7-one

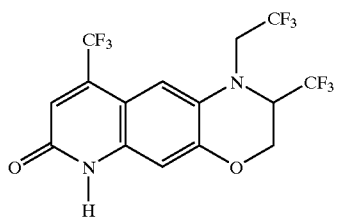

Compound 146B
(+)-1,2,3,6-Tetrahydro-(2,2,2-trifluoroethyl)-
2,9-bis(trifluoromethyl)-7H-[1,4]oxazino[3,2-g]quinolin-7-one

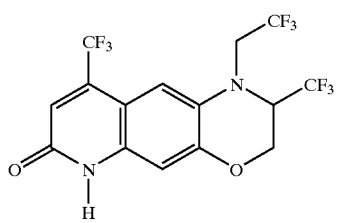

Compound 146C
(−)-1,2,3,6-Tetrahydro-(2,2,2-trifluoroethyl)-
2,9-bis(trifluoromethyl)-7H-[1,4]oxazino[3,2-g]quinolin-7-one

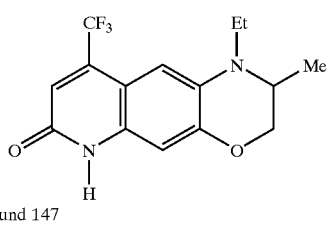

Compound 147
(±)-1-Ethyl-1,2,3,6-tetrahydro-2-methyl-9-(trifluoromethyl)-
7H-[1,4]oxazino[3,2-g]quinolin-7-one

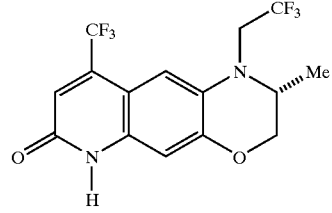

Compound 148
(2R)-(−)-1,2,3,6-Tetrahydro-2-methyl-1-(2,2,2-trifluoroethyl)-
9-(trifluoromethyl)-7H-[1,4]oxazino[3,2-g]quinolin-7-one

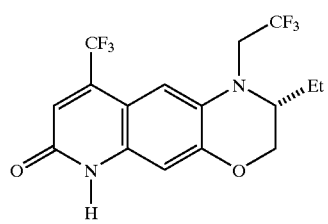

Compound 149
(2R)-2-Ethyl-1,2,3,6-tetrahydro-1-(2,2,2-trifluoroethyl)-
9-(trifluoromethyl)-7H-[1,4]oxazino[3,2-g]quinolin-7-one

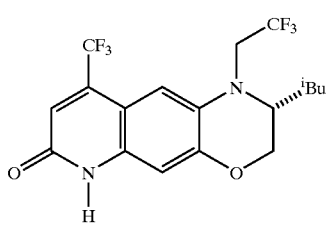

Compound 150
(2R)-1,2,3,6-Tetrahydro-2-isobutyl-1-(2,2,2-trifluoroethyl)-
9-(trifluoromethyl)-7H-[1,4]oxazino[3,2-g]quinolin-7-one

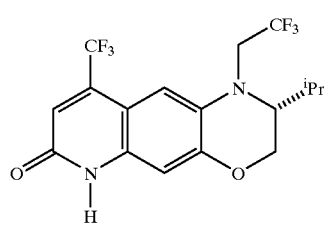

Compound 151
(2R)-1,2,3,6-Tetrahydro-2-isopropyl-1-(2,2,2-trifluoroethyl)-
9-(trifluoromethyl)-7H-[1,4]oxazino[3,2-g]quinolin-7-one

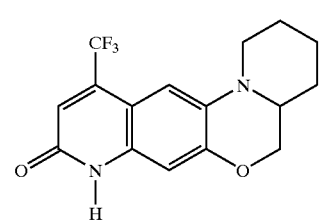

Compound 152
(±)-1,2,3,4,4a,5-Hexahydro-11-(trifluoromethyl)-
pyrido[1′,2′:4,5][1,4]oxazino[3,2-g]quinolin-9(8H)-one

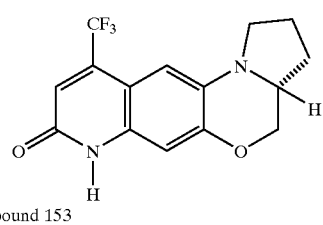

Compound 153
(R)-2,3,3a,4-Tetrahydro-10-(trifluoromethyl)-
pyrrolo[1′,2′:4,5][1,4]oxazino[3,2-g]quinolin-8(7H)-one

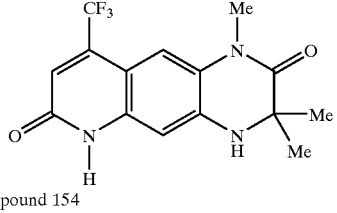

Compound 154
1,3,4,6-Tetrahydro-1,3,3-trimethyl-9-(trifluoromethyl)-
pyrazino[3,2-g]quinolin-2,7-dione 23
-continued
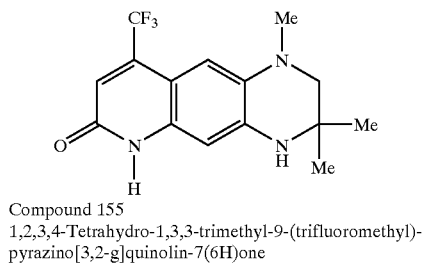
Compound 155
1,2,3,4-Tetrahydro-1,3,3-trimethyl-9-(trifluoromethyl)-
pyrazino[3,2-g]quinolin-7(6H)one
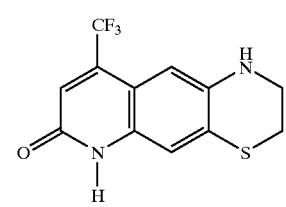
Compound 156
9-(Trifluoromethyl)-1,2,3,6-tetrahydro-
7H-[1,4]thiazino[3,2-g]quinolin-7-one
24
-continued
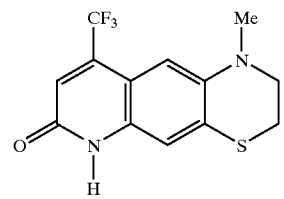
Compound 157
1-Methyl-9-(trifluoromethyl)-1,2,3,6-tetrahydro-
7H-[1,4]thiazino[3,2-g]quinolin-7-one
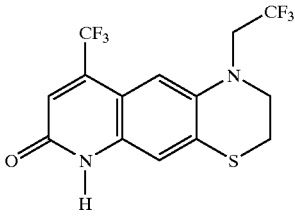
Compound 158
1-(2,2,2-Trifluoroethyl)-9-(trifluoromethyl)-1,2,3,6-tetrahydr
7H-[1,4]thiazino[3,2-g]quinolin-7-one
Scheme I
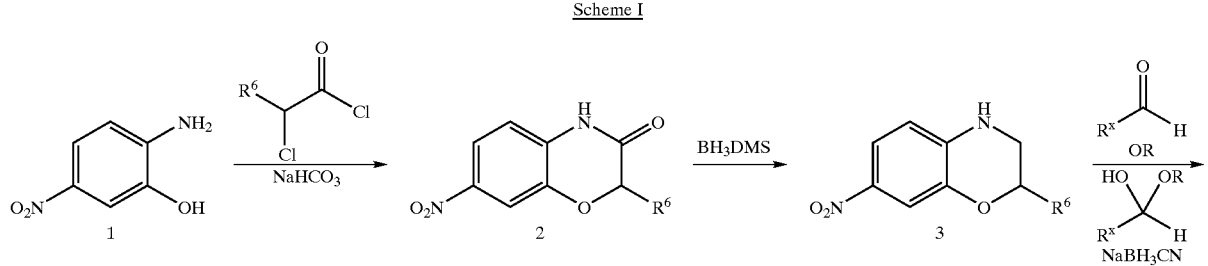
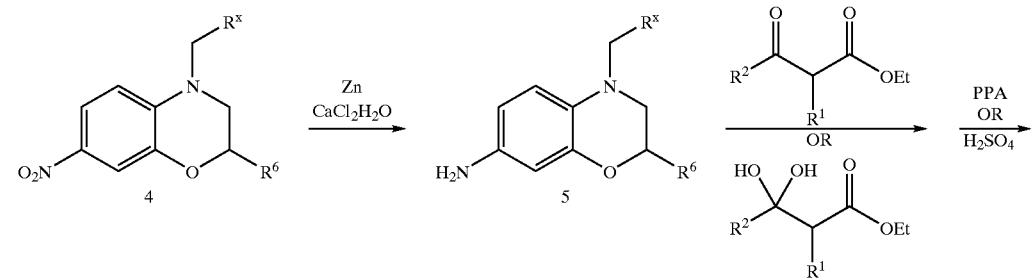

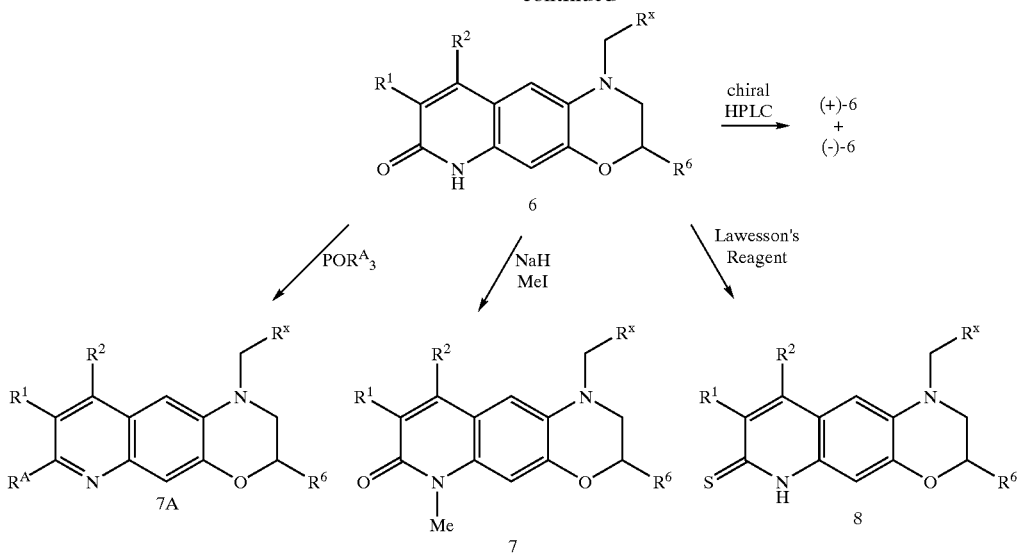

Compounds of the present invention, comprising classes of heterocyclic nitrogen compounds and their derivatives, can be obtained by routine chemical synthesis by those skilled in the art, e.g., by modification of the heterocyclic nitrogen compounds disclosed or by a total synthesis approach.

The sequences of steps for several general schemes to synthesize the compounds of the present invention are shown below. In each of the schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulas I through VI also comprise potential substituents for the analogous positions on the structures within the schemes.

The synthesis of 7H-[1,4]oxazino[3,2-g]quinolin-7-one compounds (e.g., Structures 6 and 7), is depicted in Scheme I. The process of Scheme I begins with a cyclization of a haloacetyl halide onto 2-amino-5-nitrophenol (Structure 1) with, for example, chloroacetyl chloride to afford a lactam (Structure 2). See D. R. Shridhar, et al., *Org. Prep. Proc. Int.*, 14:195 (1982). The amide is then reduced to the corresponding amine (Structure 3), with, for example, borane dimethyl sulfide. See Y. Matsumoto , et. al., *Chem. Pharm. Bull.*, 44:103–114 (1996). Treatment of a compound such as Structure 3 with an aldehyde or its corresponding hydrate or hemiacetal, for example trifluoroacetaldehyde hydrate in the presence of a reducing agent, for example, sodium cyanoborohydride, in a carboxylic acid, for example trifluoroacetic acid, affords a compound such as Structure 4. The nitro derivative is reduced to the corresponding aniline, with a reducing agent, for example, zinc and calcium chloride, to afford Structure 5. Treatment of the aniline with a β-ketoester or corresponding hydrate, for example 4,4,4-trifluoroacetoacetate, at elevated temperatures, followed by treatment with an acid, for example, sulfuric acid, affords a major product (Structure 6). The cyclization of anilines as described above is known as a Knorr cyclization. See, G. Jones, *Comprehensive Heterocyclic Chemistry*, Katritzky, A. R.; Rees, C. W., eds. Pergamon, New York, 1984. Vol. 2, chap. 2.08, pp 421–426, the disclosure of which is herein incorporated by reference. In turn, the quinolinone nitrogen may be alkylated by, for example, treatment with sodium hydride followed by iodomethane, to afford a compound of Structure 7. Alternatively, a quinolinone compound of Structure 6 can be converted to the corresponding quinoline by treatment with a dehydrating agent, for example, oxyphosphoryl chloride, to afford a compound of Structure 7A.

Alternatively, a quinolinone compound of Structure 6 can be transformed to the corresponding thio-compound by treatment with, for example, Lawesson's reagent [2,4-bis(4-methoxyphenyl)-1,3-dithia-2,4-diphosphetane-2,4-disulfide] to give a 7H-[1,4]oxazino[3,2-g]quinolin-thione (e.g., Structure 8). See J. Voss, *Encyclopedia of Reagents for Organic Synthesis*, Paquette, L. A., Ed. John Wiley and Sons, New York, 1995; Vol. 1, pp 530–533, the disclosure of which is herein incorporated by reference. Alternatively, a compound of Structure 6 (or chiral synthetic precursors of Structure 6) can be separated into its corresponding enantiomers, (+)-6 and (−)-6 by chiral HPLC, with, for example, a preparative Chiralpak AD column eluted with hexanes:isopropanol.

Scheme II

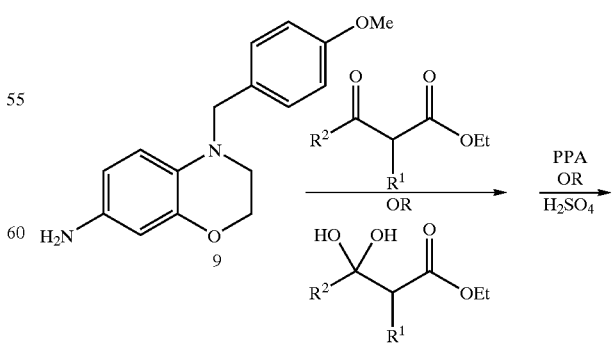

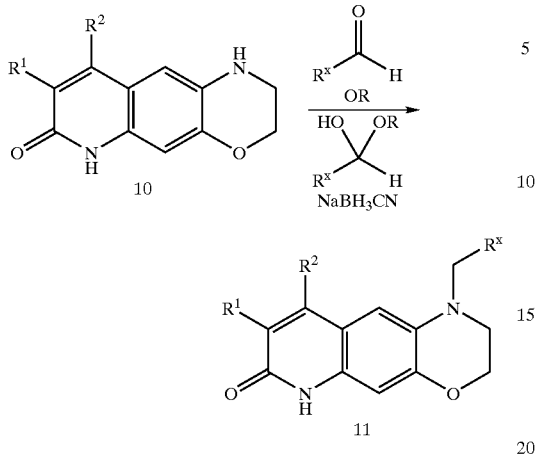

An alternate synthesis of 7H-[1,4]oxazino[3,2-g] quinolin-7-one compounds (e.g., Structures 10 and 11) is shown in Scheme II. The process of Scheme II begins with a Knorr cyclization of 7-amino-3,4-dihydro-4-p-methoxybenzyl-2H-1,4-benzoxazine, and a β-ketoester promoted by an acid, for example, sulfuric acid to afford a compound of Structure 10. Alkylation of the quinolinone nitrogen may be achieved by treatment with an aldehyde or its corresponding hydrate, for example cyclopropanecarboxaldehyde in the presence of a reducing agent, for example, sodium cyanoborohydride, to afford the alkylated derivative of the corresponding quinolinone compound (e.g., Structure 11).

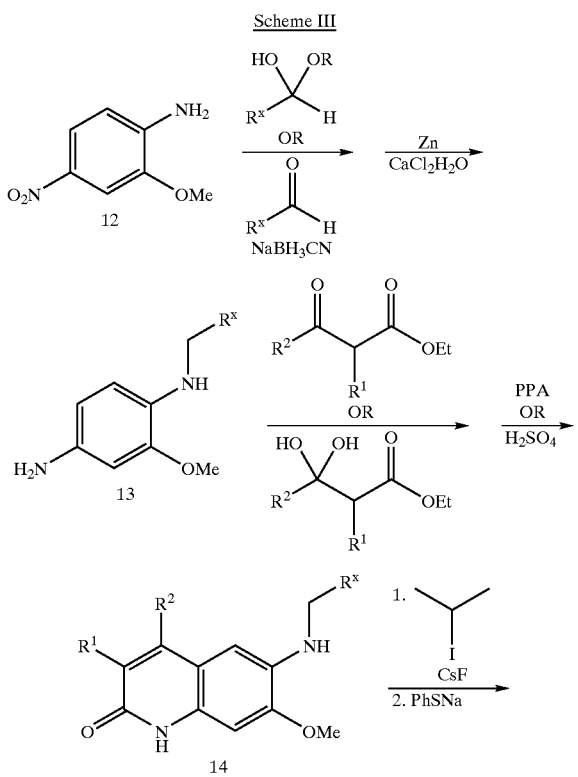

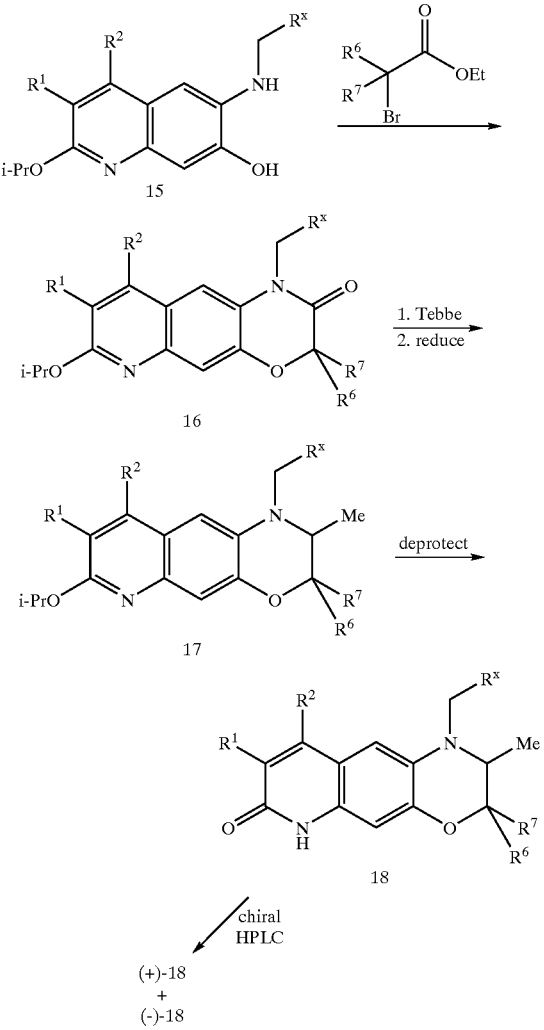

An additional synthetic route into quinoline compounds (e.g., Structures 16 and 18) is shown in Scheme III. The process of Scheme III begins with reductive amination of 2-methoxy-4-nitroaniline with an aldehyde or its corresponding hydrate, for example trifluoroacetaldehyde hydrate in the presence of a reducing agent, for example, sodium cyanoborohydride, in an acid, for example trifluoroacetic acid, to afford the corresponding N-alkylated amine. The nitro derivative is reduced to the corresponding aniline, with a reducing agent, for example, zinc and calcium chloride, to afford a compound of Structure 13. Knorr cyclization of the aniline by heating with a β-ketoester or corresponding hydrate, for example 4,4,4-trifluoroacetoacetate, followed by treatment with an acid, for example, sulfuric acid, affords a product of Structure 14. Protection of the pyridone ring, with, for example isopropyl iodide mediated by a base, for example, cesium fluoride, affords the corresponding imino ether. See T. Sato, et al., *Synlett* 1995, 845–846. Demethylation of the anisole is accomplished by treatment with, for example, sodium thiophenolate to afford a compound of Structure 15. See C. Hansson, et al., *Synthesis* 1975, 191. Treatment of aminophenol derivative 15 with an α-bromoester, for example, ethyl bromoacetate, and a base, with for example, potassium carbonate, affords a quinolinone compound (Structure 16). Treatment of quinolinone compounds such as Structure 16 with an alkylidenation reagent, for example, Tebbe's reagent, followed by reduction with, for example, sodium cyanoborohydride, in an acid, for example acetic acid, affords a quinoline compound (e.g., Structure 17). See S. H. Pine, et. al., *J. Org. Chem.* 1985, 50, 1212, for the methylenation of amides. Deprotection can be accomplished in one of two ways. Treatment of the iminoether (Structure 17) with a mineral acid, for example hydrochloric acid, affords a 7H-[1,4]oxazino[3,2-g]quinolin-7-one compound (Structure 18). Alternatively, this transformation can be carried out with a Lewis acid, for example boron trichloride, to afford Structure 18. See T. Sala, et al., *J. Chem. Soc., Perkin Trans. I*, 1979, 2593. Quinolinone compounds of Structure 18 (or any chiral synthetic precursor of 18) can be separated into their corresponding enantiomers, (+)-18 and (−)-18 by chiral HPLC, with, for example, a preparative Chiralpak AD column eluted with hexanes:isopropanol.

compound (e.g., Structure 16) followed by hydroboration of the resultant enamine to afford a hydroxyalkyl quinoline compound (Structure 19). See C. T. Goralski, et. al. *Tetrahedron Lett.* 1994, 35, 3251, for the hydroboration of enamines. Hydrolysis of the imino ether with an acid, for example hydrochloric acid, affords a hydroxy quinolinone compound (e.g., Structure 20).

Alternatively, hydrolysis of the imino ether of a hydroxyalkyl quinoline compound (e.g., Structure 19) can be carried out with an acid, for example hydrochloric acid, in acetic acid, to afford an acyloxyalkyl quinolinone compound (Structure 21)

Alternatively, a hydroxy quinoline compound (e.g., Structure 19) can be O-alkylated by treatment with a base, for example, sodium hydride, and an alkylating agent, with, for example methyl iodide, to afford an alkoxyalkyl quinoline compound (e.g., Structure 22). Imino ether hydrolysis of

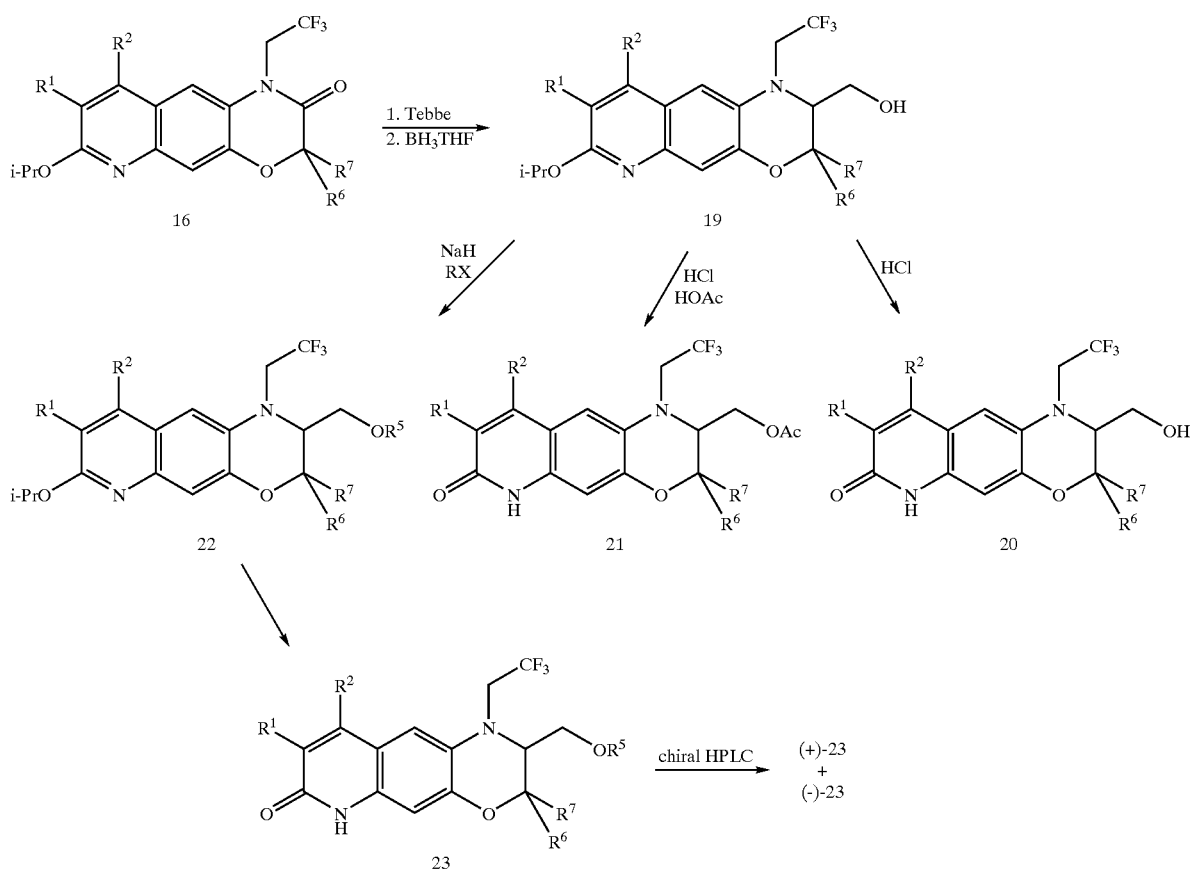

The process of converting quinolinone compounds (e.g., Structure 16) into corresponding hydroxyalkyl quinoline compounds (e.g., Structure 19) and then further converting into corresponding hydroxyalkyl, acyloxyalkyl, and alkyloxyalkyl quinolinone derivatives (e.g., Structures 20, 21, and 23 respectively) is shown in Scheme IV. The process of Scheme IV begins with a Tebbe olefination of a quinolinone Structure 22 with an acid, for example hydrochloric acid in acetic acid, affords an alkoxyalkyl quinoline compound (Structure 23). Compound such as Structures 20, 21, or 23 can be separated into their corresponding enantiomers, (+)-20 and (−)-20, (+)-21 and (−)-21, or (+)-23 and (−)-23 by chiral HPLC, with, for example, a preparative Chiralpak AD column eluted with hexanes:isopropanol.

Scheme V

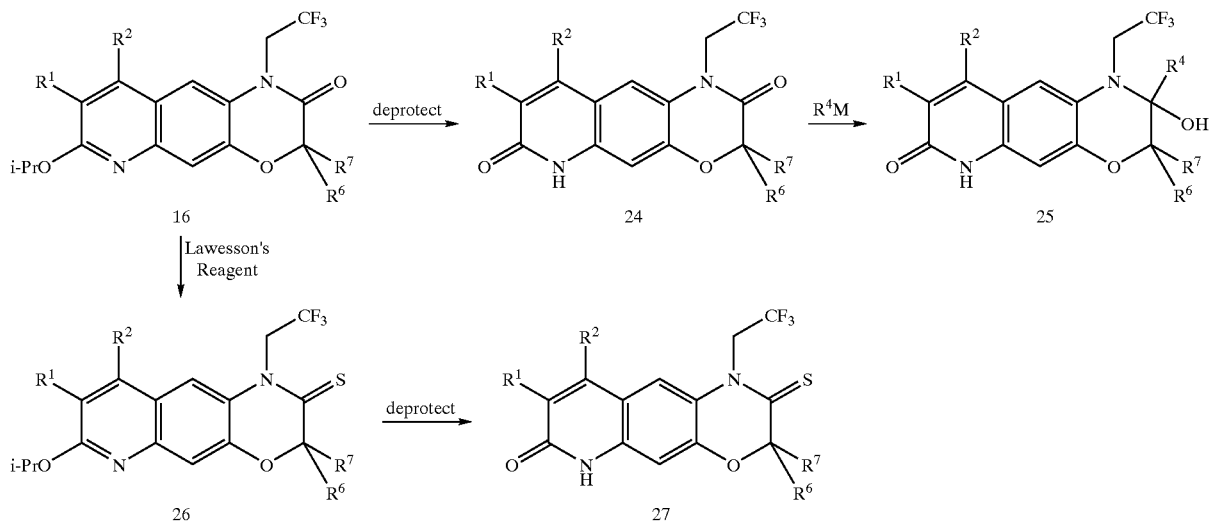

Quinolinone compounds (e.g., Structure 16) may be converted into corresponding quinoline-diones (e.g., Structure 24), hydroxy quinolinones (e.g., Structure 25), and quinoline-thiones (e.g., Structures 26 and 27) by the processes shown in Scheme V. The process of Scheme V begins with the deprotection of the imino ether of Structure 16 by treatment with a mineral acid, for example, hydrochloric acid, to afford a quinoline-dione compound of Structure 24. Alternatively, this transformation can be carried out with a Lewis acid, for example, boron trichloride, to afford a quinoline-dione compound (e.g., Structure 24). See T. Sala, et al., supra. A quinoline-dione compound (e.g., Structure 24) can be converted to a hydroxy quinoline compound (e.g., Structure 25) by addition of an organometallic reagent, for example, methyl lithium, which affords a hydroxy quinoline compound (Structure 25).

Quinoline compounds (e.g., Structure 16) can optionally be converted into corresponding thio-compounds (e.g., Structure 25) by treatment with, for example, Lawesson's reagent [2,4-bis(4-methoxyphenyl)-1,3-dithia-2,4-diphosphetane-2,4-disulfide]. Hydrolysis of the imino ether with a Lewis acid, for example, boron trichloride, affords a quinoline-thione compound (Structure 26).

Scheme VI

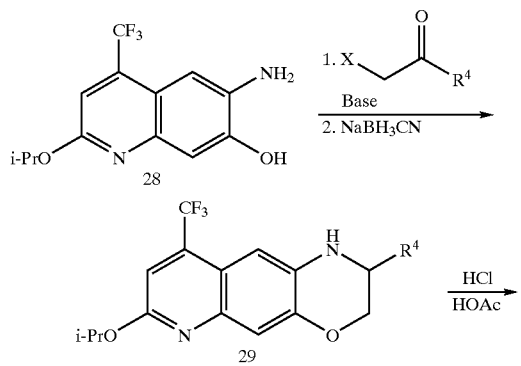

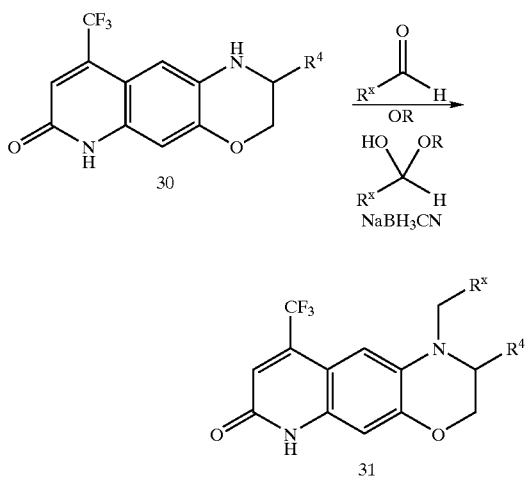

A synthesis of quinolinone compounds such as Structure 30 is shown in Scheme VI. The process of Scheme VI begins with the O-alkylation of an o-aminophenol, for example, a 6-amino-7-hydroxyquinoline, with a haloketone, for example, chloroacetone, mediated by a base, for example, potassium carbonate, followed by treatment with a reducing agent, for example, sodium cyanoborohydride, in an acid, for example, acetic acid, to afford a quinoline compound of Structure 29. Hydrolysis of the imino ether of Structure 29 with an acid, for example, hydrochloric acid in acetic acid, affords a quinolinone compound of Structure 30. Alkylation of the quinolinone nitrogen is achieved by treatment of quinolinone compounds (e.g., Structure 30) with an aldehyde or its corresponding hydrate, for example, cyclopropanecarboxaldehyde, with a reducing agent, for example, sodium cyanoborohydride, in an acid, for example, acetic acid, affords a compound of Structure 31.

Scheme VIA

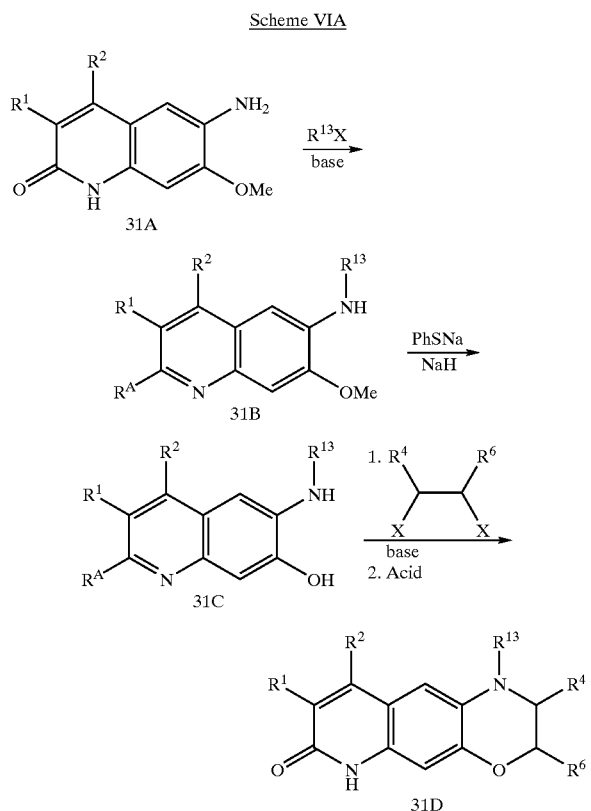

An additional route to quinolinone compounds such as Structure 31D is shown in Scheme VIA. The process of Scheme VIA begins with the alkylation of a 6-aminoquinolinone with, for example, 6-amino-7-methoxy-4-trifluoromethyl-1H-quinolin-2-one, with an alkyl halide, for example, isopropyl iodide, mediated by a base, for example, cesium fluoride, to afford a compound of structure 31B. Demethylation of the methyl ether is accomplished by treatment with, for example, sodium thiophenolate to afford a compound of Structure 31C. Annulation of the oxazine ring can be accomplished by treatment with a vicinal dihalide, for example, 1,2-dibromoethane, mediated by a base, for example potassium carbonate, to afford the corresponding 1,4-oxazine, which in turn is converted to a compound of Structure 31D by treatment with an acid, for example, hydrochloric acid in acetic acid at elevated temperatures.

Scheme VII

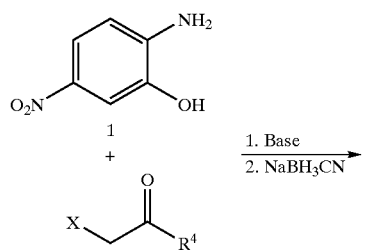

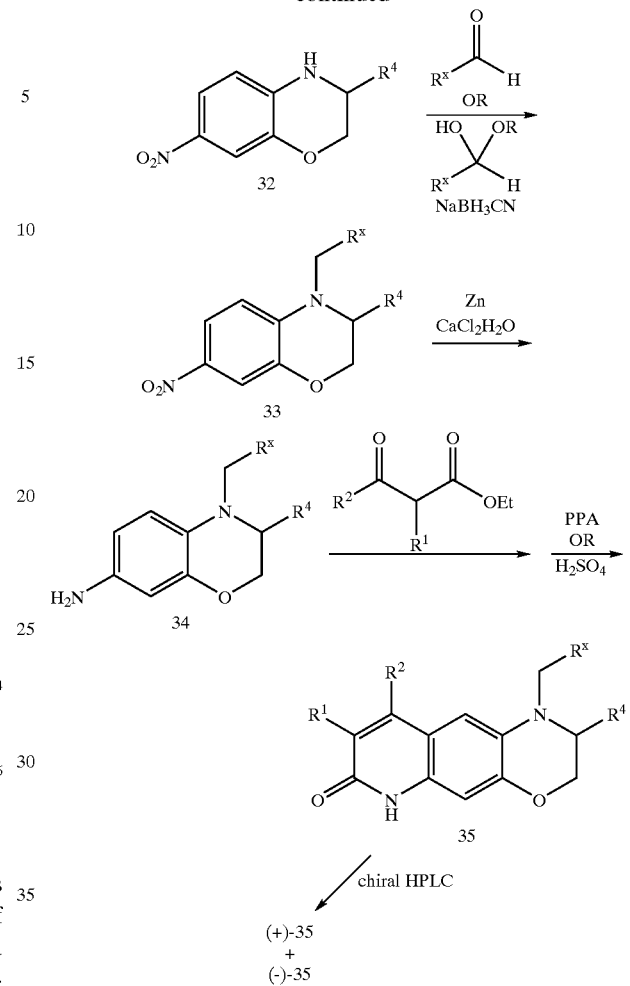

Quinolinones (e.g., Structure 35) are prepared from benzoxazines (e.g., Structure 34) by the synthetic route outlined in Scheme VII. Scheme VII begins with an alkylation of a haloketone onto 2-amino-5-nitrophenol (Structure 1) with, for example, 2-bromobutanone, mediated by a base, for example, potassium carbonate, followed by treatment with a reducing agent, for example, sodium cyanoborohydride, in an acid, for example acetic acid, to afford a benzoxazine compound (e.g., Structure 32). The benzoxazine is alkylated at the benzoxazine nitrogen by treatment of a benzoxazine compound (e.g., Structure 32) with an aldehyde, its corresponding hydrate or hemiacetal, with for example, trifluoroacetaldehyde hydrate in the presence of a reducing agent, for example, sodium cyanoborohydride, in an acid, for example trifluoroacetic acid. This procedure affords an alkylated benzoxazine compound (e.g., Structure 33). The nitro derivative of the alkylated benzoxazine compound (Structure 33) is reduced to the corresponding aniline by catalytic hydrogenation or with a reducing agent, for example, zinc and calcium chloride, to afford benzoxazine compound (e.g., Structure 34). Knorr cyclization of an aminobenzoxazine (e.g., Structure 34) by heating with a β-ketoester or corresponding hydrate, with for example, 4,4,4-trifluoroacetoacetate, followed by treatment with an acid, for example, sulfuric acid, affords a quinolinone product (e.g., Structure 35).

Scheme VIIA

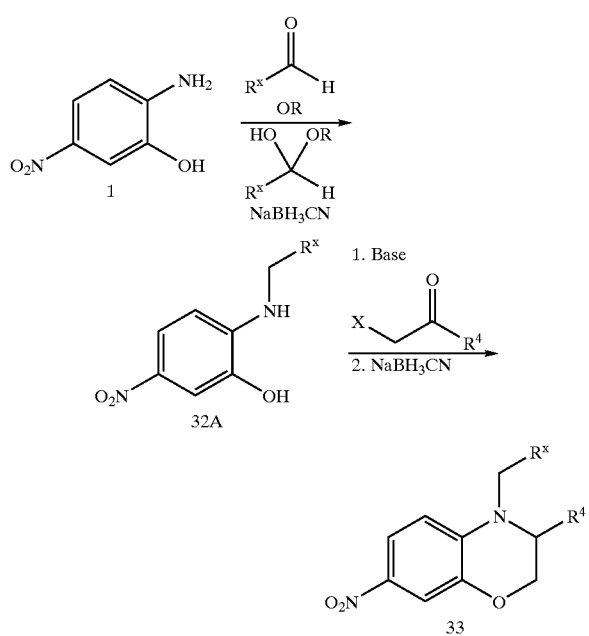

Compounds such as the 3,4-dihydro-7-nitro-2H-1,4-benzoxazines of Structure 33 are key intermediates in the preparation of quinolinones and other fused ring structures. In accordance with the current invention, we have developed a method to prepare these 3,4-dihydro-7-nitro-2H-1,4-benzoxazines in enantiomerically pure form (Structure 39) from optically pure β-aminoalcohols. A synthetic method for the preparation of enantiomerically pure, fused ring compounds, such as quinolinones 41, that relies upon such intermediates is shown in Scheme VIII.

Scheme VIII

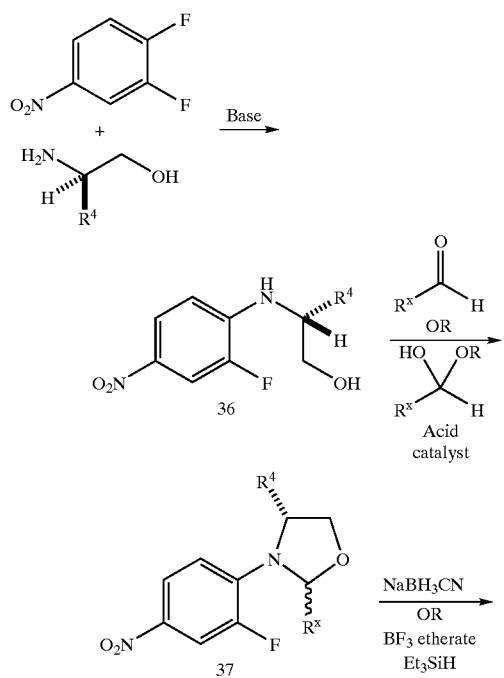

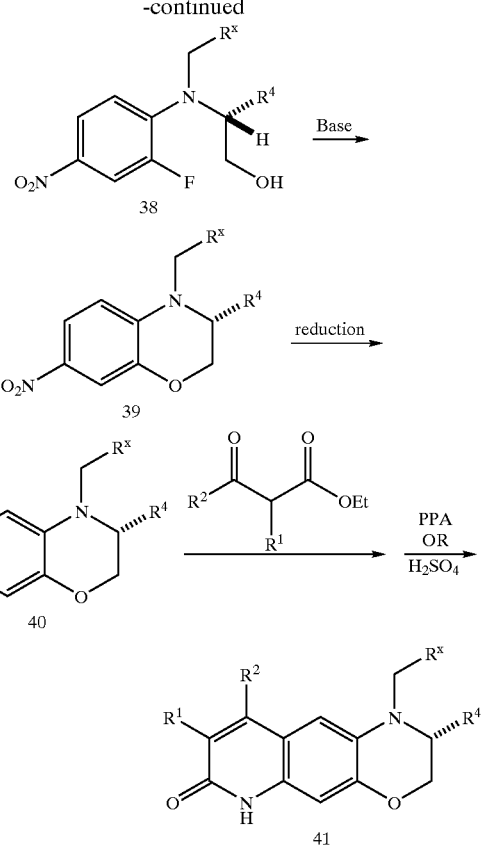

The asymmetric synthesis of Scheme VIII begins with the chemo- and regioselective N-alkylation of a β-aminoalcohol, either as a single enantiomer (R or S) or its racemate, for example, (R)-2-amino-1-propanol, onto a 3,4-dihalonitrobenzene, for example, 3,4-difluoronitrobenzene, mediated by a base, for example, sodium bicarbonate, affords an optically pure arylamino alcohol (e.g., Structure 36). Treatment of amino alcohol compounds such as Structure 36 with an aldehyde or the corresponding hydrate or hemiacetal, for example, trifluoroacetaldehyde ethyl hemiacetal, in the presence of an acid catalyst, for example p-toluenesulfonic acid, affords an optically pure oxazolidine compound (e.g., Structure 37). Treatment of an oxazolidine compound such as Structure 37 with a reducing agent, for example, triethylsilane, in the presence of an acid, for example, boron trifluoride etherate, affords an N-alkyl substituted amino alcohol compound (e.g., Structure 38). Benzoxazine compounds (e.g., Structure 39), may then be formed by cyclization of the N-alkyl substituted amino alcohol compounds (e.g., Structure 38) by treatment with a base such as sodium hydride. Reduction of nitro benzoxazine compounds (e.g., Structure 39) with a reducing agent, for example, zinc and calcium chloride affords an amino benzoxazine compound (e.g., Structure 40). Treatment of an amino benzoxazine with a β-ketoester or its corresponding hydrate, for example ethyl 4,4,4-trifluoroacetoacetate, at elevated temperatures, affords the corresponding acetanilide. Treatment of the acetanilide with an acid, for example, sulfuric acid, affords an optically pure quinolinone compound (e.g., Structure 41). An enantiomer of Structure 41, or a racemic mixture may be obtained by the synthetic route as described in Scheme VIII, by starting with the enantiomer of the β-aminoalcohol as shown (e.g., an (S)-β-amino alcohol), or a racemic mixture of the β-aminoalcohol shown (e.g., a (±)-β-amino alcohol. Accordingly, an (S)-β-amino alcohol, employed in Scheme VII, produces an (S)-quinolinone, an (R)-β-amino alcohol, employed in Scheme VII, produces an (R)-quinolinone, and a racemic mixture of the β-amino alcohol, employed in Scheme VII, produces a racemic mixture of the corresponding quinolinone.

Introduction of an N-alkyl or N-methylaryl group through the reductive cleavage of oxazolidine 37, as outlined in Scheme VIII, is generally applicable to the preparation of enantiomerically pure arylamino alcohol compounds such as Structure 38. Furthermore, the introduction of an N-(2-haloethyl) group through the reductive cleavage of an aryl oxazolidine is a novel process that has general utility in organic synthesis.

Preparation of N-Alkyl or N-Methylaryl Arylamino Alcohols

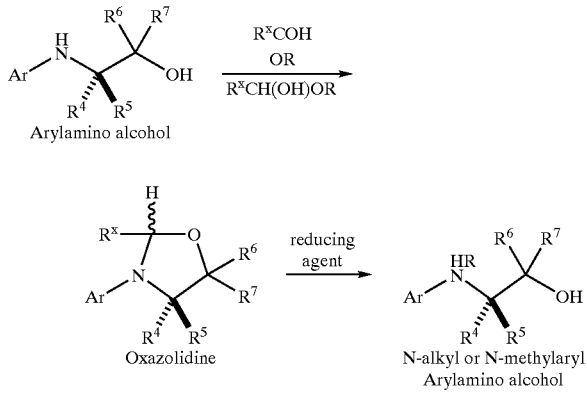

In the above process sequence, $R^{4-7}$ may optionally represent hydrogen or alkyl or aryl groups, including $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, or $C_2$–$C_8$ alkenyl and wherein the alkyl, cycloalkyl, heteroalkyl, haloalkyl, aryl, arylalkyl, heteroaryl, alkynyl, and alkenyl are optionally substituted with halogen, $C_1$–$C_4$ alkyl, or $C_1$–$C_4$ haloalkyl;

$R^x$ may represent $C_1$–$C_8$ alkyl, $C_3$–$C_8$ cycloalkyl, $C_1$–$C_8$ heteroalkyl, $C_1$–$C_8$ haloalkyl, allyl, aryl, arylalkyl, heteroaryl, $C_2$–$C_8$ alkynyl, or $C_2$–$C_8$ alkenyl and wherein the alkyl, cycloalkyl, heteroalkyl, haloalkyl, allyl, aryl, arylalkyl, heteroaryl, alkynyl, and alkenyl are optionally substituted with halogen, $C_1$–$C_4$ alkyl, or $C_1$–$C_4$ haloalkyl.

Ar represents optionally substituted aryl or heteroaryl groups, including mono- and polycyclic structures, optionally substituted at one or more positions.

Additional substitutions are also possible and can be readily determined by one skilled in the art.

The above process sequence begins with an arylamino alcohol which is then converted into an oxazolidine with an aldehyde or the corresponding hydrate or hemiacetal in the presence of an acid catalyst. The oxazolidine is then converted to an N-alkylarylamino alcohol by addition of a reducing agent such as triethylsilane or sodium cyanoborohydride in the presence of a Lewis acid such as boron trifluoride etherate or a protic acid such as trifluoroacetic acid as a catalyst. Additional aldehydes and their corresponding hydrates as well as reducing agents may be used and are readily determined by those skilled in the art.

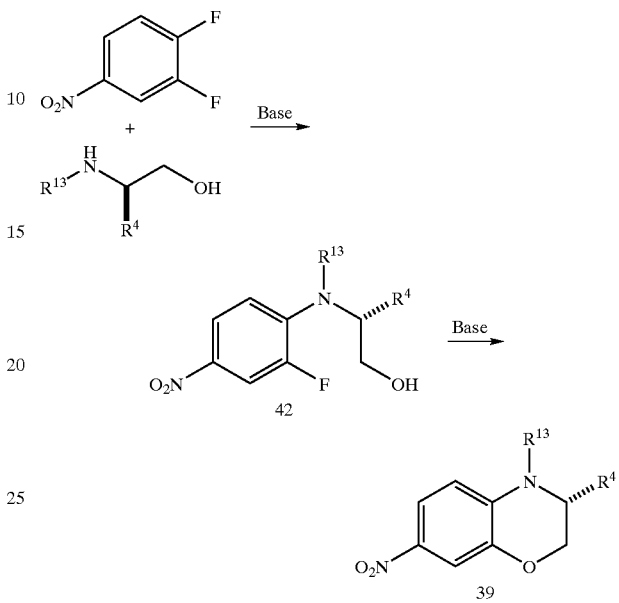

Scheme IX describes an alternative to the route of Scheme VIII for formation of enantiomerically pure benzoxazine compounds such as Structure 39. The route of Scheme IX offers direct access to compounds of Structure 39 in which $R^4$ and $R^{13}$ taken together form a ring structure. The process of Scheme IX begins with reaction of a secondary aminoalcohol, either a single enantiomer (R or S) or its racemate, for example 2-piperidinemethanol, with a 3,4-dihalonitrobenzene, for example, 3,4-difluoronitrobenzene, to afford an N-aryl substituted tertiary aminoalcohol compound such as Structure 42. Cyclization of Structure 42, mediated by treatment with a base, for example, sodium hydride, affords a benzoxazine compound (e.g., Structure 39). Benzoxazine compounds such as Structure 39 may then further be employed in the synthesis of quinolinone compounds as described herein.

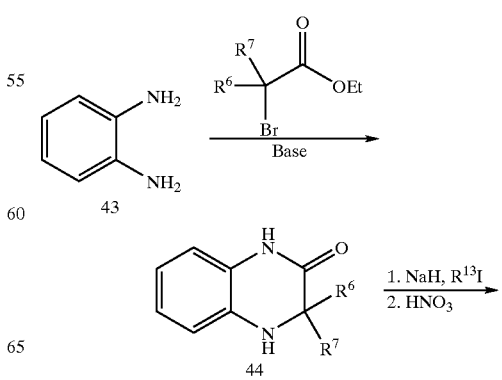

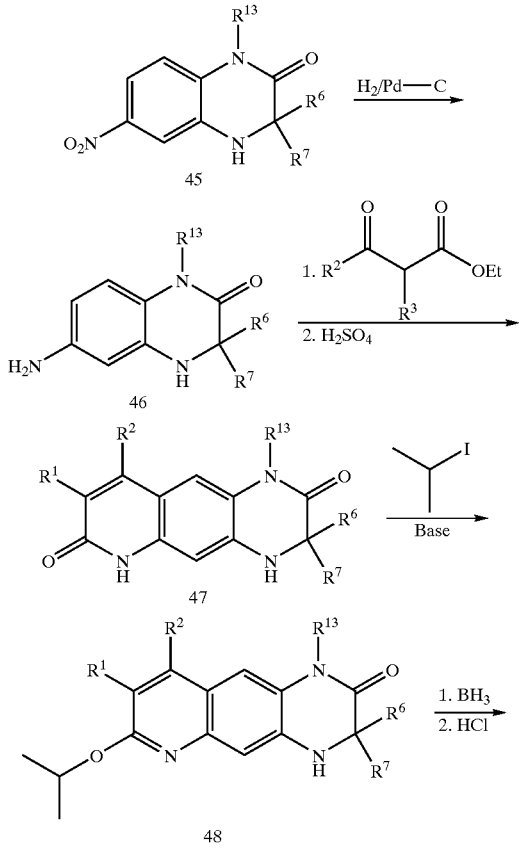
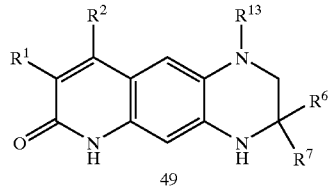

Pyrazino-quinolinone compounds (e.g., Structure 49) may be prepared by the process described in Scheme X. The process of Scheme X begins with the alkylation of a 1,2-phenylenediamine, for example, 1,2-phenylenediamine, with an α-haloester, for example ethyl 2-bromoisobutyrate, mediated by a base, for example diisopropylethylamine, to afford a compound of Structure 44. Nitration of 44 with, for example, nitric acid in sulfuric acid, affords a compound of Structure 45. The nitro group of 45 can be reduced to the corresponding aniline, with, for example, palladium on carbon under a hydrogen atmosphere, to afford a compound of Structure 46. Treatment of the aniline with a β-ketoester or its corresponding hydrate, for example 4,4,4-trifluoroacetoacetate, at elevated temperatures, affords the corresponding acetanilide. Treatment of the acetanilide with an acid, for example, sulfuric acid, affords a compound of Structure 47. Protection of the pyridone ring, with, for example isopropyl iodide mediated by a base, for example, cesium fluoride, affords the corresponding imino ether (Structure 48). Reduction of the amide with, for example, borane dimethyl sulfide, affords the corresponding amine. Hydrolysis of this imino ether with an acid, for example, hydrochloric acid in acetic acid, affords a pyrazino-quinolinone compound such as Structure 49.

Scheme XI

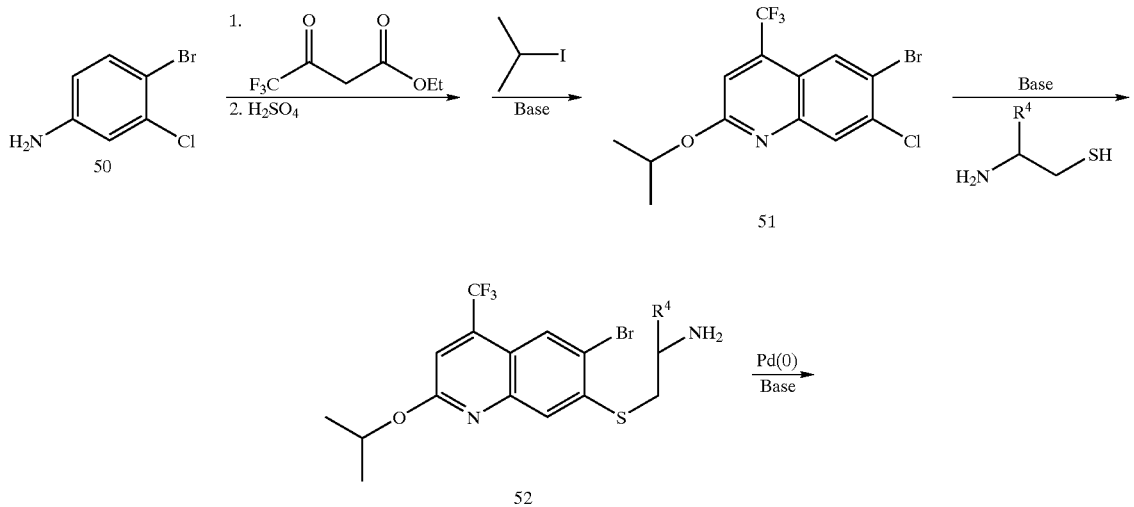

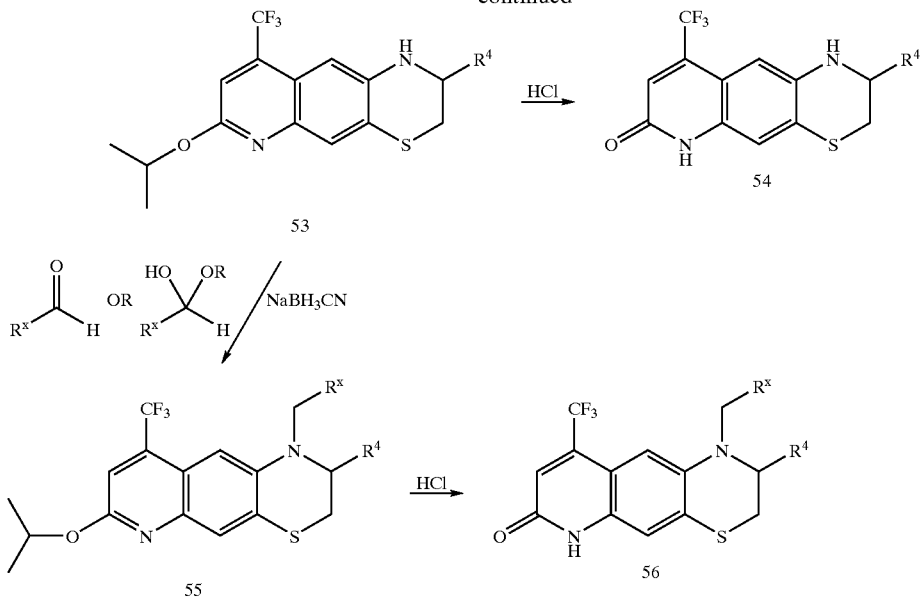

Thiazino-quinolinone compounds (e.g., Structure 56) are prepared as shown in Scheme XI. The process of Scheme XI begins with the treatment of an aniline, for example, 4-bromo-3-chloroaniline, with a β-ketoester or its corresponding hydrate, for example 4,4,4-trifluoroacetoacetate, at elevated temperatures, to afford the corresponding acetanilide. Treatment of the acetanilide with an acid, for example, sulfuric acid, affords the corresponding 1H-quinolin-2-one (an example of a Knorr cyclization as described further herein). Protection of the pyridone ring, with, for example, isopropyl iodide, mediated by a base, for example, cesium fluoride, affords a compound of Structure 51. Treatment of a compound (e.g., Structure 51) with a β-aminothiol, for example, 2-aminoethanethiol hydrochloride, mediated by a base, for example, sodium hydride, affords a compound of Structure 52. Treatment of a compound of Structure 52 with a ligated transition metal. for example palladium acetate and BINAP, in the presence of a base, for example sodium t-butoxide, at elevated temperatures, affords a compound of Structure 53, See S. Wagaw, et al., *J. Am. Chem. Soc.* 1997, 119, 8451–8458. Treatment of a compound of Structure 53 with an aldehyde or its corresponding hydrate or hemiacetal, for example, formaldehyde, affords a compound of Structure 55. Hydrolysis of the imino ether can be accomplished by treatment of a compound of Structure 55 with an acid, for example hydrochloric acid, at elevated temperatures, to afford a thiazino-quinolinone compound such as Structure 56. Alternatively, a compound of Structure 53 can be deprotected with an acid, for example hydrochloric acid, at elevated temperatures, to afford a thiazino-quinolinone compound such as Structure 54.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, any of the steroid modulator compounds of the present invention can be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of AR in a cell background or extract. They are particularly useful due to their ability to selectively activate androgen receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques which are known to those of skill in the art. These techniques include column separation, filtration, centrifugation, tagging and physical separation, and antibody complexing, among others.

The compounds and pharmaceutical compositions of the present invention can advantageously be used in the treatment of the diseases and conditions described herein. In this regard, the compounds and compositions of the present invention will prove particularly useful as modulators of male sex steroid-dependent diseases and conditions such as the treatment of acne, male-pattern baldness, male hormone replacement therapy, sexual dysfunction, wasting diseases, hirsutism, stimulation of hematopoiesis, hypogonadism, prostatic hyperplasia, osteoporosis, male contraception, impotence, cancer cachexia, various hormone-dependent cancers, including, without limitation, prostate and breast cancer and as anabolic agents.

The compounds and pharmaceutical compositions of the present invention possess a number of advantages over previously identified steroidal and non-steroidal compounds.

Furthermore, the compounds and pharmaceutical compositions of the present invention possess a number of advantages over previously identified steroid modulator compounds. For example, the compounds are extremely potent activators of AR, preferably displaying 50% maximal activation of AR at a concentration of less than 100 nM, more preferably at a concentration of less than 50 nM, more preferably yet at a concentration of less than 20 nM, and most preferably at a concentration of 10 nM or less. Also, the selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration. In addition, the compounds of the present invention, as small organic molecules, are easier to synthesize, provide greater stability and can be more easily administered in oral dosage forms than other known steroidal compounds.

The invention will be further illustrated by reference to the following non-limiting Examples.

EXAMPLE 1

1,2,3,6-Tetrahydro-1-methyl-9-(trifluoromethyl)-7H-[1,4]oxazino[3,2-g]quinolin-7-one (Compound 101, Structure 6 of Scheme I, where $R^1$=H, $R^2$= Trifluoromethyl, $R^6$=H, $R^x$=H)

General Method 1: Cyclization of an α-chloroacetyl chloride to 2-amino-5-nitrophenol. To a solution of 2-amino-5-nitrophenol (1.0 equiv), NaHCO$_3$ (2.4 equiv) in 4-methyl-2-pentanone (0.6 mL/mmol) and water (0.6 mL/mmol) was added an α-chloroacetyl chloride derivative (1.15 equiv) via syringe pump over 45 min at 0° C. The reaction mixture was allowed to warm to room temperature and then refluxed overnight. The crude reaction mixture was allowed to cool to room temperature, filtered and washed with water (3×1.2 mL/mmol) to afford the desired product as a tan solid.

7-Nitro-2H-1,4-benzoxazin-3(4H)-one (Structure 2 of Scheme I, where $R^6$=H). This compound was prepared by General Method 1 from 2-amino-5-nitrophenol (6.0 g, 39 mmol), NaHCO$_3$ (7.8 g, 93 mmol), and chloroacetyl chloride (3.58 mL, 45 mmol) to afford 6.91 g (91%) of 7-nitro-2H-1,4-benzoxazin-3(4H)-one. Data for 7-nitro-2H-1,4-benzoxazin-3(4H)-one: $R_f$ 0.44 (11.5:1 CH$_2$Cl$_2$:MeOH); $^1$H NMR (400 MHz, DMSO-d$_6$) δ 11.3 (br s, 1H), 7.90 (dd, 1H, J=8.7, 2.6), 7.76 (d, 1H, J=2.5), 7.06 (d, 1H, J=8.7), 4.73 (s, 2H).

General Method 2: Reduction of an amide Structure 2 to an amine of Structure 3. To a solution of a 2H-1,4-benzoxazin-3(4H)-one of Structure 2 (1.0 equiv) in THF (10 mL/mmol) was added borane dimethylsulfide (2.0 M or 10.0 M in THF, 4 equiv) at rt, then the solution was heated to reflux for 16–18 hrs. The mixture was cooled to room temperature, quenched slowly with methanol until gas evolution stops, then refluxed for an additional 30 min. The solvent was removed under reduced pressure and the compound purified by flash chromatography as indicated.

3,4-Dihydro-7-nitro-2H-1,4-benzoxazine (Structure 3 of Scheme I, where $R^6$=H). This compound was prepared by General Method 2 from 7-nitro-2H-1,4-benzoxazin-3(4H)-one (2.0 g, 10 mmol) and borane dimethylsulfide (2.0 M in THF, 24 mL, 48 mmol) and purified on silica gel (20:1 CH$_2$Cl$_2$:MeOH) to afford 1.84 g (98%) of 3,4-dihydro-7-nitro-2H-1,4-benzoxazine, an orange solid. Data for 3,4-dihydro-7-nitro-2H-1,4-benzoxazine: $R_f$ 0.76 (11.5:1 CH$_2$Cl$_2$:MeOH); $^1$H NMR (400 MHz, CDCl$_3$) δ 7.74 (dd, 1H, J=8.7, 2.5), 7.69 (d, 1H, J=2.5), 6.52 (d, 1H, J=8.7), 4.56 (br s, 1H), 4.26 (t, 2H, J=4.4), 3.54 (td, 2H, J=4.4, 2.5)

General Method 3: Reductive amination of a 3,4-dihydro-2H-1,4-benzoxazine derivative with sodium cyanoborohydride in acetic acid. To a solution of a 3,4-dihydro-7-nitro-2H-1,4-benzoxazine (1.0 equiv) in acetic acid (7.8 mL/mmol) was added an aldehyde component (10 equiv) and the mixture was stirred at rt for 1 h. To this mixture was added portionwise sodium cyanoborohydride (4.8 equiv) and stirred at room temperature overnight. The resulting mixture was poured over ice and neutralized with 6M NaOH to pH 7.0, extracted with CH$_2$Cl$_2$ (3×30 mL/mmol), washed with pH 7 phosphate buffer (50 mL/mmol) and brine (50 mL/mmol). The organic solution was dried (MgSO$_4$) and concentrated under reduced pressure to afford the desired product as a yellow solid.

3,4-Dihydro-4-methyl-7-nitro-2H-1,4-benzoxazine (Structure 4 of Scheme I, where $R^6$=H, $R^x$=H). This compound was prepared by General Method 3 from 3,4-dihydro-7-nitro-2H-1,4-benzoxazine (1.15 g, 6.38 mmol), paraformaldehyde (1.92 g, 64.1 mmol) and NaBH$_3$CN (1.95 g, 30.9 mmol) to afford 1.21 g (98%) of 3,4-dihydro-4-methyl-7-nitro-2H-1,4-benzoxazine, a yellow solid. Data for 3,4-dihydro-4-methyl-7-nitro-2H-1,4-benzoxazine: $R_f$ 0.83 (11.5:1 CH$_2$Cl$_2$:MeOH); $^1$H NMR (400 MHz, CDCl$_3$) δ 7.82 (dd, 1H, J=9.0, 2.6), 7.65 (d, 1H, J=3.4), 6.56 (d, 1H, J=8.9), 4.27 (t, 2H, J=4.6), 3.46 (t, 2H, J=4.5), 3.05 (s, 3H).

General Method 4: Hydrogenation of a 4-alkyl-3,4-dihydro-7-nitro-2H-1,4-benzoxazine. To a solution of a 4-alkyl-3,4-dihydro-7-nitro-2H-1,4-benzoxazine in 1:1 EtOAc:EtOH (13 mL/mmol) was added 10% Pd-C (6% by wt). The flask was flushed and evacuated with $N_2$ (3×), then stirred under an atmosphere of $H_2$ overnight. The reaction mixture was filtered through Celite, washed with EtOAc (2×20 mL/mmol) and concentrated under reduced pressure to give the desired product as a light purple/tan solid, which was purified on silica gel as indicated.

7-Amino-3,4-dihydro-4-methyl-2H-1,4-benzoxazine. (Structure 5 of Scheme I, where $R^6$=H, $R^x$=H). This compound was prepared by General Method 4 from 3,4-dihydro-4-methyl-7-nitro-2H-1,4-benzoxazine (262 mg, 1.35 mmol) and purified by flash chromatography ($CH_2Cl_2$/MeOH, 20:1) to afford 167 mg (75%) of 7-amino-3,4-dihydro-4-methyl-2H-1,4-benzoxazine. Data for 7-amino-3,4-dihydro-4-methyl-2H-1,4-benzoxazine: $R_f$ 0.36 (11.5:1 $CH_2Cl_2$:MeOH) $^1$H NMR (400 MHz, $CDCl_3$) δ 6.55 (d, 1H, J=8.2), 6.25 (d, 1H, J=2.6), 6.22 (dd, 1H, J=7.0, 2.7), 4.28 (t, 2H, J=4.4) 3.32 (br s, 2H), 3.13 (t, 2H, J=4.5), 2.79 (s, 3H).

General Method 5: Condensation of a 7-amino-3,4-dihydro-2H-1,4-benzoxazine with acetoacetates or their corresponding hydrates followed by Knorr reaction mediated by polyphosphoric acid. To a solution of a 7-amino-3,4-dihydro-2H-1,4-benzoxazine of Structure 5 (1.0 equiv) in benzene (10 mL/mmol) under $N_2$ at room temperature was added an acetoacetate derivative (1.2 equiv) and the reaction was heated at reflux for 12–16 hrs, whereupon the mixture was concentrated under reduced pressure. The crude reaction mixture was diluted in polyphosphoric acid (8 mL/mmol) and heated to 100° C. for 12–16 hrs. The resulting mixture was poured over ice and neutralized with 6M NaOH solution to pH 7.0, extracted with $CH_2Cl_2$ (3×30 mL/mmol), washed with pH 7 phosphate buffer (50 mL/mmol) and brine (50 mL/mmol). The organic solution was dried ($MgSO_4$) and concentrated under reduced pressure. Purification by flash chromatography (silica gel, 20:1, $CH_2Cl_2$/MeOH) afforded the desired quinolone as a fluorescent-yellow solid.

1,2,3,6-Tetrahydro-1-methyl-9-(trifluoromethyl)-7H-[1,4]oxazino[3,2-g]quinolin-7-one (Compound 101, Structure 6 of Scheme I, where $R^1$=H, $R^2$=trifluoromethyl, $R^6$=H, $R^x$=H). This compound was prepared by General Method 5 from 7-amino-3,4-dihydro-4-methyl-2H-1,4-benzoxazine (162 mg, 0.98 mmol), and ethyl 4,4,4-trifluoroacetoacetate (0.19 mL, 1.28 mmol) and purified by flash chromatography (19:1 $CH_2Cl_2$:MeOH) to afford 125 mg (44%) of Compound 101. Data for Compound 101: $R_f$ 0.44 (EtOAc); $^1$H NMR (400 MHz, $CDCl_3$) δ 10.65 (br s, 1H), 6.90 (s, 1H), 6.87 (s, 1H), 6.72 (s, 1H), 4.39 (t, 2H, J=4.6), 3.31 (t, 2H, J=4.5), 2.94 (s, 3H).

EXAMPLE 2

1,2,3,6-Tetrahydro-1,6-dimethyl-9-(trifluoromethyl)-7H-[1,4]oxazino [3,2-g]quinolin-7-one (Compound 102, Structure 7 of Scheme I, where $R^1$=H, $R^2$= Trifluoromethyl, $R^6$=H, $R^x$=H)

General Method 6: N-Methylation of a pyridone (compounds of Structure 6) to form a compound of Structure 7. To an oven-dried rb flask containing a pyridone of Structure 6 (1.0 equiv) in THF (5 mL/mmol) was added portionwise sodium hydride (60% dispersion in mineral oil, 1.2 equiv) under $N_2$. After 30 min, iodomethane (1.2 equiv) was added and the mixture was allowed to stir under $N_2$ an additional 8–10 hrs. The reaction mixture was then diluted with pH 7 phosphate buffer (50 mL/mmol), extracted with $CH_2Cl_2$ (3×30 mL) and washed with brine (50 mL/mmol). The organic solution was dried ($MgSO_4$) and concentrated under reduced pressure. Purification by flash chromatography (silica gel, 20:1, $CH_2Cl_2$MeOH) afforded the desired product as a fluorescent-yellow solid.

1,2,3,6-Tetrahydro-1,6-dimethyl-9-(trifluoromethyl)-7H-[1,4]oxazino[3,2-g]quinolin-7-one (Compound 102, Structure 7 of Scheme I, where $R^1$=H, $R^2$=trifluoromethyl, $R^6$=H, $R^x$=H). This compound was prepared by General Method 6 from 3,4-dihydro-4-methyl-6-(trifluoromethyl)-8-pyridono-[5,6-g]-2H-1,4-benzoxazine (23.9 mg, 0.08 mmol), iodomethane (6.3 μL, 0.10 mmol) and sodium hydride (4.0 mg, 0.10 mmol) and purified by flash chromatography (19:1 $CH_2Cl_2$:MeOH) to afford 13.7 mg (55%) of Compound 102. Data for Compound 102: $R_f$ 0.54 (11.5:1 $CH_2Cl_2$:MeOH); $^1$H NMR (400 MHz, $CDCl_3$) δ 6.96 (s, 1H), 6.95 (s, 1H), 6.93 (s, 1H), 4.42 (t, 2H, J=4.4), 3.66 (s, 3H), 3.31 (t, 2H, J=4.6), 2.95 (s, 3H).

EXAMPLE 3

1-Ethyl-1,2,3,6-tetrahydro-9-(trifluoromethyl)-7H-[1,4]oxazino[3,2-g]quinolin-7-one (Compound 103, Structure 6 of Scheme I, where $R^1$=H, $R^2$= Trifluoromethyl, $R^6$=H, $R^x$=$CH_3$)

4-Ethyl-3,4-dihydro-7-nitro-2H-1,4-benzoxazine (Structure 4 of Scheme I, where $R^6$=H, $R^x$=$CH_3$). This compound was prepared by General Method 3 (EXAMPLE 1) from 3,4-dihydro-7-nitro-2H-1,4-benzoxazine (EXAMPLE 1) (1.15 g, 6.39 mmol), acetaldehyde (3.59 mL, 64.2 mmol) and $NaBH_3CN$ (1.95 g, 31 mmol) to afford 984 mg (74%) of 4-ethyl-3,4-dihydro-7-nitro-2H-1,4-benzoxazine, a yellow solid. Data for 4-ethyl-3,4-dihydro-7-nitro-2H-1,4-benzoxazine: $R_f$ 0.85 (11.5:1 $CH_2Cl_2$:MeOH); $^1$H NMR (400 MHz, $CDCl_3$) δ 7.81 (dd, 1H, J=9.6, 2.6), 7.66 (d, 1H, J=2.7), 6.29 (d, 1H, J=9.2), 4.23 (t, 2H, J=4.7), 3.47 (t, 2H, J=4.7), 3.45 (q, 2H, J=7.2), 1.22 (t, 3H, J=7.0).

7-Amino-4-ethyl-3,4-dihydro-2H-1,4-benzoxazine (Structure 5 of Scheme I, where $R^6$=H, $R^x$=$CH_3$). This compound was prepared by General Method 4 (EXAMPLE 1) from 4-ethyl-3,4-dihydro-7-nitro-2H-1,4-benzoxazine (264 mg, 1.3 mmol) and purified by flash chromatography ($CH_2Cl_2$/MeOH, 20:1) to afford 173 mg (77%) of 7-amino-4-ethyl-3,4-dihydro-2H-1,4-benzoxazine. Data for 7-amino-4-ethyl-3,4-dihydro-2H-1,4-benzoxazine: $R_f$ 0.52 (11.5:1 $CH_2Cl_2$:MeOH); $^1$H NMR (400 MHz, $CDCl_3$) δ 6.56 (d, 1H, J=8.1), 6.26–6.22 (m, 2H), 4.23 (t, 2H, J=4.4), 3.29 (br s, 2H), 3.24 (q, 2H, J=7.1), 3.19 (t, 2H, J=4.4), 1.11 (t, 31H, J=7.0).

1-Ethyl-1,2,3,6-tetrahydro-9-(trifluoromethyl)-7H-[1,4] oxazino[3,2-g]quinolin-7-one (Compound 103, Structure 6 of Scheme I, where $R^1$=H, $R^2$=trifluoromethyl, $R^6$=H, $R^x$=$CH_3$). This compound was prepared by General Method 5 (EXAMPLE 1) from 7-amino-4-ethyl-3,4-dihydro-2H-1,4-benzoxazine (170 mg, 0.95. mmol), and ethyl 4,4,4-trifluoroacetoacetate (0.16 mL, 1.14 mmol) and purified by flash chromatography (19:1 $CH_2Cl_2$:MeOH) to afford 100 mg (35%) of Compound 103. Data for Compound 103: $R_f$ 0.21 (11.5:1 $CH_2Cl_2$:MeOH); $^1$H NMR (400 MHz, $CDCl_3$) δ 11.47 (br s, 1H), 6.92 (s, 1H), 6.88 (s, 1H), 6.81 (s, 1H), 4.35 (t, 2H, J=4.5), 3.4 (q, 2H, J=7.1), 3.34 (t, 2H, J=4.5), 1.19 (t, 3H, J=7.1). Anal. Calcd for $C_{14}H_{13}F_3N_2O_2$: C, 56.38; H, 4.39; N, 9.39. Found: C, 56.04; H, 4.32; N, 9.22.

EXAMPLE 4

1-Ethyl-1,2,3,6-tetrahydro-6-methyl-9-(trifluoromethyl)-7H-[1,4]oxazino[3,2-g]quinolin-7-one (Compound 104, Structure I of Scheme I, where $R^1$=H, $R^2$=Trifluoromethyl, $R^6$=H, $R^x$=$CH_3$)

This compound was prepared by General Method 6 (EXAMPLE 2) from Compound 103 (18.5 mg, 0.06 mmol), iodomethane (5.8 μL, 0.09 mmol) and sodium hydride (3.6 mg, 0.09 mmol) and purified by flash chromatography (19:1 $CH_2Cl_2$:MeOH) to afford 13.5 mg (71%) of Compound 104. Data for Compound 104: $R_f$ 0.57 (2:3 EtOAc:hexanes); $^1$H NMR (400 MHz, $CDCl_3$) δ 6.98 (s, 1H), 6.93 (s, H), 6.85 (s, 1H), 4.38 (t, 2H, J=4.5), 3.66 (s, 3H), 3.4 (q, 2H, J=7.1), 3.35 (t, 2H, J=4.6), 1.19 (t, 3H, J=7.1).

EXAMPLE 5

1,2,3,6-Tetrahydro-1-(2,2,2-trifluoroethyl)-9-(trifluoromethyl)-7H-[1,4]oxazino[3,2-g]quinolin-7-one (Compound 105, Structure 6 of Scheme I, where $R^1$=H, $R^2$=Trifluoromethyl, $R^6$=H, $R^x$=$CF_3$)

General Method 7: Reductive amination of a 7-nitro-2H-1,4-benzoxazine in trifluoroacetic acid. To a solution of a 7-nitro-3,4-dihydro-2H-1,4-benzoxazine (1.0 equiv) in trifluoroacetic acid (0.5 mL/mmol) was added an aldehyde or its corresponding hydrate (10 equiv) and the mixture was stirred at rt for 2 h. To this mixture was added portionwise sodium cyanoborohydride (4.8 equiv) and stirred at room temperature overnight. The resulting mixture was poured over ice and neutralized with 6M NaOH solution to pH 7.0, extracted with $CH_2Cl_2$ (3×30 mL/mmol), washed with pH 7 phosphate buffer (50 mL/mmol) and brine (50 mL/mmol). The organic solution was dried ($MgSO_4$) and concentrated under reduced pressure to afford the desired product as a yellow solid.

3,4-Dihydro-7-nitro-4-(2,2,2-trifluoroethyl)-2H-1,4-benzoxazine (Structure 4 of Scheme I, where $R^6$=H, $R^x$=$CF_3$). This compound was prepared by General Method 7 from 3,4-dihydro-7-nitro-2H-1,4-benzoxazine (EXAMPLE 1) (388 mg, 2.1 mmol), 2,2,2-trifluoroacetaldehyde monohydrate (2.51 g, 21.6 mmol) and $NaBH_3CN$ (656 mg, 10.4 mmol) to afford 500 mg (88%) of 3,4-dihydro-7-nitro-4-(2,2,2-trifluoroethyl)-2H-1,4-benzoxazine, a yellow solid. Data for 3,4-dihydro-7-nitro-4-(2,2,2-trifluoroethyl)-2H-1,4-benzoxazine: $R_f$ 0.59 (3:2 EtOAc:hexanes); $^1$H NMR (400 MHz, $CDCl_3$) δ 7.81 (dd, 1H, J=8.8, 2.6), 7.72 (d, 1H, J=2.6), 6.72 (d, 1H, J=9.1), 4.27 (t, 2H, J=4.5), 3.94 (2H, J=8.6), 3.61 (t, 2H, J=4.5).

7-Amino-3,4-dihydro-4-(2,2,2-trifluoroethyl)-2H-1,4-benzoxazine (Structure 5 of Scheme I, where $R^6$=H, $R^x$=$CF_3$). This compound was prepared by General Method 4 (EXAMPLE 1) from 3,4-dihydro-7-nitro-4-(2,2,2-trifluoroethyl)-2H-1,4-benzoxazine (3.12 g, 12 mmol) and purified by flash chromatography ($CH_2Cl_2$/MeOH, 20:1) to afford 2.7 g (98%) of 7-amino-3,4-dihydro-4-(2,2,2-trifluoroethyl)-2H-1,4-benzoxazine. Data for 7-amino-3,4-dihydro-4-(2,2,2-trifluoroethyl)-2H-1,4-benzoxazine: $R_f$ 0.47 (3:2 EtOAc:hexanes); $^1$H NMR(400 MHz, $CDCl_3$) δ 6.56 (d, 1H, J=8.2), 6.30–6.20 (m, 2H), 4.16 (t, 2H, J=4.3), 3.65 (q, 2H, J=9.1), 3.39 (t, 2H, J=4.4), 3.36 (br s, 1H).

1,2,3,6-Tetrahydro-1-(2,2,2-trifluoroethyl)-9-(trifluoromethyl)-7H-[1,4]oxazino[3,2-g]quinolin-7-one (Compound 105, Structure 6 of Scheme I, where $R^1$=H, $R^2$=trifluoromethyl, $R^6$=H, $R^x$=$CF_3$). This compound was prepared by General Method 5 (EXAMPLE 1) from 7-amino-4-(2,2,2-trifluoroethyl)-2H-1,4-benzoxazine (2.7 g, 11.6 mmol), and ethyl 4,4,4-trifluoroacetoacetate (2.04 mL, 14 mmol) and purified by flash chromatography (3:2 EtOAc:hexanes) and recrystallized from MeOH to afford 790 mg (19%) of Compound 105. Data for Compound 105: $R_f$ 0.25 (11.5:1 $CH_2Cl_2$:MeOH); $^1$H NMR (400 MHz, $CDCl_3$) δ 11.95 (br s, 1H), 7.04 (br s, 1H), 6.91 (s, 1H), 6.90 (s, 1H), 4.33 (t, 2H, J=4.5), 3.88 (q, 2H, J=8.9), 3.56 (t, 2H, J=4.5). Anal. Calcd for $C_{14}H_{10}F_6N_2O_2$: C, 47.74; H, 2.86; N, 7.95. Found: C, 47.81; H; 2.80; N, 7.87.

EXAMPLE 6

8-Fluoro-1,2,3,6-tetrahydro-1-(2,2,2-trifluoroethyl)-9-(trifluoromethyl)-7H-[1,4]oxazino[3,2-g]quinolin-7-one (Compound 106, Structure 6 of Scheme I, where $R^1$=F, $R^2$=Trifluoromethyl, $R^6$=H, $R^x$=$CF_3$)

This compound was prepared by General Method 5 (EXAMPLE 1) from 7-amino-3,4-dihydro-4-(2,2,2-trifluoroethyl)-2H-1,4-benzoxazine (EXAMPLE 5) (24 mg, 0.1 mmol), and ethyl 2,4,4,4-tetrafluoro-3,3-dihydroxybutanoate (27 mg, 0.12 mmol) and purified by flash chromatography (1:1 EtOAc:hexanes) to afford 8 mg (21%) of Compound 106. Data for Compound 106: $R_f$ 0.15 (19:1 $CH_2Cl_2$:MeOH); $^1$H NMR (400 MHz, $CDCl_3$) δ 11.38 (br s, 1H), 7.08 (s, 1H), 6.86 (s, 1H), 4.32 (t, 2H, J=4.5), 3.88 (q, 2H, J 8.8), 3.56 (t, 2H, J=4.4).

EXAMPLE 7

8-Chloro-1,2,3,6-tetrahydro-1-(2,2,2-trifluoroethyl)-9-(trifluoromethyl)-7H-[1,4]oxazino[3,2-g]quinolin-7-one (Compound 107, Structure 6 of Scheme I, where $R^1$=Cl, $R^2$=Trifluoromethyl, $R^6$=H, $R^x$=$CF_3$)

This compound was prepared by General Method 5 (EXAMPLE 1) from 7-amino-3,4-dihydro-4-(2,2,2-trifluoroethyl)-2H-1,4-benzoxazine (EXAMPLE 5) (21 mg, 0.1 mmol), and ethyl 2-chloro-4,4,4-trifluoroacetoacetate (23 mg, 0.1 mmol)and purified by reverse phase HPLC (ODS, 75:25 MeOH:water, 3 mL/min) to afford 2 mg (6%) of Compound 107. Data for Compound 107: $R_f$ 0.12 (19:1 $CH_2Cl_2$:MeOH); $^1$H NMR (400 MHz, $CDCl_3$) δ 10.22 (br s, 1H), 7.15 (s, 1H), 6.75 (s, 1H), 4.33 (t, 2H, J=4.5), 3.87 (q, 2H, J=8.7), 3.56 (2H, J=4.4).

EXAMPLE 8

9-(Difluoromethyl)-1,2,3,6-tetrahydro-1-(2,2,2-trifluoroethyl)-7H-[1,4]oxazino[3,2-g]quinolin-7-one (Compound 108, Structure 6 of Scheme I, where $R^1$=H, $R^2$=Difluoromethyl, $R^6$=H, $R^x$=$CF_3$)

This compound was prepared by General Method 5 (EXAMPLE 1) from 7-amino-3,4-dihydro-4-(2,2,2-trifluoroethyl)-2H-1,4-benzoxazine (EXAMPLE 5) (310 mg, 1.3 mmol), and ethyl 4,4-difluoroacetoacetate (243 mg, 1.5 mmol) and purified by flash chromatography (19:1 $CH_2Cl_2$:MeOH) to afford 50 mg (11%) of Compound 108. Data for Compound 108: $R_f$ 0.22 (3:2 EtOAc:hexanes); $^1$H NMR (400 MHz, $CDCl_3$) 10.92 (br s, 1H), 7.06 (s, 1H), 6.82 (s, 1H), 6.72 (t, 1H, J=54.2), 6.71 (s, 1H), 4.32 (t, 2H, J=4.4), 3.85 (q, 2H, J=8.9), 3.54 (t, 2H, J=4.4).

EXAMPLE 9

1,2,3,6-Tetrahydro-6-methyl-1-(2,2,2-trifluoroethyl)-9-(trifluoromethyl)-7H-[1,4]oxazino[3,2-g]quinolin-7-one (Compound 109, Structure 7 of Scheme I, where $R^1$=H, $R^2$=Trifluoromethyl, $R^6$=H, $R^x$=$CF_3$)

This compound was prepared by General Method 6 (EXAMPLE 2) from Compound 105 (EXAMPLE 5) (85.0 mg, 0.24 mmol), iodomethane (18 μL, 0.29 mmol) and sodium hydride (11.6 mg, 0.29 mmol) and purified by flash chromatography (3:2 EtOAc:hexanes) to afford 73 mg (83%) of Compound 109. Data for Compound 109: $R_f$ 0.47

(3:2 EtOAc:hexanes); $^1$H NMR (400 MHz, CDCl$_3$) 7.09 (s, 1H), 6.95 (s, 1H), 6.89 (s, 1H), 4.36 (t, 2H, J=4.4), 3.88 (q, 2H, J=8.9), 3.66 (s, 3H), 3.57 (t, 2H, J=4.4).

EXAMPLE 9A

7-Chloro-2,3-dihydro-1-(2,2,2-trifluoroethyl)-9-(trifluoromethyl)-1H-[1,4]oxazino[3,2-g]quinoline (Compound 109A, Structure 7A of Scheme I, where $R^1$=H, $R^2$=Trifluoromethyl, $R^6$=H, $R^x$=CF$_3$, $R^A$=Cl)

A solution of Compound 105 (EXAMPLE 5) (25 mg, 0.07 mmol) in 3 mL POCl$_3$ was heated at 80° C. for 2 h. The reaction was quenched with NaHCO$_3$ (sat'd) in ice and neutralized to pH=7. The mixture was extracted with CH$_2$Cl$_2$, and the organic layers were washed with brine, dried over MgSO4, filtered, and concentrated. Flash chromatography (95:5 CH$_2$Cl$_2$:MeOH) afforded 20 mg (77%) of Compound 109A, a yellow solid. Data for Compound 109A: $^1$H NMR (400 MHz, CDCl$_3$) 7.48 (s, 1H), 7.46 (s, 1H), 7.16 (s, 1H), 4.38 (t, 2H, J=4.6), 4.00 (q, 2H, J=8.8), 3.66 (t, 2F1, J=4.4).

EXAMPLE 10

1,2,3,6-Tetrahydro-1-(2,2,2-trifluoroethyl)-9-(trifluoromethyl)-7H-[1,4]oxazino[3,2-g]quinolin-7-thione (Compound 110, Structure 8 of Scheme I, where $R^1$=H, $R^2$=Trifluoromethyl, $R^6$=H, $R^x$=CF$_3$)

General Method 8: Conversion of a pyridone to a thiopyridone. To a solution of a pyridone of Structure 6 (1.0 equiv) in benzene (0.6 mL/mmol) was added Lawesson's reagent (1.0 equiv) and heated to 60° C. for 12–16 hours. The reaction mixture was allowed to cool to room temperature, partitioned with H$_2$O/ether (200 mL/100 mL), extracted with ether (2×30 mL), and washed with brine (50 mL/mmol). The organic solution was dried (MgSO$_4$) and concentrated under reduced pressure to give the desired product as an orange solid, which was purified on silica gel as indicated.

1,2,3,6-Tetrahydro-1-(2,2,2-trifluoroethyl)-9-(trifluoromethyl)-7H-[1,4]oxazino[3,2-g]quinolin-7-thione (Compound 110, Structure 8 of Scheme I, where $R^1$=H, $R^2$=Trifluoromethyl, $R^6$=H, $R^x$=CF$_3$). This compound was prepared by General Method 8 from Compound 105 (EXAMPLE 5) (50.0 mg, 0.15 mmol) and Lawesson's reagent (57.0 mg, 0.15 mmol) and purified by flash chromatography (19:1 CH$_2$Cl$_2$:MeOH) to afford 12 mg (23%) of Compound 110. Data for Compound 110: $^1$H NMR (400 MHz, CDCl$_3$) 11.47 (br s, 1H), 7.04 (s, 2H), 6.91 (s, 1H), 4.35 (t, 2H, J=4.6), 3.97 (q, 2H, J=8.8), 3.63 (t, 2H, J=4.6).

EXAMPLE 11

1,2,3,6-Tetrahydro-1-propyl-9-(trifluoromethyl)-7H-[1,4]oxazino[3,2-g]quinolin-7-one (Compound 111, Structure 6 of Scheme I, where $R^1$=H, $R^2$= Trifluoromethyl, $R^6$=H, $R^x$=CH$_3$CH$_2$)

7-Nitro-4-propyl-2H-1,4-benzoxazine (Structure 4 of Scheme I, where $R^6$=H, $R^x$=CH$_3$CH$_2$). This compound was prepared by General Method 3 (EXAMPLE 1) from 3,4-dihydro-7-nitro-2H-1,4-benzoxazine (EXAMPLE 1) (530 mg, 2.9 mmol), propionaldehyde (1.61 g, 28 mmol) and NaBH$_3$CN (872 mg, 14 mmol) to afford 450 mg (69%) of 3,4-dihydro-7-nitro-4-propyl-2H-1,4-benzoxazine, an orange oil. Data for 3,4-dihydro-7-nitro-4-propyl-2H-1,4-benzoxazine: R$_f$ 0.57 (2:1 EtOAc:hexanes); $^1$H NMR (400 MHz, CDCl$_3$) δ 7.80 (dd, 1H, J=9.1, 2.6), 7.66 (d, 1H, J=2.6), 6.56 (d, 1H, J=9.0), 4.22 (t, 2H, J=4.5), 3.49 (t, 2H, J=4.5), 3.33 (t, 2H, J=7.5), 1.67 (sext, 2H, J=7.4), 0.98 (t, 3H, J=7.4).

7-Amino-3,4-dihydro-4-propyl-2H-1,4-benzoxazine (Structure 5 of Scheme I, where $R^6$=H, $R^x$=CH$_3$CH$_2$). This compound was prepared by General Method 4 (EXAMPLE 1) from 3,4-dihydro-7-nitro-4-propyl-2H-1,4-benzoxazine (50 mg, 0.2 mmol) and purified by flash chromatography (CH$_2$Cl$_2$/MeOH, 20:1) to afford 36 mg (84%) of 7-amino-3,4-dihydro-4-propyl-2H-1,4-benzoxazine. Data for 7-amino-3,4-dihydro-4-propyl-2H-1,4-benzoxazine: R$_f$ 0.43 (2:1 EtOAc:hexanes); $^1$H NMR (400 MHz, CDCl$_3$) δ 6.53 (d, 1H. J=8.9), 6.25–6.20 (m, 2H), 4.21 (t, 2H, J=4.4), 3.28 (br s, 2H), 3.21 (t, 2H, J=4.4), 3.08 (t, 2H, J=7.5), 1.60 (sext, 2H, J=7.4), 0.94 (t, 3H, J=7.4).

1,2,3,6-Tetrahydro-1-propyl-9-(trifluoromethyl)-7H-[1,4]oxazino[3,2-g]quinolin-7-one (Compound 111, Structure 6 of Scheme I, where $R^1$=H, $R^2$=Trifluoromethyl, $R^6$=H, $R^x$=CH$_3$CH$_2$). This compound was prepared by General Method 5 (EXAMPLE 1) from 7-amino-3,4-dihydro-4-propyl-2H-1,4-benzoxazine (395 mg, 2.0 mmol), and ethyl 4,4,4-trifluoroacetoacetate (0.36 mL, 2.5 mmol) and purified by flash chromatography (3:2 EtOAc:hexanes) and recrystallized from MeOH to afford 100 mg (16%) of Compound 111. Data for Compound 111: R$_f$ 0.24 (3:2 EtOAc:hexanes); $^1$H NMR (400 MHz, CDCl$_3$) 11.79 (br s, 1H), 6.88 (s, 1H), 6.87 (s, 1H), 6.83 (s, 1H), 4.32 (t, 2H, J=4.5), 3.37 (t, 2H, J=4.5), 3.26 (t, 2H, J=7.4), 1.66 (sext, 2H, J=7.4), 0.99 (t, 3H, J=7.4).

EXAMPLE 12

1,2,3,6-Tetrahydro-1-isobutyl-9-(trifluoromethyl)-7H-[1,4]oxazino[3,2-g]quinolin-7-one (Compound 112, Structure 6 of Scheme I, where $R^1$=H, $R^2$= Trifluoromethyl, $R^6$=H, $R^x$=(CH$_3$)$_2$CH)

3,4-Dihydro-4-isobutyl-7-nitro-2H-1,4-benzoxazine (Structure 4 of Scheme I, where $R^6$=H, $R^x$=(CH$_3$)$_2$CH). This compound was prepared by General Method 3 (EXAMPLE 1) from 3,4-dihydro-7-nitro-2H-1,4-benzoxazine (EXAMPLE 1) (550 mg, 3.0 mmol), isobutyraldehyde (1.65 g, 22.8 mmol) and NaBH$_3$CN (959 mg, 15 mmol) to afford 713 mg (99%) of 3,4-dihydro-4-isobutyl-7-nitro-2H-1,4-benzoxazine, an yellow solid. Data for 3,4-dihydro-4-isobutyl-7-nitro-2H-1,4-benzoxazine: R$_f$ 0.75 (3:2 EtOAc:hexanes); $^1$H NMR (400 MHz, CDCl$_3$) δ 7.78 (dd, 1H, J=9.0, 2.6), 7.66 (d, 1H, J=2.6), 6.55 (d, 1H, J=9.2), 4.21 (t, 2H, J=4.5), 3.52 (t, 2H, J=4.6), 3.16 (d, 2H, J=7.4), 3.12 (hept, 1H, J=6.9), 0.97 (d, 6H, J=6.7).

7-Amino-3,4-dihydro-4-isobutyl-2H-1,4-benzoxazine (Structure 5 of Scheme I, where $R^6$=H, $R^x$=(CH$_3$)$_2$CH). This compound was prepared by General Method 4 (EXAMPLE 1) from 3,4-dihydro-4-isobutyl-7-nitro-2H-1,4-benzoxazine (712 mg, 3.0 mmol) and purified by flash chromatography (CH$_2$Cl$_2$/MeOH, 20:1) to afford 621 mg (99%) of 7-amino-4-isobutyl-2H-1,4-benzoxazine. Data for 7-amino-3,4-dihydro-4-isobutyl-2H-1,4-benzoxazine: R$_f$ 0.43 (3:2 EtOAc:hexanes); $^1$H NMR (400 MHz, CDCl$_3$) δ 6.49 (d, 1H, J=9.1), 6.23 (m, 2H), 4.20 (t, 2H, J=4.4), 3.28 (br s, 2H), 3.23 (t, 2H, J=4.4), 2.85 (d, 2H, J=7.2), 2.04–1.92 (m, 1H), 0.94 (d, 6H, J=6.5).

1,2,3,6-Tetrahydro-1-isobutyl-9-(trifluoromethyl)-7H-[1,4]oxazino[3,2-g]quinolin-7-one (Compound 112, Structure 6 of Scheme I, where $R^1$=H, $R^2$=trifluoromethyl, $R^6$=H, R$^x$=(CH$^3$)$_2$CH). This compound was prepared by General Method 5 (EXAMPLE 1) from 7-amino-3,4-dihydro-4-isobutyl-2H-1,4-benzoxazine (620 mg, 3.0 mmol), and ethyl 4,4,4-trifluoroacetoacetate (0.527 mL, 3.6 mmol) and purified by flash chromatography (3:2 EtOAc:hexanes) and recrystallized from MeOH to afford 241 mg (25%) of Compound 112. Data for Compound 112: R$_f$ 0.2 (3:2 EtOAc:hexanes); $^1$H NMR (400 MHz, CDCl$_3$) δ 10.62 (br s, 1H), 6.87 (s, 2H), 6.74 (s, 1H), 4.31 (t, 2H, J=4.5), 3.41 (t, 2H, J=4.5), 3.05 (d, 2H, J=7.0), 2.05–1.95 (m, 1H), 0.98 (d, 6H, J=6.5).

EXAMPLE 13

1,2,3,6-Tetrahydro-1-isobutyl-6-methyl-9-(trifluoromethyl)-7H-[1,4]oxazino[3,2-g]quinolin-7-one (Compound 113, Structure 7 of Scheme I, where R$^1$=H, R$^2$=Trifluoromethyl, R$^6$=H, R$^x$=(CH$_3$)$_2$CH)

This compound was prepared by General Method 6 (EXAMPLE 2) from Compound 112 (10.0 mg, 0.03 mmol), iodomethane (3.0 μL, 0.03 mmol) and sodium hydride (1.5 mg, 0.03 mmol) and purified by flash chromatography (19:1 CH$_2$Cl$_2$:MeOH) to afford 8.3 mg (80%) of Compound 113. Data for Compound 113: $^1$H NMR (400 MHz, CDCl$_3$) δ 6.93 (s, 2H), 6.85 (s, 1H), 4.34 (t, 2H, J=4.5), 3.65 (s, 3H), 3.43 (t, 2H, J=4.5), 3.06 (d, 2H, J=7.2), 2.09 (m, 1H), 0.99 (d, 6H, J=6.6).

EXAMPLE 14

(±)-1,2,3,6-Tetrahydro-3-methyl-1-(2,2,2-trifluoroethyl)-9-(trifluoromethyl)-7H-[1,4]oxazino[3,2-g]quinolin-7-one (Compound 114, Structure 6 of Scheme I, where R$^1$=H, R$^2$=Trifluoromethyl, R$^6$=Me, R$^x$=CF$_3$)

(±)-2-Methyl-7-nitro-2H-1,4-benzoxazin-3(4H)-one (Structure 2 of Scheme I, where R$^6$=Me). This compound was prepared by General Method 1 (EXAMPLE 1) from 2-amino-5-nitrophenol (3.0 g, 20 mmol), NaHCO$_3$ (3.9 g, 46 mmol), and 2-chloropropionyl chloride (2.2 mL, 22 mmol) to afford 3.1 g (77%) of (±)-2-methyl-7-nitro-2H-1,4-benzoxazin-3(4H)-one. Data for (±)-2-methyl-7-nitro-2H-1,4-benzoxazin-3(4H)-one: R$_f$ 0.45 (11.5:1 CH$_2$Cl$_2$:MeOH); $^1$H NMR (400 MHz, DMSO) δ 11.28 (br s, 1H), 7.92 (dd, 1H, J=8.6, 2.2), 7.77 (d, 1H, J=2.6), 7.07 (d, 1H, J=8.7), 4.85 (q, 1H, J=6.7), 1.46 (d, 3H, J=6.8).

(±)-3,4-Dihydro-2-methyl-7-nitro-2H-1,4-benzoxazine (Structure 3 of Scheme I, where R$^6$=Me). This compound was prepared by General Method 2 (EXAMPLE 1) from (±)-2-methyl-7-nitro-2H-1,4-benzoxazin-3(4H)-one (1.8 g, 8.6 mmol) and borane dimethylsulfide (10.0–10.2 M in THF, 3.5 mL, 35 mmol) and purified on silica gel (20:1 CH$_2$Cl$_2$:MeOH) to afford 1.57 g (94%) of 3,4-dihydro-2-methyl-7-nitro-2H-1,4-benzoxazine, an orange solid. Data for 3,4-dihydro-2-methyl-7-nitro-2H-1,4-benzoxazine: R$_f$ 0.75 (11.5:1 CH$_2$Cl$_2$:MeOH); $^1$H NMR (400 MHz, CDCl$_3$) δ 7.73 (dd, 1H, J=8.7, 2.6), 7.69 (d, 1H, J=2.2), 6.52 (d, 1H, 8.7), 4.56 (br s, 1H), 4.20 (m, 1H), 3.47 (ddd, 1H, J=12.1, 3.8, 2.7), 3.21 (ddd, 1H, J=12.0, 8.1, 1.2), 1.40 (d, 3H, J=6.1).

(±)-3,4-Dihydro-2-methyl-7-nitro-4-(2,2,2-trifluoroethyl)-2H-1,4-benzoxazine (Structure 4 of Scheme I, where R$^6$=Me, R$^x$=CF$_3$). This compound was prepared by General Method 7 (EXAMPLE 5) from (±)-3,4-dihydro-2-methyl-7-nitro-2H-1,4-benzoxazine (400 mg, 2.0 mmol), 2,2,2-trifluoroacetaldehyde monohydrate (2.4 g, 20.6 mmol) and NaBH$_3$CN (628 mg, 10.0 mmol) to afford 550 mg (96%) of (±)-3,4-dihydro-2-methyl-7-nitro-4-(2,2,2-trifluoroethyl)-2H-1,4-benzoxazine, a yellow solid. Data for (±)-3,4-dihydro-2-methyl-7-nitro-4-(2,2,2-trifluoroethyl)-2H-1,4-benzoxazine: R$_f$ 0.85 (3:2 EtOAc:hexanes); $^1$H NMR (400 MHz, CDCl$_3$) δ 7.81 (dd, 1H, J=9.2, 2.6), 7.72 (d, 1H, J=2.6), 6.72 (d, 1H, J=9.1), 4.23 (m, 1H), 4.23–3.82 (m, 2H), 3.47 (dd, 1H, J=12.1, 2.6), 3.37 (dd, 1H, J=12.2, 8.2), 1.41 (d, 3H, J=6.1).

(±)-7-Amino-3,4-dihydro-2-methyl-4-(2,2,2-trifluoroethyl)-2H-1,4-benzoxazine (Structure 5 of Scheme I, where R$^6$=Me, R$^x$=CF$_3$). This compound was prepared by General Method 4 (EXAMPLE 1) from (±)-3,4-dihydro-2-methyl-7-nitro-4-(2,2,2-trifluoroethyl)-2H-1,4-benzoxazine (394 mg, 1.4 mmol) and purified by flash chromatography (CH$_2$Cl$_2$/MeOH, 20:1) to afford 345 mg (98%) of (±)-7-amino-3,4-dihydro-2-methyl-4-(2,2,2-trifluoroethyl)-2H-1,4-benzoxazine. Data for (±)-7-amino-3,4-dihydro-2-methyl-4-(2,2,2-trifluoroethyl)-2H-1,4-benzoxazine: R$_f$ 0.60 (11.5:1 CH$_2$Cl$_2$:MeOH); $^1$H NMR (400 MHz, CDCl$_3$) δ 6.57 (d, 1H, J=9.2), 6.27–6.22 (m, 2H), 6.24 (s, 1H), 4.18 (m, 1H), 3.75–3.62 (m, 3H), 3.27 (dd, 1H, J=12.0, 9.8), 3.10 (dd, 1H, J=12.0, 8.5), 1.34 (d, 3H, J=6.3).

(±)-1,2,3,6-Tetrahydro-3-methyl-1-(2,2,2-trifluoroethyl)-9-(trifluoromethyl)-7H-[1,4]oxazino[3,2-g]quinolin-7-one (Compound 114, Structure 6 of Scheme I, where R$^1$=H, R$^2$=trifluoromethyl, R$^6$=Me, R$^x$=CF$_3$). This compound was prepared by General Method 5 (EXAMPLE 1) from (±)-7-amino-3,4-dihydro-2-methyl-4-(2,2,2-trifluoroethyl)-2H-1,4-benzoxazine (345 mg, 1.4 mmol), and ethyl 4,4,4-trifluoroacetoacetate (0.24 mL, 1.6 mmol) and purified by flash chromatography (19:1 CH$_2$Cl$_2$:MeOH) to afford 52 mg (34%) of Compound 114. Data for Compound 114: R$_f$ 0.26 (11.5:1 CH$_2$Cl$_2$:MeOH); $^1$H NMR (400 MHz, CDCl$_3$) δ 10.84 (br s, 1H), 7.05 (s, 1H), 6.90 (s, 1H), 6.82 (s, 1H), 4.35 (m, 1H), 3.91 (m, 1H), 3.83 (m, 1H), 3.44 (dd, 1H, J=12.1, 2.0), 3.21 (dd, 1H, J=11.7, 7.8), 1.42 (d, 3H, J=6.2). Anal. Calcd for C$_{15}$H$_{12}$F$_6$N$_2$O$_2$: C, 49.19; H, 3.30; N, 7.65. Found: C, 49.19; H, 3.23; N, 7.54.

EXAMPLE 15

(−)-1,2,3,6-Tetrahydro-3-methyl-1-(2,2,2-trifluoroethyl)-9-(trifluoromethyl)-7H-[1,4]oxazino[3,2-g]quinolin-7-one (Compound 115, Structure 6 of Scheme I, where R$^1$=H, R$^2$=Trifluoromethyl, R$^6$=Me, R$^x$=CF$_3$) and (±)-1,2,3,6-Tetrahydro-3-methyl-1-(2,2,2-trifluoroethyl)-9-(trifluoromethyl)-7H-[1,4]oxazino[3,2-g]quinolin-7-one (Compound 116, Structure 6 of Scheme I, where R$^1$=H, R$^2$=Trifluoromethyl, R$^6$=Me, R$^x$=CF$_3$)

General Method 9: Resolution of Compounds of Structure 6, 18, or 23 to their corresponding enantiomers via chiral HPLC. A preparative Chiralpak AD column (10 μm particle size, 20×250 mm OR 10×250 mm, Daicel Chemical Industries, Ltd.) on a Beckman Gold HPLC was equilibrated with an eluent of hexanes:isopropanol at a flow rate of 4.5–5 mL/min. A solution of the racemic compound in MeOH, EtOH, or acetone was prepared and injections were monitored to insure that baseline separation is achieved. Compound elution was monitored by absorbance detection at 254 nM. Sequential injections were performed until the specified amounts were obtained. The solvents of the separated enantiomers were removed in vacuo. Purity of the collected fractions were verified by injection of analytical amounts and in each case only a single enantiomer was detected.

(−)-1,2,3,6-Tetrahydro-3-methyl-1-(2,2,2-trifluoroethyl)-9-(trifluoromethyl)-7H-[1,4]oxazino[3,2-g]quinolin-7-one (Compound 115, Structure 6 of Scheme I, where $R^1$=H, $R^2$=trifluoromethyl, $R^6$=Me, $R^x$=CF$_3$) and (+)-1,2,3,6-tetrahydro-3-methyl-1-(2,2,2-trifluoroethyl)-9-(trifluoromethyl)-7H-[1,4]oxazino[3,2-g]quinolin-7-one (Compound 116, Structure 6 of Scheme I, where $R^1$=H, $R^2$=trifluoromethyl, $R^6$=Me, $R^x$=CF$_3$).

This compound was prepared according to General Method 9 from Compound 114 (10 mg, 0.03 mmol) on a semiprep Chiralpak AD column (10×250 mm) and eluted with hexanes/isopropanol (95:5), to afford 3 mg of Compound 115, a yellow solid, and 2.0 mg of Compound 116, a yellow solid. Data for Compound 115: HPLC (Chiralpak AD, 4×250 mm, 95:5 hexanes:isopropanol, 0.8 mL/min) $t_R$ 16.9 min; $[\alpha]_D$=−78 (c=0.18). Data for Compound 116: HPLC (Chiralpak AD, 4×250 mm, 95:5 hexanes:isopropanol, 0.8 mL/min) $t_R$ 20.0 min; $[\alpha]_D$=+70 (c=0.12).

EXAMPLE 16

(±)-1,2,3,6-Tetrahydro-1,3-dimethyl-9-(trifluoromethyl)-7H-[1,4]oxazino[3,2-g]quinolin-7-one (Compound 117, Structure 6 of Scheme I, where $R^1$=H, $R^2$=Trifluoromethyl, $R^6$=Me, $R^x$=H)

(±)-3,4-Dihydro-2,4-dimethyl-7-nitro-2H-1,4-benzoxazine (Structure 4 of Scheme I, where $R^6$=Me, $R^x$=H). This compound was prepared from General Method 3 (EXAMPLE 1) from (±)-3,4-dihydro-2-methyl-7-nitro-2H-1,4-benzoxazine (150 mg, 0.77 mmol), paraformaldehyde (233 mg, 7.8 mmol) and NaBH$_3$CN (235 mg, 3.7 mmol) to afford 160 mg (99%) of (±)-3,4-dihydro-2,4-dimethyl-7-nitro-2H-1,4-benzoxazine. Data for (±)-3,4-dihydro-2,4-dimethyl-7-nitro-2H-1,4-benzoxazine: $R_f$ 0.77 (3:2 EtOAc:hexanes); $^1$H NMR (400 MHz, CDCl$_3$) δ 7.81 (dd, 1H, J=9.1, 2.5), 7.66 (d, 1H, J=2.5), 6.55 (d, 1H, J=8.9), 4.26–4.23 (m, 1H), 3.32 (dd, 1H, J=12.1, 2.7), 3.22 (dd, 1H, J=12.0, 8.2), 3.03 (s, 3H), 1.39 (d, 3H, J=6.5).

(±)-7-Amino-3,4-dihydro-2,4-dimethyl-2H-1,4-benzoxazine (Structure 5 of Scheme I, where $R^6$=Me, $R^x$=H). This compound was prepared from General Method 4 EXAMPLE 1) from (±)-3,4-dihydro-2,4-dimethyl-7-nitro-2H-1,4-benzoxazine (160 mg, 0.77 mmol) and purified by flash chromatography (CH$_2$Cl$_2$/MeOH, 20:1) to afford 134 mg (97%) of (±)-7-amino-3,4-dihydro-2,4-dimethyl-2H-1,4-benzoxazine. Data for (±)-7-amino-3,4-dihydro-2,4-dimethyl-2H-1,4-benzoxazine: $R_f$ 0.35 (11.5:1 CH$_2$Cl$_2$:MeOH); $^1$H NMR (400 MHz, CDCl$_3$) δ 6.54 (d, 1H, J=8.0), 6.25–6.20 (m, 2H), 4.36–4.33 (m, 1H), 3.31 (br s, 2H), 3.08 (dd, 1H, J=11.4, 2.3), 2.82 (dd, 1H, 11.4, 8.2), 2.78 (s, 3H), 1.33 (d, 3H, J=6.2).

(±)-1,2,3,6-Tetrahydro-1,3-dimethyl-9-(trifluoromethyl)-7H-[1,4]oxazino[3,2-g]quinolin-7-one (Compound 117, Structure 6 of Scheme I, where $R^1$=H, $R^2$=trifluoromethyl, $R^6$=Me, $R^x$=H). This compound was prepared by General Method 5 (EXAMPLE 1) from (±)-7-amino-3,4-dihydro-2,4-dimethyl-2H-1,4-benzoxazine (75 mg, 0.42 mmol), and ethyl 4,4,4-trifluoroacetoacetate (0.07 mL, 0.48 mmol) and purified by flash chromatography (19:1 CH$_2$Cl$_2$:MeOH) to afford 50 mg (40%) of Compound 117. Data for Compound 117: $R_f$ 0.42 (11.5:1 CH$_2$Cl$_2$:MeOH); $^1$H NMR (400 MHz, CDCl$_3$) δ 11.17 (br s, 1H), 6.88 (s, 1H), 6.87 (s, 1H), 6.78 (s, 1H), 4.45 (m, 1H), 3.24 (dd, 1H, J=11.7, 2.5), 3.02 (dd, 1H, J=11.5, 8.2), 2.93 (s, 3H), 1.40 (d, 3H, J=6.5).

EXAMPLE 17

(±)-3-Ethyl-1,2,3,6-tetrahydro-1-(2,2,2-trifluoroethyl)-9-(trifluoromethyl)-7H-[1,4]oxazino [3,2-g]quinolin-7-one (Compound 118, Structure 6 of Scheme I, where $R^1$=H, $R^2$=Trifluoromethyl, $R^6$=Et, $R^x$=CF$_3$)

(±)-2-Ethyl-7-nitro-2H-1,4-benzoxazin-3(4H)-one (Structure 2 of Scheme I, where $R^6$=Et). This compound was prepared by General Method 1 (EXAMPLE 1) from 2-amino-5-nitrophenol (3.0 g, 19.5 mmol), NaHCO$_3$ (3.9 g, 46.5 mmol), and 2-chlorobutyryl chloride (3.1 g, 22.4 mmol) to afford 1.2 g (28%) of (±)-2-ethyl-7-nitro-2H-1,4-benzoxazin-3(4H)-one. Data for (±)-2-ethyl-7-nitro-2H-1,4-benzoxazin-3(4H)-one: $R_f$ 0.48 (19:1 CH$_2$Cl$_2$:MeOH); $^1$H NMR (400 MHz, DMSO-d$_6$) δ 11.29 (br s, 1H), 7.91 (dd, 1H, J=8.7, 2.6), 7.79 (d, 1H, J=2.4), 7.06 (d, 1H, J=8.7), 4.71–4.68 (m, 1H), 1.88–1.76 (m, 2H), 1.00 (t, 3H, J=7.2).

(±)-2-Ethyl-3,4-dihydro-7-nitro-2H-1,4-benzoxazine (Structure 3 of Scheme I, where $R^6$=Et). This compound was prepared by General Method 2 (EXAMPLE 1) from (±)-2-ethyl-7-nitro-2H-1,4-benzoxazin-3(4H)-one (1.2 g, 5.4 mmol) and borane dimethylsulfide (10.0–10.2 M in THF, 2.2 mL, 22 mmol) and purified on silica gel (1.8:1 hexanes:EtOAc) to afford 723 mg (65%) of (±)-2-ethyl-3,4-dihydro-7-nitro-2H-1,4-benzoxazine, an orange solid. Data for (±)-2-ethyl-3,4-dihydro-7-nitro-2H- 1,4-benzoxazine: $R_f$ 0.85 (11.5:1 CH$_2$Cl$_2$:MeOH); $^1$H NMR (400 MHz, CDCl$_3$) δ 7.73 (dd, 1H, J=8.5, 2.4), 7.71 (d, 1H, J=2.3), 6.50 (d, 1H, J=8.6), 4.53 (br s, 1H), 3.99–3.94 (m, 1H), 3.48 (dd, 1H, J=8.9, 3.0), 3.23 (dd, 1H, J=10.9, 8.0), 1.75–1.61 (m, 2H), 1.07 (t, 3H, J=7.5).

(±)-2-Ethyl-3,4-dihydro-7-nitro-4-(2,2,2-trifluoroethyl)-2H-1,4-benzoxazine (Structure 4 of Scheme I, where $R^6$=Et, $R^x$=CF$_3$). This compound was prepared by General Method 7 (EXAMPLE 5) from (±)-2-ethyl-3,4-dihydro-7-nitro-2H-1,4-benzoxazine (250 mg, 1.2 mmol), 2,2,2-trifluoroacetaldehyde monohydrate (1.4 g, 12 mmol) and NaBH$_3$CN (366 mg, 5.8 mmol) to afford 346 mg (99%) of (±)-2-ethyl-3,4-dihydro-7-nitro-4-(2,2,2-trifluoroethyl)-2H-1,4-benzoxazine. Data for (±)-2-ethyl-3,4-dihydro-7-nitro-4-(2,2,2-trifluoroethyl)-2H-1,4-benzoxazine: $R_f$ 0.75 (3:2 EtOAc:hexanes); $^1$H NMR (400 MHz, CDCl$_3$) δ 7.80 (dd, 1H, J=8.9, 2.6), 7.73 (d, 1H, J=2.5), 6.70 (d, 1H, J=9.0), 4.03–3.81 (m, 3H), 3.48 (dd, 1H, J=12.1, 2.6), 3.39 (dd, 1H, J=12.1, 8.0), 1.80–1.62 (m, 2H), 1.08 (t, 3H, J=7.4).

(±)-7-Amino-2-ethyl-3,4-dihydro-4-(2,2,2-trifluoroethyl)-2H-1,4-benzoxazine (Structure 5 of Scheme I, where $R^6$=Et, $R^x$=CF$_3$). This compound was prepared by General Method 4 (EXAMPLE 1) from (±)-2-ethyl-3,4-dihydro-7-nitro-4-(2,2,2-trifluoroethyl)-2H-1,4-benzoxazine (170 mg, 0.6 mmol) and purified by flash chromatography (CH$_2$Cl$_2$/MeOH, 20:1) to afford 151 mg (99%) of (±)-7-amino-2-ethyl-3,4-dihydro-4-(2,2,2-trifluoroethyl)-2H-1,4-benzoxazine. Data for (±)-7-amino-2-ethyl-3,4-dihydro-4-(2,2,2-trifluoroethyl)-2H-1,4-benzoxazine: $R_f$ 0.62 (3:2 EtOAc:hexanes); $^1$H NMR (400 MHz, CDCl$_3$) δ 6.56 (d, 1H, J=8.0), 6.25–6.20 (m, 2H), 3.93 (m, 1H), 3.70–3.64 (m, 3H), 3.43 (br s, 1H), 3.31 (m, 1H), 3.12 (dd, 1H, J=11.9, 8.1), 1.74–1.59 (m, 2H), 1.04 (t, 3H, J=7.5).

(±)-3-Ethyl-1,2,3,6-tetrahydro-1-(2,2,2-trifluoroethyl)-9-(trifluoromethyl)-7H-[1,4]oxazino[3,2-g]quinolin-7-one (Compound 118, Structure 6 of Scheme I, where $R^1$=H, $R^2$=trifluoromethyl, $R^6$=Et, $R^x$=CF$_3$). This compound was prepared by General Method 5 (EXAMPLE 1) from (±)-7-amino-2-ethyl-3,4-dihydro-4-(2,2,2-trifluoroethyl)-2H-1,4-benzoxazine (100 mg, 0.38 mmol), and ethyl 4,4,4-trifluoroacetoacetate (0.81 mg, 0.44 mmol) and purified by flash chromatography (19:1 CH$_2$Cl$_2$:MeOH) to afford 75 mg (51%) of Compound 114. Data for Compound 114: $R_f$ 0.18 (19:1 CH$_2$Cl$_2$:MeOH); $^1$H NMR (400 MHz, CDCl$_3$) δ 12.05 (br s, 1H), 7.03 (s, 1H), 6.95 (s, 1H), 6.92 (s, 1H), 4.15–4.05 (m, 1H), 3.98–3.88 (m, 1H), 3.88–3.75 (m, 1H), 3.44 (dd, 1H, J=11.8, 2.5), 3.32 (dd, 1H, J=11.9, 8.1), 1.76 (m, 1H), 1.68 (m, 1H), 1.09 (t, 3H, J=7.6).

EXAMPLE 18

(±)-3-Ethyl-1,2,3,6-tetrahydro-1-methyl-9-(trifluoromethyl)-7H-[1,4]oxazino[3,2-g]quinolin-7-one (Compound 119, Structure 6 of Scheme I, where $R^1$=H, $R^2$=Trifluoromethyl, $R^6$=Et, $R^x$=H)

(±)-2-Ethyl-3,4-dihydro-4-methyl-7-nitro-2H-1,4-benzoxazine (Structure 4 of Scheme I, where $R^6$=Et, $R^x$=H). This compound was prepared by General Method 3 (EXAMPLE 1) from 2-ethyl-3,4-dihydro-7-nitro-2H-1,4-benzoxazine (EXAMPLE 17) (120 mg, 0.57 mmol), paraformaldehyde (174 mg, 5.8 mmol) and $NaBH_3CN$ (176 mg, 2.8 mmol) to afford 127 mg (99%) of 2-ethyl-3,4-dihydro-4-methyl-7-nitro-2H-1,4-benzoxazine. Data for 2-ethyl-3,4-dihydro-4-methyl-7-nitro-2H-1,4-benzoxazine: $R_f$ 0.89 (11.5:1 $CH_2Cl_2$:MeOH); $^1$H NMR (400 MHz, $CDCl_3$) δ 7.81 (dd, 1H, J=9.0, 2.5), 7.67 (d, 1H, J=2.5), 6.54 (d, 1H, J=9.0), 4.01 (m, 1H), 3.34 (dd, 1H, J=12.0, 2.7), 3.23 (dd, 1H, J=12.0, 8.1), 3.03 (s, 3H), 1.79–1.72 (m, 1H), 1.67–1.60 (m, 1H), 1.07 (t, 3H, J=7.5).

(±)-7-Amino-2-ethyl-3,4-dihydro-4-methyl-2H-1,4-benzoxazine (Structure 4 of Scheme I, where $R^6$=Et, $R^x$=H). This compound was prepared by General Method 4 (EXAMPLE 1) from (±)-2-ethyl-3,4-dihydro-4-methyl-7-nitro-2H-1,4-benzoxazine (130 mg, 0.6 mmol) and purified by flash chromatography ($CH_2Cl_2$/MeOH, 19:1) to afford 80 mg (71%) of (±)-7-amino-2-ethyl-3,4-dihydro-4-methyl-2H-1,4-benzoxazine. Data for (±)-7-amino-2-ethyl-3,4-dihydro-4-methyl-2H-1,4-benzoxazine: $R_f$ 0.5 (19:1 $CH_2Cl_2$/MeOH); $^1$H NMR (400 MHz, $CDCl_3$) δ 6.53 (dd, 1H, J=9.1, 2.7), 6.25–6.20 (m, 2H), 4.11 (m, 1H), 3.10 (dd, 1H, J=11.4, 2.1), 2.84 (dd, 1H, J=11.3, 8.1), 2.78 (s, 3H), 1.75–1.70 (band, 1H), 1.64–1.58 (m, 1H), 1.03 (t, 2H, J=7.5).

(±)-3-Ethyl-1,2,3,6-tetrahydro-1-methyl-9-(trifluoromethyl)-7H-[1,4]oxazino[3,2-g]quinolin-7-one (Compound 119, Structure 6 of Scheme I, where $R^1$=H, $R^2$=trifluoromethyl, $R^6$=Et, $R^x$=H). This compound was prepared by General Method 5 (EXAMPLE 1) from (±)-7-amino-2-ethyl-3,4-dihydro-4-methyl-2H-1,4-benzoxazine (80 mg, 0.4 mmol), and ethyl 4,4,4-trifluoroacetoacetate (0.92 mg, 0.5 mmol) and purified by flash chromatography (19:1 $CH_2Cl_2$:MeOH) to afford 26 mg (20%) of Compound 119. Data for Compound 119: $R_f$ 0.19 (19:1 $CH_2Cl_2$:MeOH); $^1$H NMR (400 MHz, $CDCl_3$) δ 11.5 (br s, 1H), 6.89 (s, 2H), 6.83 (s, 1H), 4.22 (m, 1H), 3.26 (dd, 1H, J=11.6, 2.4), 3.05 (dd, 1H, J=11.6, 8.2), 2.94 (s, 3H), 1.76 (m, 1H), 1.67 (m, 1H), 1.08 (t, 3H, J=7.5).

EXAMPLE 19

1,2,3.6-Tetrahydro-9-(trifluoromethyl)-7H-[1,4]oxazino[3,2-g]quinolin-7-one (Compound 120, Structure 10 of Scheme II, where $R^1$=H, $R^2$=Trifluoromethyl)

3,4-Dihydro-4-(p-methoxybenzyl)-7-nitro-2H-1,4-benzoxazine (Structure 4 of Scheme I, where $R^6$=H, $R^x$=4-anisyl). This compound was prepared by General Method 3 (EXAMPLE 1) from 3,4-dihydro-7-nitro-2H-1,4-benzoxazine (EXAMPLE 1) (305 mg, 1.7 mmol), p-anisaldehyde (2.3 g, 17 mmol) and $NaBH_3CN$ (532 mg, 8.4 mmol) to afford 361 mg (70%) of 3,4-dihydro-4-(p-methoxybenzyl)-7-nitro-2H-1,4-benzoxazine, an yellow solid. Data for 3,4-dihydro-4-(p-methoxybenzyl)-7-nitro-2H-1,4-benzoxazine: $R_f$ 0.79 (3:2 EtOAc:hexanes); $^1$H NMR (400 MHz, $CDCl_3$) δ 7.76 (dd, 1H, J=9.0, 2.6), 7.70 (d, 1H, J=2.5), 7.14 (d, 2H, J=8.6), 6.88 (d, 2H, J=8.6), 6.63 (d, 1H, J=9.1), 4.54 (s, 2H), 4.26 (t, 2H, J=4.5), 3.80 (s, 3H), 3.51 (t, 2H, J=4.6).

General Method 10: Reduction of a nitrobenzene derivative to an aniline with zinc/calcium chloride dihydrate. To a solution of the nitrobenzene derivative (1.0 equiv) in ethanol:water (95:5) was added zinc dust (4.30 equiv) and calcium chloride dihydrate (2.15 equiv) at room temperature, whereupon the mixture was then heated to reflux. Color change of the solution from yellow to colorless indicated that the reaction was complete, with a reaction time of approximately 4–5 hours. The reaction mixture was filtered hot through a pad of celite and washed with hot EtOAc (100 mL). The solvent was removed under reduced pressure and partitioned with water (150 mL) and EtOAc (150 mL). The aqueous layer was then adjusted to a pH of 3–4 with 20% HCl, extracted with EtOAc (3×100 mL), washed with brine (100 mL), dried ($MgSO_4$) and concentrated under reduced pressure. Purification by flash chromatography (silica gel, 20:1, $CH_2Cl_2$:MeOH) gave the desired product.

7-Amino-3,4-dihydro-4-(p-methoxybenzyl)-2H-1,4-benzoxazine (Structure 5 of Scheme I, where $R^6$=H, $R^x$=4-anisyl). This compound was prepared by General Method 10 from 3,4-dihydro-4-(p-methoxybenzyl)-7-nitro-2H-1,4-benzoxazine (1.0 g, 3.3 mmol) and purified by flash chromatography ($CH_2Cl_2$/MeOH, 20:1) to afford 900 mg (99%) of 7-amino-3,4-dihydro-4-(p-methoxybenzyl)-2H-1,4-benzoxazine. Data for 7-amino-3,4-dihydro-4-(p-methoxybenzyl)-2H-1,4-benzoxazine: $R_f$ 0.60 (24:1 $CH_2Cl_2$:MeOH); $^1$H NMR (400 MHz, $CDCl_3$) δ 7.22 (d, 2H, J=8.6), 6.86 (d, 2H, J=8.6), 6.60 (d, 1H, J=8.4), 6.34 (d, 1H, J=2.5), 6.30 (dd, 1H, J=8.5, 2.4), 4.25 (s, 2H), 4.21 (t, 2H, J=4.5), 3.80 (s, 3H), 3.17 (t, 2H, J=4.3).

(±)-1,2,3,6-Tetrahydro-9-(trifluoromethyl)-7H-[1,4]oxazino[3,2-g]quinolin-7-one (Compound 120, Structure 10 of Scheme II, where $R^1$=H, $R^2$=trifluoromethyl). This compound was prepared by General Method 5 (EXAMPLE 1) from 7-amino-3,4-dihydro-4-(p-methoxybenzyl)-2H-1,4-benzoxazine (1.78 g, 6.58 mmol) and ethyl 4,4,4,-trifluoroacetoacetate (1.15 mL, 7.9 mmol), and purified by flash chromatography (19:1 $CH_2Cl_2$:MeOH) to afford 533 mg (30%) of Compound 120. Data Compound 120: $R_f$ 0.17 (3:2 EtOAc:hexanes); $^1$H NMR (400 MHz, $CDCl_3$) δ 10.73 (br s, 1H), 6.94 (s, 1H), 6.87 (s, 1H), 6.75 (s, 1H), 4.35 (t, 2H, J=4.4), 3.99 (br s, 1H), 3.50–3.42 (m, 1H).

EXAMPLE 20

1-Cyclopropylmethyl-1,2,3,6-tetrahydro-9-(trifluoromethyl)-7H-[1,4]oxazino[3,2-g]quinolin-7-one (Compound 121, Structure 10 of Scheme II, where $R^1$=H, $R^2$=Trifluoromethyl, $R^x$=cyclopropyl)

This compound was prepared by General Method 3 (EXAMPLE 1) from Compound 120 (EXAMPLE 19) (55 mg, 0.21 mmol), cyclopropanecarboxaldehyde (100 mg, 1.5 mmol) and $NaBH_3CN$ (65 mg, 1.01 mmol) to afford 64 mg (98%) of Compound 121. Data for Compound 121: $R_f$ 0.29 (19:1 $CH_2Cl_2$:MeOH); $^1$H NMR (500 MHz, $CDCl_3$) δ 11.04 (br s, 1H), 7.00 (s, 1H), 6.88 (s, 1H), 6.78 (s, 1H), 4.36 (t, 2H, J=4.4), 3.46 (t, 2H, J=4.4), 3.19 (d, 2H, J=6.3), 1.05 (m, 1H), 0.62–0.58 (m, 2H), 0.27 (m, 2H).

EXAMPLE 21

1,2,3,6-Tetrahydro-1-(2-pyridylmethyl)-9-(trifluoromethyl)-7H-[1,4]oxazino[3,2-g]quinolin-7-one (Compound 122, Structure 11 of Scheme II, where $R^1$=H, $R^2$=Trifluoromethyl, $R^x$=2-pyridyl).

This compound was prepared by General Method 3 (EXAMPLE 1) Compound 120 (EXAMPLE 19) (19 mg, 0.07 mmol), 2-pyridinecarboxaldehyde (75.6 mg, 0.7 mmol) and NaBH$_3$CN (22 mg, 0.3 mmol) to afford 9 mg (36%) of Compound 122. Data for Compound 122: R$_f$ 0.17 (19:1 CH$_2$Cl$_2$:MeOH); $^1$H NMR (500 MHz, CDCl$_3$) δ 11.48 (br s, 1H), 8.61 (d, 1H, J=5.5), 7.64 (t, 1H, J=6.9), 7.29 (d, 1H, J=7.8), 7.19 (dd, 1H, J=7.2, 5.5), 6.84 (s, 1H), 6.82 (s, 2H), 4.60 (s, 2H), 4.42 (t, 2H, J=4.4), 3.60 (t, 2H, J=4.5).

EXAMPLE 22

(±)-1,2,3,6-Tetrahydro-2-methyl-1-(2,2,2-trifluoroethyl)-9-(trifluoromethyl)-7H-[1,4]oxazino[3,2-g]quinolin-7-one (Compound 123, Structure 18 of Scheme III, where R$^2$=CF$_3$, R$^x$=Trifluoromethyl, R$^1$, R$^6$, R$^7$=H)

(2-Methoxy-4-nitrophenyl)-2,2,2-(trifluoroethyl)amine. This compound was prepared according to General Method 7 (EXAMPLE 5) from 2-amino-5-nitroanisole (5.38 g, 32.0 mmol), trifluoroacetaldehyde hydrate (26.5 mL, 37.1 g, 0.320 mol), NaBH$_3$CN (10.0 g, 0.160 mol) in 107 mL trifluoroacetic acid to afford 7.6 g (95%) of (2-methoxy-4-nitrophenyl)-2,2,2-(trifluoroethyl)amine, a light brown crystalline solid, after recrystallization (1:1 EtOAc:hexanes, 30 mL). Data for (2-methoxy-4-nitrophenyl)-2,2,2-(trifluoroethyl)amine: R$_f$ 0.52 (2:1 hexanes:EtOAc); $^1$H NMR (400 MHz, acetone-d$_6$) δ 7.87 (dd, 1H, J=8.9, 2.4), 7.69 (d, 1H, J=2.4), 6.96 (d, 1H, J=8.9), 6.38 (broad s, 1H), 4.20 (qd, 2H, J=9.3,7.1), 4.00 (s, 3H).

(4-Amino-2-methoxyphenyl)-2,2,2-(trifluoroethyl)amine (Structure 13 of Scheme III, where R$^x$=CF$_3$). This compound was prepared according to General Method 10 (EXAMPLE 19) from (2-methoxy-4-nitrophenyl)-2,2,2-(trifluoroethyl)amine (8.40 g, 33.6 mmol), zinc dust (9.66 g, 0.148 mmol), and calcium chloride dihydrate (10.9 g, 73.9 mmol) in 300 mL 95% EtOH/water to afford to 6.7 g (90%) of (4-amino-2-methoxyphenyl)-2,2,2-(trifluoroethyl)amine, a deep purple oil. Data for (4-amino-2-methoxyphenyl)-2,2,2-(trifluoroethyl)amine: R$_f$ 0.25 (1:1 hexanes:EtOAc); $^1$H NMR (400 MHz, CDCl$_3$) δ 6.54 (d, 1H, J=8.1), 6.20–6.30 (m, 2H), 4.15 (broad s, 1H), 3.81 (s, 3H), 3.68 (qd, 2H, J=9.0, 7.4), 3.38 (broad s, 2H).

7-Methoxy-6-[2,2,2-(trifluoroethyl)amino]-4-trifluoromethyl-1H-quinolin-2-one (Structure 14 of Scheme III, where R$^1$=H, R$^2$=trifluoromethyl, R$^x$=trifluoromethyl).

General Method 11: Condensation of an aniline with an acetoacetate derivative in benzene or toluene followed by a Knorr reaction in sulfuric acid. A solution of an aniline (1.0 equiv) in benzene or toluene (10 mL/mmol) and an acetoacetate derivative (1.2 equiv) was heated at reflux for 12–16 hrs. The resulting mixture was cooled to room temperature and concentrated under reduced pressure. The crude reaction mixture was diluted in concentrated sulfuric acid (8 mL/mmol) and heated to 100° C. for 6–16 hrs. The resulting mixture was poured over ice and neutralized with 6M NaOH solution to pH 7.0, extracted with CH$_2$Cl$_2$ (3×30 mL/mmol), washed with pH 7 phosphate buffer (50 mL/mmol) and brine (50 mL/mmol). The organic solution was dried (MgSO$_4$) and concentrated under reduced pressure. Purification was performed either by flash chromatography (silica gel, 20:1, CH$_2$Cl$_2$/MeOH) or by another specified method to afford the desired quinolone as a fluorescent-yellow solid.

7-Methoxy-6-[2,2,2-(trifluoroethyl)amino]-4-trifluoromethyl-1H-quinolin-2-one (Structure 14 of Scheme III, where R$^1$=H, R$^2$=trifluoromethyl, R$^x$=trifluoromethyl).

This compound was prepared according to General Method 11 from (5.72 g, 26.0 mmol) and ethyl 4,4,4-trifluoroacetoacetate (4.56 mL, 5.74 g, 31.2 mmol) in 87 mL toluene, followed by treatment with 65 mL concentrated H$_2$SO$_4$ to afford 2.72 g (30.7%) of 7-methoxy-6-[2,2,2-(trifluoroethyl)amino]-4-trifluoromethyl-1H-quinolin-2-one, a fluffy yellow solid, after rinsing the crude material with a 1:1 mixture of EtOAc:hexanes (60 mL). Data for 7-methoxy-6-[2,2,2-(trifluoroethyl)amino]-4-trifluoromethyl-1H-quinolin-2-one: R$_f$ 0.19 (4:1 EtOAc:CH$_2$Cl$_2$); $^1$H NMR (400 MHz, acetone-d$_6$) δ 10.87 (broad s, 1H), 7.04 (s, 1H), 6.99 (broad s, 1H), 6.73 (s, 1H), 5.54 (broad m, 1H), 4.07 (app quint, 2H, J=8.4), 3.98 (s, 3H).

General Method 12: Transformation of a pyridone to an isopropyl imino ether with isopropyl iodide and cesium fluoride. To a suspension of pyridone (1 equiv) and CsF (4 equiv) in DMF (0.25 M) was added 2-iodopropane (4 equiv). The suspension was stirred for 18 h, whereupon it was poured into cold water (25 mL/mmol) and extracted with EtOAc (2×25 mL/mmol). The organic layers were washed sequentially with water (2×15 mL/mmol) and brine (15 mL/mmol), dried over MgSO$_4$, filtered, and concentrated to afford a yellow brown solid, which was used without further purification.

2-Isopropyloxy-7-methoxy-6-[2,2,2-(trifluoroethyl)amino]-4-(trifluoromethyl)quinoline: This compound was prepared by General Method 12 from 7-methoxy-6-[2,2,2-(trifluoroethyl)amino]-4-trifluoromethyl-1H-quinolin-2-one (2.42 g, 7.11 mmol), CsF (4.32 g, 28.5 mmol), and 2-iodopropane (2.84 mL, 4.84 g, 28.5 mmol) in 28 mL DMF to afford 2.47 g (90.6%) of 2-isopropyloxy-7-methoxy-6-[2,2,2-(trifluoroethyl)amino]-4-(trifluoromethyl)quinoline, a yellow brown solid, which was used without further purification. Data for 2-isopropyloxy-7-methoxy-6-[2,2,2-(trifluoroethyl)amino]-4-(trifluoromethyl)quinoline: R$_f$ 0.24 (9:1 hexanes:EtOAc); $^1$H NMR (400 MHz, CDCl$_3$) δ 7.18 (s, 1H), 7.02 (s, 1H), 7.01 (broad s, 1H), 5.48 (heptet, 1H, J=6.3), 4.87 (broad t, 1H, J=6.7), 4.02 (s, 3H), 3.88 (app quint, 2H, J=8.8), 1.39 (d, 6H, J=6.3).

7-Hydroxy-2-isopropyloxy-6-[2,2,2-(trifluoroethyl)amino]4-(trifluoromethyl)quinoline (Structure 15 of Scheme III, where R$^1$=H, R$^2$=trifluoromethyl, R$^x$=trifluoromethyl): To a suspension of sodium hydride (60% mineral oil dispersion, 1.72 g, 6.13 mmol) in 20.6 mL DMF was added thiophenol (4.53 mL, 4.86 g, 44.1 mmol) at 0° C. After the bubbling subsided, a solution of isopropyloxy-7-methoxy-6-[2,2,2-(trifluoroethyl)amino]-4-(trifluoromethyl)quinoline (2.34 g, 6.13 mmol) in 10 mL DMF was added and the mixture was heated to 110° C. After 5 h, the mixture was poured into cold water and neutralized with 21 mL 2 M NaHSO$_4$, and the aqueous layer was extracted with ethyl acetate (2×200 mL). The organic layers were washed sequentially with water (2×100 mL) and brine (100 mL), dried over MgSO$_4$, filtered and concentrated. Flash chromatography (hexanes:EtOAc, 2:1) afforded 1.71 g (75.8%) of 2-isopropyloxy-7-hydroxy-6-[2,2,2-(trifluoroethyl)amino]-4-(trifluoromethyl)quinoline, a yellow solid. Data for 7-hydroxy-2-isopropyloxy-6-[2,2,2-(trifluoroethyl)amino]-4-(trifluoromethyl)quinoline: R$_f$ 0.21 (4:1 hexanes:EtOAc); $^1$H NMR (400 MHz, CDCl$_3$) δ 7.18 (s, 1H), 7.05 (broad s, 1H), 7.01 (s, 1H), 6.0 (v broad s, 1H), 5.42 (hept, 1H, J=6.1), 4.69 (broad t, 1H, J=6.9), 3.88 (m, 2H), 1.37 (d, 6H, J=6.1).

General Method 13: Cyclization of an α-bromoester onto an o-aminophenol to form a compound of Structure 16. To a suspension of an aminophenol of Structure 15 (1 equiv) and K$_2$CO$_3$ (2.05 equiv) in DMF (0.25 M) was added the α-bromoester (1.05 equiv). The mixture was heated to 80° C. for 1 h, then heated to 110° C. for 4 h, then the reaction was partitioned between EtOAc (50 mL/mmol), water (25 mL/mmol) and sat'd NH$_4$Cl (25 mL/mmol). The aqueous layer was extracted with EtOAc (25 mL/mmol), and the combined organic layers were washed sequentially with water (2×25 ml/mmol), brine (25 mL/mmol), dried over MgSO$_4$, filtered and concentrated. This material was used without purification, or was purified as indicated.

7-Isopropoxy-1-(2,2,2-trifluoroethyl)-9-(trifluoromethyl)-1H-[1,4]oxazino[3,2-g]quinolin-2(3H)-one (Structure 16 of Scheme III, where R$^2$=CF$_3$, R$^x$=trifluoromethyl, R$^1$, R$^6$, R$^7$=H): This compound was prepared by General Method 13 from 2-isopropyloxy-7-hydroxy-6-[(2,2,2-trifluoroethyl)amino]-4-(trifluoromethyl)quinoline (1.51 g, 4.10 mmol), K$_2$CO$_3$ (1.16 g, 8.40 mmol) and ethyl bromoacetate (0.719 g, 4.30 mmol) in 16.4 mL DMF to afford 1.57 g (94%) of 7-isopropoxy-1-(2,2,2-trifluoroethyl)-9-(trifluoromethyl)-1H-[1,4]oxazino[3,2-g]quinolin-2(3H)-one, a light yellow-brown solid, R$_f$ 0.50 (4:1 hexanes:EtOAc); $^1$H NMR (400 MHz, CDCl$_3$) δ 7.57 (broad s, 1H), 7.48 (s, 1H), 7.11 (s, 1H), 5.53 (hept, 1H, J=6.2), 4.79 (s, 2H), 4.71 (q, 2H, J=8.4), 1.41 (d, 6H).

General Method 14: Methenylation of a tertiary amide of Structure 16 and subsequent reduction with NaBH$_3$CN. To a solution of a substituted 7-isopropoxy-1-(2,2,2-trifluoroethyl)-9-(trifluoromethyl)-1H-[1,4]oxazino[3,2-g]quinolin-2(3H)-one derivative (1 equiv) in THF (0.15 M) was added Tebbe reagent (0.5 M in toluene, 1.1 equiv) at 0° C. After 1 h, ether (50 mL/mmol) and methanol (0.7 mL/mmol) were added sequentially, and the brown solution was allowed to warm to rt. After 30 min, the mixture was filtered through Celite, rinsed with ether, and concentrated to a deep orange-brown solid. The solid was passed quickly through a plug of silica gel or basic alumina to afford an orange solid which was carried on directly. To a suspension of the above solid and NaBH$_3$CN (5 equiv) in dichloroethane (0.2 M) was added acetic acid (2.5 mL/mmol) dropwise at 0° C. The mixture bubbled vigorously, and was allowed to warm to rt. After 1 d the orange solution was poured into NaHCO$_3$ (40 mL/mmol) and extracted with EtOAc (2×40 mL/mmol). The organic layers were washed with brine (30 mL/mmol), dried over MgSO$_4$, filtered, and concentrated. The material was purified as indicated.

(±)-2,3-Dihydro-7-isopropoxy-2-methyl-1-(2,2,2-trifluoroethyl)-9-(trifluoromethyl)-1H-[1,4]oxazino[3,2-g]quinoline (Structure 17 of Scheme III, where R$^2$=CF$_3$, R$^x$=trifluoromethyl, R$^1$, R$^6$, R$^7$=H). This compound was made from General Method 14 from 7-isopropoxy-1-(2,2,2-trifluoroethyl)-9-(trifluoromethyl)-1H-[1,4]oxazino[3,2-g]quinolin-2(3H)-one (0.689 g, 1.69 mmol), Tebbe's reagent (3.7 mL, 1.9 mmol) in 11 mL THF to afford 0.728 g of (±)-2,3-dihydro-7-isopropoxy-2-methylene-1-(2,2,2-trifluoroethyl)-9-(trifluoromethyl)-1H-[1,4]oxazino[3,2-g]quinoline, an orange solid after filtration through silica gel. $^1$H NMR (400 MHz, CDCl$_3$) δ 7.64 (broad s, 1H), 7.49 (s, 1H), 7.29 (s, 1H), 5.59 (hept, 1H, J=6.2), 4.95 (s, 2H), 4.91 (q, 2H, J=9.1), 1.58 (d, 6H, J=6.2). Subsequent treatment of the above solid (0.728 g) as described in General Method 14 with NaBH$_3$CN (0.531 g, 8.45 mmol) and 4.2 mL acetic acid in 8.4 mL dichloroethane afforded 0.366 g (53%) of (±)-2,3-dihydro-7-isopropoxy-2-methyl-1-(2,2,2-trifluoroethyl)-9-(trifluoromethyl)-1H-[1,4]oxazino[3,2-g]quinoline, a yellow solid, after flash chromatography (hexanes:EtOAc, 9:1). R$_f$ 0.28 (9:1 hexanes:EtOAc); $^1$H NMR (400 MHz, CDCl$_3$) δ 7.29 (s, 1H), 7.12 (s, 1H), 7.00 (s, 1H), 5.48 (hept, 1H, J=6.2), 4.26 (dd, ABX, 1H, J=10.7, 2.4), 4.16 (dd, ABX, 1H, J=10.7, 2.8), 3.97–4.07 (m, 1H), 3.77–3.87 (m, 1H), 3.61–3.68 (m, 1H), 1.38 (d, 6H, J=6.2). General Method 15: Hydrolysis of an isopropyl imino ether to a pyridone. A solution of the imino ether in a 3:1 acetic acid:concentrated HCl (0.1–0.2 M) solution was heated at 60–110° C. for 4–16 h. The solution was poured into sat'd NaHCO$_3$ (80 mL/mmol), extracted with EtOAc (2×80 mL/mmol), washed with brine (60 mL/mmol), dried over MgSO$_4$, filtered, concentrated, and purified as indicated.

(±)-1,2,3,6-Tetrahydro-2-methyl-1-(2,2,2-trifluoroethyl)-9-(trifluoromethyl)-7H-[1,4]oxazino[3,2-g]quinolin-7-one (Compound 123, Structure 18 of Scheme III, where R$^1$, R$^6$, R$^7$=H, R$^2$=CF$_3$, R$^x$=trifluoromethyl). This compound was prepared according to General Method 15 from (±)-2,3-dihydro-7-isopropoxy-2-methyl-1-(2,2,2-trifluoroethyl)-9-(trifluoromethyl)-1H-[1,4]oxazino[3,2-g]quinoline (0.362 g, 0.887 mmol) in 1.6 mL conc. HCl and 4.8 mL acetic acid heated to 110° C. for 5 h. The product was isolated by purification by flash chromatography (92:8 CH$_2$Cl$_2$:MeOH), followed by recrystallization from methanol to afford 0.164 g (50%) of Compound 123, a yellow solid. Data for Compound 123: HPLC (ODS, 7:3 MeOH:water, 3.0 mL/min) t$_R$ 13.56 min; $^1$H NMR (400 MHz, CDCl$_3$) 11.07 (broad s, 1H), 7.08 (broad s, 1H), 6.96 (s, 1H), 6.75 (s, 1H), 4.25–4.30 (m, 2H), 4.05–4.25 (m, 2H), 3.72–3.82 (m, 1H), 1.28 (d, 3H, J=6.6); $^{13}$C(100 MHz, DMSO-d$_6$) 160.0, 147.7, 135.6 (q, J=30.4), 134.3 (m), 129.9, 125.8 (q, J=282), 122.7 (q, J=275), 118.4 (broad s), 108.1, 106.0, 102.8, 68.8, 51.7, 50.9 (q, J=32.2), 15.0.

EXAMPLE 23

(+)-1,2,3,6-Tetrahydro-2-methyl-1-(2,2,2-trifluoroethyl)-9-(trifluoromethyl)-7H-[1,4]oxazino [3,2-g]quinolin-7-one (Compound 124, Structure (+)-18 of Scheme III, where R$^1$, R$^6$, R$^7$=H, R$^2$=CF$_3$, R$^x$=Trifluoromethyl), and (−)-1,2,3,6-Tetrahydro-2-methyl-1-(2,2,2-trifluoroethyl)-9-(trifluoromethyl)-7H-[1,4]oxazino[3,2-g]quinolin-7-one (Compound 125, Structure (−)-18 of Scheme III, where R$^1$, R$^6$, R$^7$=H, R$^2$=CF$_3$, R$^x$= Trifluoromethyl)

This compound was prepared according to General Method 9 (EXAMPLE 15) from Compound 123 (EXAMPLE 22) (10 mg, 0.03 mmol) on a semiprep Chiralpak AD column (20×250 mm) eluted hexanes/isopropanol (93:7), to afford 3.3 mg of Compound 124, a yellow solid, and 3.0 mg of Compound 125, a yellow solid. Data for Compound 124: HPLC (Chiralpak AD, 93:7 hexanes:isopropanol, 5.0 mL/min) t$_R$ 35.4 min; [α]$_D$=+39.3. Data for Compound 125: HPLC (Chiralpak AD, 93:7 hexanes:isopropanol, 5.0 mL/min) t$_R$ 40.9 min; [α]$_D$=−41.3.

EXAMPLE 24

(±)-trans-1,2,3,6-Tetrahydro-2,3-dimethyl-1-(2,2,2-trifluoroethyl)-9-(trifluoromethyl)-7H-[1,4]oxazino [3,2-g]quinolin-7-one (Compound 126, Structure 18 of Scheme III, where R$^1$=H, R$^2$=CF$_3$, R$^6$=H, R$^7$= Me, R$^x$=Trifluoromethyl)

7-Isopropoxy-3-methyl-1-(2,2,2-trifluoroethyl)-9-(trifluoromethyl)-1H-[1,4]oxazino[3,2-g]quinolin-2(3H)-one (Structure 16 of Scheme III, where R$^1$=H, R$^2$=CF$_3$, R$^6$=H, R$^7$=Me, R$^x$=trifluoromethyl). This compound was prepared according to General Method 13 (EXAMPLE 22) from 2-isopropyloxy-7-hydroxy-6-[2,2,2-(trifluoroethyl)amino]-4-(trifluoromethyl)quinoline (EXAMPLE 22) (55 mg, 0.15 mmol), ethyl 2-bromopropionate (29 mg, 0.16 mmol) and K$_2$CO$_3$ (46 mg, 0.33 mmol) in 1.5 mL DMF to afford 61 mg (96%) of 7-isopropoxy-3-methyl-1-(2,2,2-trifluoroethyl)-9-(trifluoromethyl)-1H-[1,4]oxazino[3,2-g]quinolin-2 (3H)-one. Data for 7-isopropoxy-3-methyl-1-(2,2,2-trifluoroethyl)-9-(trifluoromethyl)-1H-[1,4]oxazino[3,2-g]quinolin-2 (3H)-one: $R_f$ 0.31 (9:1 hexanes:EtOAc); $^1$H NMR (400 MHz, CDCl$_3$) δ 7.55 (broad s, 1H), 7.48 (s, 1H), 7.11 (s, 1H), 5.53 (hept, 1H, J=6.2), 4.81 (q, 2H, J=6.8), 4.60–4.76 (m, 2H), 1.64 (d, 3H, J=6.8), 1.41 (d, 6H, J=6.2).

(±)-trans-2,3-dihydro-7-isopropoxy-2,3-dimethyl-1-(2,2,2-trifluoroethyl)-9-(trifluoromethyl)-1H-[1,4]oxazino[3,2-g]quinoline (Structure 17 of Scheme III, where $R^1$=H, $R^2$=CF$_3$, $R^6$=H, $R^7$=Me, $R^x$=trifluoromethyl) and (±)-cis-2,3-dihydro-7-isopropoxy-2,3-dimethyl-1-(2,2,2-trifluoroethyl)-9-(trifluoromethyl)-1H-[1,4]oxazino[3,2-g]quinoline (Structure 17 of Scheme III, where $R^1$=H, $R^2$=CF$_3$, $R^6$=Me, $R^7$=H, $R^x$=trifluoromethyl). This compound was prepared according to General Method 14 (EXAMPLE 22) from 7-isopropoxy-3-methyl-1-(2,2,2-trifluoroethyl)-9-(trifluoromethyl)-1H-[1,4]oxazino[3,2-g]quinolin-2(3H)-one (19 mg, 0.046 mmol), Tebbe reagent (0.10 mL, 0.050 mmol) in 0.5 mL THF followed by reduction with NaBH$_3$CN (17 mg, 0.27 mmol) in 0.23 mL HOAc and 0.46 mL dichloroethane to afford 15 mg (78%) of a 3:1 mixture of diastereomers after flash chromatography (4:1 hexanes:EtOAc). The diastereomers were separated on a Beckman HPLC (ODS Ultrasphere semi-prep column, 5 μm, 10×250 mm, 3.0 mL/min, 80% MeOH/water) to afford 3.5 mg (18%) of (±)-trans-2,3-dihydro-7-isopropoxy-2,3-dimethyl-1-(2,2,2-trifluoroethyl)-9-(trifluoromethyl)-1H-[1,4]oxazino[3,2-g]quinoline, a yellow solid, and 6.5 mg (34%) of (±)-cis-2,3-dihydro-7-isopropoxy-2,3-dimethyl-1-(2,2,2-trifluoroethyl)-9-(trifluoromethyl)-1H-[1,4]oxazino[3,2-g]quinoline. Data for (±)-trans-(±)-2,3-dihydro-7-isopropoxy-2,3-dimethyl-1-(2,2,2-trifluoroethyl)-9-(trifluoromethyl)-1H-[1,4]oxazino[3,2-g]quinoline: HPLC (ODS, 10×250 mm, 80% MeOH/water, 3 mL/min) $t_R$ 50 min; $R_f$ 0.54 (4:1 hexanes:EtOAc); $^1$H NMR (400 MHz, CDCl$_3$) δ 7.26 (s, 1H), 7.09 (broad s, 1H), 6.98 (s, 1H), 5.48 (hept, 1H, J=6.2), 4.40 (qd, 1H, J=6.5, 2.2), 3.96–4.09 (m, 1H), 3.72–3.85 (m, 1H), 3.42 (qd, J=6.5, 2.0, 1H), 1.35–1.42 (m, 9H), 1.14 (d, 3H, J=6.5).

Data for (±)-cis-2,3-dihydro-7-isopropoxy-2,3-dimethyl-1-(2,2,2-trifluoroethyl)-9-(trifluoromethyl)-1H-[1,4]oxazino[3,2-g]quinoline: HPLC (ODS, 10×250 mm, 80% MeOH/water, 3 mL/min) $t_R$ 57 min; $R_f$ 0.51 (4:1 hexanes:EtOAc); $^1$H NMR (400 MHz, CDCl$_3$) δ 7.27 (s, 1H), 7.09 (broad s, 1H), 6.99 (s, 1H), 5.48 (hept, 1H, J=6.2), 4.33 (qd, 1H, J=6.5, 1.8), 4.03–4.16 (m, 1H), 3.72–3.84 (m, 1H), 3.36 (qd, J=6.7, 1.5), 1.38 (d, 6H, J=6.2), 1.36 (d, 3H, J=6.5), 1.27 (d, 3H, J=6.6).

(±)-trans-1,2,3,6-Tetrahydro-2,3-dimethyl-1-(2,2,2-trifluoroethyl)-9-(trifluoromethyl)-7H-[1,4]oxazino[3,2-g]quinolin-7-one (Compound 126, Structure 18 of Scheme III, where $R^1$=H, $R^2$=CF$_3$, $R^6$=H, $R^7$=Me, $R^x$=trifluoromethyl). This compound was prepared according to General Method 15 (EXAMPLE 22) from (±)-trans-2,3-dihydro-7-isopropoxy-2,3-dimethyl-1-(2,2,2-trifluoroethyl)-9-(trifluoromethyl)-1H-[1,4]oxazino[3,2-g]quinoline (3.5 mg, 0.0083 mmol) in 0.2 mL conc. HCl and 0.5 mL acetic acid heated to 110° C. for 3 h, affording 2.5 mg (78%) of Compound 126 after flash chromatography (92:8 CH$_2$Cl$_2$:MeOH). Data for Compound 126: $R_f$ 0.20 (92:8 CH$_2$Cl$_2$:MeOH): $^1$H NMR (400 MHz, CDCl$_3$) δ 11.50 (broad s, 1H), 7.01 (broad s, 1H), 6.90 (s, 1H), 6.87 (s, 1H), 4.32 (qd, 1H, J=6.3, 1.9), 3.93–4.08 (m, 1H), 3.67–3.82–3.82 (m, 1H), 3.32 (qd, J=6.5, 1.3), 1.34 (d, 3H, J=6.4), 1.23 (d, 3H, J=6.5).

EXAMPLE 25

(±)-cis-1,2,3,6-Tetrahydro-2,3-dimethyl-1-(2,2,2-trifluoroethyl)-9-(trifluoromethyl)-7H-[1,4]oxazino[3,2-g]quinolin-7-one (Compound 127, Structure 18 of Scheme III, where $R^1$=H, $R^2$=CF$_3$, $R^6$=Me, $R^7$=H, $R^x$=Trifluoromethyl)

This compound was prepared according to General Method 15 (EXAMPLE 22) from (±)-cis-2,3-dihydro-7-isopropoxy-2,3-dimethyl-1-(2,2,2-trifluoroethyl)-9-(trifluoromethyl)-1H-[1,4]oxazino[3,2-g]quinoline (EXAMPLE 24) (6.0 mg, 0.014 mmol) in 0.2 mL conc. HCl and 0.5 mL acetic acid heated to 110° C. for 3 h, affording 4.5 mg (85%) of Compound 127 after flash chromatography (92:8 CH$_2$Cl$_2$:MeOH). Data for Compound 127: $R_f$ 0.20 (92:8 CH$_2$Cl$_2$:MeOH); $^1$H NMR (400 MHz, CDCl$_3$) δ 12.06 (broad s, 1H), 7.02 (broad s, 1H), 6.92 (s, 1H), 6.90 (s, 1H), 4.37 (qd, 1H, J=6.4, 1.8), 3.83–3.98 (m, 1H), 3.68–3.82 (m, 1H), 3.38 (qd, 1H, J=6.7, 1.6), 1.37 (d, 3H, J=6.4), 1.11 (d, 3H, J=6.6).

EXAMPLE 26

(±)-trans-3-Ethyl-1,2,3,6-tetrahydro-2-methyl-1-(2,2,2-trifluoroethyl)-9-(trifluoromethyl)-7H-[1,4]oxazino[3,2-g]quinolin-7-one (Compound 128, Structure 18 of Scheme III, where $R^1$=H, $R^2$=CF$_3$, $R^6$=H, $R^7$=Et, $R^x$=Trifluoromethyl)

(±)-3-Ethyl-7-isopropoxy-1-(2,2,2-trifluoroethyl)-9-(trifluoromethyl)-1H-[4]oxazino[3,2-g]quinolin-2(3H)-one (Structure 16 of Scheme III, where $R^1$=H, $R^2$=CF$_3$, $R^6$=H, $R^7$=Et, $R^x$=trifluoromethyl). This compound was prepared according to General Method 13 (EXAMPLE 22) from 2-isopropyloxy-7-hydroxy-6-[2,2,2-(trifluoroethyl)amino]-4-(trifluoromethyl)quinoline (EXAMPLE 22) (70 mg, 0.19 mmol), ethyl 2-bromobutanoate (41 mg, 0.21 mmol) and K$_2$CO$_3$ (58 mg, 0.42 mmol) in 1.9 mL DMF to afford 63 mg (76%) of (±)-3-ethyl-7-isopropoxy-1-(2,2,2-trifluoroethyl)-9-(trifluoromethyl)-1H-[1,4]oxazino[3,2-g]quinolin-2(3H)-one. Data for (±)-3-ethyl-7-isopropoxy-1-(2,2,2-trifluoroethyl)-9-(trifluoromethyl)-1H-[1,4]oxazino[3,2-g]quinolin-2(3H)-one: $R_f$ 0.47 (5.7:1 hexanes:EtOAc); $^1$H NMR (400 MHz, CDCl$_3$) 7.54 (broad s, 1H), 7.49 (s, 1H), 7.11 (s, 1H), 5.53 (hept, 1H, J=6.2), 4.72–4.83 (m, 1H), 4.66 (dd, 1H, J=8.5, 4.8), 4.55–4.65 (m, 1H), 1.85–2.10 (m, 2H), 1.41 (d, 6H, J=6.2), 1.11 (t, 3H, J=7.4).

(±)-trans-3-Ethyl-2,3-dihydro-7-isopropoxy-2-methyl-1-(2,2,2-trifluoroethyl)-9-(trifluoromethyl)-1H-[1,4]oxazino[3,2-g]quinoline (Structure 17 of Scheme III, where $R^1$=H, $R^2$=CF$_3$, $R^6$=H, $R^7$=Et, $R^x$=trifluoromethyl) and (±)-cis-3-ethyl-2,3-dihydro-7-isopropoxy-2-methyl-1-(2,2,2-trifluoroethyl)-9-(trifluoromethyl)-1H-[1,4]oxazino[3,2-g]quinoline (Structure 17 of Scheme III, where $R^1$=H, $R^2$=CF$_3$, $R^6$=Et, $R^7$=H, $R^x$=trifluoromethyl). This compound was prepared according to General Method 14 (EXAMPLE 22) from 3-ethyl-7-isopropoxy-1-(2,2,2-trifluoroethyl)-9-(trifluoromethyl)-1H-[1,4]oxazino[3,2-g]quinolin-2 (3H)-one (39 mg, 0.089 mmol), Tebbe reagent (0.20 mL, 0.098 mmol) in 0.9 mL THF followed by reduction with NaBH$_3$CN (34 mg, 0.53 mmol) in 0.45 mL HOAc and 0.90 mL dichloroethane to afford 9 mg (23%) of (±)-cis-3-ethyl-2,3-dihydro-7-isopropoxy-2-methyl-1-(2,2,2-trifluoroethyl)-9-(trifluoromethyl)-1H-[1,4]oxazino[3,2-g]quinoline, a yellow solid, and 7 mg of a 1:1 mixture of diastereomers after flash chromatography (9:1 hexanes:EtOAc). The diastereomers were separated on a Beckman HPLC (ODS Ultrasphere semi-prep column, 5 μm, 10×250 mm, 3.0 mL/min, 90% MeOH/water) to afford 3 mg (8%) of (±)-trans-3-ethyl-2,3-dihydro-7-isopropoxy-2-methyl-1-(2,2,2-trifluoroethyl)-9-(trifluoromethyl)-1H-[1,4]oxazino[3,2-g]quinoline, a yellow solid. Data for (±)-trans-3-ethyl-2,3-dihydro-7-isopropoxy-2-methyl-1-(2,2,2-trifluoroethyl)-9-(trifluoromethyl)-1H-[1,4]oxazino[3,2-g]quinoline: HPLC (ODS, 10×250 mm, 90% MeOH/water, 3 mL/min) $t_R$ 16.2 min; $R_f$ 0.25 (9:1 hexanes:EtOAc); $^1$H NMR (400 MHz, benzene-$d_6$) δ 7.70 (s, 1H), 7.28 (broad s, 1H), 7.02 (s, 1H), 5.55 (hept, 1H, J=6.2), 3.41–3.52 (m, 2H), 2.90–3.01 (m, 1H), 2.63 (broad q, 1H, J=6.3), 1.48–1.57 (m, 1H), 1.30 (d, 3H, J=6.5), 1.28 (d, 3H, J=6.5), 1.11–1.20 (m, 1H), 0.78 (t, 3H, J=7.5), 0.76 (d, 3H, J=6.5). Data for (±)-cis-3-ethyl-2,3-dihydro-7-isopropoxy-2-methyl-1-(2,2,2-trifluoroethyl)-9-(trifluoromethyl)-1H-[1,4]oxazino[3,2-g]quinoline: HPLC (ODS, 10×250 mm, 90% MeOH/water, 3 mL/min) $t_R$ 19.4 min; $R_f$ 0.28 (9:1 hexanes:EtOAc); $^1$H NMR (400 MHz, CDCl$_3$) δ 7.29 (s, 1H), 7.09 (s, 1H), 6.98 (s, 1H), 5.47 (hept, 1H, J=6.2), 4.09 (ddd, 1H, J=7.9, 5.5, 2.0), 3.96–4.06 (m, 1H), 3.74–3.84 (m, 1H), 3.47 (qd, 1H, J=6.5, 2.0), 1.65–1.88 (m, 1H), 1.50–1.62 (m, 1H), 1.37 (d, 6H, J=6.2), 1.12 (d, 3H, J=6.6, 1.10 (t, 3H, J=7.4).

(±)-trans-3-Ethyl-1,2,3,6-tetrahydro-2-methyl-1-(2,2,2-trifluoroethyl)-9-(trifluoromethyl)-7H-[1,4]oxazino[3,2-g]quinolin-7-one (Compound 128, Structure 18 of Scheme III, where $R^1$=H, $R^2$=CF$_3$, $R^6$=H, $R^7$=Et, $R^x$=trifluoromethyl). This compound was prepared according to General Method 15 from (±)-trans-3-ethyl-2,3-dihydro-7-isopropoxy-2-methyl-1-(2,2,2-trifluoroethyl)-9-(trifluoromethyl)-1H-[1,4]oxazino[3,2-g]quinoline (3 mg, 0.007 mmol) in 0.1 mL conc. HCl and 1.5 mL acetic acid heated at 100° C. for 18 h to afford 1.7 mg (63%) of Compound 128, a yellow solid. Data for Compound 128: $^1$H NMR (400 MHz, CDCl$_3$) δ 11.83 (broad s, 1H), 6.99 (broad s, 1H), 6.91 (s, 2H), 3.92–4.05 (m, 2H), 3.68–3.79 (m, 1H), 3.41 (qd, 1H, J=6.7, 1.4), 1.66–1.75 (m, 1H), 1.53–1.62 (m, 1H), 1.24 (d, 3H, J=6.6), 1.01 (t, 3H, J=7.5).

EXAMPLE 27

(±)-cis-3-Ethyl-1,2,3,6-tetrahydro-2-methyl-1-(2,2,2-trifluoroethyl)-9-(trifluoromethyl)-7H-[1,4]oxazino [3,2-g]quinolin-7-one (Compound 129, Structure 18 of Scheme III, where R=H, $R^{-CF}$$_3$, $R^{-Et, R7}$=H, $R^x$= Trifluoromethyl)

This compound was prepared according to General Method 15 (EXAMPLE 22) from (±)-cis-3-ethyl-2,3-dihydro-7-isopropoxy-2-methyl-1-(2,2,2-trifluoroethyl)-9-(trifluoromethyl)-1H-[1,4]oxazino[3,2-g]quinoline (EXAMPLE 26) (8 mg, 0.018 mmol) in 0.1 mL conc. HCl and 1.5 mL acetic acid heated at 100° C. for 18 h to afford 5 mg (71%) of Compound 129, a yellow solid. Data for Compound 129: $R_f$ 0.19 (19:1 CH$_2$Cl$_2$:MeOH); $^1$H NMR (400 MHz, CDCl$_3$) δ 12.48 (broad s, 1H), 7.02 (broad s, 1H), 6.97 (s, 1H), 6.93 (s, 1H), 4.04–4.10 (m, 1H), 3.86–3.97 (m, 1H), 3.69–3.80 (m, 1H), 3.42 (dq, 1H, J=6.5, 1.9), 1.73–1.83 (m, 1H), 1.50–1.60 (m, 1H), 1.07–1.11 (m, 6H).

EXAMPLE 28

(±)-1,2,3,6-Tetrahydro-2-(hydroxymethyl)-1-(2,2,2-trifluoroethyl)-9-(trifluoromethyl)-7H-[1,4]oxazino [3,2-g]quinolin-7-one (Compound 130, Structure 20 of Scheme IV, where $R^1$, $R^6$, $R^7$=H, R= Trifluoromethyl)

(±)-2,3-Dihydro-2-(hydroxymethyl)-7-isopropoxy-1-(2,2,2-trifluoroethyl)-9-(trifluoromethyl)-1H-[1,4]oxazino[3,2-g]quinoline (Structure 19 of Scheme IV, where $R^1$, $R^6$, $R^7$=H, $R^2$=trifluoromethyl): To a solution of 7-isopropoxy-1-(2,2,2-trifluoroethyl)-9-(trifluoromethyl)-1H-[1,4]oxazino[3,2-g]quinolin-2(3H)-one (EXAMPLE 22) (0.183 g, 0.448 mmol) in 4.8 mL THF was added Tebbe reagent (0.99 mL, 0.49 mmol) at 0° C. After 1 h, ether (22 mL) and MeOH (0.32 mL) were added sequentially and the mixture was allowed to warm to rt. The slurry was filtered through Celite and concentrated, and the resultant residues was filtered through a short plug of basic alumina (4:1 hexanes:EtOAc) to afford 0.20 g of (±)-2,3-dihydro-7-isopropoxy-2-methylene-1-(2,2,2-trifluoroethyl)-9-(trifluoromethyl)-1H-[1,4]oxazino[3,2-g]quinoline. This residue was dissolved in 2.2 mL THF, and BH$_3$THF solution (1M, 0.49 mL, 0.49 mmol) was added dropwise at 0° C. After 15 min, the mixture was allowed to warm to rt, whereupon 0.1 mL MeOH was added and the solution allowed to stir for 16 h. The solvent was removed in vacuo, and the residue was redissolved in 2.2 mL THF and 0.45 mL MeOH, whereupon 0.10 mL 6N NaOH and a 35% H$_2$O$_2$ solution (0.055 mL, 60.9 mg, 0.63 mmol) was added. A precipitate was formed which was filtered with 20 mL THF. The filtrate was concentrated, and the resultant solid was dissolved in 1 mL MeOH, acidified with 0.05 mL conc. HCl, and the solution concentrated in vacuo. The residue was treated with 0. 1 mL 6N NaOH, and partitioned between water (20 mL) and EtOAc (20 mL). The aqueous layer was extracted with EtOAc (2×20 mL), and the combined organic layers were washed with brine (20 mL), dried over MgSO$_4$, filtered, and concentrated. Flash chromatography (2:1 hexanes:EtOAc) afforded 91 mg (48%) of (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline, a light amber oil. Data for (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline: $R_f$ 0.34 (2:1 hexanes:EtOAc); $^1$H NMR (400 MHz, CDCl$_3$) δ 7.30 (s, 1H), 7.17 (broad s, 1H), 7.01 (s, 1H), 5.48 (hept, 1H, J=6.2), 4.50 (dd, 1H, J=11.1, 1.6), 4.12–4.25 (m, 1H), 3.96–4.09 (m, 1H), 3.78–3.90 (m, 2H), 3.61–3.67 (m, 1H), 1.71 (t, 1H, J=5.1), 1.38 (d,6H, J=6.2).

(±)-1,2,3,6-Tetrahydro-2-(hydroxymethyl)-1-(2,2,2-trifluoroethyl)-9-(trifluoromethyl)-7H-[1,4]oxazino[3,2-g]quinolin-7-one (Compound 130. Structure 20 of Scheme IV, where $R^1$, $R^6$, $R^7$=H, $R^2$=trifluoromethyl). A solution of (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline (20 mg, 0.047 mmol) in 1.0 mL conc. HCl was heated at 90° C. for 4 h, whereupon the solution was poured into cold sat'd NaHCO$_3$ (20 mL) and extracted with EtOAc (2×20 mL). The combined organic layers were washed with brine (20 mL), dried over MgSO$_4$, filtered, and concentrated. Flash chromatography (2:1 hexanes:EtOAc) afforded 12 mg (67%) of Compound 130, a yellow solid. Data for Compound 130: $R_f$ 0.21 (3:2 EtOAc: CH$_2$Cl$_2$); $^1$H NMR (400 MHz, acetone-$d_6$) δ 10.95 (broad s, 1H), 7.10 (broad s, 1H), 6.95 (s, 1H), 6.74 (s, 1H), 4.58 (dd, 1H, J=10.9, 1.5), 4.20–4.42 (m, 3H), 4.17 (dd, 1H, J=10.9, 2.2), 3.72–3.81 (m, 1H), 3.59–3.73 (m, 2H).

EXAMPLE 29

(±)-1,2,3,6-Tetrahydro-2-(acetoxymethyl)-1-(2,2,2-trifluoroethyl)-9-(trifluoromethyl)-7H-[1,4]oxazino [3,2-g]quinolin-7-one (Compound 131, Structure 21 of Scheme IV, where $R^1$, $R^6$, $R^7$=H, $R^2$= Trifluoromethyl).

This compound was prepared by General Method 15 (EXAMPLE 22) from (±)-2,3-dihydro-2-(hydroxymethyl)-

7-isopropoxy-1-(2,2,2-trifluoroethyl)-9-(trifluoromethyl)-1H-[1,4]oxazino[3,2-g]quinoline (EXAMPLE 28) (4.6 mg, 0.011 mmol) in 0.1 mL conc. HCl and 0.5 mL HOAc heated at 100° C. for 3 h to afford 1.6 mg (35%) of Compound 131, a yellow solid. Data for Compound 131: $R_f$ 0.21 (3:2 EtOAc:CH$_2$Cl$_2$); $^1$H NMR (400 MHz, CDCl$_3$) δ 11.25 (broad s, 1H), 7.10 (broad s, 1H), 6.93 (s, 1H), 6.89 (s, 1H), 4.44 (dd, 1H, J=11.0, 1.3), 4.26 (dd, 1H, ABX, J=11.3, 6.0), 4.15 (dd, 1H, J=11.0, 2.5), 4.10 (dd, ABX, J=11.4, 7.9), 4.02–4.14 (m, 1H), 3.84–3.96 (m, 1H), 3.68–3.74 (m, 1H), 2.09 (s, 3H).

EXAMPLE 30

(±)-1,2,3,6-Tetrahydro-2-(methoxymethyl)-1-(2,2,2-trifluoroethyl)-9-(trifluoromethyl)-7H-[1,14]oxazino[3,2-g]quinolin-7-one (Compound 132, Structure 23 of Scheme IV, where $R^1$, $R^6$, $R^7$=H, $R^2$= Trifluoromethyl, $R^5$=Me)

General Method 16: Alkylation of an alcohol of Structure 19 to compound of Structure 22 with an alkyl halide. To a solution of a compound of Structure 19 (1 equiv) and sodium hydride (60% mineral oil dispersion, 4 equiv) in THF (0.03–0.04 M) was added the specified alkyl halide (4 equiv). After TLC analysis show the consumption of starting material (6–18 h), the reaction mixture was quenched with 1 M phosphate buffer (500 mL/mmol), extracted with EtOAc (2×500 mL/mmol). The organic layers were washed with brine, dried over MgSO$_4$, filtered, and concentrated, and purified as indicated.

(±)-2,3-Dihydro-7-isopropoxy-2-(methoxymethyl)-1-(2,2,2-trifluoroethyl)-9-(trifluoromethyl)-1H-[1,4]oxazino[3,2-g]quinoline (Structure 22 of Scheme IV, where $R^1$, $R^6$, $R^7$=H, $R^2$=trifluoromethyl, $R^5$=Me). This compound was prepared by General Method 16 from (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline (EXAMPLE 28) (10 mg, 0.024 mmol), NaH (4.7 mg, 0.12 mmol) and iodomethane (17 mg, 0.12 mmol) in 0.6 mL THF to afford 8.3 mg (81%) of (±)-2,3-dihydro-7-isopropoxy-2-(methoxymethyl)-1-(2,2,2-trifluoroethyl)-9-(trifluoromethyl)-1H-[1,4]oxazino[3,2-g]quinoline, a yellow solid, after flash chromatography (5:1 hexanes:EtOAc). Data for (±)-2,3-dihydro-7-isopropoxy-2-(methoxymethyl)-1-(2,2,2-trifluoroethyl)-9-(trifluoromethyl)-1H-[1,4]oxazino[3,2-g]quinoline: $R_f$ 0.21 (3:1 hexanes: EtOAc); $^1$H NMR (400 MHz, CDCl$_3$) δ 7.29 (s, 1H), 7.14 (broad s, 1H), 7.00 (s, 1H), 5.48 (hept, 1H, J =6.2), 4.43 (dd, 1H, J=11.0, 1.6), 4.16 (dd, J=11.0, 2.6), 3.98–4.21 (m, 2H), 3.67–3.73 (m, 1H), 3.50–3.60 (m, 2H), 3.37 (s, 3H), 1.38 (d, 6H, J=6.2).

(±)-1,2,3,6-Tetrahydro-2-(methoxymethyl)-1-(2,2,2-trifluoroethyl)-9-(trifluoromethyl)-7H-[1,4]oxazino[3,2-g]quinolin-7-one (Compound 132, Structure 23 of Scheme IV, where $R^1$, $R^6$, $R^7$=H, $R^2$=trifluoromethyl, $R^5$=Me). This compound was prepared according to General Method 15 (EXAMPLE 22) from (±)-2,3-dihydro-7-isopropoxy-2-(methoxymethyl)-1-(2,2,2-trifluoroethyl)-9-(trifluoromethyl)-1H-[1,4]oxazino[3,2-g]quinoline (8.3 mg, 0.019 mmol) in 0.1 mL conc. HCl and 0.5 mL acetic acid heated at 100° C. for 4.5 h to afford 6.0 mg (80%) of Compound 132, a yellow solid. Data for Compound 132: $R_f$ 0.48 (2:1 EtOAc:CH$_2$Cl$_2$); $^1$H NMR (400 MHz, CDCl$_3$) δ 12.09 (broad s, 1H), 7.06 (broad s, 1H), 6.94 (s, 1H), 6.92 (s, 1H), 4.43 (dd, 1H, J=10.9, 1.2), 4.14 (dd, 1H, J=10.9, 2.3), 3.93–4.12 (m, 2H), 3.63–3.70 (m, 1H), 3.44–3.56 (m, 2H), 3.36 (s, 3H).

EXAMPLE 31

(+)-1,2,3,6-Tetrahydro-2-(methoxymethyl)-1-(2,2,2-trifluoroethyl)-9-(trifluoromethyl)-7H-[1,4]oxazino[3,2-g]quinolin-7-one (Compound 133, Structure (+)-23 of Scheme IV, where $R^1$, $R^6$, $R^7$=H, $R^2$= Trifluoromethyl, $R^5$=Me) and (−)-1,2,3,6-Tetrahydro-2-(methoxymethyl)-1-(2,2,2-trifluoroethyl)-9-(trifluoromethyl)-7H-[1,4]oxazino[3,2-g]quinolin- 7-one (Compound 134, Structure (−)-23 of Scheme IV, where $R^1$, $R^6$, $R^7$=H, $R^2$= Trifluoromethyl, $R^5$=Me)

This compound was prepared according to General Method 9 (EXAMPLE 15) from Compound 132 (5 mg, 0.013 mmol) on a semiprep Chiralpak AD column (20×250 mm), hexanes/isopropanol (95:5), to afford 1.8 mg of Compound 133, a yellow solid, and 1.8 mg of Compound 134, a yellow solid. Data for Compound 133: HPLC (Chiralpak AD, 95:5 hexanes:isopropanol, 5.0 mL/min) $t_R$ 35.7 min; $[α]_D$=+40.0.

Data for Compound 134: HPLC (Chiralpak AD, 93:7 hexanes:isopropanol, 5.0 mL/min) $t_R$ 40.9 min; $[α]_D$=−43.8.

EXAMPLE 32

(±)-2-(Ethoxymethyl)-1,2,3,6-tetrahydro-1-(2,2,2-trifluoroethyl)-9-(trifluoromethyl)-7H-[1,4]oxazino[3,2-g]quinolin-7-one (Compound 135, Structure 23 of Scheme IV, where $R^1$, $R^6$, $R^7$=H, $R^2$= Trifluoromethyl, $R^5$=Et)

(±)-2-(Ethoxymethyl)-2,3-dihydro-7-isopropoxy-1-(2,2,2-trfluoroethyl)-9-(trifluoromethyl)-1H-[1,4]oxazino[3,2-g]quinoline (Structure 22 of Scheme IV, where $R^1$, $R^6$, $R^7$=H, $R^2$=trifluoromethyl, $R^5$ =Et). This compound was prepared according to General Method 16 (EXAMPLE 30) from (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline (EXAMPLE 28) (10 mg, 0.024 mmol), NaH (4.7 mg, 0.12 mmol) and iodoethane (17 mg, 0.12 mmol) in 1.0 mL THF to afford 9.8 mg (89%) of (±)-2-(ethoxymethyl)-2,3-dihydro-7-isopropoxy-1-(2,2,2-trifluoroethyl)-9-(trifluoromethyl)-1H-[1,4]oxazino[3,2-g]quinoline, a yellow oil, after flash chromatography (5:1 hexanes:EtOAc). Data for (±)-2-(ethoxymethyl)-2,3-dihydro-7-isopropoxy-1-(2,2,2-trifluoroethyl)-9-(trifluoromethyl)-1H-[1,4]oxazino[3,2-g]quinoline: $R_f$ 0.60 (5:1 hexanes: EtOAc); 1H NMR (400 MHz, CDCl$_3$) δ 7.29 (s, 1H), 7.14 (broad s, 1H), 7.00 (s, 1H), 5.48 (hept, 1H, J=6.2), 4.45 (dd, 1H, J=10.9, 1.5), 4.16 (dd, J=10.9, 2.5), 4.00–4.20 (m, 2H), 3.70 (broad t, 1H, J=6.8), 3.54–3.63 (m, 2H), 3.50 (q, 2H, J=6.9), 1.38 (d, 6H, J=6.2), 1.20 (t, 3H, J=7.0).

(±)-2-(Ethoxymethyl)-1,2,3,6-tetrahydro-1-(2,2,2-trifluoroethyl)-9-(trifluoromethyl)-7H-[1,4]oxazino[3,2-g]quinolin-7-one (Compound 135, Structure 23 of Scheme IV. where $R^1$, $R^6$, $R^7$=H, $R^2$=trifluoromethyl, $R^5$=Et). This compound was prepared according to General Method 15 (EXAMPLE 22) from 2-(ethoxymethyl)-2,3-dihydro-7-isopropoxy-1-(2,2,2-trifluoroethyl)-9-(trifluoromethyl)-1H-[1,4]oxazino[3,2-g]quinoline (9.8 mg, 0.022 mmol) in 0.1 mL conc. HCl and 0.5 mL acetic acid heated at 100° C. for 4 h to afford 6.0 mg (67%) of Compound 135, a yellow solid. Data for Compound 135: $R_f$ 0.25 (11.5:1 CH$_2$Cl$_2$:MeOH); $^1$H NMR (400 MHz, CDCl$_3$) δ 12.3 (broad s, 1H), 7.06 (broad s, 1H), 6.95 (s, 1H), 6.92 (s, 1H), 4.44 (broad d, 1H, J=11.0), 4.14 (dd, 1H, J=10.9, 2.2), 3.95–4.10 (m, 2H), 3.67 (broad t, 1H, J=6.9), 3.45–3.60 (m, 4H), 1.19 (t, 3H, J=7.0).

EXAMPLE 33

(±)-1,2,3,6-Tetrahydro-2-(1-propoxymethyl)-1-(2,2,2-trifluoroethyl)-9-(trifluoromethyl)-7H-[1,4]oxazino[3,2-g]quinolin-7-one (Compound 136, Structure 23 of Scheme IV, where $R^1$, $R^6$, $R^7$=H, $R^2$=Trifluoromethyl, $R^5$=n-Pr)

(±)-2,3-Dihydro-7-isopropoxy-2-(1-propoxymethyl)-1-(2,2,2-trifluoroethyl)-9-(trifluoromethyl)-1H-[1,4]oxazino[3,2-g]quinoline (Structure 22 of Scheme IV, where $R^1$, $R^6$, $R^7$=H, $R^2$=trifluoromethyl, $R^5$=n-Pr). This compound was prepared according to General Method 16 (EXAMPLE 30) from (±)-2,3-dihydro-2-(hydroxymethyl)-7-isopropoxy-1-(2,2,2-trifluoroethyl)-9-(trifluoromethyl)-1H-[1,4]oxazino[3,2-g]quinoline (EXAMPLE 28) (11 mg, 0.026 mmol), NaH (5.0 mg, 0.12 mmol) and 1-iodopropane (21 mg, 0.12 mmol) in 1.0 mL THF to afford 6 mg (50%) of (±)-2,3-dihydro-7-isopropoxy-2-(1-propoxymethyl)-1-(2,2,2-trifluoroethyl)-9-(trifluoromethyl)-1H-[1,4]oxazino[3,2-g]quinoline, a yellow oil, after flash chromatography (5:1 hexanes:EtOAc). Data for (±)-2,3-dihydro-7-isopropoxy-2-(1-propoxymethyl)-1-(2,2,2-trifluoroethyl)-9-(trifluoromethyl)-1H-[1,4]oxazino[3,2-g]quinoline: $R_f$ 0.57 (5:1 hexanes: EtOAc); $^1$H NMR (400 MHz, CDCl$_3$) δ 7.28 (s, 1H), 7.13 (broad s, 1H), 7.00 (s, 1H), 5.48 (hept, 1H, J=6.2), 4.44 (dd, 1H, J=10.9, 1.8), 4.17 (dd, 1H, J=11.0, 2.5), 4.00–4.20 (m, 2H), 3.71 (broad t, 1H, J=6.8), 3.54–3.64 (m, 2H), 3.40 (broad t, 2H, J=6.6), 1.52–1.62 (m, 2H), 1.38 (d, 6H, J=6.2), 0.91 (t, 3H, J=7.4).

(±)-1,2,3,6-Tetrahydro-2-(1-propoxymethyl)-1-(2,2,2-trifluoroethyl)-9-(trifluoromethyl)-7H-[1,4]oxazino[3,2-g]quinolin-7-one (Compound 136, Structure 23 of Scheme IV, where $R^1$, $R^6$, $R^7$=H, $R^2$=trifluoromethyl, $R^5$=n-Pr). This compound was prepared according to General Method 15 (EXAMPLE 22) from (±)-2,3-dihydro-7-isopropoxy-2-(1-propoxymethyl)-1-(2,2,2-trifluoroethyl)-9-(trifluoromethyl)-1H-[1,4]oxazino[3,2-g]quinoline (6.0 mg, 0.013 mmol) in 0.1 mL conc. HCl and 0.5 mL acetic acid heated at 100° C. for 4 h to afford 3.1 mg (56%) of Compound 136, a yellow solid. Data for Compound 136: $R_f$ 0.25 (11.5:1 CH$_2$Cl$_2$:MeOH); $^1$H NMR (400 MHz, CDCl$_3$) δ 11.75 (broad s, 1H), 7.06 (broad s, 1H), 6.92 (s, 1H), 6.90 (s, 1H), 4.44 (dd, 1H, J=10.9, 1.7), 4.14 (dd, 1H, J=10.9, 2.5), 3.94–4.08 (m, 2H), 3.65–3.70 (m, 1H), 3.47–3.59 (m, 2H), 3.39 (t, 2H, J=6.6), 1.50–1.62 (m, 2H), 0.91 (t, 3H).

EXAMPLE 34

1,6-Dihydro-1-(2,2,2-trifluoroethyl)-9-(trifluoromethyl)-3H-[1,4]oxazino[3,2-g]-quinolin-2,7-dione (Compound 137, Structure 24 of Scheme V, where $R^1$, $R^6$, $R^7$=H, $R^2$=Trifluoromethyl)

This Compound was prepared according to General Method 15 (EXAMPLE 22) from 7-isopropoxy-1-(2,2,2-trifluoroethyl)-9-(trifluoromethyl)-1H-[1,4]oxazino[3,2-g]quinolin-2(3H)-one (EXAMPLE 22) (72 mg, 0.18 mmol), in 0.5 mL conc. HCl and 2.0 mL acetic acid heated at 60° C. for 16 h to afford 42 mg (65%) of Compound 137, an off-white solid, after flash chromatography (92:8 CH$_2$Cl$_2$:MeOH). Data for Compound 137: $R_f$ 0.34 (92:8 CH$_2$Cl$_2$:MeOH); $^1$H NMR (400 MHz, acetone-d$_6$) δ 11.11 (broad s, 1H), 7.52 (s, 1H), 7.18 (s, 1H), 6.86 (s, 1H), 4.95 (q, 2H, J=9.0), 4.90 (s, 2H).

EXAMPLE 35

(±)-1,2,3,6-Tetrahydro-2-hydroxy-2-methyl-1-(2,2,2-trifluoroethyl)-9-(trifluoromethyl)-7H-[1,4]oxazino[3,2-g]quinolin-7-one (Compound 138, Structure 25 of Scheme V, where, $R^1$, $R^6$, $R^7$=H, $R^4$=Me, $R^2$=Trifluoromethyl)

To a solution of Compound 137 (EXAMPLE 34) (0.012 g, 0.033 mmol) in 1 mL THF and 0.1 mL HMPA and was added MeLi solution (1.4 M in ether, 0.12 mL, 0.16 mmol) at −78° C. for 0.5 h. The reaction was quenched with 20 mL phosphate buffer (pH=7) and extracted with EtOAc (2×20 mL). The organic fractions were dried over Na$_2$SO$_4$, filtered, and concentrated. Flash chromatography (5% methanol/CH$_2$Cl$_2$) gave 8 mg (62% yield) of Compound 138, a yellow solid. $^1$H NMR (400MHz, acetone-d$_6$) 10.92 (br s, 1H), 7.13 (br s, 1H), 6.96 (s, 1H), 6.75 (s, 1H), 4.34–4.24 (m, 1H), 4.23 (d, 1H, J=11.6), 4.19 (d, 1H, J=10.8), 4.07–3.96 (m, 1H), 1.49 (s, 3H).

EXAMPLE 36

1,6-Dihydro-3-methyl-1-(2,2,2-trifluoroethyl)-9-(trifluoromethyl)-3H-[1,4]oxazino[3,2-g]-quinolin-2,7-dione (Compound 139, Structure 24 of Scheme V, where $R^1$, $R^6$=H, $R^2$=Trifluoromethyl, $R^7$=Me) A mixture of 7-isopropoxy-1-(2,2,2-trifluoroethyl)-9-(trifluoromethyl)-1H-[1,4]oxazino[3,2-g]quinolin-2(3H)-one (EXAMPLE 22) (7.0 mg, 0.017 mmol) in 0.5 mL 57% HI was heated to 65° C. for 16 h, whereupon it was poured onto cold NaHCO$_3$ (25 mL). The mixture was extracted with EtOAc (25 mL), and the organic layer was washed sequentially with 1 M phosphate buffer (10 mL) and brine (10 mL), dried over MgSO$_4$, filtered, and concentrated. Flash chromatography (92:8 CH$_2$Cl$_2$:MeOH) afforded 1.4 mg (22%) of Compound 139, an off-white solid. Data for Compound 139: $R_f$ 0.37 (92:8 CH$_2$Cl$_2$:MeOH); $^1$H NMR (400 MHz, acetone-d$_6$) δ 11.09 (broad s, 1H), 7.52 (s, 1H), 7.19 (s, 1H), 6.86 (s, 1H), 4.80–5.05 (m, 3H), 1.59 (d, 3H, J=6.7).

EXAMPLE 37

1,2,3,6-Tetrahydro-1-(2,2,2-trifluoroethyl)-9-(trifluoromethyl)-2-thioxo-7H-[1,4]oxazino[3,2-g]quinolin-7-one (Compound 140, Structure 27 of Scheme V, where $R^1$, $R^6$, $R^7$=H, $R^2$=Trifluoromethyl)

7-Isopropoxy-1-(2,2,2-trifluoroethyl)-9-(trifluoromethyl)-1H-[1,4]oxazino[3,2-g]quinolin-2(3H)-thione (Structure 26 of Scheme V, where $R^1$, $R^6$, $R^7$=H, $R^2$=trifluoromethyl). A mixture of 7-isopropoxy-1-(2,2,2-trifluoroethyl)-9-(trifluoromethyl)-1H-[1,4]oxazino[3,2-g]quinolin-2(3H)-one (EXAMPLE 22) (48.4 mg, 0.119 mmol) and Lawesson's reagent (0.144 g, 0.356 mmol) in 2.4 mL toluene was heated at reflux for 6 h, whereupon the mixture was partitioned between EtOAc (40 mL) and water (20 mL). The aqueous layer was extracted with EtOAc (20 mL), and the combined organic layers were washed with brine (20 mL), dried over MgSO4, filtered, and concentrated. Flash chromatography (9:1 hexanes:EtOAc) afforded 41 mg of 7-isopropoxy-1-(2,2,2-trifluoroethyl)-9-(trifluoromethyl)-1H-[1,4]oxazino[3,2-g]quinolin-2(3H)-thione, a yellow oil. Data for 7-isopropoxy-1-(2,2,2-trifluoroethyl)-9-(trifluoromethyl)-1H-[1,4]oxazino[3,2-g]quinolin-2 (3H)-thione: $R_f$ 0.36 (9:1 hexanes:EtOAc); $^1$H NMR (400 MHz, CDCl$_3$) δ 7.72 (broad s, 1H), 7.48 (s, 1H), 7.13 (s, 1H), 5.54 (hept, 1H, J=6.2), 5.32–5.42 (m, 2H), 5.05 (s, 2H), 1.41 (d, 6H, J=6.2).

1,2,3,6-Tetrahydro-1-(2,2,2-trifluoroethyl)-9-(trifluoromethyl)-2-thioxo-7H-[1,4]oxazino[3,2-g]quinolin-7-one (Compound 140, Structure 27 of Scheme V, where $R^1$, $R^6$, $R^7$=H, $R^2$=Trifluoromethyl). To a solution of 7-isopropoxy-1-(2,2,2-trifluoroethyl)-9-(trifluoromethyl)-

1H-[1,4]oxazino[3,2-g]quinolin-2(3H)-thione (30 mg, 0.071 mmol) in 1.4 mL CH$_2$Cl$_2$ was added BCl$_3$ (1 M in CH$_2$Cl$_2$, 1.2 mL, 1.2 mmol). After 8 h, the mixture was quenched with saturated NaHCO$_3$ (15 mL) and extracted with EtOAc (2×15 mL). The organic layers were washed with brine (15 mL), dried over MgSO$_4$, filtered, and concentrated. Flash chromatography (3:2 CH$_2$Cl$_2$:EtOAc) afforded 17 mg (63%) of Compound 140, an off-white solid. Data for Compound 140: R$_f$ 0.36 (3:2 CH$_2$Cl$_2$:EtOAc); $^1$H NMR (400 MHz, acetone-d$_6$) δ 11.22 (broad s, 1H), 7.72 (broad s, 1H), 7.19 (s, 1H), 6.90 (s, 1H), 5.62–5.75 (m, 2H), 5.16 (s, 2H).

EXAMPLE 38

(±)-1,2,3,6-Tetrahydro-2-methyl-9-(trifluoromethyl)-7H-[1, 4]oxazino[3,2-g]quinolin-7-one (Compound 141, Structure 30 of Scheme VI, where R$^4$=Me)

(2-Methoxy-4-nitrophenyl)-(4-methoxybenzyl)amine. This compound was prepared according to General Method 3 (EXAMPLE 1) from 2-amino-5-nitroanisole (1.00 g, 5.95 mmol), p-anisaldehyde (1.62 g, 11.9 mmol), NaBH$_3$CN (0.373 g, 5.95 mmol) in 100 mL acetic acid to afford 1.25 g (75%) of (2-methoxy-4-nitrophenyl)-(4-methoxybenzyl) amine, an orange solid, after washing the crude product with 4:1 hexanes:EtOAc. Data for (2-methoxy-4-nitrophenyl)-(4-methoxybenzyl)amine: R$_f$ 0.80 (3:2 EtOAc:hexanes); $^1$NMR (500 MHz, CDCl$_3$) δ 7.88 (dd, 1H, J=8.8, 2.4), 7.64 (d, 1H, J=2.4), 7.22–7.28 (m, 2H), 6.85–6.90 (m, 2H), 6.51 (d, 1H, J=9.0), 5.31 (broad s, 1H), 4.38 (d, 2H, J=5.4), 3.93 (s, 3H), 3.82 (s, 3H).

(4-Amino-2-methoxylhenyl)-(4-methoxybenzyl)amine (Structure 13 of Scheme III, where R$^x$=4-anisyl). This compound was prepared by General Method 10 (EXAMPLE 19) from (2-methoxy-4-nitrophenyl)-(4-methoxybenzyl) amine (1.92 g, 6.65 mmol), zinc dust (1.87 g, 28.6 mmol), and calcium chloride dihydrate (2.10 g, 14.3 mmol) in 350 mL 95:5 EtOH:water to afford 1.23 g (70%) of (4-amino-2-methoxyphenyl)-(4-methoxybenzyl)amine, a light purple solid, after flash chromatography (CH$_2$Cl$_2$:MeOH 19:1). Data for (4-amino-2-methoxyphenyl)-(4-methoxybenzyl) amine: R$_f$ 0.80 (19:1 CH$_2$Cl$_2$:MeOH); $^1$H NMR (400 MHz, CDCl$_3$) δ 7.30 (d, 2H, J=8.6), 6.87 (d, 2H, J=8.6), 6.47 (d, 1H, J=8.1), 6.28 (d, 1H, J=2.4), 6.23 (dd, 1H, J=8.1, 2.4), 4.20 (s, 2H), 4.10 (v broad s, 1H), 3.80 (s, 3H), 3.79 (s, 3H), 3.31 (broad s, 2H).

6-Amino-7-methoxy-4-(trifluoromethyl)-1H-quinolin-2-one. This compound was prepared according to General Method 11 (EXAMPLE 22) from (4-amino-2-methoxyphenyl)-(4-methoxybenzyl)amine (1.23 g, 4.76 mmol) and ethyl 4,4,4-trifluoroacetoacetate (1.05 g, 5.71 mmol) in 60 mL benzene followed by treatment with 10 mL concentrated H$_2$SO$_4$ to afford 0.734 (60%) of 6-amino-7-methoxy-4-(trifluoromethyl)-1H-quinolin-2-one, a yellow solid, after rinsing with MeOH:ether:hexanes. Data for 6-amino-7-methoxy-4-(trifluoromethyl)-1H-quinolin-2-one: R$_f$ 0.28 (19:1 CH$_2$Cl$_2$:MeOH); $^1$H NMR (500 MHz, CDCl$_3$) δ 12.2 (v broad s, 1H), 7.06 (broad s, 1H), 6.93 (s, 1H), 6.79 (s, 1H), 4.01 (s, 3H), 3.94 (broad s, 2H).

6-Amino-2-isopropoxy-7-methoxy-4-(trifluoromethyl) quinoline. This compound was prepared according to General Method 12 (EXAMPLE 22) from 6-amino-7-methoxy-4-(trifluoromethyl)-1H-quinolin-2-one (500 mg, 1.9 mmol), CsF (1.18 g, 7.7 mmol), isopropyl iodide (1.31 g, 7.7 mmol) in 8 mL DMF to afford 308 mg (53%) of 6-amino-2-isopropyloxy-7-methoxy-4-(trifluoromethyl)quinoline, a light yellow oil, and 190 mg (29%) of 2-isopropyloxy-7-methoxy-6N-(isopropyl)amino-4-(trifluoromethyl) quinoline, after flash chromatography (7:3 hexanes:EtOAc). Data for 6-amino-2-isopropyloxy-7-methoxy-4-(trifluoromethyl)quinoline: R$_f$ 0.51 (4:1 hexanes:EtOAc); $^1$H NMR (500 MHz, CDCl$_3$) δ 7.18 (s, 1H), 7.13 (broad s, 1H), 7.00 (s, 1H), 5.48 (hept, 1H, J=6.3), 4.11 (broad s, 2H), 4.01 (s, 3H), 1.40 (d, 6H, J=6.3).

6-Amino-7-hydroxy-2-isopropyloxy-4-(trifluoromethyl) quinoline (Structure 28 of Scheme VI). To a suspension of sodium hydride (60% mineral oil dispersion, 180 mg, 4.6 mmol, rinsed with hexanes) in 3.5 mL DMF was added thiophenol (550 mg, 5.0 mmol) at 0° C., whereupon a solution of 6-amino-2-isopropyloxy-7-methoxy-4-(trifluoromethyl)quinoline (200 mg, 0.67 mmol) in 2 mL DMF was added. The mixture was heated at 110° C. for 6 h, then poured into ice, and the pH was adjusted to 5 by the addition of 2N NaHSO$_4$. The mixture was extracted with EtOAc (2×30 mL), washed sequentially with water (30 mL) and brine (30 mL), dried over Na$_2$SO$_4$, filtered, and concentrated. Flash chromatography (4:1 hexanes:EtOAc) afforded 147 mg (77%) of 6-amino-2-isopropyloxy-7-methoxy-4-(trifluoromethyl)quinoline, a tan solid. Data for 6-amino-2-isopropyloxy-7-methoxy-4-(trifluoromethyl) quinoline: R$_f$ 0.14 (4:1 hexanes:EtOAc); $^1$H NMR (500 MHz, CDCl$_3$) δ 7.19 (broad s, 1H), 7.16 (s, 1H), 6.99 (s, 1H), 5.60 (v. broad s, 1H), 5.45 (hept, 1H, J=6.2), 4.00 (v. broad s, 2H), 1.38 (d, 6H, J=6.3).

General Method 17. Alkylation of an α-halo-ketone to an o-aminophenol and subsequent reductive cyclization to a 1,4-oxazine. derivative. To a solution of 2-amino-5-nitrophenol (1.0 equiv) in acetone (0.6 mL/mmol) was added an a-halo ketone (1.1 equiv) and K$_2$CO$_3$ (1.1 equiv) at 0° C. under N$_2$. The reaction mixture was allowed to warm to room temperature and stirred for 6–8 hours. The crude reaction mixture was then evaporated under reduced pressure and washed with water (3×100 mL) and the resulting solid was dried under high vacuum. To this crude solid (1.0 equiv) in trifluoroacetic acid (0.26 M) was added portionwise NaBH$_3$CN (1.0 equiv) and stirred at room temperature under N$_2$ overnight. The resulting mixture was poured over ice and neutralized with 6M NaOH to pH 7.0, extracted with EtOAc (3×30 mL/mmol), washed with brine (50 mL/mmol). The organic solution was dried (MgSO$_4$) and concentrated under reduced pressure. Purification by flash chromatography (silica gel, 19:1, CH$_2$Cl$_2$/MeOH) afforded the desired 1,4-oxazine derivative.

(±)-2,3-Dihydro-7-isopropoxy-2-methyl-9-(trifluoromethyl)-1H-[1,4]oxazino[3,2-g]quinoline (Structure 29 of Scheme VI, where R$^4$=Me). This compound was prepared by General Method 17 from 6-amino-3,4-dihydro-7-hydroxy-2-isopropoxy-4-(trifluoromethyl) quinoline (15 mg, 0.05 mmol), chloroacetone (5.0 μL, 0.06 mmol), and K$_2$CO$_3$ (8.0 mg, 0.06 mmol) to afford 13 mg of crude solid. The crude solid (13 mg, 0.04 mmol), NaBH$_3$CN (2.5 mg, 0.04 mmol) and trifluoroacetic acid afforded 10.0 mg (77%) of (±)-2,3-dihydro-7-isopropoxy-2-methyl-9-(trifluoromethyl)-1H-[1,4]oxazino[3,2-g]quinoline. Data for (±)-2,3-dihydro-7-isopropoxy-2-methyl-9-(trifluoromethyl)-1H-[1,4]oxazino[3,2-g]quinoline: R$_f$ 0.84 (2:3, EtOAc:hexanes); $^1$H NMR (400 MHz, CDCl$_3$) δ 7.24 (s, 1H), 7.02 (d, 1H, J=2.0), 6.97 (s, 1H), 5.48 (m, 1H), 4.30 (dd, 1H, J=10.6, 2.7), 4.12 (br s, 1H), 3.88 (dd, 1H, J=10.7, 8.3), 3.64 (m, 1H), 1.38 (d, 6H, J=6.3), 1.24 (d, 3H, J=6.8).

(±)-1,2,3,6-Tetrahydro-2-methyl-9-(trifluoromethyl)-7H-[1,4]oxazino[3,2-g]quinolin-7-one (Compound 141, Structure 30 of Scheme VI, where R$^4$=Me). This compound was prepared by General Method 15 (EXAMPLE 22) from (±)-2,3-dihydro-7-isopropoxy-2-methyl-9-(trifluoromethyl)-1H-[1,4]oxazino[3,2-g]quinoline (10.0 mg, 0.03 mmol) in 0.2 mL HCl and 1 mL HOAc heated at 80° C. for 6 h to afford 7.0 mg (77%) of Compound 141, a yellow solid, after purification by flash chromatography (3:2, EtOAc/hexanes). Data for Compound 141: $R_f$ 0.31 (3:2, EtOAc:hexanes); $^1$H NMR (400 MHz, CDCl$_3$) δ 12.14 (br s, 1H), 6.94 (s, 1H), 6.89 (s, 2H), 4.29 (dd, 1H, J=8.3, 2.0), 3.94 (br s, 1H), 3.86 (dd, 1H, J=10.5, 8.5), 3.58 (m, 1H), 1.23 (d, 3H, J=6.3).

EXAMPLE 39

(±)-1-Cyclopropylmethyl-1,2,3,6-tetrahydro-2-methyl-9-(trifluoromethyl)-7H-[1,4]oxazino[3,2-g]quinolin-7-one (Compound 142, Structure 31 of Scheme VI, where $R^4$=Me, $R^x$=Cyclopropyl)

This compound was prepared by General Method 3 (EXAMPLE 1) from Compound 141 (7.0 mg, 0.02 mmol), cyclopropane carboxaldehyde (17.3 mg, 0.2 mmol) and NaBH$_3$CN (7.7 mg, 0.1 mmol) to afford 6.6 mg (82%) of Compound 142. Data for Compound 142: $R_f$ 0.36 (3:2, EtOAc:hexanes); $^1$H NMR (400 MHz, CDCl$_3$) δ 11.58 (br s, 1H), 6.98 (s, 1H), 6.89 (s, 1H), 6.85 (s, 1H), 4.26 (dd, 1H, J=10.7, 2.4), 4.14 (dd, 1H, J=10.5, 2.7), 3.72 (m, 1H), 3.32 (dd, 1H, J=14.6, 5.8), 3.02 (dd, 1H, J=14.6, 4.3), 1.22 (d, 3H, J=6.3), 1.05 (m, 1H), 0.63 (m, 2H), 0.3 (m, 2H).

EXAMPLE 40

(±)-2-Ethyl-1,2,3,6-tetrahydro-9-(trifluoromethyl)-7H-[1,4 oxazino[3,2-g]quinolin-7-one (Compound 143, Structure 30 of Scheme VI, where $R^4$=Et)

(±)-2-Ethyl-2,3-dihydro-7-isopropoxy-9-(trifluoromethyl)-1H-[1,4]oxazino[3,2-g]quinoline (Structure 29 of Scheme VI, where $R^4$=Et). This compound was prepared by General Method 17 (EXAMPLE 38) from 6-amino-7-hydroxy-2-isopropoxy-4-(trifluoromethyl)quinoline (EXAMPLE 36) (15 mg, 0.05 mmol), 1-bromo-2-butanone (6.0 μL, 0.06 mmol), and K$_2$CO$_3$ (8.0 mg, 0.06 mmol) to afford 16 mg of crude solid. The crude solid (16 mg, 0.05 mmol), NaBH$_3$CN (3.0 mg, 0.05 mmol) and trifluoroacetic acid afforded 13 mg (81%) of (±)-2-ethyl-2,3-dihydro-7-isopropoxy-9-(trifluoromethyl)-1H-[1,4]oxazino[3,2-g]quinoline. Data for (±)-2-ethyl-2,3-dihydro-7-isopropoxy-9-(trifluoromethyl)-1H-[1,4]oxazino[3,2-g] quinoline: $R_f$ 0.78 (2:3, EtOAc:hexanes) $^1$H NMR (400 MHz, CDCl$_3$) δ 7.22 (s, 1H), 7.01 (s, 1H), 6.96 (s, 1H), 5.47 (m, 1H), 4.33 (dd, 1H, J=10.6, 2.5), 4.20 (br s, 1H), 3.95 (dd, 1H, J=10.6, 7.9), 3.40 (m, 1H), 1.58 (m, 2H), 1.37 (d, 6H, J=6.1), 1.06 (t, 3H, J=7.5).

(±)-2-Ethyl-1,2,3,6-tetrahydro-9-(trifluoromethyl)-7H-[1,4]oxazino[3,2-g]quinolin-7-one (Compound 143, Structure 30 of Scheme VI, where $R^4$=Et). This compound was prepared by General Method 15 (EXAMPLE 22) from (±)-2-ethyl-2,3-dihydro-7-isopropoxy-9-(trifluoromethyl)-1H-[1,4]oxazino[3,2-g]quinoline (13.0 mg, 0.04 mmol) and was purified by flash chromatography (3:2, EtOAc/hexanes) to yield 8.1 mg (72%) of Compound 143. Data Compound 143: $R_f$ 0.34 (3:2, EtOAc:hexanes); $^1$H NMR (400 MHz, CDCl$_3$) δ 12.11 (br s, 1H), 6.95 (s, 1H), 6.89 (s, 1H), 6.88 (s, 1H), 4.34 (dd, 1H J=10.2, 2.5), 4.02 (br s, 1H), 3.93 (dd, 1H, J=10.7, 7.8), 3.35 (m, 1H), 1.56 (m, 2H), 1.06 (t, 3H, J=7.5).

EXAMPLE 41

(±)-1-(Cyclopropylmethyl)-2-ethyl-1,2,3,6-tetrahydro-9-(trifluoromethyl)-7H-[1,4]oxazino[3,2-aquinolin-7-one (Compound 144, Structure 31 of Scheme VI, where $R^4$=Et, $R^x$=Cyclopropyl)

This compound was prepared by General Method 3 (EXAMPLE 1) from Compound 143 (8.1 mg, 0.03 mmol), cyclopropane carboxaldehyde (19.1 mg, 0.2 mmol) and NaBH$_3$CN (8.5 mg, 0.1 mmol) and purified by HPLC (75:25 MeOH:water, semi-prep ODS column @ 3 mL/min) to afford 4.0 mg (44%) of Compound 144. Data for Compound 144: $R_f$ 0.30 (3:2, EtOAc:hexanes); $^1$H NMR (400 MHz, CDCl$_3$) δ 11.72 (br s, 1H), 6.96 (s, 1H), 6.89 (s, 1H), 6.85 (s, 1H), 4.34 (dd, 1H, J=10.7, 1.9), 4.15 (dd, 1H, J=10.7, 2.4), 3.39 (m, 2H), 3.0 (m, 1H), 1.59 (m, 2H), 1.06 (m, 1H), 0.98 (t, 3H, J=7.8), 0.62 (m, 2H), 0.29 (m, 2H).

EXAMPLE 41A 1,2,3,6-Tetrahydro-1-isopropyl-9-(trifluoromethyl)-7H-[1,4]oxazino[3,2-g]quinolin-7-one (Compound 144A, Structure 31D of Scheme VIA, where $R^1$=$R^4$=$R^6$=H, $R^2$=Trifluoromethyl, $R^{13}$=Isopropyl)

2-Isopropyloxy-6-isopropylamino-7-methoxy-4-(trifluoromethyl)quinoline (Structure 31B of Scheme VIA, where $R^1$=H, $R^2$=trifluoromethyl, $R^{13}$=isopropyl, $R^A$=isopropyloxy). A suspension of 6-amino-7-methoxy-4-trifluoromethyl-1H-quinolin-2-one (0.50 g, 1.9 mmol), CsF (1.18 g, 7.7 mmol) and isopropyl iodide (1.31 g (7.7 mmol) in 8 mL DMF was stirred at 30° C. for 18 h, whereupon the mixture was quenched with pH 7 phosphate buffer and extracted with EtOAc (2×). The combined organic layers were washed sequentially with water (2×) and brine, dried over Na$_2$SO$_4$, filtered and concentrated. Flash chromatography (7:3, hexanes:EtOAc) afforded 0.19 g (32%) of 2-isopropyloxy-6-isopropylamino-7-methoxy-4-(trifluoromethyl)quinoline, an oil. Data for Compound 2-isopropyloxy-6-isopropylamino-7-methoxy-4-(trifluoromethyl)quinoline: $^1$H NMR (400 MHz, CDCl$_3$) δ 7.13 (s, 1H), 6.99 (s, 1H), 6.87 (s, 1H), 5.47 (sept, 1H, J=6.2), 4.37 (d, 1H, J=7.4), 3.99 (s, 3H), 3.70–3.80 (m, 1H), 1.39 (d, 6H, J=6.2), 1.30 (d, 6H, J=6.2).

2-Isopropyloxy-7-hydroxy-6-isopropylamino-4-(trifluoromethyl)quinoline (Structure 31C of Scheme VIA, where $R^1$=H, $R^2$=trifluoromethyl, $R^{13}$=isopropyl, $R^A$=isopropyloxy). A solution of 2-isopropyloxy-6-isopropylamino-7-methoxy-4-(trifluoromethyl)quinoline (0.10 g, 0.30 mmol), thiophenol (0.24 g, 2.2 mmol), and NaH (60% dispersion in mineral oil, 78 mg, 2.0 mmol) in 2 mL DMF was heated at 110° C. for 5 h, whereupon the mixture was poured over ice, and adjusted to pH 5 with 2M NaHSO$_4$. The aqueous layer was extracted with EtOAc (2×), and the combined organic layers were washed sequentially with water (2×) and brine, dried over MgSO$_4$, filtered and concentrated. Flash chromatography (4:1 hexanes:EtOAc) afforded 90 mg (95%) of 2-isopropyloxy-7-hydroxy-6-isopropylamino-4-(trifluoromethyl)quinoline, a yellow oil. Data for 2-isopropyloxy-7-hydroxy-6-isopropylamino-4-(trifluoromethyl)quinoline: $^1$H NMR (400 MHz, CDCl$_3$) δ 7.16 (s, 1H), 6.98 (s, 1H), 6.92 (s, 1H), 5.37 (sept, 1H, J=6.2), 3.70 (sept, 1H, J=6.3), 1.35 (d, 6H, J=6.2), 1.29 (d, 6H, J=6.3).

1,2,3,6-Tetrahydro-1-isopropyl-9-(trifluoromethyl)-7H-[1,4]oxazino[3,2-g]quinolin-7-one (Compound 144A, Structure 31D of Scheme VIA, where $R^1$=$R^4$=$R^6$=H, $R^2$=trifluoromethyl, $R^{13}$=isopropyl). A suspension of 2-isopropyloxy-7-hydroxy-6-isopropylamino-4-(trifluoromethyl)quinoline (60 mg, 0.18 mmol), 1,2-dibromoethane (62 mg, 0.33 mmol) and K$_2$CO$_3$ (47 mg, 0.34 mmol) in 3 mL acetone and 1.5 mL water was heated at reflux for 18 h, whereupon the mixture was partitioned between water and EtOAc. The aqueous layer was extracted with EtOAc, and the combined organic layers were washed with brine, dried over Na$_2$SO$_4$, filtered, and concentrated.

Flash chromatography (4:1 hexanes:EtOAc) afforded 27 mg of a yellow oil which was carried on directly by treatment with 0.05 mL concentrated HCl and 0.5 mL HOAc and heated at 0° C. for 4 h, whereupon the reaction was poured over ice and adjusted to pH 7 with 25% aqueous NaOH. The aqueous layer was extracted with EtOAc (3×), and the combined organic layers were washed with brine, dried over $Na_2SO_4$, filtered, and concentrated. Flash chromatography (3:2 hexanes:EtOAc) afforded 10 mg (30%) of Compound 144A, a yellow solid. Data for Compound 144A: $^1$H NMR (500 MHz, $CDCl_3$) δ 12.0 (broad s, 1H), 6.99 (s, 1H), 6.87 (s, 1H), 6.80 (s, 1H), 4.34 (t, 2H, J=4.6, 2H), 4.08 (sept, 1H, J=6.3), 3,26 (t, 2H, J=4.6), 1.22 (d, 6H, J=6.3).

EXAMPLE 42

(±)-2-Ethyl-1,2,3 6-tetrahydro-1-(2,2,2-trifluoroethyl)-9-(trifluoromethyl)-7H-[1,4]oxazino[3,2-g]quinolin-7-one (Compound 145, Structure 35 of Scheme VII, where $R^1$=H, $R^2$=$CF_3$, $R^4$=Et, $R^x$=Trifluoromethyl)

(±)-3-Ethyl-3,4-dihydro-7-nitro-2H-1,4-benzoxazine (Structure 32 of Scheme VII, where $R^4$=Et). This compound was prepared by General Method 17 (EXAMPLE 38) from 2-amino-5-nitrophenol (2.0 g, 13.0 mmol), 1-bromo-2-butanone (1.45 mL, 14.2 mmol), and $K_2CO_3$ (1.97 g, 14.2 mmol) to afford 3.0 g of crude solid. The crude solid (3.0 g, 13.3 mmol), $NaBH_3CN$ (837 mg, 13.3 mmol) and trifluoroacetic acid afforded 1.96 g (70%) (±)-3-ethyl-3,4-dihydro-7-nitro-2H-1,4-benzoxazine after purification by flash chromatography (19:1, $CH_2Cl_2$/MeOH). Data for (±)-3-ethyl-3,4-dihydro-7-nitro-2H-1,4-benzoxazine: $R_f$ 0.57 (2:3 EtOAc:hexanes); $^1$H NMR (500 MHz, $CDCl_3$) δ 7.74 (dd, 1H, J=8.7, 2.6), 7.69 (d, 1H, J=2.6), 6.51 (d, 1H, J=8.8), 4.59 (br s, 1H), 4.25 (dd, 1H, J=10.7, 3,2), 3.86 (dd, 1H, J=10.7, 7.1), 3.43 (m, 1H), 1.6 (m, 2H), 1.05 (t, 3H, J=7.4).

(±)-3-Ethyl-3,4-dihydro-7-nitro-4-(2,2,2-trifluoroethyl)-2H-1,4-benzoxazine (Structure 33 of Scheme VII, where $R^4$=Et, $R^x$=$CF_3$). This compound was prepared by General Method 7 (EXAMPLE 5) from (±)-3-ethyl-3,4-dihydro-7-nitro-2H-1,4-benzoxazine (200 mg, 0.96 mmol), 2,2,2-trifluoroacetaldehyde monohydrate (1.12 g, 9.6 mmol) and $NaBH_3CN$ (292 mg, 4.6 mmol) to afford 100 mg (36%) of 3-ethyl-3,4-dihydro-7-nitro-4-(2,2,2-trifluoroethyl)-2H-1,4-benzoxazine, a yellow solid. Data for (±)-3-ethyl-3,4-dihydro-7-nitro-4-(2,2,2-trifluoroethyl)-2H-1,4-benzoxazine: $R_f$ 0.69 (2:3 EtOAc:hexanes); $^1$H NMR (500 MHz, $CDCl_3$) δ 7.80 (dd, 1H, J=8.9, 2.6), 7.71 (d, 1H, J=2.6), 6.72 (d, 1H, J=9.0), 4.34 (dd, 1H, J=10.9, 1.4), 4.19–4.05 (m, 1H), 4.02 (dd, 1H, J=11.0, 2.3), 3.87–3.72 (m, 1H), 1.72–1.62 (m, 2H), 1.00 (t, 34H, J=7.4).

(±)-7-Amino-3-ethyl-3,4-dihydro-4-[2,2,2 (trifluoroethyl)]-2H-1,4-benzoxazine (Structure 34 of Scheme VII, where $R^4$=Et, $R^x$=$CF_3$). This compound was prepared by General Method 4 (EXAMPLE 1) from (±)-3-ethyl-3,4-dihydro-7-nitro-4-(2,2,2-trifluoroethyl)-2H-1,4-benzoxazine (100 mg, 0.34 mmol) and purified by flash chromatography (EtOAc:hexanes, 3:2) to afford 83 mg (93%) of (±)-7-amino-3-ethyl-3,4-dihydro-4-(2,2,2-trifluoroethyl)-2H-1,4-benzoxazine. Data for (±)-7-amino-3-ethyl-3,4-dihydro-4-[2,2,2 (trifluoroethyl)]-2H-1,4-benzoxazine: $R_f$ 0.63 (3:2 EtOAc:hexanes); $^1$H NMR (400 MHz, $CDCl_3$) δ 6.64 (d, 1H, J=8.3), 6.28 (dd, 1H, J=8.5, 2.7), 6.23 (d, 1H, J=2.4), 4.15 (d, 1H, J=10.7), 3.96 (dd, 1H, J=10.7, 2.4), 3.65 (m, 1H), 3.40 (br s, 1H), 3.03 (m, 1H), 1.53 (m, 2H), 0.96 (t, 3H, J=7.6).

(±)-2-Ethyl-1,2,3,6-tetrahydro-1-(2,2,2-trifluoroethyl)-9-(trifluoromethyl)-7H-[1,4]oxazino[3,2-g]quinolin-7-one (Compound 145, Structure 35 of Scheme VII, where $R^1$=H, $R^2$=$CF_3$, $R^4$=Et, $R^x$=trifluoromethyl). This compound was prepared by General Method 5 (EXAMPLE 1) from (±)-7-amino-3-ethyl-3,4-dihydro-4-(2,2,2-trifluoroethyl)-2H-1,4-benzoxazine (83 mg, 0.32 mmol) and ethyl 4,4,4-trifluoroacetoacetate (70 mg, 0.38 mmol) and purified by flash chromatography (3:2 EtOAc:hexanes) to yield 54 mg (44%) of Compound 145. Data for Compound 145: $R_f$ 0.36 (3:2 EtOAc:hexanes); 1H NMR (500 MHz, $CDCl_3$) δ 11.67 (br s, 1h), 7.07 (s, 1H), 6.91 (s, 1H), 6.89 (s, 1H), 4.35 (dd, 1H, J=10.7. 2.0), 4.15 (dd, 1H, J=10.7, 2.4), 4.04–3.97 (m, 1H), 3.75 (m, 1H), 3,28 (m, 1H), 1.64 (m, 2H), 1.00 (t, 3H, J=7.3).

EXAMPLE 43

(±)-1,2-Diethyl-1,2,3,6-tetrahydro-9-(trifluoromethyl)-7H-[1,4]oxazino[3,2-g]quinolin-7-one (Compound 146, Structure 35 of Scheme VII, where $R^1$=H, $R^2$=$CF_3$, $R^4$=Et, $R^x$=$CH_3$)

(±)-3,4-Diethyl-3,4-dihydro-7-nitro-2H-1,4-benzoxazine (Structure 33 of Scheme VII, where $R^4$=Et, $R^x$=$CH_3$). This compound was prepared by General Method 3 (EXAMPLE 1) from 3-ethyl-3,4-dihydro-7-nitro-2H-1,4-benzoxazine (EXAMPLE 42) (200 mg, 0.96 mmol), acetaldehyde (424 mg, 9.6 mmol) and $NaBH_3CN$ (293 mg, 4.6 mmol) to afford 170 mg (75%) of (±)-3,4-diethyl-3,4-dihydro-7-nitro-2H-1, 4-benzoxazine, a yellow solid. Data for (±)-3,4-diethyl-3,4-dihydro-7-nitro-2H-1,4-benzoxazine: $R_f$ 0.80 (3:2 EtOAc:hexanes); $^1$H NMR (500 MHz, $CDCl_3$) δ 7.80 (dd, 1H, J=8.9, 2.6), 7.66 (d, 1H, J=2.6), 6.55 (d, 1H, J=9.2), 4.07 (dd, ABX, 1H, J=10.7, 2.5), 3.96 (dd, ABX, 1H, J=10.7, 2.6), 3.60 (m, 1H), 3.55–3.35 (m, 2H), 1.29 (d, 3H, J=6.6), 1.24 (t, 3H, J=7.0).

(±)-7-Amino-3,4-diethyl-3,4-dihydro-2H-1,4-benzoxazine (Structure 34 of Scheme VII, where $R^4$=Et, $R^x$=$CH_3$). This compound was prepared by General Method 4 (EXAMPLE 1) from (±)-3,4-diethyl-3,4-dihydro-7-nitro-2H-1,4-benzoxazine (170 mg, 0.72 mmol) and purified by flash chromatography (EtOAc:hexanes, 3:2) to afford 39 mg (25%) of (±)-7-amino-3,4-diethyl-3,4-dihydro-2H-1,4-benzoxazine. Data for (±)-7-amino-3,4-diethyl-3,4-dihydro-2H-1,4-benzoxazine: (3:2 EtOAc:hexanes); $^1$H NMR (500 MHz, $CDCl_3$) δ 6.57 (d, 1H, J=8.3), 6.26–6.20 (m, 2H), 4.12 (dd, ABX, 1H, J=10.3, 2.4), 3.92 (dd, ABX, 1H, J=10.7, 2.4), 3.32–3,28 (m, 3H), 3.15–3.10 (m, 1H), 3.01 (m, 1H), 1.57–1.48 (m, 2H), 1.15 (t, 3H, J=7.0), 0.94 (t, 3H, J=7.3).

(±)-1,2-Diethyl-1,2,3,6-tetrahydro-9-(trifluoromethyl)-7H-[1,4]oxazino[3,2-g]quinolin-7-one (Compound 146, Structure 35 of Scheme VII, where $R^1$=H, $R^2$=$CF_3$, $R^4$=Et, $R^x$=$CH_3$. This compound was prepared by General Method 5 (EXAMPLE 1) from (±)-7-amino-3,4-diethyl-3,4-dihydro-2H-1,4-benzoxazine (39 mg, 0.18 mmol) and ethyl 4,4,4-trifluoroacetoacetate (42 mg, 0.22 mmol) and purified by flash chromatography (19:1, $CH_2Cl_2$/MeOH) to yield 15 mg (25%) of Compound 146. Data for Compound 146: $R_f$ 0.28 (19: 1, $CH_2Cl_2$:MeOH); $^1$H NMR (500 MHz, $CDCl_3$) δ 11.50 (br s, 1H), 6.89 (s, 1H), 6.88 (s, 1H), 6.84 (s, 1H), 4.32 (dd, ABX, 1H, J=10.7, 2.0), 4.06 (dd, ABX, 1H, J=10.7, 2.7), 3.51–3.47 (m, 1H), 3.30–3,23 (m, 2H), 1.66–1.60 (m, 2H), 1.25 (t, 3H, J=7.3), 0.98 (t, 3H, J=7.3).

EXAMPLE 43A (±)-1,2,3,6-Tetrahydro-1-(2,2,2-trifluoroethyl)-2,9-bis(trifluoromethyl)-7H-[1,4]oxazino[3,2-g]quinolin-7-one (Compound 146A, Structure 35 of Scheme VII, where $R^1$=H, $R^2$, $R^4$=Trifluoromethyl, $R^x$=$CF_3$)

2-(Trifluoroethyl)amino-5-nitrophenol (Structure 32A of Scheme VIIA, where $R^x$=$CF_3$). This compound was prepared by General Method 7 (EXAMPLE 5) from 2-amino-5-nitrophenol (5.0 g, 32 mmol), 2,2,2-trifluoroacetaldehyde ethyl hemiacetal (9.4 g, 65 mmol) and NaBH$_3$CN (4.1 g, 65 mmol) in 90 mL trifluoroacetic acid to afford 5.5 g (72%) of 2-(trifluoroethyl)amino-5-nitrophenol, a yellow solid, after flash chromatography (3:1 hexanes:EtOAc). Data for 2-(trifluoroethyl)amino-5-nitrophenol: $^1$H NMR (400 MHz, acetone-d$_6$) 9.48 (broad s, 1H), 7.79 (dd, 1H, J=9.1, 2.4), 7.67 (d, 1H, J=2.4), 6.96 (d, 1H, J=8.8), 6.20 (broad s, 1H), 4.26–4.18 (m, 2H).

(±)-3,4-Dihydro-7-nitro-4-(2,2,2-trifluoroethyl)-3-(trifluoromethyl)-2H-1,4-benzoxazine (Structure 33 of Scheme VIIA, where R$^4$=trifluoromethyl, R$^x$=CF$_3$). This compound was prepared by General Method 17 (EXAMPLE 38) from 2-(trifluoroethyl)amino-5-nitrophenol (1.00 g, 4.23 mmol), 3-bromo-1,1,1-trifluoroacetone (4.84 g, 25.4 mmol), and K$_2$CO$_3$ (2.34 g, 16.9 mmol) to afford 1.5 g of crude solid. This was combined with another lot of the same reaction (4.2 mmol) and purified by flash chromatography (1:1 hexanes:EtOAc) to afford 1.0 g (40%) of a yellow oil. This material (725 mg, 2.47 mmol) was treated with 20 mL trifluoroacetic acid and NaBH$_3$CN (776 mg, 12.4 mmol) to afford 0.26 g (38%) (±)-3,4-dihydro-7-nitro-3-(trifluoromethyl)-2H-1,4-benzoxazine after purification by flash chromatography (3:1 hexanes:EtOAc). Data for (±)-3,4-dihydro-7-nitro-3-(trifluoromethyl)-2H-1,4-benzoxazine: $^1$H NMR (400 MHz, CDCl$_3$) 7.87 (dd, 1H, J=9.1, 2.8), 7.81 (d, 1H, J=2.5), 6.92 (d, 1H, J=9.1), 4.73 (d, 1H, J=12.1), 4.48–4.39 (m, 1H), 4.13–4.06 (m, 2H), 3.99–3.88 (m, 1H).

(±)-7-Amino-3,4-dihydro-4-(2,2,2-trifluoroethyl)-3-(trifluoromethyl)-2H-1,4-benzoxazine (Structure 34 of Scheme VII, where R$^4$=trifluoromethyl, R$^x$=CF). This compound was prepared by General Method 4 (EXAMPLE 1) from (+)-3,4-dihydro-7-nitro-4-(2,2,2-trifluoroethyl)-3-(trifluoromethyl)-2H-1,4-benzoxazine (45 mg, 0.16 mmol) and 10% Pd-C (30 mg) and purified by flash chromatography (EtOAc:hexanes, 1:1) to afford 26 mg (65%) of (±)-7-amino-3,4-dihydro-4-(2,2,2-trifluoroethyl)-3-(trifluoromethyl)-2H-1,4-benzoxazine. Data for (±)-7-amino-3,4-dihydro-4-(2,2,2-trifluoroethyl)-3-(trifluoromethyl)-2H-1,4-benzoxazine: $^1$H NMR (400 MHz, CDCl$_3$) 6.68 (d, 1H, J=8.4), 6.32–6.28 (m, 2H), 4.56 (dd, 1H, J=12.0, 0.96), 4.16–4.00 (m, 2H), 3.84–3.69 (m, 2H), 3.60–3.32 (m, 2H).

(±)-1,2,3,6-Tetrahydro-1-(2,2,2-trifluoroethyl)-2,9-bis(trifluoromethyl)-7H-[1,4]oxazino[3,2-g]quinolin-7-one (Compound 146A, Structure 35 of Scheme VII, where R$^1$=H, R$^2$, R$^4$=trifluoromethyl, R$^x$=CF$_3$). This compound was prepared by General Method 11 (EXAMPLE 22) from (±)-7-amino-3,4-dihydro-4-(2,2,2-trifluoroethyl)-3-(trifluoromethyl)-2H-1,4-benzoxazine (26 mg, 0.11 mmol) and ethyl 4,4,4-trifluoroacetoacetate (58 mg, 0.32 mmol) in 1.5 mL toluene followed by treatment with 1 mL H$_2$SO$_4$ afforded 35 mg (90%) of Compound 146A. Data for Compound 146A: $^1$H NMR (400 MHz, CDCl$_3$) 12.6 (broad s, 1H), 7.19 (broad s, 1H), 7.04 (s, 1H), 6.96 (s, 1H), 4.73 (d, 11H, J=11.7), 4.42–4.31 (m, 1H), 4.23–4.19 (m, 1H), 4.02–3.95 (m, 1H), 3.96–3.84 (m, 1H).

EXAMPLE 43B (±)-1,2,3,6-Tetrahydro-1-(2,2,2-trifluoroethyl)-2,9-bis(trifluoromethyl)-7H-[1,4]oxazino[3,2-g]quinolin-7-one (Compound 146B, Structure (+)-35 of Scheme VII, where R$^1$=H, R$^2$, R$^4$=Trifluoromethyl, R$^x$=CF$_3$) and (--)-1,2,3,6-Tetrahydro-1-(2,2,2-trifluoroethyl)-2,9-bis(trifluoromethyl)-7H-[1,4]oxazino[3,2-g]quinolin-7-one (Compound 146C, Structure (–)-35 of Scheme VIIA, where R$^1$=H, R$^2$, R$^4$=Trifluoromethyl, R$^x$=CF$_3$)

This compound was prepared according to General Method 9 (EXAMPLE 15) from Compound 146A (EXAMPLE 42A) (10 mg, 0.03 mmol) on a semiprep Chiralpak AD column (20×250 mm) eluted hexanes/isopropanol (95:5), to afford 4.5 mg of Compound 146B, an orange solid, and 4.7 mg of Compound 146C, an orange solid. Data for Compound 146B: HPLC (Chiralpak AD, 95:5 hexanes:isopropanol, 5.0 mL/min) t$_R$ 54.1 min; [α]$_D$=+62.7.

Data for Compound 146C: HPLC (Chiralpak AD, 95:5 hexanes:isopropanol, 5.0 mL/min) t$_R$ 64.3 min; [α]$_D$=−60.4.

EXAMPLE 44

(±)-1-Ethyl-1,2,3,6-tetrahydro-2-methyl-9-(trifluoromethyl)-7H-[1,4]oxazino[3,2-g]quinolin-7-one (Compound 147, Structure 35 of Scheme VII, where R$^1$=H, R$^2$=Trifluoromethyl, R$^4$=Me, R$^x$=CH$_3$)

(±)-3,4-Dihydro-3-methyl-7-nitro-2H-1,4-benzoxazine (Structure 32 of Scheme VII, where R$^4$=Me). This compound was prepared by General Method 17 (EXAMPLE 38) from 2-amino-5-nitrophenol (4.0 g, 25.9 mmol), chloroacetone (2.27 mL, 28.5 mmol), and K$_2$CO$_3$ (3.94 g, 28.5 mmol) to afford 3.5 g of crude solid. The crude solid (3.0 g, 14.2 mmol), NaBH$_3$CN (892 mg, 14.2 mmol) and trifluoroacetic acid afforded 2.68 g (97%) of 3,4-dihydro-3-methyl-7-nitro-2H-1,4-benzoxazine. Data for (±)-3,4-dihydro-3-methyl-7-nitro-2H-1,4-benzoxazine: R$_f$ 0.51 (2:3, EtOAc:hexanes); $^1$H NMR (400 MHz, CDCl$_3$) δ 7.74 (dd, 1H, J=8.7, 2.6), 7.70 (d, 1H, J=2.3), 6.50 (d, 1H, 8.7), 4.46 (br s, 1H), 4.23 (dd, 1H, J=10.5, 2.8), 3.76 (dd, 1H, J=10.5, 7.8), 3.67 (m, 1H), 1.25 (d, 3H, J=6.4).

(±)-4-Ethyl-3,4-dihydro-3-methyl-7-nitro-2H-1,4-benzoxazine (Structure 33 of Scheme VII, where R$^4$=Me, R$^x$=CH$_3$). This compound was prepared by General Method 3 (EXAMPLE 1) from (±)-3,4-dihydro-3-methyl-7-nitro-2H-1,4-benzoxazine (200 mg, 1.0 mmol), acetaldehyde (455 mg, 10.3 mmol) and NaBH$_3$CN (314 mg, 5.0 mmol) to afford 144 mg (63%) of 4-ethyl-3,4-dihydro-3-methyl-7-nitro-2H-1,4-benzoxazine. Data for (±)-4-ethyl-3,4-dihydro-3-methyl-7-nitro-2H-1,4-benzoxazine: R$_f$ 0.80 (3:2 EtOAc:hexanes); $^1$H NMR (500 MHz, CDCl$_3$) δ 7.80 (dd, 1H, J=8.9, 2.6), 7.66 (d, 1H, J=2.6), 6.55 (d, 1H, J=9.2), 4.07 (dd, 1H, J=10.7,2.5), 3.96 (dd, 1H, J=10.7, 2.6), 3.60 (m, 1H), 3.55–3.35 (m, 2H), 1.29 (d, 3H, J=6.6), 1.24 (t, 3H, J=7.0).

(±)-7-Amino-4-ethyl-3,4-dihydro-3-methyl-2H-1,4-benzoxazine (Structure 34 of Scheme VII, where R$^4$=Me, R$^x$=CH$_3$). This compound was prepared by General Method 4 (EXAMPLE 1) from (±)-4-ethyl-3,4-dihydro-3-methyl-7-nitro-2H-1,4-benzoxazine (140 mg, 0.62 mmol) and purified by flash chromatography (EtOAc:hexanes, 3:2) to afford 90 mg (74%) of (±)-7-amino-4-ethyl-3,4-dihydro-3-methyl-2H-1,4-benzoxazine. Data for (±)-7-amino-4-ethyl-3,4-dihydro-3-methyl-2H-1,4-benzoxazine: R$_f$ 0.48 (3:2 EtOAc:hexanes) $^1$H NMR (400 MHz, CDCl$_3$) δ 6.53 (d, 1H, J=8.0), 6.26–6.20 (m, 2H), 4.04 (dd, 1H, J=10.5, 2.6), 3.94 (dd, 1H, J=10.4, 4.3), 3.37–3.26 (m, 4H), 3.17–3.07 (m, 1H), 1.13 (m, 6H).

(±)-1-Ethyl-1,2,3,6-tetrahydro-2-methyl-9-(trifluoromethyl)-7H-[1,4]oxazino[3,2-g]quinolin-7-one (Compound 147, Structure 35 of Scheme VII, where R$^1$=H, R$^2$=trifluoromethyl, R$^4$=Me, R$^x$=CH$_3$). This compound was prepared by General Method (EXAMPLE 1) from (±)-7-amino-4-ethyl-3,4-dihydro-3-methyl-2H-1,4-benzoxazine (90 mg, 0.47 mmol) and ethyl 4,4,4-trifluoroacetoacetate (103 mg, 0.56 mmol) and purified by flash chromatography (3:2 EtOAc:hexanes) to yield 46 mg (30%) of Compound 147. Data for Compound 147: $R_f$ 0.37 (3:2, EtOAc:hexanes); $^1$H NMR (400 MHz, CDCl$_3$) δ 12.07 (br s, 1H), 6.89 (s, 1H), 6.88 (s, 2H), 4.18 (dd, 1H, J=10.5, 2.5), 4.09 (dd, 1H, J=10.6, 3.4), 3.54–3.51 (m, 1H), 3.47–3.40 (m, 1H), 3.31–3,24 (m, 1H), 1.23 (m, 6H).

EXAMPLE 45

(2R-)-(−)-1,2,3 6-Tetrahydro-2-methyl-1-(2,2,2-trifluoroethyl)-9-(trifluoromethyl)-7H-[1,4]oxazino [3,2-g]quinolin-7-one benzoxazine (Compound 148, Structure 41 of Scheme VIII, where R$^1$=H, R$^2$=Trifluoromethyl, R$^4$Me, R$^x$=CF$_3$)

General Method 18: Displacement of a halonitroaromatic compound with an amino alcohol. A mixture of the halonitrobenzene (1.2 equiv) and the amino alcohol (1 equiv) was dissolved in absolute ethanol (3.3 M) or DMF. To this solution was added sodium bicarbonate (1 equiv). The suspension was heated at reflux temperature for 12 h when TLC indicated complete conversion of the amino alcohol. After cooling to room temperature, the reaction mixture was filtered with the aid of additional ethanol and the filtrate was concentrated under reduced pressure, which was then purified as indicated.

(2R)-(+)-2-(2-Fluoro-4-nitrophenyl)amino-1-propanol (Structure 36 of Scheme VIII, where R$^4$=Me). This compound was prepared according to General Method 18 from 3,4-difluoronitrobenzene (76.2 g 0.48 mol), R-(+)-2-amino-1-propanol (30 g, 0.40 mol) and sodium bicarbonate (33.6 g, 0.40 mol) in 120 mL ethanol to afford 68.4 g (80%) of (2R)-(+)-2-(2-fluoro-4-nitrophenyl)amino-1-propanol, a yellow solid, after recrystallization from ethanol. Data for (2R)-(+)-2-(2-fluoro-4-nitrophenyl)amino-1-propanol: mp 128.2–129.7° C; [α]$_D$=+22.6 (EtOH, c 3.1); $^1$H NMR (400 MHz, CDCl$_3$) δ 7.99 (1H, dd, J=11.4), 7.89 (1H, dd, J=2.5, 11.6), 6.72 (1H, dd, J=8.7), 4.75 (1H, bs), 3.8 (2H, m), 3.69 (1H, m), 1.31 (3H, d, J=6.4).

General Method 19: Formation of an oxazolidine from an aminoalcohol and a carbonyl derivative, or its corresponding hydrate or hemiacetal. A r.b. flask equipped with a Dean-Stark condenser was charged sequentially with the amino alcohol (1 equiv), benzene (0.3–0.5 M), trifluoroacetaldehyde ethyl hemiacetal (5 equiv), and p-toluenesulfonic acid (catalytic). The reaction mixture was refluxed with azeotropic removal of water for 10–12 h. After cooling to room temperature the reaction mixture was concentrated under reduced pressure. The residue was dissolved in ethyl acetate and washed with aqueous sodium bicarbonate, brine and dried over anhydrous MgSO$_4$. After filtration, the solvents were removed under reduced pressure to afford the desired oxazolidine.

cis-(2S,4R)-(−)-3-(2-Fluoro-4-nitrophenyl)-4-methyl-2-trifluoromethyloxazolidine and trans-(2R,4R)-(+)-3-(2-Fluoro-4-nitrophenyl)-4-methyl-2-trifluoromethyloxazolidine (Structure 37 of Scheme VIII, where R$^4$=Me, R$^x$=CF$_3$). These compounds were prepared according to General Method 19 from (2R)-(+)-2-(2-fluoro-4-nitrophenyl)amino-1-propanol (68 g, 0.317 mole), 750 mL of benzene, trifluoroacetaldehyde ethyl hemiacetal (229 g, 1.58 mole), and 100 mg of p-toluenesulfonic acid (100 mg, 0.53 mmol) to afford cis-(2S,4R)-(−)-3-(2-fluoro-4-nitrophenyl)-4-methyl-2-trifluoromethyloxazolidine and trans-(2R,4R)-(+)-3-(2-fluoro-4-nitrophenyl)-4-methyl-2-trifluoromethyloxazolidine as a low melting solid. The product was found to be a mixture of two diastereoisomers (cis/trans 4:1). Crystallization from ethyl acetate-hexanes furnished the major (cis) isomer as pale yellow needles and the minor (trans) isomer as a glassy solid. The combined yield of both compounds was 93.2 g (100%).

Data for cis-(2S,4R)-(−)-3-(2-fluoro-4-nitrophenyl)-4-methyl-2-trifluoromethyloxazolidine: mp 46–50° C; [α]$_D$=−60.9 (CHCl$_3$, c 10.3); 1H NMR (CDCl$_3$) δ 8.01 (1H, m ), 7.98 (1H, dd, J=2.5, 12.3), 6.96 (1H, dd, J=9.0), 5.75 (1H, q, J=4.7), 4.33 (1H, m), 4.19 (1H, m), 3.99 (1H, m), 1.45 (3H, d, J=6.26). Data for trans-(2R,4R)-(+)-3-(2-fluoro-4-nitrophenyl)-4-methyl-2-trifluoromethyloxazolidine: [α]$_D$=+258.9 (CHCl$_3$, c 8.25); $^1$H NMR (CDCl$_3$) δ 8.02 (1H, dd), 7.98 (1H, dd, J=2.5, 12.9), 6.96 (1H, dd, J=8.5), 5.83 (1H, q, J=4.7), 4.48 (1H, m), 4.40 (1H, m), 3.95 (1H, m), 1.23 (3H, d, J=6.0).

(2R)-(−)-2-[2-Fluoro-4-nitro(2,2,2-trifluoroethyl) anilino]-1-propanol (Structure 38 of Scheme VIII, where R$^4$=Me, R$^x$=CF$_3$). A 1-L three-necked RB flask equipped with an addition funnel and mechanical stirrer was charged sequentially with cis-(2S,4R)-(−)-3-(2-fluoro-4-nitrophenyl)-4-methyl-2-trifluoromethyloxazolidine and trans-(2R,4R)-(+)-3-(2-fluoro-4-nitrophenyl)-4-methyl-2-trifluoromethyloxazolidine (93 g, 0.36 mole), 600 mL of dry chloroform, and triethylsilane (183.7 g, 1.58 mol). The solution was cooled to −78° C. and TiCl$_4$ (90 g, 0.474 mol) was added dropwise via addition funnel. After the addition was complete, the reaction mixture was allowed to warm to room temperature and stirred for another 24 h. The reaction mixture was quenched with ice and then neutralized with aqueous Na$_2$CO$_3$. The organic layers were washed with water, brine and dried over MgSO$_4$. After filtration, the solvents were evaporated under reduced pressure and the residue was purified by silica gel column chromatography (ethyl acetate:hexanes 1:9) to afford 57 g (61%) of(2R)-(−)-2-[2-fluoro-4-nitro(2,2,2-trifluoroethyl)anilino]-1-propanol, as a glassy solid. Data for (2R)-(−)-2-[2-fluoro-4-nitro(2,2,2-trifluoroethyl)anilino]-1-propanol [α]$_D$=−205.9 (EtOH, c 10.15) $^1$H NMR (CDCl$_3$) δ 7.99 (1H, dd, J=2.5, 9.0), 7.95 (1H, dd, J=2.6, 14,7), 7.32 (1H, dd, J=8.6), 3.94 (1H, m), 3.74 (2H, m), 3.65 (1H, m), 1.86 (1H, bs), 1.19 (3H, d, J=6.7).

General Method 20: Intramolecular cyclization of an alcohol of Structure 38 or 42 on a haloaromatic to form a benzoxazine. A solution of the aminoalcohol (1 equiv) in dry THF (1M) was added to a suspension of NaH (1.5 equiv) in dry THF (2M) and the mixture was heated at reflux. After cooling, methanol (50 mL/mol) was added to consume excess sodium hydride. The reaction mixture was poured into ice-cold water and extracted with ethyl acetate. The organic portions were combined, washed with brine and dried over MgSO$_4$. After filtration, the solvents were evaporated under reduced pressure and purified as indicated.

(3R)-(+)-3,4-Dihydro-3-methyl-7-nitro-4-(2,2,2-trifluoroethyl)-2H-1,4-benzoxazine (Structure 39 of Scheme VIII, where R$^4$=Me, R$^x$=CF$_3$).

This compound was prepared according to General Method 20 from (2R)-(−)-2-[2-fluoro-4-nitro(2,2,2-trifluoroethyl)anilino]-1-propanol (57 g, 0.193 mol) in 200 mL and NaH (6.93 g, 0.289 mole) in 400 mL of dry THF heated at reflux for 3 h to afford 36.5 g (68%) of (3R)-(+)-2,3-dihydro-3-methyl-7-nitro-4-(2,2,2-trifluoroethyl)-2H-1, 4-benzoxazine, a yellow crystalline solid, after flash chromatography. Data for (3R)-(+)-2,3-dihydro-3-methyl-7-nitro-4-(2,2,2-trifluoroethyl)-2H-1,4-benzoxazine: mp 95.5–96.4° C.; [α]$_D$=+57.8 (EtOH, c 2.25); $^1$H NMR (CDCl$_3$) δ 7.80 (1H, dd, J=2.5, 9.1), 7.73 (1H, d, J=2.6), 6.71 (1H, d, J=9.1), 4.13 (2H, m ), 4.03 (11H, m), 3.84 (1H, m), (1H, m), 1.31 (3H, d, J=6.6).

(3R)-(−)-7-Amino-3,4-dihydro-3-methyl-4-(2,2,2-trifluoroethyl)-2H-1,4-benzoxazine (Structure 40 of Scheme VIII, where $R^4$=Me, $R^x$=$CF_3$). This compound was prepared according to General Method 4 (EXAMPLE 1) from (3R)-(+)-2,3-dihydro-3-methyl-7-nitro-4-(2,2,2-trifluoroethyl)-2H-1,4-benzoxazine (35.5 g, 0.128 mol) and 10% palladium on carbon (3 g) in 400 mL of ethyl acetate to afford 31 g (98%) of (3R)-(−)- 7-amino-2,3-dihydro-3-methyl-4-trifluoroethyl-2H-1,4benzoxazine, an off-white solid, after purification by silica gel column chromatography (ethyl acetate-hexanes). Data for (3R)-(−)-7-amino-2,3-dihydro-3-methyl-4-trifluoroethyl-2H-1,4benzoxazine: $[\alpha]_D$=−39.4 (EtOH, c 1.7) $^1$H NMR (CDCl$_3$) δ 6.58 (1H, d, J=8.2), 6.40 (1H, m), 6.37 (1H, m), 4.05 (1H, dd, J=2.3, 11.0), 3.98 (1H, dd, J=2.9, 10.6), 3.66 (2H, m), 3.38 (1H, m), 3.40 (NH2), 1.18 (3H, d, J=6.6).

(2R-)-(−)-1,2,3,6-Tetrahydro-2-methyl-1-(2,2,2-trifluoroethyl)-9-(trifluoromethyl)-7H-[1,4]oxazino[3,2-g]quinolin-7-one benzoxazine (Compound 148, Structure 41 of Scheme VIII, where $R^1$=H, $R^2$=trifluoromethyl, $R^4$=Me, $R^x$=$CF_3$).

A mixture of (3R)-(−)-7-amino-3,4-dihydro-3-methyl-4-trifluoroethyl-2H-1,4-benzoxazine (4.14 g, 16.8 mmol) and of ethyl 4,4,4-trifluoroacetoacetate (4.64 g, 25 mmol) were taken up in 85 mL of wet toluene (5% H$_2$O). The reaction mixture was refluxed for 24 h. After cooling to room temperature, the solvents were evaporated under reduced pressure. The crude anilide obtained as a glassy solid was then treated with 50 mL of concentrated H$_2$SO$_4$. The reaction mixture was then slowly warmed to 70° C. and then to 98° C. After 45 min, the heating bath was removed and the reaction mixture was allowed to cool to room temperature and then poured on to crushed ice with vigorous stirring. The yellow precipitate formed was filtered, washed with distilled water, and dried under vacuum. The crude product thus obtained was purified by silica gel column chromatography (ethyl acetate:hexanes), followed by recrystallization from ethyl acetate-hexanes to afford 2.6 g (42.3%) of Compound 148, a bright-yellow crystalline solid. Data for Compound 148: mp 219–223.1° C.; $[\alpha]_D$=−81.7 (EtOH, c 2.4); $^1$H NMR (CDCl$_3$) δ 7.05 (1H, s), 6.91 (1H, s), 6.89 (1H, s), 4.23 (1H, dd, J=2.4, 10.8), 4.14 (1H, dd, J=2.7, 10.7), 3.92 (1H, m), 3.78 (1H, m), 3.61 (1H, m) 1.27 (3H, d J=6.6).

EXAMPLE 46

(2R-)-2-Ethyl-1,2,3 6-tetrahydro-1-(2,2,2-trifluoroethyl)-9-(trifluoromethyl )-7H-[1,4]oxazino[3,2-g]quinolin-7-one (Compound 149, Structure 41 of Scheme VIII, where $R^1$=H, $R^2$=Trifluoromethyl, $R^4$=Et, $R^x$=$CF_3$)

(2R)-2-(2-Fluoro-4-nitrophenyl)amino-1-butanol (Structure 36 of Scheme VIII, where $R^4$=Et). This compound was prepared according to General Method 18 (EXAMPLE 45) from 3,4-difluoronitrobenzene (5.34 mL, 0.048 mol), R-(−)-2 amino-1-butanol (4.14 mL, 0.044 mol) and sodium bicarbonate (3.68 g, 0.044 mol) in 133 mL anhydrous DMF heated at 90° C. for 12 hrs to afford 9.9 g (99%) of (2R)-2-(2-fluoro-4-nitrophenyl)amino-1-butanol, a yellow oil, after flash chromatography (gradient elution, hexanes:ethyl acetate 95:5 to 50:50). Data for (2R)-2-(2-fluoro-4-nitrophenyl)amino-1-butanol: $^1$H NMR (500 MHz, CDCl$_3$) δ 7.98 (dd, J=8.8, 1.5, 1H), 7.89 (dd, J=11.7, 2.4, 1H), 6.71 (dd, J=8.8, 8.8, 1H), 4.72 (bs, 1H), 3.81 (m, 1H), 3.73 (m, 1H), 3.55 (m, 1H), 1.76 (m, 1H), 1.63 (m, 1H), 1.02 (t, J=7.8, 3H).

(4R)-3-(2-Fluoro4-nitrophenyl)-4-ethyl-2-(trifluoromethyl)-1,3-oxazolidine (Structure 37 of Scheme VIII, where $R^4$=Et, $R^x$=$CF_3$). This compound was prepared according to General Method 19 (EXAMPLE 45) from (2R)-2-(2-fluoro-4-nitrophenyl)amino-1-butanol (1.6 g, 70 mmol), trifluoroacetaldehyde ethyl hemiacetal (4.9 g, 34 mmol) and p-toluenesulfonic acid (0.13 g, 0.68 mmol) in 70 mL anhydrous benzene to afford 1.8 g (85%) of (4R)-3-(2-fluoro-4-nitrophenyl)-4-ethyl-2-trifluoromethyloxazolidine, after flash chromatography (gradient elution, hexanes:ethyl acetate 90:10 to 50:50). Data for (4R)-3-(2-fluoro-4-nitrophenyl)-4-ethyl-2-trifluoromethyloxazolidine: $^1$H NMR (500 MHz, CDCl$_3$) δ 8.01 (m, 1H), 7.98 (m, 1H), 6.95 (dd, J=8.8, 8.8, 1H), 5.68 (m, 1H), 4.30 (m, 1H), 4.08 (m, 1H), 3.92 (m, 1H), 2.00 (m, 1H), 1.67 (m, 1H), 0.97 (t, J=7.8, 3H).

(2R )-2-[2-Fluoro-4-nitro(2,2,2-trifluoroethyl)anilino]-1-butanol (Structure 38 of Scheme VIII, where $R^4$=Et, $R^x$=$CF_3$). To a solution of (4R)-3-(2-fluoro-4-nitrophenyl)-4-ethyl-2-trifluoromethyloxazolidine (9.2 g, 29.8 mmol) and Et$_3$SiH (19.1 mL, 119 mmol) in 100 mL chloroform was added BF$_3$OEt$_2$ (7.56 mL, 60 mmol). The reaction was heated to reflux for 12 hrs, whereupon additional BF$_3$OEt$_2$ (7.56 mL, 60 mmol) was added, and the mixture heated at reflux for an additional 12 hrs. After cooling, MeOH (5 mL) was added and the reaction was allowed to stir at r.t. for an hour. The reaction was poured in water (250 mL) and extracted with ethyl acetate (3×250 mL). The organic layers were combined, washed sequentially with water (250 mL) and brine (250 mL), dried (MgSO$_4$), filtered, and concentrated under reduced pressure to a brown oil. Flash chromatography (gradient elution, hexanes:ethyl acetate 95:5 to 50:50) afforded 5.4 g (59%) of (2R )-2-[2-fluoro-4-nitro(2,2,2-trifluoroethyl)anilino]-1-butanol. Data for (2R )-2-[2-fluoro-4-nitro(2,2,2-trifluoroethyl)anilino]-1-butanol: $^1$H NMR (500 MHz, CDCl$_3$) δ 7.98 (dd, J=8.8, 2.4, 1H), 7.94 (dd, J=13,2, 2.9, 1H), 7.37 (dd, J=8.8, 8.8, 1H), 4.12 (m, 1H), 3.87 (m, 1H), 3.77 (m, 1H), 3.70 (m, 1H), 3.57 (m, 1H), 1.78 (dd, J=6.8, 4.4, 1H), 1.58 (dq, J=7.8, 2.9, 2H), 0.95 (t, J=7.3, 1H).

(3R)-3-Ethyl-3,4-dihydro-7-nitro-4-(2,2,2-trifluoroethyl)-2H-1,4-benzoxazine (Structure 39 of Scheme VIII, where $R^4$=Et, $R^x$=$CF_3$). This compound was prepared according to General Method 20 from (2R )-2-[2-fluoro-4-nitro(2,2,2-trifluoroethyl)anilino]-1-butanol (5.4 g, 17.3 mmol) in 45 mL THF and NaH (1.4 g, 35 mmol) in 10 mL THF heated at reflux for 1 hr to afford 3.78 g (75%) of (3R)-3-ethyl-3,4-dihydro-7-nitro-4-(2,2,2-trifluoroethyl)-2H-1,4-benzoxazine, after flash chromatography (gradient elution, hexanes:ethyl acetate 95:5 to 50:50). Data for (3R)-3-ethyl-3,4-dihydro-7-nitro-4-(2,2,2-trifluoroethyl)-2H-1,4-benzoxazine: $^1$H NMR (500 MHz, CDCl$_3$) δ 7.81 (dd, J=8.8, 2.4, 1H), 7.73 (d, J=2.9, 1H), 6.72 (d, J=8.8, 1H), 4.34 (dd, J=11.2, 1.5, 1H), 4.13 (m, 1H), 4.03 (dd, J=11.2, 2.4, 1H), 3.8 (m, 1H), 3.37 (m, 1H), 1.67 (m, 1H), 1.01 (t, J=7.3, 3H).

(3R)-7-Amino-3-ethyl-3,4-dihydro-4-(2,2,2-trifluoroethyl)-2H-1,4-benzoxazine (Structure 40 of Scheme VIII, where $R^4$=Me, $R^x$=$CF_3$). This compound was prepared according to General Method 4 (EXAMPLE 1) from (3R)-3-ethyl-3,4-dihydro-7-nitro-4-(2,2,2-trifluoroethyl)-2H-1,4-benzoxazine (5.6 g, 19.3 mmol) and 10% Pd/C (cat.) in 60 mL ethyl acetate to afford 4.8 g (95%) of (3R)-7-amino-3, 4-dihydro-3-ethyl-4-trifluoroethyl-2H-1,4benzoxazine as a tan solid, which was carried on directly to the next step.

(2R)-2-Ethyl-1,2,3,6-tetrahydro-1-(2,2,2-trifluoroethyl)-9-(trifluoromethyl)-7H-[1,4]oxazino[3,2-g]quinolin-7-one (Compound 149, Structure 41 of Scheme VIII, where $R^1$=H, $R^2$=trifluoromethyl, $R^4$=Et, $R^x$=$CF_3$). This compound was prepared by General Method 11 (EXAMPLE 22) from (3R)-7-amino-3-ethyl-3,4-dihydro-4-trifluoroethyl-2H-1,4-benzoxazine (4.8 g, 18.4 mmol) and ethyl-4,4,4-trifluoroacetoacetate (8.1 mL, 55.2 mmol) in 58 mL toluene heated at reflux for 3d, followed by workup and treatment with 35 mL concentrated $H_2SO_4$ heated to 90° C. for 0.5 h to afford 1.5 g (21%) of Compound 149, a yellow solid, after flash chromatography (gradient elution, hexanes:ethyl acetate 95:5 to 50:50) followed by additional purification using reverse phase HPLC (Kromasil C18, 50×250 mm; 65:35 MeOH:water; flow rate of 80 mL/min.). Data for Compound 149: $^1$H NMR (500 MHz, $CDCl_3$) δ 11.75 (bs, 1H), 7.06 (s, 1H), 6.91 (s, 1H), 6.89 (s, 1H), 6.89 (s, 1H), 4.34 (dd, J=10.7, 1.5, 1H), 4.14 (dd, J=11.2, 2.4, 1H), 3.99 (m, 1H), 3.75 (m, 1H), 3,28 (m, 1H), 1.64 (dq, J=7.6, 7.3, 2H), 1.00 (t, J=7.3, 3H).

EXAMPLE 47

(2R)-1,2,3,6-Tetrahydro-2-isobutyl-1-(2,2,2-trifluoroethyl)-9-(trifluoromethyl)-7H-[1,4]oxazino3,2-g]quinolin-7-one (Compound 150, Structure 41 of Scheme VIII, where $R^1$=H, $R^2$=Trifluoromethyl, $R^4$=Isobutyl, $R^x$=$CF_3$)

(2R)-2-(2-Fluoro-4-nitrophenyl)amino-4-methyl-1-pentanol (Structure 36 of Scheme VIII, where $R^4$=isobutyl). This compound was prepared according to General Method 18 (EXAMPLE 45) from 3,4-difluoronitrobenzene (8.73 g, 54.9 mmol), R-2-amino-4-methyl-1-pentanol (5.00 g, 42.7 mmol) in EtOH heated at reflux for 16 h to afford 6.0 g (55%) of (2R)-2-(2-fluoro-4-nitrophenyl)amino-4-methyl-1-pentanol, a yellow solid, after flash chromatography (gradient elution, hexanes:EtOAc 9:1 to 1:1). Data for (2R)-2-(2-fluoro-4-nitrophenyl)amino-4-methyl-1-pentanol: $R_f$ 0.3 (3: 1 hexanes:EtOAc); $^1$H NMR (400 MHz, $CDCl_3$) δ 8.01–7.97 (m, 1H), 7.90 (dd, 1H J=11.7, 2.7), 6.74 (dd, 1H, J=8.6, 8.6), 4.62–4.57 (m, 1H), 3.82–3.74 (m, 1H), 3.75–3.62 (m, 2H), 1.77–1.65 (m, 1H), 1.61–1.45 (m, 2H), 0.99 (d, 31H, J=6.6), 0.93 (d, 3H, J=6.6).

(4R)-3-(2-Fluoro-4-nitrophenyl)-4isobutyl-2-(trifluoromethyl)-1,3-oxazolidine (Structure 37 of Scheme VIII, where $R^4$=isobutyl, $R^x$=$CF_3$. This compound was prepared according to General Method 19 (EXAMPLE 45) from (2R)-2-(2-fluoro-4-nitrophenyl)amino-4-methyl-1-pentanol (6.0 g, 23 mmol) trifluoroacetaldehyde ethyl hemiacetal (30.4 g, 211 mmol) and p-toluenesulfonic acid (0.020 g, 0.10 mmol) in 250 mL benzene to afford 5.15 g (65%) of (4R)-3-(2-fluoro-4-nitrophenyl)-4-isobutyl-2-trifluoromethyloxazolidine. Data for (4R)-3-(2-fluoro-4-nitrophenyl)-4-isobutyl-2-trifluoromethyloxazolidine as a mixture of diastereomers: $R_f$ 0.8 (3:1 hexanes:EtOAc); $^1$H NMR (400 MHz, $CDCl_3$) δ 8.03–7.94 (m, 2H), 6.96–6.88 (m, 1H), 5.81 (q, 1H, minor diast., J=4.7), 5.69 (q, 1H, major diast., J=4.7), 4.45–4.40 (m, 1H, minor diast.), 4.36–4.28 (m, 1H, major diast.), 4.11–4.01 (m, 2H), 1.82–1.74 (m, 1H), 1.66–1.52 (m, 2H), 1.02 (d, 3H, major diast., J=6.4), 0.99–0.95 (m, 3H), 0.91 (d, 3H, minor diast., J=6.6).

(2R)-2-[2-Fluoro-4-nitro(2,2,2-trifluoroethyl)anilino]-4-methyl-1-pentanol (Structure 38 of Scheme VIII, where $R^4$=isobutyl, $R^x$=$CF_3$. To a solution of (4R)-3-(2-fluoro-4-nitrophenyl)-4-isobutyl-2-trifluoromethyloxazolidine (4.8 g, 14.3 mmol) and $Et_3SiH$ (21.6 g, 186 mmol) in 60 mL chloroform was added $BF_3OEt_2$ (14.2, 60 mmol, added in portions) The reaction was heated at reflux for 1 d After cooling, the reaction was poured in water (200 mL) and extracted with chloroform (3×150 mL). The organic layers were combined, washed sequentially with water (200 mL) and brine (200 mL), dried ($MgSO_4$), filtered, and concentrated under reduced pressure to a brown oil. Flash chromatography (gradient elution, hexanes:ethyl acetate 95:5 to 3:1) afforded 2.1 g (44%) of (2R)-2-[2-fluoro-4-nitro(2,2,2-trifluoroethyl)anilino]-4-methyl- -pentanol, an orange oil. Data for (2R)-2-[2-fluoro-4-nitro(2,2,2-trifluoroethyl)anilino]-4-methyl-1-pentanol: $R_f$ 0.8 (3:1 hexanes:EtOAc); $^1$H NMR (400 MHz, $CDCl_3$) δ 7.98 (dd, 1H, J=9.3, 2.4), 7.94 (dd, 1H, J=12.9, 2.5), 7.40 (dd, 1H, J=8.7, 8.7), 4.21–4.10 (m, 1H), 3.89–3.78 (m, 1H), 3.79–3.65 (m, 3H), 1.96–1.89 (m, 1H), 1.67–1.54 (m, 1H), 1.55–1.44 (m, 1H), 1.32–1.22 (m, 1H), 0.91 (d, 3H, J=6.6), 0.77 (d, 3H, J=6.6).

(3R)-3,4-Dihydro-3-isobutyl-7-nitro-4-(2,2,2-trifluoroethyl)-2H-1,4-benzoxazine (Structure 39 of Scheme VIII, where $R^4$=isobutyl, $R^x$=$CF_3$. This compound was prepared according to General Method 20 (EXAMPLE 45) from (2R)-2-[2-fluoro-4-nitro(2,2,2-trifluoroethyl)anilino]-4-methyl-1-pentanol (1.95 g, 5.76 mmol) in 30 mL THF and NaH (1.4 g, 35 mmol) in 25 mL THF heated at reflux for I hr to afford 0.87 g (50%) of (3R)-3,4-dihydro-3-isobutyl-7-nitro4-(2,2,2-trifluoroethyl)- 2H-1,4-benzoxazine, a yellow oil. Data for (3R)-3,4-dihydro-3-isobutyl-7-nitro-4-(2,2,2-trifluoroethyl)-2H-1,4-benzoxazine: $R_f$ 0.6 (3:1 hexanes:EtOAc); $^1$H NMR (400 MHz, $CDCl_3$) δ 7.79 (dd, 1H, J=9.1, 2.7), 7.71 (d, 1H, J=2.5), 6.72 (d, 1H, J=9.1), 4.30 (dd, 1H, ABx,J=11.0, 1.5), 4.19–4.06 (m, 1H), 4.06–4.01 (m, 1H), 3.82–3.73 (m, 1H), 3.53–3.47 (m, 1H), 1.71–1.61 (m, 2H), 1.38–1.29 (m, 1H), 0.99 (d, 3H, J=6.5), 0.96 (d, 3H, J=6.5).

(3R)-7-Amino-3,4-dihydro-3-isobutyl-4-(2,2,2-trifluoroethyl)-2H-1,4 benzoxazine (Structure 40 of Scheme VIII, where $R^4$=isobutyl, $R^x$=$CF_3$). This compound was prepared according to General Method 4 (EXAMPLE 1) from (3R)-3,4-dihydro-3-isobutyl-7-nitro-4-(2,2,2-trifluoroethyl)-2H-1,4-benzoxazine (0.22 g, 0.69 mmol) and 10% Pd/C (0.075 g) in 5 mL ethyl acetate to afford 0.13 g (65%) of (3R)-7-amino-3,4-dihydro-3-isobutyl-4-trifluoroethyl-2H-1,4-benzoxazine. Data for (3R)-7-amino-3,4-dihydro-3-isobutyl-4-trifluoroethyl-2H-1,4-benzoxazine: $R_f$ 0.3 (3:1 hexanes:EtOAc); $^1$H NMR (400 MHz, $CDCl_3$) δ 6.63 (d, 1H, J=8.5), 6.27 (dd, 1H, J=8.5, 2.6), 6.23 (d, 1H, J=2.5), 4.10 (dd, 1H, ABx, J=10.6, 1.8), 3.97 (dd, 1H, ABx, J=10.6, 2.3), 3.70–3.51 (m, 2H), 3.38 (broad s, 2H), 3.19–3.13 (m, 1H), 1.75–1.63 (m, 1H), 1.47–1.25 (m, 2H), 0.93 (d, 3H, J=6.6), 0.89 (d, 3H, J=6.6).

(2R)-1,2,3,6-Tetrahydro-2-isobutyl-1-(2,2,2-trifluoroethyl)-9-(trifluoromethyl)-7H-[1,4]oxazino[3,2-g]quinolin-7-one (Compound 150, Structure 41 of Scheme VIII, where $R^1$=H, $R^2$=trifluoromethyl, $R^4$=isobutyl, $R_x$=CF3). This compound was prepared by General Method 11 (EXAMPLE 22) from (3R)-7-amino-3,4-dihydro-3-isobutyl-4-trifluoroethyl-2H-1,4-benzoxazine (0.13 g, 0.45 mmol) and ethyl-4,4,4-trifluoroacetoacetate (0.25 g, 1.4 mmol) in 6 mL toluene heated at reflux for 3 h, followed by workup and treatment with 3 mL concentrated $H_2SO_4$ heated to 95° C. for 1 h to afford 17 mg (9%) of Compound 150, a yellow solid, after purification by flash chromatography (95:5 $CH_2Cl_2$:MeOH) and recrystallization from EtOAc:hexanes. Data for Compound 150: $R_f$ 0.2 (19:1 $CH_2Cl_2$;MeOH); $^1$H NMR (400 MHz, $CDCl_3$) δ 12.58 (broad s, 1H), 7.05 (broad s, 1H), 6.97 (s, 1H), 6.91 (s, 1H), 4.30 (dd, 1H, ABX, J=11.0, 1.1), 4.16 (dd, 1H, ABX, J=11.0, 1.3), 4.01–3.91 (m, 1H), 3.75–3.65 (m, 1H), 3.42–3.37 (m, 1H), 1.71–1.62 (m, 1H), 1.62–1.54 (m, 1H), 1.35–1.27 (m, 1H), 0.96 (d, 3H, J=6.9), 0.93 (d, 3H, J=7.5).

EXAMPLE 48

(2R)-1,2,3,6-Tetrahydro-2-isopropyl-1-(2,2,2-trifluoroethyl)-9-(trifluoromethyl)-7H-[1,4]oxazino[3,2-g]quinolin-7-one (Compound 151, Structure 41 of Scheme VIII, where $R^1$=H, $R^2$=Trifluoromethyl, $R^4$=Isopropyl, $R_x$=$CF_3$)

(2R)-2-(2-Fluoro-4-nitrophenyl)amino-3-methyl-1-butanol (Structure 36 of Scheme VIII, where $R^4$=isopropyl).

This compound was prepared according to General Method 18 (EXAMPLE 45) from 3,4-difluoronitrobenzene (9.9 g, 62 mmol), R-2-amino-3-methyl-1-butanol (5.00 g, 48.5 mmol) in 6 mL EtOH heated at reflux for 22 h to afford 8.3 g (71%) of (2R)-2-(2-fluoro-4-nitrophenyl)amino-3-methyl-1-butanol, a yellow solid, after flash chromatography. Data for (2R)-2-(2-fluoro-4-nitrophenyl)amino-3-methyl-1-butanol: $R_f$ 0.8 (1:1 hexanes:EtOAc); $^1$H NMR (400 MHz, CDCl$_3$) δ 8.00–7.96 (m, 1H), 7.90 (dd, 1H, J=11.6, 2.4), 6.73 (dd, 1H, J=8.5, 8.5), 4.75–4.69 (m, 1H), 3.87–3.79 (m, 1H), 3.79–3.70 (m, 1H), 3.47–3.39 (m, 1H), 2.06–1.97 (m, 1H), 1.03 (d, 31H, J=3.6), 1.01 (d, 3H, J=3.6).

(4R)-3-(2-Fluoro-4-nitrophenyl)-4-isopropyl-2-(trifluoromethyl)-1,3-oxazolidine (Structure 37 of Scheme VIII, where R$^4$=isopropyl, R$_x$=CF$_3$. This compound was prepared according to General Method 19 (EXAMPLE 45) from (2R)-2-(2-fluoro-4-nitrophenyl)amino-3-methyl-1-butanol (8.3 g, 34 mmol) trifluoroacetaldehyde ethyl hemiacetal (86.4 g, 0.600 mol) and p-toluenesulfonic acid (20 mg, 0.10 mmol) in 220 mL benzene to afford 5.2 g (47%) of (4R)-3-(2-fluoro-4-nitrophenyl)-4-isopropyl-2-trifluoromethyloxazolidine. Data for (4R)-3-(2-fluoro-4-nitrophenyl)-4-isopropyl-2-trifluoromethyloxazolidine: $R_f$ 0.7 (3:1 hexanes:EtOAc); $^1$H NMR (400 MHz, CDCl$_3$) δ 8.04–7.97 (m, 2H), 7.22 (dd, 1H, J=8.7, 8.7), 5.34 (quartet, 1H, J=4.6), 4.27 (dd, 1H, J=8.0, 8.0), 4.1 1 (dd, 1H, J=7.4, 7.4), 3.81 (quartet, 1H, J=7.1), 2.02–1.93 (m, 1H), 0.96 (d, 6H, J=6.8).

(2R)-2-[2-Fluoro-4-nitro(2,2,2-trifluoroethyl)anilinol-3-methyl-1-butanol (Structure 38 of Scheme VIII, where R$^4$=isopropyl, R$_x$=CF$_3$. To a solution of (4R)-3-(2-fluoro-4-nitrophenyl)-4-isopropyl-2-trifluoromethyloxazolidine (1.8 g, 5.6 mmol) and Et$_3$SiH (1.88 g, 16.1 mmol) in 15 mL CHCl$_3$ was added TiCl$_4$ (6 mL of a 1M solution in CH$_2$Cl$_2$, 6 mmol) at −78° C. The solution was stirred for 2 h, then allowed to warm to 0° C. and stirred for 2 h. The mixture was poured into 150 mL water and neutralized with 6N NaOH. The aqueous layer was extracted with CHCl$_3$ (3×100 mL), and the combined organic layers washed with brine (150 mL), dried over MgSO$_4$, filtered and concentrated. Flash chromatography (gradient elution, hexanes:EtOAc 9:1 to 3:1) afforded 1.6 g (88%) of (2R)-2-[2-fluoro-4-nitro(2,2,2-trifluoroethyl)anilino]-3-methyl-1-butanol, an orange oil. Data for (2R)-2-[2-fluoro-4-nitro(2,2,2-trifluoroethyl)anilino]-3-methyl-1-butanol: $R_f$ 0.3 (3:1 hexanes:EtOAc); $^1$H NMR (400 MHz, CDCl$_3$) δ 7.96 (dd, 1H, J=8.8, 2.3), 7.92 (dd, 1H, J=13.4, 2.5), 7.37 (dd, 1H, J=8.8, 8.8), 4.33–4.23 (m, 1H), 4.03–3.86 (m, 2H), 3.81–3.74 (m, 1H), 3.36–3,27 (m, 1H), 1.97–1.88 (m, 1H), 1.85 (broad s, 1H), 0.99 (d, 3H, J=6.6), 0.94 (d, 3H, J=6.6).

(3R)-3,4-Dihydro-3-isopropyl-7-nitro-4-(2,2,2-trifluoroethyl)-2H-1,4-benzoxazine (Structure 39 of Scheme VIII, where R$^4$=isopropyl. R$_x$=CF$_3$. This compound was prepared according to General Method 20 (EXAMPLE 45) from (2R)-2-[2-fluoro-4-nitro(2,2,2-trifluoroethyl)anilino]-3-methyl-1-butanol (1.58 g, 4.87 mmol) in 30 mL THF and NaH (0.351 g, 14.6 mmol) in 10 mL THF heated at reflux for 0.5 hr to afford 0.80 g (54%) of (3R)-3,4-dihydro-3-isopropyl-7-nitro-4-(2,2,2-trifluoroethyl)-2H-1,4-benzoxazine, a yellow oil, after purification by flash chromatography (gradient elution, hexanes:EtOAc 9:1 to 3:1). Data for (3R)-3,4-dihydro-3-isopropyl-7-nitro-4-(2,2,2-trifluoroethyl)-2H-1,4-benzoxazine: $R_f$ 0.5 (3:1 hexanes:EtOAc); $^1$H NMR (400 MHz, CDCl$_3$) δ 7.81 (dd, 1H, J=9.1, 2.5), 7.72 (d, 1H, J=2.6), 6.79 (d, 1H, J=9.1), 4.49 (dd, 1H, ABX, J=11.1, 0.92), 4.37–4.26 (m, 1H), 3.95 (dd, 1H, J=11.1, 2.4), 3.80–3.69 (m, 1H), 3.14 (d, 1H, J=8.5), 2.08–1.98 (m, 1H), 1.01 (d, 3H, J=6.9), 0.99 (d, 3H, J=6.9).

(3R)-7-Amino-3,4-dihydro-3-isopropyl-4-(2,2,2-trifluoroethyl)-2H-1,4-benzoxazine (Structure 40 of Scheme VIII, where R$^4$=isopropyl. R$_x$=CF,). This compound was prepared according to General Method 4 (EXAMPLE 1) from (3R)-3,4-dihydro-3-isopropyl-7-nitro-4-(2,2,2-trifluoroethyl)-2H-1,4-benzoxazine (0.350 g, 1.15 mmol) and 10% Pd/C (0.14 g) in 7 mL EtOAc to afford 0.284 g (90%) of (3R)-7-amino-3,4-dihydro-3-isopropyl-4-(2,2,2-trifluoroethyl)- 2H-1,4benzoxazine after purification by flash chromatography (gradient elution, hexanes:EtOAc 9:1 to 3:1). Data for (3R)-7-amino-3,4-dihydro-3-isopropyl-4-(2,2,2-trifluoroethyl)-2H-1,4-benzoxazine: $R_f$ 0.2 (3:1 hexanes:EtOAc); $^1$H NMR (400 MHz, CDCl$_3$) δ 6.71 (d, 1H, J=8.5), 6.27 (dd, 1H, J=8.5, 2.6), 6.20 (d, 1H, J=2.5), 4.34 (dd, 1H, ABX, J=11.0, 1.5), 3.84 (dd, 1H, ABX, J=11.3, 2.2), 3.71–3.47 (m, 2H), 3.41 (broad s, 2H), 2.62 (d, 1H, J=9.8), 1.81–1.70 (m, 1H), 0.98 (d, 3H, J=6.7), 0.96 (d, 3H, J=6.7).

(2R)-1,2,3,6-Tetrahydro-2-isopropyl-1-(2,2,2-trifluoroethyl)-9-(trifluoromethyl)-7H-[1,4]oxazino[3,2-g]quinolin-7-one (Compound 151, Structure 41 of Scheme VIII, where R$^1$=H, R$^2$=trifluoromethyl, R$^4$=isopropyl, R$_x$=CF$_3$). This compound was prepared according to General Method 11 (EXAMPLE 22) from (3R)-7-amino-3,4-dihydro-3-isopropyl-4-(2,2,2-trifluoroethyl)-2H-1,4-benzoxazine (0.284 g, 1.04 mmol) and ethyl 4,4,4-trifluoroacetoacetate (0.573 g, 3.11 mmol) in 8 mL toluene followed by workup and treatment with 6 mL conc. sulfuric acid to afford 0.15 g (38%) of Compound 151, a yellow solid, after flash chromatography (19:1 CH$_2$Cl$_2$:MeOH). Further purification was performed by reverse phase HPLC (ODS, 5 microm, 10×250 mm), 80% MeOH:water, 2.6 mL/min). Data for Compound 151: $R_f$ 0.2 (19:1 CH$_2$Cl$_2$:MeOH); $^1$H NMR (400 MHz, CDCl$_3$) δ 12.52 (broad s, 1H), 7.14 (broad s, 1H), 6.95 (s, 1H), 6.92 (s, 1H), 4.50 (d, 1H, J=11.0), 4.18–4.06 (m, 1H), 4.05 (dd, 1H, ABX, J 11.0, 2.5), 3.75–3 .60 (m, 1H), 2.98 (d, 1H, J=8.7), 1.98–1.88 (m, 1H), 1.00 (d, 3H, J=7.3), 0.98 (d, 3H, J=7.3).

EXAMPLE 49

(±)-1,2,3,4,4a,5-Hexahydro-11-(trifluoromethyl)-pyrido[1',2':4.5][1,4]oxazino[3,2-g]quinolin-9 (8H)-one (Compound 152, Structure 41 of Scheme VIII, where R$^1$=H, R$^2$=Trifluoromethyl, R$^4$, R$^x$=—(CH$_2$)$_3$)

(±)-[1-(2-Fluoro-4-nitrophenyl)-2-piperidinyl]-methanol] (Structure 42 of Scheme IX, where R$^4$, R$^x$=—(CH$_2$)$_4$—. A solution of 3,4-difluoronitrobenzene (1.00 g, 6.28 mmol) and (±)-2-piperidinemethanol (0.724 g, 6.28 mmol) in 1.5 mL EtOH was heated at 50° C. for 18 h, then heated at reflux for 24 h. The solvent was concentrated and the crude reaction purified by flash chromatography (7:3 hexanes:EtOAc) to afford 0.85 g (53%) of (±)-[1-(2-fluoro-4-nitrophenyl)-2-piperidinyl]-methanol], an orange oil. Data for (±)-[1-(2-fluoro-4-nitrophenyl)-2-piperidinyl]-methanol]: $R_f$ 0.36 (3:7, EtOAc:hexanes); $^1$H NMR (400 MHz, CDCl$_3$) δ 7.95 (dd, 1H, J=8.8, 2.4), 7.88 (dd, 1H, J=13,2, 2.4), 7.01 (t, 1H, J=8.8), 4.04–3.97 (m, 2H), 3.74–3.68 (m, 1H), 3.45–3.42 (m, 1H), 3.34–3,28 (m, 1H), 1.89–1.82 (m, 1H), 1.77–1.61 (m, 6H).

(±)-3-Nitro-6,6a,7,8,9,10-hexahydropyrido[2,1-c][1,4]benzoxazine (Structure 39 of Scheme IX, where R$^4$, R$^x$=—(CH$_2$)$_4$—). A suspension of (+)-[I-(2-fluoro-4-nitrophenyl)-2-piperidinyl]-methanol (0.586 g, 2.30 mmol) and sodium hydride (60% mineral oil suspension, 0.101 g, 2.54 mmol) in 10 mL THF was heated at reflux for 16 h. The mixture was neutralized with phosphate buffer (pH 7), and the resultant solution was extracted twice with EtOAc. The combined organic layers were washed with brine, dried over $Na_2SO_4$, filtered, and concentrated. Flash chromatography (7:3 hexanes:EtOAc) afforded 0.410 g (76%) of (±)-3-nitro-6,6a,7,8,9, 10-hexahydropyrido[2,1-c][1,4]benzoxazine, a yellow-orange solid. Data for (±)-3-nitro-6,6a,7,8,9,10-hexahydropyrido[2,1-c][1,4]benzoxazine: $R_{f\ o.}$ 71 (2:3, EtOAc:hexanes) $^1$H NMR (400 MHz, $CDCl_3$) δ 7.78 (dd, 1H, J=9.3, 2.9), 7.64 (d, 1H, J=2.9), 6.75 (d, 1H, J=9.3), 4.23 (dd, 1H, J=10.7, 2.9), 3.96 (dd, 1H, J=10.7, 7.8), 3.93 (m, 1H), 3,22–3.17 (m, 1H), 2.78 (td, 1H, J=12.8, 3.0), 1.95–1.92 (m, 1H), 1.88–1.84 (m, 1H), 1.75–1.71 (m, 1H), 1.66–1.60 (m, 1H), 1.58–1.48 (m, 1H), 1.35–1.27 (m, 1H).

(±)-3-Amino-6,6a,7,8,9,10-hexahydropyrido[2,1-c][1,4]benzoxazine (Structure 40 of Scheme VIII, where $R^4$, $R^x$=—$(CH_2)_3$—). This compound was prepared according to General Method 4 (EXAMPLE 1) from (±)-3-nitro-6,6a,7,8,9,10-hexahydropyrido[2,1-c][1,4]benzoxazine (0.300 g, 1.30 mmol) to afford 0.232 g (88%) of (±)-3-amino-6,6a,7,8,9,10-hexahydropyrido[2,1-c][1,4]benzoxazine, a colorless oil, after flash chromatography (gradient elution 3:7 EtOAc:hexanes, then 3:2 EtOAc:hexanes). Data for (+)-3-amino-6,6a,7,8,9,10-hexahydropyrido[2,1-c][1,4]benzoxazine: $R_f$ 0.5 (2:3, EtOAc:hexanes); $^1$H NMR (400 MHz, $CDCl_3$) δ 6.66 (d, 1H, J=8.3), 6.24 (dd, 1H, J=8.5, 2.7), 6.21 (d, 1H, J=2.4), 4.11 (dd, 1H, J=10.7, 2.4), 3.97 (dd, 1H, J=10.7, 9.0), 3.69 (dd, 1H, J=13.7, 11.2), 3.33 (br s, 2H), 2.85–2.80 (m, 1H), 2.43 (td, 1H, J=11.7, 2.9), 1.87–1.78 (m, 2H), 1.69–1.60 (m, 2H), 1.45–1.36 (m, 1H), 1.28–1.19 (m, 1H).

(±)-1,2,3,4,4a,5-Hexahydro-11-(trifluoromethyl)-pyrido[1',2':4,5][1,4]oxazino[3,2-g]quinolin-9(8H)-one (Compound 152, Structure 41 Scheme VIII, where $R^1$=H, $R^2$=trifluoromethyl, $R^4$, $R^x$=—$(CH_2)_3$). This compound was prepared according to General Method 11 (EXAMPLE 22) from (±)-3-amino-6,6a,7,8,9,10-hexahydropyrido[2,1-c][1,4]benzoxazine (0.232 g, 1.13 mmol), ethyl 4,4,4-trifluoroacetoacetate (0.250 g, 1.36 mmol) in 11 mL benzene followed by treatment with conc. $H_2SO_4$ to afford 0.110 g (30%) of Compound 152, a yellow fluffy solid. Data for Compound 152: $R_f$ 0.15 (2:3, EtOAc:hexanes); $^1$H NMR (400 MHz, $CDCl_3$) δ 10.73 (br s, 1H), 7.09 (s, 1H), 6.87 (s, 1H), 6.73 (s, 1H), 4.26 (dd, 1H, J=10.5, 2.6), 4.06 (dd, 1H, J=10.5,9.0), 3.80 (m, 1H), 3.02–2.97 (m, 1H), 2.60 (td, 1H, J=12.2, 2.9), 1.92 (m, 2H), 1.74–1.65 (m, 2H), 1.50–1.42 (m, 1H), 1.29–1.21 (m, 1H).

EXAMPLE 50

(R)-2,3,3a,4-Tetrahydro-10-(trifluoromethyl)-1H-pyrrolo[1',2':4,5][1,4]oxazino[3,2-g]quinolin-8(7H)-one (Compound 153, Structure 41 of Scheme VIII, where $R^1$=H, $R^2$=trifluoromethyl, $R^4$, $R^x$=—$(CH_2)_2$—)

(R)-[1-(2-Fluoro-4-nitrophenyl)-2-pyrrolidinyl]-methanol (Structure 42 of Scheme IX, where $R^1$=H, $R^x$=—$(CH_2)_2$—). A suspension of 3,4-difluoronitrobenzene (1.57 g, 9.8 mmol), (R)-2-pyrrolidinemethanol (1.0 g, 9.8 mmol) and $K_2CO_3$ (1.36 g, 9.8 mmol) in 30 mL DMF was heated at 75° C. for 20 h, whereupon the mixture was partitioned between water (100 mL) and EtOAc (100 mL). The aqueous layer was extracted with EtOAc (100 mL), and the combined organic layers washed with brine, dried over $Na_2SO_4$, filtered, and concentrated. Flash chromatography (19:1 $CH_2Cl_2$:MeOH) afforded 2.27 g (96%) of (R)-[1-(2-fluoro-4-nitrophenyl)-2-pyrrolidinyl]-methanol, an orange solid. Data for (R)-[1-(2-fluoro-4-nitrophenyl)-2-pyrrolidinyl]-methanol: $R_f$ 0.17 (7:3 hexanes:EtOAc); $^1$H NMR (400 MHz, $CDCl_3$) δ 7.94 (dd, 1H, J=9.1, 2.6), 7.89 (dd, 1H, J=14.4, 2.6), 6.68 (t, 1H, J=9.0), 4.25–4.32 (m, 1H), 3.60–3.75 (m, 3H), 3.40–3.50 (m, 1H), 1.95–2.15 (m, 4H), 1.43 (t, 1H, J=5.8).

(R)-2,3,3a,4-Tetrahydro-7-nitro-1H-pyrrolo[2,1-c][1,4]benzoxazine (Structure 42 of Scheme IX where $R^4$, $R^x$=—$(CH_2)_2$—). A suspension of (R)-[1-(2-fluoro-4-nitrophenyl)-2-pyrrolidinyl]-methanol (2.27 g, 9.4 mmol) and NaH (60% mineral oil suspension, 0.737 g, 18.9 mmol) in 35 mL THF was heated at reflux for 1 h. The reaction was quenched with phosphate buffer, and the aqueous layer was extracted with EtOAc. The solution was filtered through Celite, and the organic layer was washed with brine, dried over $MgSO_4$, filtered, and concentrated. Flash chromatography (3:2 EtOAc:hexanes) afforded 476 mg (22%) of (R)-2,3,3a,4-tetrahydro-7-nitro-1H-pyrrolo[2,1-c][1,4]benzoxazine, an orange solid. Data for (R)-2,3,3a,4-tetrahydro-7-nitro-1H-pyrrolo[2,1-c][1,4]benzoxazine: $R_f$ 0.55 (3:2 hexanes:EtOAc); $^1$H NMR (400 MHz, $CDCl_3$) δ 7.87 (dd, 1H, J=9,2,2,4), 7.74 (d, 1H, J=2.4), 6.44 (d, 1H, J=8.8), 4.56 (dd, 1H, J=10.3, 3.4), 3.65–3.72 (m, 1H), 3.60 (broad t, 1H, J=8.6), 3.44 (t, 1H, J=10.0), 3.36 (td, 1H, J=9.8, 7.3), 2.15–2.25 (m, 2H), 2.05–2.15 (m, 1H), 1.45–1.55 (m, 1H).

(R)-7-Amino-2,3,3a,4-tetrahydro-1H-pyrrolo[2,1-c][1,4]benzoxazine (Structure 40 of Scheme VIII, where $R^4$, $R^x$=—$(CH_2)_2$—). This compound was prepared according to General Method 4 (EXAMPLE 1) from (R)-2,3,3a,4-tetrahydro-7-nitro-1H-pyrrolo[2,1-c][1,4]benzoxazine (0.470 g, 2.10 mmol) to afford 0.39 g (98%) of (R)-2,3,3a,4-tetrahydro-7-nitro-1H-pyrrolo[2,1-c][1,4]benzoxazine. Data for (R)-7-amino-2,3,3a,4-tetrahydro-1H-pyrrolo[2,1-c][1,4]benzoxazine: $R_f$ 0.55 (3:2 hexanes:EtOAc); $^1$H NMR (400 MHz, $CDCl_3$) δ 6.50 (d, 1H, J=8.3), 6.32 (d, 1H, J=2.4), 6.29 (dd, 1H, J=8.3, 2.4), 4.31 (dd, 1H,.J=8.3, 1.5), 3.37–3.50 (m, 3H), 3.31 (broad s, 2H), 3.13 (broad q, 1H, J=8.3), 2.07–2.15 (m, 1H), 1.90–2.05 (m, 2H), 1.40–1.50 (m, 1H).

(R)-2,3,3a,4-Tetrahydro-10-(trifluoromethyl)-1H-pyrrolo[1',2':4,5][1,4]oxazino[3,2-g]quinolin-8(7H)-one (Compound 153, Structure 41 of Scheme VIII, where $R^1$=H, $R^2$=trifluoromethyl, $R^4$, $R^x$=—$(CH_2)_2$—. This compound was prepared according to General Method 11 (EXAMPLE 22) from (R)-7-amino-2,3,3a,4-tetrahydro-1H-pyrrolo[2,1-c][1,4]benzoxazine (0.390 g, 2.05 mmol) and ethyl 4,4,4-trifluoroacetoacetate (0.378 g, 2.05 mmol) in 14 mL benzene, followed by workup and treatment with 7 mL concentrated sulfuric acid to afford 120 mg (20%) of Compound 153, a yellow solid after flash chromatography (92:8 $CH_2Cl_2$:MeOH). Further purification was performed by reverse phase HPLC (ODS, 5 micron, 10×250 mm, 3 mL/min). Data for Compound 153: $^1$H NMR (400 MHz, $CDCl_3$) δ 11.42 (broad s, 1H), 6.91 (s, 1H), 6.89 (s, 1H), 6.76 (broad s, 1H), 4.54 (dd, 1H, J=9.6, 2.7), 3.61 (t, 1H, J=9.6), 3.50–3.60 (m, 1H), 3.40–3.50 (m, 1H), 3.30–3.40 (m, 1H), 2.12–2.22 (m, 2H), 2.00–2.10 (m, 1H), 1.40–1.50 (m, 1H).

EXAMPLE 51

1,3,4,6-Tetrahydro-1,3,3-trimethyl-9-(trifluoromethyl)pyrazino[3,2-g]quinolin-2,7-dione (Compound 154, Structure 47 of Scheme X, where $R^1$=H, $R^2$=Trifluoromethyl, $R^6$=$R^7$=$R^{13}$=Me)

3,4-Dihydro-3,3-dimethylquinoxalin-2 (1H)-one (Structure 44 of Scheme X, where $R^6$=$R^7$=Me). In a 200-mL r.b. flask, a solution of 1,2-phenylenediamine (2.12 g, 19.6 mmol), diisopropylethylamine (4.55 ml, 25.5 mmol, 1.3 equiv), ethyl-2-bromoisobutyrate (4.97 mL, 25.5 mmol, 1.3 equiv) in DMF (20 mL) was heated to 110° C. overnight, cooled, partitioned between EtOAc (100 mL) and H$_2$O (30 mL). The aqueous layer was extracted with EtOAc (2×50 mL). The combined organic layers were washed sequentially with 1 M HCl (40 mL), H$_2$O (40 mL), saturated NaHCO$_3$ (40 ml), H$_2$O (40 mL) and brine (30 mL), dried (MgSO$_4$), filtered, and concentrated. The crude product was purified by recrystallization (CH$_2$Cl$_2$/hexane) to give 2.09 g (60%) of 3,4-dihydro-3,3-dimethylquinoxalin-2 (1l)-one as white crystals. Data for 3,4-dihydro-3,3-dimethylquinoxalin-2 (1H)-one: $^1$H NMR (400 MHz, CDCl$_3$) δ 7.84 (bs, 1H), 6.89 (dd, J=7.3, 7.3, 1H), 6.76 (dd, J=7.2, 7.3, 1H), 6.70 (d, J=7.6 , 1H), 6.67 (d, J=6.9, 1H), 3.69 (bs, 1H), 1.41 (s, 6H).

3,4-Dihydro-1,3,3-trimethylquinoxalin-2(1H)-one. In a 200-mL r.b. flask, a solution of 3,4-dihydro-3,3-dimethylquinoxalin-2(1H)-one (1.00 g, 5.66 mmol) in dry THF was treated with NaH (0.28 g, 7.09 mmol, 1.25 equiv). The reaction mixture was stirred at room temperature for 30 minutes before iodomethane (0.39 mL, 6.24 mmol, 1.1 equiv) was added to the reaction flask. The reaction was then stirred at room temperature overnight then partitioned between EtOAc (100 mL) and H$_2$O (20 mL). The aqueous layer was extracted with EtOAc (2×30 mL). The combined organic layers were then washed with brine (20 mL), dried (MgSO$_4$), filtered, and concentrated to a thick oil. Purification by flash chromatography (25% EtOAc/hexane) afforded 830 mg (78%) of 3,4-dihydro-1,3,3-trimethylquinoxalin-2 (1H)-one as a white solid. Data for 3,4-dihydro-1,3,3-trimethylquinoxalin-2(1H)-one: $^1$H NMR (400 MHz, CDCl$_3$) δ 6.90 (m, 3H), 6.67 (d, J=7.7, 1H), 3.69 (bs, 1H), 3.36 (s, 3H), 1.37 (s, 6H).

3,4-Dihydro-1,3,3-trimethyl-6-nitroquinoxalin-2 (1 H)-one (Structure 45 of Scheme X, where R$^6$=R$^7$=R$^{13}$=Me). In a 50-mL r.b. flask, a solution of 3,4-dihydro-1,3,3-trimethylquinoxalin-2(1H)-one (830 mg, 4.36 mmol) in 20 mL of conc. H$_2$SO$_4$ was cooled to −15° C. A solution of HNO$_3$ (336 mg, 4.80 mmnol, 1.1 equiv) dissolved in conc. H$_2$SO$_4$ (1 mL) was then added dropwise via syringe in order to maintain a temperature below −5° C. After complete addition the reaction was allowed to stir at −15° C. for 15 min, warmed to rt, poured over NaOH (15 g) pellets and ice. After complete solution of the NaOH pellets, the red precipitate was filtered, redissolved in EtOAc (150 mL), washed with H$_2$O (20 mL), brine (20 mL), dried (MgSO$_4$), filtered, and concentrated to give a orange solid. No further purification is required to obtain 960 mg (94%) of 3,4-dihydro-1,3,3-trimethyl-6-nitroquinoxalin-2(1H)-one as an orange solid. Data for 3,4-dihydro-1,3,3-trimethyl-6-nitroquinoxalin-2 (1H)-one: $^1$H NMR (400 MHz, CDCl$_3$) δ 7.76 (dd, J=8.8, 2.5, 1H), 7.55 (d, J=2.4, 1H), 6.96 (d, J=8.9, 1H), 4.04 (bs, 1H), 3.42 (s, 3H), 1.41 (s, 6H).

6-Amino-3,4-dihydro-1,3,3-trimethylquinoxalin-2(1H)-one (Structure 46 of Scheme X, where R$^6$=R$^7$=R$^{13}$=Me). In a Parr shaker apparatus, a solution 3,4-dihydro-1,3,3-trimethyl-6-nitroquinoxalin-2(1lH)-one (960 mg, 4.08 mmol) in 50 mL of EtOAc:EtOH (1:1) and a catalytic amount of 10% Pd on activated carbon (96 mg, 10 wt-%) were shaken under an atmosphere of hydrogen gas at 45 psi overnight. The reaction mixture was filtered through a pad of celite. The filtrate and EtOH washings were combined and concentrated to give 838 mg (100%) of 6-amino-3,4-dihydro-1,3,3-trimethylquinoxalin-2(1H)-one, purple brown solid. Data for 6-amino-3,4-dihydro-1,3,3-trimethylquinoxalin-2(1H)-one: $^1$H NMR (400 MHz, CDCl$_3$) δ 6.69 (d, J=8.42, 1H), 6.19 (dd, J=8.5, 2.4, 1H), 6.05 (d, J=2.4, 1H), 3.55 (bs, 1H), 3.31 (s, 3H), 1.35 (s, 6H).

1,3,4,6-Tetrahydro-1,3,3-trimethyl-9-(trifluoromethyl)pyrazino[3,2-g]quinolin-2,7-dione (Compound 154, Structure 47 of Scheme X, where R$^1$=H, R$^2$=trifluoromethyl, R$^6$=R$^7$=R$^{13}$=Me). In a 100-mL r.b. flask, a solution of 6-amino-3,4-dihydro-1,3,3-trimethylquinoxalin-2(1H)-one (500 mg, 2.44 mmol) and ethyl-4,4,4-trifluoroacetoacetate (0.46 mL, 3.16 mmol, 1.3 equiv) in toluene (40 mL) was heated to reflux with stirring overnight. Removal of solvent followed be treatment of the crude product with conc H$_2$SO$_4$ (10 mL) at 100° C. for 10 h, cooled to rt, poured onto ice and the pH adjusted to 7 with NaOH pellets. The aqueous phase was extracted with EtOAc (4×50 mL), combined, washed with brine, dried (MgSO$_4$), filtered, and concentrated to a brown oil. Purification by flash chromatography (EtOAc/hexane, 25% to 50%, gradient elution) afforded 80 mg (10%) of Compound 154 as a yellow solid. Data for Compound 154: $^1$H NMR (400 MHz, DMSO-d$_6$) δ 12.07 (s, 1H), 7.22 (s, 1H), 7.01 (s, 1H), 6.73 (s, H), 6.61 (s, 1H), 3.30 (s, 3H), 1.29 (s, 6H).

EXAMPLE 52

1,2,3,4-Tetrahydro-1,3,3-trimethyl-9-(trifluoromethyl)pyrazino[3,2-g]quinolin-7(6H-one (Compound 155, Structure 49 of Scheme X, where R$^1$=H, R$^2$=Trifluoromethyl, R$^6$=R$^7$=R$^{13}$=Me)

1,2,3,4-Tetrahydro-7-isopropoxy-1,3,3-trimethyl-9-(trifluoromethyl)pyrazino[3,2-g]quinolin-2-one (Structure 48 of Scheme X, where R$^1$=H, R=trifluoromethyl, R$^6$=R$^7$=R$^{13}$=Me). This compound was made according to General Method 12 (EXAMPLE 22) from Compound 154 (EXAMPLE 51) (40 mg, 0.12 mmol), cesium fluoride (28 mg, 0.18 mmol, 1.5 equiv), and 2-iodopropane (0.02 mL, 0.18 mmol, 1.5 equiv). The crude reaction mixture was purified by silica gel chromatography (EtOAc/hexane, 25% to 50% gradient elution) to afford 26 mg (56%) of 1,2,3,4-tetrahydro-7-isopropoxy-1,3,3-trimethyl-9-(trifluoromethyl)pyrazino[3,2-g]quinolin-2-one as an off-white solid. Data for 1,2,3,4-tetrahydro-7-isopropoxy-1,3,3-trimethyl-9-(trifluoromethyl)pyrazino[3,2-g]quinolin-2-one: $^1$H NMR (400 MHz, CDCl$_3$) δ 7.34 (s, 1H), 7.06 (s, 1H), 6.96 (s, 1H), 5.49 (sep, J=6.3, 1H), 4.17 (s, 1H), 3.47 (s, 3H), 1.45 (s, 6H), 1.39 (d, J=6.3, 6H).

1,2,3,4-Tetrahydro-7-isopropoxy-1,3,3-trimethyl-9-(trifluoromethyl)pyrazino[3,2-g]quinoline. This compound was made according to General Method 2 (EXAMPLE 1) from 1,2,3,4-tetrahydro-7-isopropoxy-1,3,3-trimethyl-9-(trifluoromethyl)pyrazino[3,2-g]quinolin-2-one (25 mg, 0.07 mmol) and BH$_3$-DMS (0.14 mL, 0.27 mmol, 4.0 equiv). Purification by silica gel chromatography (EtOAc/hexane, 10% to 25% gradient) afforded 5 mg (25%) of 1,2,3,4-tetrahydro-7-isopropoxy-1,3,3-trimethyl-9-(trifluoromethyl)pyrazino[3,2-g]quinoline as a pale yellow solid. Data for 1,2,3,4-tetrahydro-7-isopropoxy-1,3,3-trimethyl-9-(trifluoromethyl)pyrazino[3,2-g]quinoline: $^1$H NMR (400 MHz, CDCl$_3$) δ 6.84 (s, 1H), 6.82 (s, 1H), 6.77 (s, 1H), 5.43 (sept, J=6.1, 1H), 3.04 (s, 2H), 3.02 (s, 3H), 1.39 (d, J=6.0, 6H), 1.29 (s, 6H).

1,2,3,4-Tetrahydro-1,3,3-trimethyl-9-(trifluoromethyl)pyrazino[3 2-g]quinolin-7(6H)-one (Compound 155, Structure 49 of Scheme X, where R=H, R=trifluoromethyl, R$^6$=R$^7$=R$^{13}$=Me). This compound was made according to General Method 15 (EXAMPLE 22) from 1,2,3,4-tetrahydro-7-isopropoxy-1,3,3-trimethyl-9-

(trifluoromethyl)pyrazino[3,2-g]quinoline (5 mg, 0.02 mmol) to yield 2 mg (45%) of Compound 155, a yellow solid. Data for Compound 155: $^1$H NMR (400 MHz, DMSO-d$_6$) δ 11.75 (broad s, 1H), 6.97 (s, 1H), 6.39 (s, 1H), 6.37 (s, 1H), 5.23 (bs, 1H), 2.86 (s, 2H), 2.82 (s, 3H), 1.17 (s, 6H).

EXAMPLE 53

9-(Trifluoromethyl)-1,2,3,6-tetrahydro-7H-[1,4] thiazino[3,2-g]quinolin-7-one (Compound 156, Structure 54 of Scheme XI, where R$^4$=H)

6-Bromo-7-chloro-2-isopropoxy-4-(trifluoromethyl) quinoline (Structure 51 of Scheme XI). This compound was prepared according to General Method 11 (EXAMPLE 22) from 4-bromo-3-chloroaniline (2.06 g, 10.0 mmol), ethyl 4,4,4-trifluoroacetoacetate (2.30 g, 12.5 mmol) in 50 mL toluene followed by heating in 33 mL conc. H$_2$SO$_4$ to afford 2.08 g (64%) of 6-bromo-7-chloro-4-(trifluoromethyl)-quinolin-2(1H)-one, an off-white solid. This material was converted to the corresponding imino ether according to General Method 12 (EXAMPLE 22) with isopropyl iodide (4.32 g, 25.4 mmol) and CsF (3.85 g, 25.4 mmol) in 32 mL DMF to afford 1.34 g (57%) of 6-bromo-7-chloro-2-isopropoxy-4-(trifluoromethyl)quinoline, a white solid, after flash chromatography (hexanes). Data for 6-bromo-7-chloro-2-isopropoxy-4-(trifluoromethyl)quinoline: $^1$H NMR (400 MHz, CDCl$_3$) δ 8.22 (broad s, 1H), 8.00 (s, 1H), 7.17 (s, 1H), 5.51 (hept, 1H, J=6.2), 1.40 (d, 6H, J=6.2).

2-{[6-Bromo-2-isopropoxy-4-(trifluoromethyl)-7-quinolinyl]sulfanyl}-1-ethanamine (Structure 52 of XI, where R$^4$=H). A solution of 6-bromo-7-chloro-2-isopropoxy-4-(trifluoromethyl)quinoline (0.500 g, 1.36 mmol), 2-aminoethanethiol hydrochloride (0.185 g, 1.63 mmol), NaH (60% in mineral oil, 0.136 g, 3.40 mmol) in 6.8 mL DMF was stirred at 0° C., then allowed to warm to rt. After 4 h, the mixture was poured into a cold saturated NH$_4$Cl:water (60 mL, 1:1). The solution was extracted with EtOAc (2×60 mL), and the combined organic layers washed sequentially with water (30 mL), brine (30 mL), dried over MgSO$_4$, filtered, and concentrated. Flash chromatography (9:1 CH$_2$Cl$_2$:MeOH) afforded 0.404 g (73%) of 2-{[6-bromo-2-isopropoxy-4-(trifluoromethyl)-7-quinolinyl]sulfanyl}-1-ethanamine, a yellow-brown solid. Data for 2-{[6-bromo-2-isopropoxy-4-(trifluoromethyl)-7-quinolinyl]sulfanyl}-1-ethanamine: $^1$H NMR (400 MHz, CDCl$_3$) δ 8.13 (broad s, 1H), 7.63 (s, 1H), 7.10 (s, 1H), 5.54 (hept, 1H, J=6.2), 3.17–3.25 (m, 2H), 3.08–3.15 (m, 2H), 1.41 (d, 6H, J=6.2).

2,3-Dihydro-7-isopropoxy-9-(trifluoromethyl)-1H-[1,4] thiazino[3,2-g]quinoline (Structure 53 of Scheme XI, where R$^4$=H). A 10 mL Schlenk flask was charged with palladium acetate (10.7 mg, 0.0476 mmol), R-BINAP (32.6 mg, 0.0524 mmol) and sodium t-butoxide (0.137 g, 1.43 mmol). The flask was placed under vacuum, then bled with nitrogen. This process was repeated twice. The solids were dissolved in 3 mL toluene, and a solution of 2-{[6-bromo-2-isopropoxy-4-(trifluoromethyl)-7-quinolinyl]sulfanyl}-1-ethanamine (0.390 g, 0.953 mmol) in 3.3 mL toluene was added. The flask was heated to 100° C. for 4 h, whereupon the reaction was quenched with sat'd NH$_4$Cl (30 mL) and water (30 mL). The mixture was extracted with EtOAc (2×60 mL), and the combined organic layers washed with brine (30 mL), dried over MgSO$_4$, filtered, and concentrated. Flash chromatography (4:1 hexanes:EtOAc) afforded 0.242 g (77%) of 2,3-dihydro-7-isopropoxy-9-(trifluoromethyl)-1H-[1,4]thiazino[3,2-g]quinoline, a yellow solid. Data for 2,3-dihydro-7-isopropoxy-9-(trifluoromethyl)-1H-[1,4] thiazino[3,2-g]quinoline: $^1$H NMR (400 MHz, CDCl$_3$) δ 7.56 (s, 1H), 6.99 (s, 1H), 6.90 (broad s, 1H), 5.44 (hept, 1H, J=6.2), 4.35 (broad s, 1H), 3.64–3.70 (m, 2H), 3.11–3.16 (m, 2H), 1.37 (d, 6H, J=6.2).

9-(Trifluoromethyl)-1,2,3,6-tetrahydro-7H-[1,4]thiazino [3,2-g]quinolin-7-one (Compound 156, Structure 54 of Scheme XI, where R$^4$=H). This compound was prepared according to General Method 15 (EXAMPLE 22) from 2,3-dihydro-7-isopropoxy-9-(trifluoromethyl)-1H-[1,4] thiazino[3,2-g]quinoline (15 mg, 0.046 mmol) and 0.15 mL conc. HCl and 0.5 mL HOAc to afford 12 mg (91%) of Compound 156, a yellow solid. Data for Compound 156: $^1$H NMR (400 MHz, ace-d$_6$) δ 10.8 (v broad s, 1H), 7.12 (s, 1H), 6.92 (broad s, 1H), 6.75 (s, 1H), 5.74 (broad s, 1H), 3.58–3.64 (m, 2H), 3.12–3.20 (m, 2H).

EXAMPLE 54

1-Methyl-9-(trifluoromethyl)-1,2,3,6-tetrahydro-7H-[1,4]thiazino[3,2-g]quinolin-7-one (Compound 157, Structure 56 of Scheme XI, where R$^4$=H, R$^x$=Me)

2,3-Dihydro-1-methyl-7-isopropoxy-9-(trifluoromethyl)-1H-[1,4]thiazino[3,2-g]quinoline (Structure 55 of Scheme XI, where R$^4$=H, R$^x$=Me). To a solution of 2,3-dihydro-7-isopropoxy-9-(trifluoromethyl)-1H-[1,4]thiazino[3,2-g] quinoline (11 mg, 0.033 mmol) and paraformaldehyde (9.9 mg, 0.33 mmol) in 0.5 mL acetic acid was added NaBH$_3$CN (12 mg, 0.19 mmol). After 16 h, the solution was quenched with sat'd NaHCO$_3$ (20 mL), and was extracted with EtOAc (20 mL). The organic layer was washed sequentially with sat'd NaHCO$_3$ (10 mL) and brine (10 mL), dried over MgSO$_4$, filtered and concentrated to afford 11 mg (97%) of 2,3-dihydro-1-methyl-7-isopropoxy-9-(trifluoromethyl)-1H-[1,4]thiazino[3,2-g]quinoline, a yellow solid. Data for 2,3-dihydro-1-methyl-7-isopropoxy-9-(trifluoromethyl)-1H-[1,4]thiazino[3,2-g]quinoline: $^1$H NMR (400 MHz, CDCl$_3$) δ 7.60 (s, 1H), 7.01 (s, 1H), 6.98 (broad s, 1H), 5.45 (hept, 1H, J=6.2), 3.58–3.64 (m, 2H), 3.14–3.20 (m, 2H), 3.05 (s, 3H), 1.37 (d, 6H, j=6.2).

1-Methyl-9-(trifluoromethyl)-1,2,3,6-tetrahydro-7H-[1,4] thiazino[3,2-g]quinolin-7-one (Compound 157, Structure 56 of Scheme XI, where R$^4$=H, R$^x$=H). This compound was prepared according to General Method 15 (EXAMPLE 22) from 2,3-dihydro-1-methyl-7-isopropoxy-9-(trifluoromethyl)-1H-[1,4]thiazino[3,2-g]quinoline (11 mg, 0.032 mmol) and 0.2 mL HCl and 0.6 mL HOAc heated at 80° C. for 3 h to afford 7 mg (73%) of Compound 157, a yellow solid, after flash chromatography (23:2 CH$_2$Cl$_2$:MeOH). Data for Compound 157: $^1$H NMR (400 MHz, CDCl$_3$) δ 11.5 (broad s, 1H), 7.11 (s, 1H), 6.95 (s, 1H), 6.90 (broad s, 1H), 3.52–3.60 (m, 2H), 3.15–3.20 (m, 2H), 3.01 (s, 3H).

EXAMPLE 55

1-(2,2,2-trifluoroethyl)-9-(trifluoromethyl)-1,2,3,6-tetrahydro-7H-[1,4]thiazino[3,2-g]quinolin-7-one (Compound 158, Structure 56 of Scheme XI, where R$^4$=H, R$^x$=CF$_3$)

2,3-Dihydro-7-isopropoxy-1-(2,2,2-trifluoroethyl)-9-(trifluoromethyl)-1H-[1,4]thiazino[3,2-g]quinoline (Structure 55 of Scheme XI, where R$^4$=H, R$^x$=CF$_3$). This compound was prepared according to General Method 7 (EXAMPLE 5) from 2,3-dihydro-7-isopropoxy-9-(trifluoromethyl)-1H-[1,4]thiazino[3,2-g]quinoline (11 mg, 0.034 mmol), trifluoroacetaldehyde ethyl hemiacetal (49 mg, 0.34 mmol) and NaBH$_3$CN (14 mg, 0.22 mmol) in 0.7 mL TFA to afford 7.8 mg (56%) of 2,3-dihydro-7-isopropoxy-1-(2,2,2-trifluoroethyl)-9-(trifluoromethyl)-1H-[1,4]thiazino[3,2-g]quinoline, a yellow oil, after flash chromatography (9:1 hexanes:EtOAc). Data for 2,3-dihydro-7-isopropoxy- 1-(2,2,2-trifluoroethyl)-9-(trifluoromethyl)-1H-[1,4]thiazino[3,2-g]quinoline: $^1$H NMR (400 MHz, CDCl$_3$) δ 7.62 (s, 1H), 7.21 (broad s, 1H), 7.03 (s, 1H), 5.46 (hept, 1H, J=6.1), 3.97 (q, 2H, J=8.8), 3.77–3.83 (m, 2H), 3.08–3.14 (m, 2H), 1.38 (d, 6H, J=6.1).

1-(2,2,2-Trifluoroethyl)-9-(trifluoromethyl)-1,2,3,6-tetrahydro-7H-[1,4]thiazino[3,2-g]quinolin-7-one (Compound 158. Structure 56 of Scheme XI, where R$^4$=H, R$^x$=CF$_3$). This compound was prepared according to General Method 15 (EXAMPLE 22) from 2,3-dihydro-7-isopropoxy-1-(2,2,2-trifluoroethyl)-9-(trifluoromethyl)-1H-[1,4]thiazino[3,2-g]quinoline (7.8 mg, 0.019 mmol) in 0.2 mL HCl and 0.6 mL HOAc to afford 3.6 mg (51%) of Compound 158, a yellow solid, after flash chromatography (23:2 CH$_2$Cl$_2$:MeOH). Data for Compound 158: $^1$H NMR (400 MHz, ace-d$_6$) δ 10.8 (broad s, 1H), 7.21 (s, 1H), 7.15 (broad s, 1H), 6.80 (s, 1H), 4.18 (q, 2H, J=9.3), 3.77–3.83 (m, 2H), 3.18–3.24 (m, 2H).

EXAMPLE 56

Steroid Receptor Activity

Utilizing the "cis-trans" or "co-transfection" assay described by Evans et al., Science, 240:889–95 (May 13, 1988), the disclosure of which is herein incorporated by reference, the compounds of the present invention were tested and found to have strong, specific activity as both agonists, partial agonists and antagonists of AR. This assay is described in further detail in U.S. Pat. Nos. 4,981,784 and 5,071,773, the disclosures of which are incorporated herein by reference.

The co-transfection assay provides a method for identifying functional agonists and partial agonists that mimic, or antagonists that inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay, and in standard IR binding assays, according to the following illustrative Examples.

Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum (CH-FBS) then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following plasmids: pRShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor", 266 *J. Biol. Chem.*, 510 (1991).

The reporter plasmid, MTV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11beta,17beta)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]pronanamide; Schering-Plough) as an AR antagonist; estradiol (Sigma) as an ER agonist and ICI 164,384 (N-butyl-3,17-dihydroxy-N-methyl-(7-alpha,17-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-alpha-[acetylthio]-17-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

TABLE 1

Agonist, partial agonist, antagonist and binding activity of androgen receptor modulator compounds of present invention and the reference agonist compound, dihydrotestosterone (DHT), and reference antagonists compound, 2-hydroxyflutamide (Flut) and Casodex (Cas), on hAR in CV-1 cells.

| Compd No. | AR Agonist CV-1 Cells | | AR Antagonist CV-1 Cells | |
|---|---|---|---|---|
| | Efficacy (%) | Potency (nM) | Efficacy (%) | Potency (nM) |
| 101 | 56 | 18 | na | na |
| 102 | na[1] | na | 58 | 22 |
| 103 | 92 | 6.4 | 24 | 8000 |
| 104 | na | na | 68 | 26 |
| 105 | 88 | 3.5 | na | na |
| 106 | 80 | 4 | na | na |
| 107 | 92 | 26 | na | na |
| 108 | 80 | 14 | na | na |
| 109 | na | na | 57 | 24 |
| 110 | 90 | 44 | na | na |
| 111 | 88 | 2.4 | na | na |
| 112 | 80 | 2.6 | na | na |
| 113 | na | na | 78 | 61 |
| 114 | 94 | 6.2 | na | na |
| 115 | 82 | 7.8 | na | na |
| 116 | 24 | 39 | 35 | 14 |
| 117 | 36 | 40 | na | na |
| 118 | 76 | 11 | na | na |
| 119 | 20 | 39 | na | na |
| 120 | na | na | 69 | 112 |
| 121 | 69 | 1.4 | na | na |
| 122 | na | na | 75 | 632 |
| 123 | 91 | 3.4 | na | na |
| 124 | 54 | 3.6 | na | na |
| 125 | 74 | 0.70 | na | na |
| 128 | na | na | 42 | 1345 |
| 129 | 42 | 1340 | 76 | 13 |
| 130 | 48 | 8.9 | na | na |
| 131 | 46 | 31 | na | na |
| 132 | 72 | 1.7 | na | na |
| 137 | na | na | 84 | 18 |
| 145 | 69 | 6 | 30 | 5024 |
| DHT | 100 | 6 | na | na |
| Fluox | 120 | 2.8 | na | na |
| Flut | na | na | 83 | 25 |
| Cas | na | na | 81 | 201 |

[1]na = not active (i.e. efficacy of < 20 and potency of > 10,000 nM for the cotransfection assay, and Ki > 1000 nM for the binding assay).
nt = not tested.

TABLE 2

Overall agonist and antagonist potency of selected androgen receptor modulator compounds of present invention and the reference agonist and antagonist compounds shown in Table 1 on PR, AR, ER, GR and MR.

| Cmpd No. | PR Potency | | AR Potency | | ER Potency | | GR Potency | MR Potency |
|---|---|---|---|---|---|---|---|---|
| | Agon (nM) | Antag (nM) | Agon (nM) | Antag (nM) | Agon (nM) | Antag (nM) | Antag (nM) | Antag (nM) |
| 101 | na | na | 18 | na | na | na | 6500 | na |
| 102 | na | 4100 | na | 22 | na | 5900 | 3200 | na |
| 103 | na | 4500 | 6.4 | 8000 | na | na | na | na |
| 104 | na | 2000 | na | 26 | na | na | 830 | 1800 |
| 105 | na | 3000 | 3.5 | na | na | na | 6700 | na |
| 114 | na | na | 6.2 | na | na | na | na | na |
| 121 | na | 415 | 1.4 | na | na | na | 1050 | 2570 |

TABLE 2-continued

Overall agonist and antagonist potency of selected androgen receptor modulator compounds of present invention and the reference agonist and antagonist compounds shown in Table 1 on PR, AR, ER, GR and MR.

| Cmpd No. | PR Potency | | AR Potency | | ER Potency | | GR Potency | MR Potency |
|---|---|---|---|---|---|---|---|---|
| | Agon (nM) | Antag (nM) | Agon (nM) | Antag (nM) | Agon (nM) | Antag (nM) | Antag (nM) | Antag (nM) |
| 123 | na | 2470 | 3.4 | na | na | na | 3160 | na |
| 137 | na | na | na | 18 | na | na | na | na |
| Fluox | 1210 | 224 | 2.8 | na | na | na | 263 | 193 |
| Prog | 4 | na | 1300 | na | na | na | na | nt |
| RU486 | na | 0.1 | na | 12 | na | 1500 | 0.7 | 1100 |
| DHT | na | 1800 | 6 | na | 1700 | na | na | nt |
| Flut | na | 1900 | na | 26 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of >20 and potency of >10,000); nt = not tested.

EXAMPLE —57

The activity of selected compounds of the present invention as AR agonists was investigated in an immature castrated male rat model, a recognized test of the androgen of a given compound, as described in L. G. Hershberger et al., "Myotrophic Activity of 19-Nortestosterone and Other Steroids Determined by Modified Levator Ani Muscle Method" 83 *Proc. Soc. Exptl. Biol. Med.*, 175 (1953), and P. C. Walsh and R. F. Gittes "Inhibition of extratesticular stimuli to prostatic growth in the castrated rat by antiandrogens", 86 *Endocrinology*, 624 (1970); the disclosures of which are herein incorporated by reference.

The basis of this assay is the fact that the male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone (DHT), within the prostate by 5-alpha-reductase. Adrenal androgens also contribute about 20% of total DHT in the rat prostate, and about 40% of that in 65-year-old men. F. Labrie et al. 16 *Clin. Invest. Med.*, 475–92 (1993). However, this is not a major pathway, since in both animals and humans, castration leads to almost complete involution of the prostate and seminal vesicles without concomitant adrenalectomy. Therefore, under normal conditions, the adrenals do not support significant growth of prostatic tissue. M. C. Luke and D. S. Coffey, "The Physiology of Reproduction" ed. by E. Knobil and J. D. Neill, 1, 1435–1487 (1994). Since the male sex organs are the tissues most responsive to modulation of androgen activity, this model is used to determine the androgen-dependent growth of the sex accessory organs in immature castrated rats. In addition to the prostate and seminal vesicles, the levator ani demonstrates androgen dependent growth (Herschberger, supra). Androgens which show the greatest levator ani growth also show the greatest anabolic activity by nitrogen retention methods. Hence, the levator ani is a useful endpoint to measure myotrophic effects on muscle. Compounds which show anabolic activities could be useful in the treatment of muscle-wasting disorders. Further, compounds which possess such anabolic activity without concomitant androgenic activity (tissue selectivity) would be of practical therapeutic value. Male immature rats (50–40 g, 21-day-old, Sprague-Dawley, Harlan) were castrated under metofane anesthesia. Immediately after surgery, animals groups were dosed for 3 days as follows:

(1) control vehicle.
(2) Fluoxymesterone (Fluox) (1.0, 3.0, and 100 mg/kg, oral administration daily); and
(3) a compound of the present invention (different doses, oral administration daily) to demonstrate agonist activity At the end of the 3-day treatment, the animals were sacrificed, and the ventral prostates (VP), seminal vesicles (SV), and levator ani (LA) were collected and weighed. The sexual organ weights were first standardized as mg per 100 g of body weight, and the increase in organ weight induced by the compounds of the present invention was compared to the castrate control animals. The organ weight of the intact control animals is considered fully efficacious (100%). Super-anova (one factor) was used for statistical analysis.

The gain and loss of sexual organ weights reflect the changes of cell number (DNA content) and cell mass (protein content), depending upon the serum androgen concentration. See Y. Okuda et al., 145 *J Urol.*, 188–191 (1991), the disclosure of which is herein incorporated by reference. Therefore, measurement of organ wet weights is sufficient to indicate the bioactivity of androgens and androgen antagonists. In immature castrated rats, replacement of exogenous androgens increased the weights of the ventral prostate (VP), the seminal vesicles (SV), and the levator ani (LA) in a dose-dependent manner as shown in Table 4.

TABLE 4

Androgen Induced Ventral Prostate, Seminal Vesicle, and Levator Ani Growth in castrated immature rats at oral dosing, once daily, for 3 days, with fluoxymesterone (fluox) and Compound 105.

| Treatment (mg/kg) | VP (wet wt)[1] | VP eff (% of intact)[2] | SV (wet wt)[1] | SV eff (% intact)[2] | LA (wet wt)[1] | LA eff (% intact)[2] |
|---|---|---|---|---|---|---|
| Cx | 24.2 ± 1.8 | 0.0 ± 8.1 | 7.7 ± 1.0 | 0.0 ± 20 | 27.7 ± 3.2 | 0.0 ± 163 |
| intact | 46.6 ± 3.4 | 100 ± 15 | 12.8 ± 1.3 | 100 ± 25 | 29.5 ± 1.0 | 100 ± 60 |
| 105 (3) | 26.9 ± 1.1 | 12 ± 5 | 8.5 ± 0.7 | 15 ± 13 | 33.0 ± 2.4 | 306 ± 140 |
| 105 (10) | 35.9 ± 2.7 | 52 ± 12 | 9.9 ± 0.4 | 42 ± 8.2 | 36.3 ± 1.3 | 498 ± 73 |
| 105 (30) | 30.1 ± 2.1 | 26 ± 9 | 11.7 ± 1.4 | 78 ± 26 | 35.8 ± 1.2 | 469 ± 71 |
| 105 (100) | 42.1 ± 1.6 | 80 ± 7 | 14.4 ± 1.0 | 131 ± 19 | 39.7 ± 0.6 | 696 ± 36 |
| Fluox (1) | 49.3 ± 4.1 | 112 ± 18 | 24.3 ± 3.7 | 325 ± 73 | 44.6 ± 4.0 | 977 ± 230 |
| Fluox (3) | 57.5 ± 2.4 | 148 ± 10 | 31.8 ± 4.2 | 472 ± 82 | 45.3 ± 3.1 | 1020 ± 180 |
| Fluox (100) | 82.3 ± 7.2 | 259 ± 32 | 46.7 ± 1.7 | 762 ± 34 | 49.8 ± 5.4 | 1280 ± 310 |

[1]Weight of organ in mg/100 g body weight.
[2]% Efficacy compared to intact control (100% is full maintenance).

TABLE 5

Androgen Induced Ventral Prostate, Seminal Vesicle, and Levator Ani Growth in castrated immature rats at oral dosing, once daily, for 3 days, with fluoxymesterone (fluox) and Compound 123.

| Treatment (mg/kg) | VP (wet wt)[1] | VP eff (% of intact)[2] | SV (wet wt)[1] | SV eff (% of intact)[1] | LA (wet wt)[1] | LA eff (% of intact)[2] |
|---|---|---|---|---|---|---|
| Cx | 26.6 ± 2.1 | 0.0 ± 12 | 9.4 ± 0.8 | 0.0 ± 11 | 30.0 ± 3.6 | 0.0 ± 163 |
| intact | 44.0 ± 5.1 | 100 ± 29 | 17 ± 1.5 | 100 ± 19 | 32.1 ± 3.0 | 100 ± 137 |
| 123 (3) | 28.8 ± 2.8 | 13 ± 16 | 10.6 ± 0.9 | 15 ± 12 | 32.4 ± 3.6 | 109 ± 165 |
| 123 (10) | 38.6 ± 0.6 | 69 ± 3.6 | 9.3 ± 0.3 | −1 ± 4.2 | 34.4 ± 1.6 | 203 ± 75 |
| 123 (30) | 37.9 ± 3.1 | 65 ± 18 | 13.9 ± 0.8 | 57 ± 9.9 | 42.1 ± 2.7 | 554 ± 124 |
| 123 (100) | 44.6 ± 5.3 | 101 ± 30 | 19.6 ± 1.5 | 129 ± 19 | 48.5 ± 2.0 | 844 ± 91 |
| Fluox (1) | 31.8 ± 3.8 | 30 ± 22 | 22.4 ± 3.2 | 165 ± 41 | 42.6 ± 2.6 | 574 ± 116 |
| Fluox (3) | 47.1 ± 3.4 | 118 ± 19 | 29.0 ± 2.0 | 250 ± 26 | 51.8 ± 1.4 | 995 ± 65 |
| Fluox (100) | 73.5 ± 3.5 | 269 ± 20 | 37.4 ± 1.1 | 356 ± 14 | 60.4 ± 1.1 | 1384 ± 51 |

[1]Weight of organ in mg/100 g body weight.
[2]% Efficacy compared to intact control (100% is full maintenance).

In this immature castrated rat model, a known AR agonist (fluoxymesterone) was administered orally with 1.0, 3.0, and 100 mg/kg, increasing the androgen-mediated increases in the weights of VP, SV and LA in a dose-dependent manner as shown in Table 4. Compounds 105 and 123 also exhibited AR agonist activity by promoting the androgen-mediated maintenance/increase in the weights of the VP, SV and LA as summarized in Tables 4 and 5.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention, reference is made to the following non-limiting enumerated embodiments.

What is claimed is:

1. A compound of the formula:

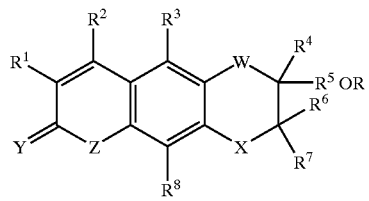

(I)

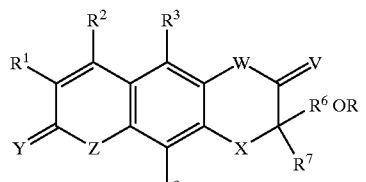

(III)

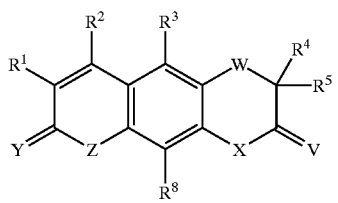

(V)

wherein:
R$^1$ is selected from the group of hydrogen, F, Cl, Br, I, NO$_2$, OR$^9$, NR$^{10}$R$^{11}$, S(O)$_m$R$^9$, C$_1$–C$_8$ alkyl, C$_1$–C$_8$ cycloalkyl, C$_1$–C$_8$ heteroalkyl, C$_1$–C$_8$ haloalkyl, C$_1$–C$_8$ aryl, C$_1$–C$_8$ arylalkyl, C$_1$–C$_8$ heteroaryl, C$_2$–C$_8$ alkynyl, and C$_2$–C$_8$ alkenyl and wherein the alkyl, cycloalkyl, heteroalkyl, haloalkyl, aryl, arylalkyl, heteroaryl, alkynyl, and alkenyl groups are optionally substituted;

$R^2$ is selected from the group of F, Cl, Br, I, $CF_3$, $CF_2Cl$, $CF_2H$, $CFH_2$, $CF_2OR^9$, $CH_2OR^9$, $OR^9$, $S(O)_mR^9$, $NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted;

$R^3$ is selected from the group of hydrogen, F, Cl, Br, I, $OR^9$, $S(O)_mR^9$, $NR^{10}R^{11}$, or $C_1$–$C_6$ alkyl, $C_1$–$C_6$ heteroalkyl and $C_1$–$C_6$ haloalkyl and wherein the alkyl, heteroalkyl and haloalkyl groups are optionally substituted;

$R^4$ and $R^5$ are each independently selected from the group of hydrogen, $OR^9$, $S(O)_mR^9$, $NR^{10}R^{11}$, $C(Y)OR^{11}$, $C(Y)NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted, or $R^4$ and $R^5$ taken together form a saturated or unsaturated three- to seven-membered ring that is optionally substituted;

$R^6$ and $R^7$ are each independently selected from the group of hydrogen, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted, or $R^6$ and $R^7$ taken together form a saturated or unsaturated three- to seven-membered ring that is optionally substituted, or $R^6$ and $R^5$ taken together form a saturated or unsaturated three- to seven-membered ring that is optionally substituted;

$R^8$ is selected from the group of hydrogen, $C_1$–$C_4$ alkyl, $C_1$–$C_4$ heteroalkyl, $C_1$–$C_4$ haloalkyl, F, Cl, Br, I, $NO_2$, $OR^9$, $NR^{10}R^{11}$ and $S(O)_mR^9$ and wherein the alkyl, heteroalkyl and haloalkyl groups are optionally substituted;

$R^9$ is selected from the group of hydrogen, $C_1$–$C_6$ alkyl, $C_1$–$C_6$ heteroalkyl, $C_1$–$C_6$ haloalkyl, aryl, heteroaryl, arylalkyl, $C_2$–$C_4$ alkynyl and $C_2$–$C_8$ alkenyl and wherein the alkyl, heteroalkyl, haloalkyl, aryl, arylalkyl, heteroaryl, alkynyl, and alkenyl groups are optionally substituted;

$R^{10}$ is selected from the group of hydrogen, $C_1$–$C_6$ alkyl, $C_1$–$C_6$ heteroalkyl, $C_1$–$C_6$ haloalkyl, $C(Y)R^{12}$, $C(Y)OR^{12}$, aryl, heteroaryl, $C_2$–$C_4$ alkynyl, $C_2$–$C_8$ alkenyl, arylalkyl, $SO_2R^{12}$ and $S(O)R^{12}$ and wherein the alkyl, heteroalkyl, haloalkyl, aryl, arylalkyl, heteroaryl, alkynyl, and alkenyl groups are optionally substituted;

$R^{11}$ is selected from the group of hydrogen, $C_1$–$C_6$ alkyl, $C_1$–$C_6$ heteroalkyl, $C_1$–$C_6$ haloalkyl, aryl, heteroaryl, arylalkyl, $C_2$–$C_4$ alkynyl and $C_2$–$C_8$ alkenyl and wherein the alkyl, heteroalkyl, haloalkyl, aryl, arylalkyl, heteroaryl, alkynyl, and alkenyl groups are optionally substituted;

$R^{12}$ is selected from the group of hydrogen, $C_1$–$C_6$ alkyl, $C_1$–$C_6$ heteroalkyl, $C_1$–$C_6$ haloalkyl, aryl, heteroaryl, arylalkyl, $C_2$–$C_4$ alkynyl and $C_2$–$C_8$ alkenyl and wherein the alkyl, heteroalkyl, haloalkyl, aryl, arylalkyl, heteroaryl, alkynyl, and alkenyl groups are optionally substituted, $R^{13}$ is selected from the group of hydrogen, $C_1$–$C_8$ alkyl, $C_3$–$C_8$ cycloalkyl, $C_1$–$C_8$ heteroalkyl, $C_1$–$C_8$ haloalkyl, aryl, heteroaryl, arylalkyl, heteroarylalkyl, $C_2$–$C_4$ alkynyl and $C_2$–$C_8$ alkenyl and wherein the alkyl, cycloalkyl, heteroalkyl, haloalkyl, aryl, arylalkyl, heteroaryl, heteroarylalkyl, alkynyl, and alkenyl groups are optionally substituted; or $R^{13}$ and $R^4$ taken together form a saturated or unsaturated three- to seven-membered ring that is optionally substituted; or any two of $R^4$ through $R^7$, and $R^{13}$ taken together form a saturated or unsaturated three- to seven-membered ring that is optionally substituted;

$R^{14}$ and $R^{15}$ are each independently selected from the group of hydrogen, $C_1$–$C_8$ alkyl, $C_3$–$C_8$ cycloalkyl, $C_1$–$C_8$ heteroalkyl, $C_1$–$C_8$ haloalkyl, aryl, heteroaryl, arylalkyl, $C_2$–$C_8$ alkynyl and $C_2$–$C_8$ alkenyl and wherein the alkyl, cycloalkyl, heteroalkyl, haloalkyl, aryl, heteroaryl, arylalkyl, alkynyl and alkenyl are optionally substituted;

m is 0, 1 or 2;

V is selected from the group of O, S and $CR^{14}R^{15}$;

W is selected from the group of O, S, NH, $NR^{13}$, $NC(Y)R^{11}$ and $NSO_2R^{11}$;

X and Z each independently is selected from the group of O, $S(O)_m$, NH, $NR^{11}$, $NC(Y)R^{11}$, $NSO_2R^{12}$ and $NS(O)R^{12}$; and Y is O or S; wherein when W is O or S, X is selected from the group of NH, $NR^{11}$, $NC(Y)R^{11}$, $NSO_2R^{12}$, and $NS(O)R^{12}$; and wherein when X is O or $S(O)_m$, W is selected from the group of NH, $NR^{13}$, $NC(Y)R^{11}$, and $NSO_2R^{11}$;

and pharmaceutically acceptable salts thereof.

2. A compound according to claim 1, wherein Z is $NR^{11}$.

3. A compound according to claim 2, wherein $R^{11}$ is hydrogen.

4. A compound according to claim 2, wherein $R^2$ is $CF_3$.

5. A compound according to claim 1, wherein W is $NR^{13}$.

6. A compound according to claim 5, wherein $R^{13}$ and one of $R^4$ and $R^5$ together form a five or six-membered ring.

7. A compound according to claim 5, wherein $R^{13}$ is alkyl.

8. A compound according to claim 7, wherein $R^{13}$ is selected from the group of methyl, ethyl, propyl, isopropyl, cyclopropylmethyl, and t-butyl.

9. A compound according to claim 5, wherein $R^{13}$ is haloalkyl.

10. A compound according to claim 9, wherein $R^{13}$ is trifluoroethyl.

11. A compound according to claim 1, wherein each of $R^4$, $R^5$, $R^6$ and $R^7$ are independently hydrogen or optionally substituted $C_1$–$C_6$ alkyl.

12. A compound according to claim 11, wherein one of $R^4$, $R^5$, $R^6$ and $R^7$ is optionally substituted $C_1$–$C_6$ alkyl.

13. A compound according to claim 11, wherein one of $R^4$ and $R^5$ is optionally substituted $C_1$–$C_6$ alkyl.

14. A compound according to claim 13, wherein one of $R^4$ and $R^5$ is $OR^9$.

15. A compound according to any one of claims 11 or 13, wherein one of $R^6$ and $R^7$ is optionally substituted $C_1$–$C_6$ alkyl.

16. A compound according to claim 15, wherein one of $R^6$ and $R^7$ is $OR^9$.

17. A compound according to claim 1, wherein $R^3$ and $R^8$ are each hydrogen;

X and Y are each independently O or S; W is $NR^{13}$; and Z is $NR^{11}$.

18. A compound according to claim 17, wherein X and Y are each O.

19. A compound according to claim 18, wherein $R^2$ is selected from the group of halogen, $CF_3$, $C_1$–$C_8$ alkyl and $C_1$–$C_8$ haloalkyl.

20. A compound according to claim 19, wherein $R^2$ is $CF_3$.

21. A compound according to claim 20, wherein $R^{13}$ is selected from the group of $C_1$–$C_8$ alkyl, $C_3$–$C_8$ cycloalkyl, and $C_1$–$C_8$ haloalkyl.

22. A compound according to claim 21, wherein $R^{13}$ is $C_1$–$C_8$ alkyl or $C_1$–$C_8$ haloalkyl.

23. A compound according to claim 21, wherein $R^{11}$ is selected from the group of hydrogen, optionally substituted $C_1$–$C_6$ alkyl and $C_1$–$C_6$ heteroalkyl.

24. A compound according to claim 23, wherein $R^{11}$ is hydrogen or optionally substituted $C_1$–$C_6$ alkyl.

25. A compound according to claim 24, wherein $R^{11}$ is hydrogen.

26. A compound according to claim 23, wherein $R^6$ and $R^7$ are each independently selected from the group of hydrogen, $C_1$–$C_8$ alkyl, and $C_1$–$C_8$ haloalkyl.

27. A compound according to claim 26, wherein $R^6$ and $R^7$ are each independently hydrogen or $C_1$–$C_8$ alkyl.

28. A compound according to claim 27, wherein $R^6$ and $R^7$ are each hydrogen.

29. A compound according to claim 26, wherein $R^4$ and $R^5$ are each independently selected from the group of hydrogen, $C_1$–$C_8$ alkyl, and $OR^9$.

30. A compound according to claim 29, wherein $R^4$ and $R^5$ are each independently hydrogen or $C_1$–$C_8$ alkyl.

31. A compound according to claim 30, wherein $R^4$ and $R^5$ are each hydrogen.

32. A compound according to claim 1, wherein:
$R^1$ is selected from the group of hydrogen, F, Cl, Br, I, $C_1$–$C_6$ alkyl and $C_1$–$C_6$ haloalkyl;
$R^2$ is selected from the group of halogen, $CF_3$, $C_1$–$C_8$ alkyl, and $C_1$–$C_8$ haloalkyl;
$R^3$ is selected from the group of hydrogen, $C_1$–$C_8$ alkyl, and $C_1$–$C_8$ haloalkyl;
$R^4$ and $R^5$ are each independently selected from the group of hydrogen, $C_1$–$C_8$ alkyl, $C_1$–$C_4$ haloalkyl, $C_1$–$C_4$ heteroalkyl and $OR^9$;
$R^6$ and $R^7$ are each independently hydrogen or $C_1$–$C_8$ alkyl;
$R^8$ is selected from the group of hydrogen, F, Cl, Br, I, $C_1$–$C_4$ alkyl and $C_1$–$C_4$ haloalkyl;
m is 1 or 2;
W is selected from the group of O, NH, $NR^{13}$, $NC(Y)R^{11}$, and $NSO_2R^{11}$;
X and Z are each independently selected from the group of O, S and $NR^{11}$; and
Y is O.

33. A compound according to claim 32, wherein:
$R^1$, $R^3$ and $R^8$ are each hydrogen;
$R^2$ is $CF_3$ or haloalkyl;
$R^5$, $R^6$, and $R^7$ each are independently hydrogen or $C_1$–$C_8$ alkyl;
m is 1;
W is NH or $NR^{13}$;
X and Z are each independently O or $NR^{11}$; and
Y is O.

34. A compound according to claim 33, wherein:
$R^2$ is $CF_3$;
$R^4$ is selected from the group of hydrogen, $C_1$–$C_4$ alkyl, and $C_1$–$C_2$ haloalkyl;
$R^5$, $R^6$, and $R^7$ are each independently hydrogen;
W is $NR^{13}$;
X is O; and
Z is $NR^{11}$.

35. A compound of the formula:

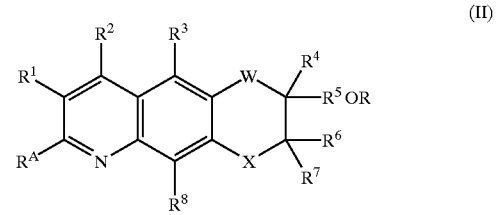

(II)

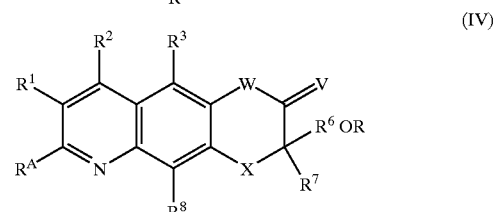

(IV)

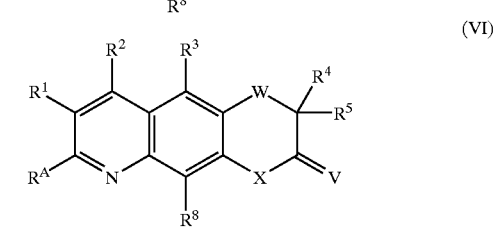

(VI)

wherein:
$R^1$ is selected from the group of hydrogen, F, Cl, Br, I, $NO_2$, $OR^9$, $NR^{10}R^{11}$, $S(O)_mR^9$, $C_1$–$C_8$ alkyl, $C_1$–$C_8$ cycloalkyl, $C_1$–$C_8$ heteroalkyl, $C_1$–$C_8$ haloalkyl, $C_1$–$C_8$ aryl, $C_1$–$C_8$ arylalkyl, $C_1$–$C_8$ heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted;

$R^2$ is selected from the group of F, Cl, Br, I, $CF_3$, $CF_2Cl$, $CF_2H$, $CFH_2$, $CF_2OR^9$, $CH_2OR^9$, $OR^9$, $S(O)_mR^9$, $NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted;

$R^3$ is selected from the group of hydrogen, F, Cl, Br, I, $OR^9$, $S(O)_mR^9$, $NR^{10}R^{11}$, or $C_1$–$C_6$ alkyl, $C_1$–$C_6$ heteroalkyl and $C_1$–$C_6$ haloalkyl and wherein the alkyl, heteroalkyl and haloalkyl groups are optionally substituted;

$R^4$ and $R^5$ are each independently selected from the group of hydrogen, $OR^9$, $S(O)_mR^9$, $NR^{10}R^{11}$, $C(Y)OR^{11}$, $C(Y)NR^{10}R^{11}$, $C_1$–$C_8$ alkyl, $C_3$–$C_8$ cycloalkyl, $C_1$–$C_8$ heteroalkyl, $C_1$–$C_8$ haloalkyl, aryl, arylalkyl, heteroaryl, $C_2$–$C_8$ alkynyl, and $C_2$–$C_8$ alkenyl and wherein the alkyl, cycloalkyl, heteroalkyl, haloalkyl, aryl, arylalkyl, heteroaryl, alkynyl, and alkenyl groups are optionally substituted, or R$^4$ and R$^5$ taken together form a saturated or unsaturated three- to seven-membered ring that is optionally substituted;

R$^6$ and R$^7$ are each independently selected from the group of hydrogen, C$_1$–C$_8$ alkyl, C$_3$–C$_8$ cycloalkyl, C$_1$–C$_8$ heteroalkyl, C$_1$–C$_8$ haloalkyl, aryl, arylalkyl, heteroaryl, C$_2$–C$_8$ alkynyl, and C$_2$–C$_8$ alkenyl and wherein the alkyl, cycloalkyl, heteroalkyl, haloalkyl, aryl, arylalkyl, heteroaryl, alkynyl, and alkenyl groups are optionally substituted, or R$^6$ and R$^7$ taken together form a saturated or unsaturated three- to seven-membered ring that is optionally substituted, or R$^6$ and R$^5$ taken together form a saturated or unsaturated three- to seven-membered ring that is optionally substituted;

R$^8$ is selected from the group of hydrogen, C$_1$–C$_4$ alkyl, C$_1$–C$_4$ heteroalkyl, C$_1$–C$_4$ haloalkyl, F, Cl, Br, I, NO$_2$, OR$^9$, NR$^{10}$R$^{11}$ and S(O)$_m$R$^9$ and wherein the alkyl, heteroalkyl and haloalkyl groups are optionally substituted;

R$^9$ is selected from the group of hydrogen, C$_1$–C$_6$ alkyl, C$_1$–C$_6$ heteroalkyl, C$_1$–C$_6$ haloalkyl, aryl, heteroaryl, arylalkyl, C$_2$–C$_4$ alkynyl and C$_2$–C$_8$ alkenyl and wherein the alkyl, heteroalkyl, haloalkyl, aryl, arylalkyl, heteroaryl, alkynyl, and alkenyl groups are optionally substituted;

R$^{10}$ is selected from the group of hydrogen, C$_1$–C$_6$ alkyl, C$_1$–C$_6$ heteroalkyl, C$_1$–C$_6$ haloalkyl, C(Y)R$^{12}$, C(Y)OR$^{12}$, aryl, heteroaryl, C$_2$–C$_4$ alkynyl, C$_2$–C$_8$ alkenyl, arylalkyl, SO$_2$R$^{12}$ and S(O)R$^{12}$ and wherein the alkyl, heteroalkyl, haloalkyl, aryl, arylalkyl, heteroaryl, alkynyl, and alkenyl groups are optionally substituted;

R$^{11}$ is selected from the group of hydrogen, C$_1$–C$_6$ alkyl, C$_1$–C$_6$ heteroalkyl, C$_1$–C$_6$ haloalkyl, aryl, heteroaryl, arylalkyl, C$_2$–C$_4$ alkynyl and C$_2$–C$_8$ alkenyl and wherein the alkyl, heteroalkyl, haloalkyl, aryl, arylalkyl, heteroaryl, alkynyl, and alkenyl groups are optionally substituted;

R$^{12}$ is selected from the group of hydrogen, C$_1$–C$_6$ alkyl, C$_1$–C$_6$ heteroalkyl, C$_1$–C$_6$ haloalkyl, aryl, heteroaryl, arylalkyl, C$_2$–C$_4$ alkynyl and C$_2$–C$_8$ alkenyl and wherein the alkyl, heteroalkyl, haloalkyl, aryl, arylalkyl, heteroaryl, alkynyl, and alkenyl groups are optionally substituted, R$^{13}$ is selected from the group of hydrogen, C$_1$–C$_8$ alkyl, C$_3$–C$_8$ cycloalkyl, C$_1$–C$_8$ heteroalkyl, C$_1$–C$_8$ haloalkyl, aryl, heteroaryl, arylalkyl, heteroarylalkyl, C$_2$–C$_4$ alkynyl and C$_2$–C$_8$ alkenyl and wherein the alkyl, cycloalkyl, heteroalkyl, haloalkyl, aryl, arylalkyl, heteroaryl, heteroarylalkyl, alkynyl, and alkenyl groups are optionally substituted; or R$^{13}$ and R$^4$ taken together form a saturated or unsaturated three- to seven-membered ring that is optionally substituted; or any two of R$^4$ through R$^7$, and R$^{13}$ taken together form a saturated or unsaturated three- to seven-membered ring that is optionally substituted;

R$^{14}$ and R$^{15}$ are each independently selected from the group of hydrogen, C$_1$–C$_8$ alkyl, C$_3$–C$_8$ cycloalkyl, C$_1$–C$_8$ heteroalkyl, C$_1$–C$_8$ haloalkyl, aryl, heteroaryl, arylalkyl, C$_2$–C$_8$ alkynyl and C$_2$–C$_8$ alkenyl and wherein the alkyl, cycloalkyl, heteroalkyl, haloalkyl, aryl, heteroaryl, arylalkyl, alkynyl and alkenyl are optionally substituted;

R$^A$ is selected from the group of F, Br, Cl, I, CN, OR$^{16}$, NR$^{16}$R$^{17}$, SR$^{16}$, CH$_2$R$^{16}$, COR$^{17}$, CO$_2$R$^{17}$, CONR$^{17}$R$^{17}$, SOR$^{17}$ and SO$_2$R$^{17}$;

R$^{16}$ is selected from the group of hydrogen, C$_1$–C$_8$ alkyl, C$_1$–C$_8$ haloalkyl, C$_1$–C$_8$ heteroalkyl, COR$^{17}$, CO$_2$R$^{17}$, CONR$^{17}$R$^{17}$, C$_2$–C$_8$ alkynyl, C$_2$–C$_8$ alkenyl, aryl, and heteroaryl and wherein the alkyl, heteroalkyl, haloalkyl, aryl, heteroaryl, alkynyl, and alkenyl groups are optionally substituted;

R$^{17}$ is selected from the group of hydrogen, C$_1$–C$_4$ alkyl, C$_1$–C$_4$ haloalkyl and C$_1$–C$_4$ heteroalkyl and wherein the alkyl, haloalkyl, and heteroalkyl groups are optionally substituted;

m is 0, 1 or 2;

n is 1 or 2;

V is selected from the group of O, S and CR$^{14}$R$^{15}$;

W is selected from the group of O, S, NH, NR$^{13}$, NC(Y)R$^{11}$ and NSO$_2$R$^{11}$; and X is selected from the group of O, S(O)$_m$, NH, NR$^{11}$, NC(Y)R$^{11}$, NSO$_2$R$^{12}$ and NS(O)R$^{12}$;

and pharmaceutically acceptable salts thereof.

36. A compound according to claim 35, wherein R$^2$ is CF$_3$.

37. A compound according to claim 35, wherein W is NR$^{13}$.

38. A compound according to claim 35, wherein R$^{13}$ and one of R$^4$ and R$^5$ together form a five or six-membered ring.

39. A compound according to claim 35, wherein R$^{13}$ is alkyl.

40. A compound according to claim 39, wherein R$^{13}$ is selected from the group of methyl, ethyl, propyl, isopropyl, cyclopropylmethyl, and t-butyl.

41. A compound according to claim 35, wherein R$^{13}$ is haloalkyl.

42. A compound according to claim 41, wherein R$^{13}$ is trifluoroethyl.

43. A compound according to claim 35, wherein each of R$^4$, R$^5$, R$^6$ and R$^7$ are independently hydrogen or optionally substituted C$_1$–C$_6$ alkyl.

44. A compound according to claim 43, wherein one of R$^4$, R$^5$, R$^6$ and R$^7$ is optionally substituted C$_1$–C$_6$ alkyl.

45. A compound according to claim 43, wherein one of R$^4$ and R$^5$ is optionally substituted C$_1$–C$_6$ alkyl.

46. A compound according to claim 45, wherein one of R$^4$ and R$^5$ is OR$^9$.

47. A compound according to any one of claim 43, wherein one of R$^6$ and R$^7$ is optionally substituted C$_1$–C$_6$ alkyl.

48. A compound according to claim 47, wherein one of R$^6$ and R$^7$ is OR$^9$.

49. A compound according to claim 35, wherein X is O.

50. A compound according to claim 49, wherein R$^2$ is selected from the group of halogen, CF$_3$, C$_1$–C$_8$ alkyl and C$_1$–C$_8$ haloalkyl.

51. A compound according to claim 50, wherein R$^2$ is CF$_3$.

52. A compound according to claim 51, wherein R$^{13}$ is selected from the group of C$_1$–C$_8$ alkyl, C$_3$–C$_8$ cycloalkyl, and C$_1$–C$_8$ haloalkyl.

53. A compound according to claim 51, wherein R$^{13}$ is C$_1$–C$_8$ alkyl or C$_1$–C$_8$ haloalkyl.

54. A compound according to claim 51, wherein R$^{11}$ is selected from the group of hydrogen, optionally substituted C$_1$–C$_6$ alkyl and C$_1$–C$_6$ heteroalkyl.

55. A compound according to claim 54, wherein R$^{11}$ is hydrogen or optionally substituted C$_1$–C$_6$ alkyl.

56. A compound according to claim 55, wherein $R^{11}$ is hydrogen.

57. A compound according to claim 54, wherein $R^6$ and $R^7$ are each independently selected from the group of hydrogen, $C_1$–$C_8$ alkyl, and $C_1$–$C_8$ haloalkyl.

58. A compound according to claim 57, wherein $R^6$ and $R^7$ are each independently hydrogen or $C_1$–$C_8$ alkyl.

59. A compound according to claim 58, wherein $R^6$ and $R^7$ are each hydrogen.

60. A compound according to claim 57, wherein $R^4$ and $R^5$ are each independently selected from the group of hydrogen, $C_1$–$C_8$ alkyl, and $OR^9$.

61. A compound according to claim 60, wherein $R^4$ and $R^5$ are each independently hydrogen or $C_1$–$C_8$ alkyl.

62. A compound according to claim 61, wherein $R^4$ and $R^5$ are each hydrogen.

63. A compound according to claim 35, wherein:
   $R^1$ is selected from the group of hydrogen, F, Cl, Br, I, $C_1$–$C_6$ alkyl and $C_1$–$C_6$ haloalkyl;
   $R^2$ is selected from the group of halogen, $CF_3$, $C_1$–$C_8$ alkyl, and $C_1$–$C_8$ haloalkyl;
   $R^3$ is selected from the group of hydrogen, $C_1$–$C_8$ alkyl, and $C_1$–$C_8$ haloalkyl;
   $R^4$ and $R^5$ are each independently selected from the group of hydrogen, $C_1$–$C_8$ alkyl, $C_1$–$C_4$ haloalkyl, $C_1$–$C_4$ heteroalkyl and $OR^9$;
   $R^6$ and $R^7$ are each independently hydrogen or $C_1$–$C_8$ alkyl;
   $R^8$ is selected from the group of hydrogen, F, Cl, Br, I, $C_1$–$C_4$ alkyl and $C_1$–$C_4$ haloalkyl;
   $R^A$ is selected from the group of F, Cl, Br, and I;
   m is 1 or 2;
   W is selected from the group of O, NH, $NR^{13}$, $NC(Y)R^{11}$, and $NSO_2R^{11}$; and
   X is selected from the group of O, S and $NR^{11}$.

64. A compound according to claim 63, wherein:
   $R^1$, $R^3$ and $R^8$ are each hydrogen;
   $R^2$ is $CF_3$ or haloalkyl;
   $R^5$, $R^6$, and $R^7$ each are independently hydrogen or $C_1$–$C_8$ alkyl;
   m is 1;
   W is NH or $NR^{13}$; and
   X is O or $NR^{11}$.

65. A compound according to claim 64, wherein:
   $R^2$ is $CF_3$;
   $R^4$ is selected from the group of hydrogen, $C_1$–$C_4$ alkyl, and $C_1$–$C_2$ haloalkyl;
   $R^5$, $R^6$, and $R^7$ are each independently hydrogen;
   W is $NR^{13}$; and
   X is O.

66. A compound according to any one of claims 1 or 35, wherein said compound is selected from the group of:
   1,2,3,6-Tetrahydro-1-methyl-9-(trifluoromethyl)-7H-[1,4]oxazino[3,2-g]quinolin-7-one,
   1,2,3,6-Tetrahydro-1,6-dimethyl-9-(trifluoromethyl)-7H-[1,4]oxazino[3,2-g]quinolin-7-one,
   1-Ethyl-1,2,3,6-tetrahydro-9-(trifluoromethyl)-7H-[1,4]oxazino[3,2-g]quinolin-7-one,
   1-Ethyl-1,2,3,6-tetrahydro-6-methyl-9-(trifluoromethyl)-7H-[1,4]oxazino[3,2-g]quinolin-7-one,
   1,2,3,6-tetrahydro-1-(2,2,2-trifluoroethyl)-9-(trifluoromethyl)-7H-[1,4]oxazino[3,2-g]quinolin-7-one,
   8-Fluoro-1,2,3,6-tetrahydro-1-(2,2,2-trifluoroethyl)-9-(trifluoromethyl)-7H-[1,4]oxazino[3,2-g]quinolin-7-one,
   8-Chloro-1,2,3,6-tetrahydro-1-(2,2,2-trifluoroethyl)-9-(trifluoromethyl)-7H-[1,4]oxazino[3,2-g]quinolin-7-one,
   9-(Difluoromethyl)-1,2,3,6-tetrahydro-1-(2,2,2-trifluoroethyl)-7H-[1,4]oxazino[3,2-g]quinolin-7-one,
   1,2,3,6-Tetrahydro-6-methyl-1-(2,2,2-trifluoroethyl)-9-(trifluoromethyl)-7H-[1,4]oxazino[3,2-g]quinolin-7-one,
   1,2,3,6-tetrahydro-1-(2,2,2-trifluoroethyl)-9-(trifluoromethyl)-7H-[1,4]oxazino[3,2-g]quinolin-7-thione,
   1,2,3,6-Tetrahydro-1-propyl-9-(trifluoromethyl)-7H-[1,4]oxazino[3,2-g]quinolin-7-one,
   1,2,3,6-Tetrahydro-1-isobutyl-9-(trifluoromethyl)-7H-[1,4]oxazino[3,2-g]quinolin-7-one,
   1,2,3,6-Tetrahydro-1-isobutyl-6-methyl-9-(trifluoromethyl)-7H-[1,4]oxazino[3,2-g]quinolin-7-one,
   (−)-1,2,3,6-Tetrahydro-3-methyl-1-(2,2,2-trifluoroethyl)-9-(trifluoromethyl)-7H-[1,4]oxazino[3,2-g]quinolin-7-one,
   (±)-1,2,3,6-Tetrahydro-3-methyl-1-(2,2,2-trifluoroethyl)-9-(trifluoromethyl)-7H-[1,4]oxazino[3,2-g]quinolin-7-one,
   (±)-1,2,3,6-Tetrahydro-1,3-dimethyl-9-(trifluoromethyl)-7H-[1,4]oxazino[3,2-g]quinolin-7-one,
   (±)-3-Ethyl-1,2,3,6-tetrahydro-1-(2,2,2-trifluoroethyl)-9-(trifluoromethyl)-7H-[1,4]oxazino[3,2-g]quinolin-7-one,
   (±)-3-Ethyl-1,2,3,6-tetrahydro-1-methyl-9-(trifluoromethyl)-7H-[1,4]oxazino[3,2-g]quinolin-7-one,
   (±)-1,2,3,6-Tetrahydro-9-(trifluoromethyl)-7H-[1,4]oxazino[3,2-g]quinolin-7-one,
   1-Cyclopropylmethyl-1,2,3,6-tetrahydro-9-(trifluoromethyl)-7H-[1,4]oxazino[3,2-g]quinolin-7-one,
   1,2,3,6-Tetrahydro-1-(pyridylmethyl)-9-(trifluoromethyl)-7H-[1,4]oxazino[3,2-g]quinolin-7-one,
   (±)-1,2,3,6-Tetrahydro-2-methyl-1-(2,2,2-trifluoroethyl)-9-(trifluoromethyl)-7H-[1,4]oxazino[3,2-g]quinolin-7-one,
   (−)-1,2,3,6-Tetrahydro-2-methyl-1-(2,2,2-trifluoroethyl)-9-(trifluoromethyl)-7H-[1,4]oxazino[3,2-g]quinolin-7-one,
   (±)-trans-1,2,3,6-Tetrahydro-2,3-dimethyl-1-(2,2,2-trifluoroethyl)-9-(trifluoromethyl)-7H-[1,4]oxazino[3,2-g]quinolin-7-one,
   (±)-cis-1,2,3,6-Tetrahydro-2,3-dimethyl-1-(2,2,2-trifluoroethyl)-9-(trifluoromethyl)-7H-[1,4]oxazino[3,2-g]quinolin-7-one,
   (±)-trans-3-Ethyl-1,2,3,6-tetrahydro-2-methyl-1-(2,2,2-trifluoroethyl)-9-(trifluoromethyl)-7H-[1,4]oxazino[3,2-g]quinolin-7-one,
   (±)-cis-3-Ethyl-1,2,3,6-tetrahydro-2-methyl-1-(2,2,2-trifluoroethyl)-9-(trifluoromethyl)-7H-[1,4]oxazino[3,2-g]quinolin-7-one,
   (±)-1,2,3,6-Tetrahydro-2-(hydroxymethyl)-1-(2,2,2-trifluoroethyl)-9-(trifluoromethyl)-7H-[1,4]oxazino[3,2-g]quinolin-7-one, (±)-1,2,3,6-Tetrahydro-2-(acetoxymethyl)-1-(2,2,2-trifluoroethyl)-9-(trifluoromethyl)-7H-[1,4]oxazino[3,2-g]quinolin-7-one, (±)-1,2,3,6-Tetrahydro-2-(methoxymethyl)-1-(2,2,2-trifluoroethyl)-9-(trifluoromethyl)-7H-[1,4]oxazino[3,2-g]quinolin-7-one, (−)-1,2,3,6-Tetrahydro-2-(methoxymethyl)-1-(2,2,2-trifluoroethyl)-9-(trifluoromethyl)-7H-[1,4]oxazino[3,2-g]quinolin-7-one, (±)-2-(Ethoxymethyl)-1,2,3,6-tetrahydro-1-(2,2,2-trifluoroethyl)-9-(trifluoromethyl)-7H-[1,4]oxazino[3,2-g]quinolin-7-one, (±)-1,2,3,6-Tetrahydro-2-(propoxymethyl)-1-(2,2,2-trifluoroethyl)-9-(trifluoromethyl)-7H-[1,4]oxazino[3,2-g]quinolin-7-one, 1,2-Dihydro-1-(2,2,2-trifluoroethyl)-9-(trifluoromethyl)-3H-[1,4]oxazino[3,2-g]quinolin-2,7-dione, (±)-1,2,3,6-Tetrahydro-2-hydroxy-2-methyl-1-(2,2,2-trifluoroethyl)-9-(trifluoromethyl)-7H-[1,4]oxazino[3,2-g]quinolin-7-one, 1,2-Dihydro-3-methyl-1-(2,2,2-trifluoroethyl)-9-(trifluoromethyl)-3H-[1,4]oxazino[3,2-g]-quinolin-2,7-dione, 1,2,3,6-Tetrahydro-1-(2,2,2-trifluoroethyl)-9-(trifluoromethyl)-2-thioxo-7H-[1,4]oxazino[3,2-g]quinolin-7-one, (±)-1,2,3,6-Tetrahydro-2-methyl-9-(trifluoromethyl)-7H-[1,4]oxazino[3,2-g]quinolin-7-one, 1-Cyclopropylmethyl-1,2,3,6-tetrahydro-2-methyl-9-(trifluoromethyl)-7H-[1,4]oxazino[3,2-g]quinolin-7-one, (±)-2-Ethyl-1,2,3,6-tetrahydro-9-(trifluoromethyl)-7H-[1,4]oxazino[3,2-g]quinolin-7-one, 1-Cyclopropylmethyl-2-ethyl-1,2,3,6-tetrahydro-9-(trifluoromethyl)-7H-[1,4]oxazino[3,2-g]quinolin-7-one, 1,2,3,6-Tetrahydro-1-isopropyl-9-(trifluoromethyl)-7H-[1,4]oxazino[3,2-g]quinolin-7-one, (±)-2-Ethyl-1,2,3,6-tetrahydro-1-(2,2,2-trifluoroethyl)-9-(trifluoromethyl)-7H-[1,4]oxazino[3,2-g]quinolin-7-one, (±)-1,2-Diethyl-1,2,3,6-tetrahydro-9-(trifluoromethyl)-7H-[1,4]oxazino[3,2-g]quinolin-7-one, (±)-1,2,3,6-Tetrahydro-1-(2,2,2-trifluoroethyl)-2,9-bis(trifluoromethyl)-7H-[1,4]oxazino[3,2-g]quinolin-7-one, (±)-1,2,3,6-Tetrahydro-1-(2,2,2-trifluoroethyl)-2,9-bis(trifluoromethyl)-7H-[1,4]oxazino[3,2-g]quinolin-7-one, (−)-1,2,3,6-Tetrahydro-1-(2,2,2-trifluoroethyl)-2,9-bis(trifluoromethyl)-7H-[1,4]oxazino[3,2-g]quinolin-7-one, (±)-1-Ethyl-1,2,3,6-tetrahydro-2-methyl-9-(trifluoromethyl)-7H-[1,4]oxazino[3,2-g]quinolin-7-one, (2R)-(−)-1,2,3,6-Tetrahydro-2-methyl-1-(2,2,2-trifluoroethyl)-9-(trifluoromethyl)-7H-[1,4]oxazino[3,2-g]quinolin-7-one, (2R)-2-Ethyl-1,2,3,6-tetrahydro-1-(2,2,2-trifluoroethyl)-9-(trifluoromethyl)-7H-[1,4]oxazino[3,2-g]quinolin-7-one, (2R)-2-Ethyl-1,2,3,6-tetrahydro-1-(2,2,2-trifluoroethyl)-9-(trifluoromethyl)-7H-[1,4]oxazino[3,2-g]quinolin-7-one, (2R)-1,2,3,6-Tetrahydro-2-isopropyl-1-(2,2,2-trifluoroethyl)-9-(trifluoromethyl)-7H-[1,4]oxazino[3,2-g]quinolin-7-one, (±)-1,2,3,4,4a,5-Hexahydro-11-(trifluoromethyl)-pyrido[1',2':4,5][1,4]oxazino[3,2-g]quinolin-7-one, (R)-2,3,3a,4-Tetrahydro-10-(trifluoromethyl)-pyrrolo[1',2':4,5][1,4]oxazino[3,2-g]quinolin-8(7H)-one, 1,3,4,6-Tetrahydro-1,3,3-trimethyl-9-(trifluoromethyl)-pyrazino[3,2-g]quinolin-2,7-dione, 1,2,3,4-Tetrahydro-1,3,3-trimethyl-9-(trifluoromethyl)-pyrazino[3,2-g]quinolin-7(6H)one, 9-(Trifluoromethyl)-1,2,3,6-tetrahydro-7H-[1,4]thiazino[3,2-g]quinolin-7-one, 1-Methyl-9-(trifluoromethyl)-1,2,3,6-tetrahydro-7H-[1,4]thiazino[3,2-g]quinolin-7-one, and 1-(2,2,2-Trifluoroethyl)-9-(trifluoromethyl)-1,2,3,6-tetrahydro-7H-[1,4]thiazino[3,2-g]quinolin-7-one.

67. A compound according to claim 35, wherein said compound is 7-Chloro-2,3-dihydro-1-(2,2,2-trifluoroethyl)-9-(trifluoromethyl)-1H-[1,4]oxazino[3,2-g]quinoline.

68. A pharmaceutical composition comprising a pharmaceutically acceptable vehicle suitable for enteral, parenteral, or topical administration, and a compound according to claim 35.

69. A method of modulating in a mammal a process mediated by one or more steroid receptors from the group consisting of progesterone receptors, androgen receptors, estrogen receptors, glucorticoid receptors, and mineralocorticoid receptors comprising administering to said mammal a pharmaceutically effective amount of a compound according to claim 35.

* * * * *